United States Patent
Maddaford et al.

(10) Patent No.: US 7,951,940 B2
(45) Date of Patent: *May 31, 2011

(54) SUBSTITUTED INDOLE COMPOUNDS HAVING NOS INHIBITORY ACTIVITY

(75) Inventors: Shawn Maddaford, Mississauga (CA); Jailall Ramnauth, Brampton (CA); Suman Rakhit, Mississauga (CA); Joanne Patman, Mississauga (CA); Paul Renton, Toronto (CA); Subhash C. Annedi, Mississauga (CA)

(73) Assignee: NeurAxon, Inc., Mississauga (CA)

( * ) Notice: Subject to any disclaimer, the term of this patent is extended or adjusted under 35 U.S.C. 154(b) by 15 days.

This patent is subject to a terminal disclaimer.

(21) Appl. No.: 12/047,963

(22) Filed: Mar. 13, 2008

(65) Prior Publication Data

US 2008/0249302 A1 Oct. 9, 2008

Related U.S. Application Data

(63) Continuation of application No. 11/404,267, filed on Apr. 13, 2006, now Pat. No. 7,375,219.

(60) Provisional application No. 60/670,856, filed on Apr. 13, 2005.

(51) Int. Cl.
*C07D 409/02* (2006.01)
*C07D 409/14* (2006.01)
*C07D 407/14* (2006.01)
*C07D 413/02* (2006.01)
*C07D 413/14* (2006.01)

(52) U.S. Cl. ........ 540/524; 544/143; 546/112; 546/135; 546/201; 546/277.4; 548/312.1; 548/466; 548/467; 548/503

(58) Field of Classification Search .................. None
See application file for complete search history.

(56) References Cited

U.S. PATENT DOCUMENTS

| | | | |
|---|---|---|---|
| 4,324,790 A | 4/1982 | Guillaume et al. | |
| 4,816,470 A | 3/1989 | Dowle et al. | |
| 4,816,560 A | 3/1989 | Verdini et al. | |
| 4,839,377 A | 6/1989 | Bays et al. | |
| 4,894,387 A | 1/1990 | Butina et al. | |
| 4,994,483 A | 2/1991 | Oxford et al. | |
| 5,037,845 A | 8/1991 | Oxford | |
| 5,070,102 A | 12/1991 | Traber et al. | |
| 5,103,020 A | 4/1992 | Albinson et al. | |
| 5,200,410 A | 4/1993 | Traber et al. | |
| 5,234,942 A * | 8/1993 | Bernstein et al. | 514/415 |
| 5,270,333 A | 12/1993 | Bays et al. | |
| 5,331,005 A | 7/1994 | Calderó Ges et al. | |
| 5,399,574 A | 3/1995 | Robertson et al. | |
| 5,466,699 A | 11/1995 | Robertson et al. | |
| 5,468,768 A | 11/1995 | Cipollina et al. | |
| 5,708,008 A | 1/1998 | Audia et al. | |
| 5,863,935 A | 1/1999 | Robertson et al. | |
| 5,874,427 A | 2/1999 | Filla et al. | |
| 5,998,438 A | 12/1999 | Slassi et al. | |
| 6,090,839 A | 7/2000 | Adams et al. | |
| 6,093,716 A | 7/2000 | Davis et al. | |
| 6,242,447 B1 | 6/2001 | Demopulos et al. | |
| 6,255,334 B1 | 7/2001 | Sands | |
| 6,380,201 B1 | 4/2002 | Johnson et al. | |
| 6,750,242 B1 | 6/2004 | Gurley et al. | |
| 6,861,443 B2 | 3/2005 | Gurley et al. | |
| 7,141,595 B2 | 11/2006 | Ramnauth et al. | |
| 7,375,219 B2 * | 5/2008 | Maddaford et al. | 540/524 |
| 2003/0064991 A1 | 4/2003 | Harriman et al. | |
| 2003/0203055 A1 | 10/2003 | Rao et al. | |
| 2004/0142935 A1 | 7/2004 | Schiemann et al. | |
| 2004/0259891 A1 | 12/2004 | Agarwal et al. | |
| 2005/0032791 A1 | 2/2005 | Merc-Vidal et al. | |
| 2005/0075348 A1 | 4/2005 | Harriman et al. | |
| 2005/0244389 A1 | 11/2005 | Fioramonti et al. | |
| 2005/0256182 A1 | 11/2005 | Sutter et al. | |
| 2006/0009512 A1 | 1/2006 | Curwen et al. | |
| 2007/0105943 A1 | 5/2007 | Nakamoto et al. | |
| 2007/0254940 A1 * | 11/2007 | Maddaford et al. | 514/414 |
| 2009/0131503 A1 | 5/2009 | Annedi et al. | |
| 2009/0163451 A1 | 6/2009 | Porreca et al. | |
| 2009/0192157 A1 | 7/2009 | Maddaford et al. | |

FOREIGN PATENT DOCUMENTS

| | | |
|---|---|---|
| CA | 2380775 | 2/2002 |
| CA | 2498644 | 2/2005 |
| EP | 0262873 | 4/1988 |
| EP | 0438230 | 7/1991 |
| EP | 0574618 | 12/1993 |
| EP | 1 571 142 A1 | 9/2005 |
| JP | 6212151 | 8/1994 |
| JP | 2000280626 | 10/2000 |
| JP | 2005129430 | 5/2005 |
| WO | WO 91/18897 | 12/1991 |
| WO | WO 92/13856 | 8/1992 |
| WO | WO 93/11106 | 6/1993 |
| WO | WO 94/03446 | 2/1994 |
| WO | WO9747302 | 12/1997 |

(Continued)

OTHER PUBLICATIONS

Perregaared et al., Journal of Medicinal Chemistry, 35(26), 4813-4822, 1992.*
Anderson et al, "Palladium-Catalyzed Amination of Aryl Nonaflates," *J. Org. Chem.*, 68: 9563-9573 (2003).
Antilla et al., "Copper-Catalyzed Coupling of Arylboronic Acids and Amines," *Org. Lett.*, 3: 2077-2079 (2001).

(Continued)

*Primary Examiner* — Fiona T Powers
(74) *Attorney, Agent, or Firm* — Clark & Elbing LLP

(57) ABSTRACT

The present invention features inhibitors of nitric oxide synthase (NOS), particularly those that selectively inhibit neuronal nitric oxide synthase (nNOS) in preference to other NOS isoforms. The NOS inhibitors of the invention, alone or in combination with other pharmaceutically active agents, can be used for treating or preventing conditions such as, for example, stroke, reperfusion injury, neurodegeneration, head trauma, CABG, migraine headache with and without aura, migraine with allodynia, central post-stroke pain (CPSP), neuropathic pain, morphine/opioid induced tolerance and hyperalgesia.

12 Claims, 23 Drawing Sheets

FOREIGN PATENT DOCUMENTS

| WO | WO9811895 | 3/1998 |
|---|---|---|
| WO | WO0000487 | 1/2000 |
| WO | WO0017198 | 3/2000 |
| WO | WO 00/38677 | 7/2000 |
| WO | WO 01/12187 | 2/2001 |
| WO | WO 01/32619 | 5/2001 |
| WO | WO 02/16318 | 2/2002 |
| WO | WO 03/051275 | 6/2003 |
| WO | WO 2004/014885 | 2/2004 |
| WO | WO2005013974 | 2/2005 |
| WO | WO2005024416 | 3/2005 |
| WO | WO2005090282 | 9/2005 |
| WO | WO 2007/063418 | 6/2007 |
| WO | WO 2007/118314 | 10/2007 |

OTHER PUBLICATIONS

Baati et al., "An Improved Method for the Preparation of Amidines via Thiophenylimidic Esters," *Synthesis*, 927-929 (1999).

Blair et al., "Effect of Ring Fluorination on the Pharmacology of Hallucinogenic Tryptamines," *J. Med. Chem.*, 43: 4701-4710 (2000).

Coe et al., "Convenient preparation of N-substituted indoles by modified Leimgruber-Batcho indole synthesis," *Tetrahedron Lett.*, 37: 6045-6048 (1996).

Cooper et al., "2-Aryl Indole NK1 Receptor Antagonists: Pptimisation of Indole Substitution," *Bioorg. Med. Chem. Lett.*, 11: 1233-1236 (2001).

Heaney et al., "1-Benzylindole," *Org. Synth.*, 54: 58 (1974) [http://www.orgsyn.org/orgsyn/prep.asp?prep=cv6p0104].

Huang et al., "New Ammonia Equivalents for the Pd-Catalyzed Amination of Aryl Halides," *Org. Lett.*, 3: 3417-3419 (2001).

Macor et al., "5-[(3-Nitropyrid-2-yl)amino]indoles: Novel Serotonin Agonists with Selectivity for the 5-HT1D Receptor. Variation of the C3 Substituent on the Indole Template Leads to Increased 5-HT1D Receptor Selectivity," *J. Med. Chem.*, 37: 2509-2512 (1994).

Macor et al., "Use of 2,5-Dimethylpyrrole as an Amino-Protecting Group in an Efficient Synthesis of 5-Amino-3-[(N-methyl-pyrrolidin-2(R)-yl)methyl]indole," *J. Org. Chem.*, 59: 7496-7498 (1994).

Perregaard et al., "Selective, centrally acting serotonin 5-HT2 antagonists. 1. 2- and 6-Substituted 1-phenyl-3-(4-piperidinyl)-1H-indoles" *J. Med. Chem.*, 35: 4813-4822 (1992).

Rowley et al., "3-(4-Fluoropiperidin-3-yl)-2-phenylindoles as High Affinity, Selective, and Orally Bioavailable h5-HT2A Receptor Antagonists," *J. Med. Chem.*, 44: 1603-1614 (2001).

Russell et al., "3-[3-(Piperidin-1-yl)propyl]indoles as Highly Selective h5-HT1D Receptor Agonists," *J. Med. Chem.*, 42: 4981-5001 (1999).

Speeter et al., "The Action of Oxalyl Chloride on Indoles: A New Approach to Tryptamines," *J. Am. Chem. Soc.*, 76: 6208-6210 (1954).

Sternfeld et al., "Synthesis and Serotonergic Activity of 3-[2-(Pyrrolidin-1-yl)ethyl]indoles: Potent Agonists for the h5-HT1D Receptor with High Selectivity over the h5-HT1B Receptor," *J. Med. Chem.*, 42: 677-690 (1999).

van Niel et al., "Fluorination of 3-(3-(Piperidin-1-yl)propyl)indoles and 3-(3-(Piperazin-1-yl)propyl)indoles Gives Selective Human 5-HT1D Receptor Ligands with Improved Pharmacokinetic Profiles," *J. Med. Chem.*, 42: 2087-2104 (1999).

Wiedenau et al., "Facile Synthesis of 2-Benzylindoles," *Synthetic Communications*, 27: 2033-2039 (1997).

Wolfe et al., "Simple, Efficient Catalyst System for the Palladium-Catalyzed Amination of Aryl Chlorides, Bromides, and Triflates," *J. Org. Chem.*, 65: 1158-1174 (2000).

Suh et al. "Novel Potent Antagonists of Transient Receptor Potential Channel, Vanilloid Subfamily Member 1: Structure-Activity Relationship of 1,3,-Diarylalkyl Thioureas Possessing New Vanilloid Equivalents," *J. Med. Chem.* 48:5823-5836 (2005).

Johnson et al. Chemical Abstracts, 128:192544, 1998.

Johnson et al. Chemical Abstracts, 128:257330, 1998.

Kitazawa et al. Chemical Abstracts, 129:302552, 1998.

Acton et al., "Benzoyl 2-Methyl Indoles as Selective PPARγ Modulators," *Bioorganic & Medicinal Chemistry Letters* 15:357-362 (2005).

Berridge, "The Mode of Action of 5-Hydroxytryptamine," *J. Exp. Biol.* 56:311-321 (1972).

Kuyper et al., "High-Affinity Inhibitors of Dihydrofolate Reductase: Antimicrobial and Anticancer Activities of 7,8-Dialkyl-1,3-diaminopyrrolo[3,2-f]quinazolines with Small Molecular Size," *J. Med. Chem.* 39:892-903 (1996).

U.S. Appl. No. 12/272,775, filed Nov. 17, 2008, Maddaford et al.

Mahindroo et al., "Novel Indole-Based Peroxisome Proliferator-Activated Receptor Agonists: Design, SAR, Structural Biology, and Biological Activities," *J. Med. Chem.* 48:8194-8208 (2005).

Abdel-Magid et al., "Reductive Amination of Aldehydes and Ketones with Sodium Triacetoxyborohydride. Studies on Direct and Indirect Reductive Amination Procedures," *J. Org. Chem.* 61(11): 3849-3862, 1996.

Adachi et al., "Aminohaloborane in Organic Synthesis IX. Exclusive Ortho Acylation Reaction of N-Monoaminoalkylanilines," *Chem. Pharm. Bull.* 33(5): 1826-1835, 1985.

Castro et al., "Enhancement of Oral Absorption in Selective 5-HT$_{1D}$ Receptor Agonists: Fluorinated 3-[3-(Piperidin-1-yl)propyl]indoles," *J. Med. Chem.*, 41(51): 2667-2670, 1998.

Dörwald, "Side Reactions in Organic Synthesis," *WILEY-VCH* (2005).

Egle et al., "3-(2-Pyrrolidin-1-ylethyl)-5-(1,2,3,6-Tetrahydropyridin-4-yl)-1H-indole Derivatives as High Affinity Human 5-HT(1B/1D) Ligands," *Bioorg. Med. Chem. Lett.* 14(3): 727-729, 2004.

Heuring and Peroutka, "Characterization of a Novel 3H-5-Hydroxytryptamine Binding Site Subtype in Bovine Brain Membranes," *J. Neurosci.* 7(3):894-903, 1987.

Hoyer et al., "Characterization of the 5-HT1B Recognition Site in Rat Brain: Binding Studies with (-)[125I]lodocyanopindolol," *Eur. J. Pharmacol.* 118(1-2):1-12, 1985.

Humphrey and Kuethe, "Practical Methodologies for the Synthesis of Indoles," *Chem. Rev.* 106(7):2875-2911, 2006.

Jordan, "Tamoxifen: A Most Unlikely Pioneering Medicine," *Nature Reviews.* 2(3):205-213 (2003).

Kim and Chung, "An Experimental Model for Peripheral Neuropathy Produced by Segmental Spinal Nerve Ligation in the Rat," *Pain* 50(3):355-363, 1992.

McKay, "The Preparation of N-Substituted-N$^1$-nitroguanidines by the Reaction of Primary Amines with N-Alkyl-N-nitroso-N$^1$-nitroguanidines," *J. Am. Chem. Soc.*, 71(6):1968-1970, 1949.

Srivastava and Banik, "Bismuth Nitrate-Catalyzed Versatile Michael Reactions," *J. Org. Chem.* 68(6):2109-2114, 2003.

Non-Final Office Action for U.S. Appl. No. 12/272,656 on Jun. 11, 2009.

International Search Report for PCT/IB2006/003873 (mailed Oct. 11, 2007).

Ahn and Basbaum, "Where do Triptans Act in the Treatment of Migraine?" *Pain* 115(1-2):1-4, 2005.

Ahn and Basbaum, "Tissue Injury Regulates Serotonin 1D Receptor Expression: Implications for the Control of Migraine and Inflammatory Pain," *J. Neurosci.* 26(32):8332-8338, 2006.

Al-Chaer et al., "A New Model of Chronic Visceral Hypersensitivity in Adult Rats Induced by Colon Irritation During Postnatal Development," *Gastroenterology* 119:1276-1285, 2000.

Arvieu et al., "Sumatriptan Inhibits the Release of CGRP and Substance P from the Rat Spinal Cord," *Neuroreport* 7(12):1973-1976, 1996.

Azpiroz et al., "Mechanisms of Hypersensitivity in IBS and Functional Disorders," *Neurogastroenterol. Motil.* 19(1 Suppl):62-88, 2007.

Bartsch et al., "Activation of 5-HT(1B/1D) Receptor in the Periaqueductal Gray Inhibits Nociception," *Ann. Neurol.* 56(3):371-381, 2004.

Bingham et al., "Inhibition of Inflammation-Induced Thermal Hypersensitivity by Sumatriptan Through Activation of 5-HT(1B/1D) Receptors," *Exp. Neurol.* 167(1):65-73, 2001.

Bornman et al., "Pathogenesis of Pain in Chronic Pancreatitis: Ongoing Enigma," *World J. Surg.* 27(11):1175-1182, 2003.

Bourdu et al., "Rectal Instillation of Butyrate Provides a Novel Clinically Relevant Model of Noninflammatory Colonic Hypersensitivity in Rats," *Gastroenterology* 128(7):1996-2008, 2005.

Bruinvels et al., "Localization of 5-HT1B, 5-HT1D alpha, 5-HT1E and 5-HT1F Receptor Messenger RNA in Rodent and Primate Brain," *Neuropharmacology* 33(3-4):367-386, 1994.

Burgess et al., "Time-Dependent Descending Facilitation from the Rostral Ventromedial Medulla Maintains, but does not Initiate, Neuropathic Pain," *J. Neurosci.* 22(12):5129-5136, 2002.

Buscher et al., "Chronic Pancreatitis Patients Show Hyperalgesia of Central Origin: A Pilot Study," *Eur. J. Pain* 10(4):363-370, 2006.

Castro et al., "Differential Distribution of [$^3$H]Sumatriptan Binding Sites (5-HT1B, 5-HT1D and 5-HT1F Receptors) in Human Brain: Focus on Brainstem and Spinal Cord," *Neuropharmacology* 36(4-5):535-542, 1997.

Cervero and Laird, "Visceral Pain," *Lancet* 353(9170):2145-2148, 1999.

De Ponti and Tonini, "Irritable Bowel Syndrome: New Agents Targeting Serotonin Receptor Subtypes," *Drugs* 61(3):317-332, 2001.

Dimcevski et al., "Pain in Chronic Pancreatitis: The Role of Reorganization in the Central Nervous System," *Gastroenterology* 132(4):1546-1556, 2007.

Dimcevski et al., "Assessment of Experimental Pain from Skin, Muscle, and Esophagus in Patients with Chronic Pancreatitis," *Pancreas* 35(1):22-29, 2007.

Ekbom, "Treatment of Cluster Headache: Clinical Trials, Design and Results," *Cephalalgia* 15(Suppl 15):33-36, 1995.

Ghelardini et al., "Involvement of Central Cholinergic System in Antinociception Induced by Sumatriptan in Mouse," *Int. J. Clin. Pharmacol. Res.* 17(2-3):105-109, 1997.

Giamberardino, "Referred Muscle Pain/Hyperalgesia and Central Sensitization," *J. Rehabil. Med.* (41 Suppl):85-88, 2003.

Hauer et al., "Gabapentin Successfully Manages Chronic Unexplained Irritability in Children with Severe Neurologic Impairment," *Pediatrics* 119(2):e519-522, 2007.

Humphrey and Goadsby, "The Mode of Action of Sumatriptan is Vascular? A Debate," *Cephalalgia* 14(6):401-410, 1994.

Jain and Kulkarni, "Antinociceptive Effect of Sumatriptan in Mice," *Indian J. Exp. Biol.* 36(10):973-979, 1998.

Jennings et al., "Effects of Sumatriptan on Rat Medullary Dorsal Horn Neurons," *Pain* 111(1-2):30-37, 2004.

Kayser et al., "The Antimigraine 5-HT 1B/1D Receptor Agonists, Sumatriptan, Zolmitriptan and Dihydroergotamine, Attenuate Pain-Related Behaviour in a Rat Model of Trigeminal Neuropathic Pain," *Br. J. Pharmacol.* 137(8):1287-1297, 2002.

Levy et al., "Disruption of Communication Between Peripheral and Central Trigeminovascular Neurons Mediates the Antimigraine Action of 5HT 1B/1D Receptor Agonists," *Proc. Natl. Acad. Sci. USA* 101(12):4274-4279, 2004.

Li et al., "Voltage-Dependent Calcium Currents in Bulbospinal Neurons of Neonatal Rat Rostral Ventrolateral Medulla: Modulation by Alpha2-Adrenergic Receptors," *J. Neurophysiol.* 79(2):583-594, 1998.

Nicholas et al., "Cellular Localization of Messenger RNA for beta-1 and beta-2 Adrenergic Receptors in Rat Brain: An in Situ Hybridization Study," *Neuroscience* 56(4):1023-1039, 1993.

Nikai et al., "Profound Reduction of Somatic and Visceral Pain in Mice by Intrathecal Administration of the Anti-migraine Drug, Sumatriptan," *Pain* 139(3):533-540, 2008.

Ottani et al., "Effect of Sumatriptan in Different Models of Pain in Rats," *Eur. J. Pharmacol.* 497(2):181-186, 2004.

Potrebic et al., "Peptidergic Nociceptors of Both Trigeminal and Dorsal Root Ganglia Express Serotonin 1D Receptors: Implications for the Selective Antimigraine Action of Triptans," *J. Neurosci.* 23(34):10988-10997, 2003.

Price et al., "SB-216641 and BRL-15572—Compounds to Pharmacologically Discriminate h5-HT1B and h5-HT1D Receptors," *Naunyn. Schmiedebergs. Arch. Pharmacol.* 356(3):312-320, 1997.

Rényi et al., "Biochemical and Behavioural Effects of Isamoltane, a beta-Adrenoceptor Antagonist with Affinity for the 5-HT1B Receptor of Rat Brain," *Naunyn. Schmiedebergs. Arch. Pharmacol.* 343(1):1-6, 1991.

Sparmann et al., "Pancreatic Fibrosis in Experimental Pancreatitis Induced by Dibutyltin Dichloride," *Gastroenterology* 112(5):1664-1672, 1997.

Stepanović-Petrović et al., "The Antinociceptive Effects of Anticonvulsants in a Mouse Visceral Pain Model," *Anesth. Analg.* 106(6):1897-1903, 2008.

Vera-Portocarrero et al., "Nociception in Persistent Pancreatitis in Rats: Effects of Morphine and Neuropeptide Alterations," *Anesthesiology* 98(2):474-484, 2003.

Vera-Portocarrero and Westlund, "Attenuation of Nociception in a Model of Acute Pancreatitis by an NK-1 Antagonist," *Pharmacol. Biochem. Behav.* 77(3):631-640, 2004.

Vera-Portocarrero et al., "Descending Facilitation from the Rostral Ventromedial Medulla Maintains Visceral Pain in Rats with Experimental Pancreatitis," *Gastroenterology* 130(7):2155-2164, 2006.

Vera-Portocarrero et al., "Reversal of Inflammatory and Noninflammatory Visceral Pain by Central or Peripheral Actions of Sumatriptan," *Gastroenterology* 135(4):1369-1378, 2008.

Verne et al., "Hypersensitivity to Visceral and Cutaneous Pain in the Irritable Bowel Syndrome," *Pain* 93(1):7-14, 2001.

Wick et al., "Transient Receptor Potential Vanilloid 1, Calcitonin Gene-Related Peptide, and Substance P Mediate Nociception in Acute Pancreatitis," *Am. J. Physiol. Gastrointest. Liver Physiol.* 290(5):G959-G969, 2006.

Winston et al., "Acute Pancreatitis Results in Referred Mechanical Hypersensitivity and Neuropeptide Up-Regulation that can be Suppressed by the Protein Kinase Inhibitor k252a," *J. Pain* 4(6):329-337, 2003.

Zhuo and Gebhart, "Facilitation and Attenuation of a Visceral Nociceptive Reflex from the Rostroventral Medulla in the Rat," *Gastroenterology* 122(4):1007-1019, 2002.

Zhuo et al., "Biphasic Modulation of Spinal Visceral Nociceptive Transmission from the Rostroventral Medial Medulla in the Rat," *J. Neurophysiol.* 87(5):2225-2236, 2002.

Zochodne and Ho, "Sumatriptan Blocks Neurogenic Inflammation in the Peripheral Nerve Trunk," *Neurology* 44(1):161-163, 1994.

Supplementary European Search Report and Communication for European Application No. 07719544.4 (dated Jan. 12, 2010).

* cited by examiner (compound Ic is compound 9; compound Id is compound 12; and compound If is compound 18)

(compound Id is compound 12)

(compound Id is compound 12)

| | n | String score : mean ± s.e.m. (arbitrary unit) |
|---|---|---|
| uninjured mice | 15 | 4.3 ± 0.4 |
| injured mice + vehicle | 15 | 0.3 ± 0.2 ††† |
| injured mice + Compound Id 1 mg/kg | 15 | 0.2 ± 0.1 ns |
| injured mice + Compound Id 3 mg/kg | 15 | 0.2 ± 0.1 ns |
| injured mice + Compound Id 6 mg/kg | 15 | 0.3 ± 0.3 ns |

Table III (compound Id is compound 12)

|  | n | Hall score : mean ± s.e.m. (arbitrary unit) |
|---|---|---|
| uninjured mice | 15 | 5.8 ± 0.2 |
| injured mice + vehicle | 15 | 2.1 ± 3.2 ††† |
| injured mice + Compound Id (1 mg/kg) | 15 | 1.7 ± 0.4 ns |
| injured mice + Compound Id (3 mg/kg) | 15 | 2.0 ± 0.3 ns |
| injured mice + Compound Id (6 mg/kg) | 15 | 2.1 ± 0.4 ns |

Table IV (compound Id is compound 12)

| | n | String score : mean ± s.e.m. (arbitrary unit) |
|---|---|---|
| uninjured mice | 15 | 4.5 ± 0.2 |
| injured mice + vehicle | 15 | 0.3 ± 0.1 ††† |
| injured mice + Compound Id (1 mg/kg) | 15 | 0.3 ± 0.2 ns |
| injured mice + Compound Id (3 mg/kg) | 15 | 1.6 ± 0.5 * |
| injured mice + Compound Id (6 mg/kg) | 15 | 1.7 ± 0.6 * |

Table V :

(compound Id is compound 12)

| | n | Grip score : mean ± s.e.m. (s) |
|---|---|---|
| uninjured mice | 15 | 30.0 ± 0.0 |
| injured mice + vehicle | 15 | 14.6 ± 3.2 ††† |
| injured mice + Compound Id 1 mg/kg | 15 | 13.4 ± 2.6 ns |
| injured mice + Compound Id 3 mg/kg | 15 | 21.9 ± 2.9 * |
| injured mice + Compound Id 6 mg/kg | 15 | 18.4 ± 3.0 ns |

Table VI :

(compound Id is compound 12)

| | n | Hall score : mean ± s.e.m. (arbitrary unit) |
|---|---|---|
| uninjured mice | 15 | 5.8 ± 0.1 |
| injured mice + vehicle | 15 | 2.7 ± 0.3 ††† |
| injured mice + Compound Id 1 mg/kg | 15 | 2.7 ± 0.4 ns |
| injured mice + Compound Id 3 mg/kg | 15 | 3.6 ± 0.4 ns |
| injured mice + Compound Id 6 mg/kg | 15 | 3.8 ± 0.1 * |

Table VII (compound Id is compound 12)

| | n | Body temperature: mean ± s.e.m. (°C) |
|---|---|---|
| uninjured mice | 15 | 36.9 ± 0.08 |
| injured mice + vehicle | 15 | 35.0 ± 0.29 ††† |
| injured mice +Compound Id 1 mg/kg | 15 | 34.4 ± 0.37 ns |
| injured mice + Compound Id 3 mg/kg | 15 | 35.3 ± 0.42 ns |
| injured mice +Compound Id 6 mg/kg | 15 | 34.8 ± 0.34 ns |

TableVIII:

(compound Id is compound 12)

| | n | Body temperature : mean ± s.e.m. (°C) |
|---|---|---|
| uninjured mice | 15 | 36.6 ± 0.11 |
| injured mice + vehicle | 15 | 37.1 ± 0.14 † |
| injured mice + Compound Id (1 mg/kg) | 15 | 36.7 ± 0.14 * |
| injured mice + Compound Id (3 mg/kg) | 15 | 36.7 ± 0.17 * |
| injured mice + Compound Id (6 mg/kg) | 15 | 36.8 ± 0.12 ns |

Table (compound Id is compound 12)

| | n | body weight loss: mean ± s.e.m. (g) |
|---|---|---|
| uninjured mice | 15 | 0.0 ± 0.2 |
| injured mice + vehicle | 14 | 5.6 ± 0.3 ††† |
| injured mice + Compound Id (1 mg/kg) | 15 | 5.5 ± 0.3 ns |
| injured mice + Compound Id (3 mg/kg) | 15 | 3.9 ± 0.6 ** |
| injured mice + Compound Id (6 mg/kg) | 15 | 5.0 ± 0.5 ns |

Table X:

(compound Id is compound 12)

Effect of Compound 12 on Population Spike Amplitude in CA1 Cells after OGD Challenge

Figure 15: a) Left PS in control cells. b) Middle; PS after 10 min OGD (control dead). C) Right: PS in OGD cells protected (control live) by 0.3 mM Ca2+.

(compound Id is compound 12)

(compound Id is compound 12)

Chung SNL Model of Tactile Allodynia –

Chung SNL Model of Thermal Hyperalgesia – compound 1i (-) is compound 32(-); compound 1i (+) is compound 32(+)

compound 1i (-) is compound 32(-); compound 1i (+) is compound 32(+)

(compound Id is compound 12)

(compound Id is compound 12)

SUBSTITUTED INDOLE COMPOUNDS HAVING NOS INHIBITORY ACTIVITY

CROSS-REFERENCE TO RELATED APPLICATIONS

This application is a continuation of U.S. application Ser. No. 11/404,267, filed Apr. 13, 2006, which claims benefit of U.S. Provisional Application No. 60/670,856, filed Apr. 13, 2005, each of which is hereby incorporated by reference.

BACKGROUND OF THE INVENTION

The present invention relates to novel substituted indole compounds having nitric oxide synthase (NOS) inhibitory activity, to pharmaceutical and diagnostic compositions containing them, and to their medical use, particularly as compounds for the treatment of stroke, reperfusion injury, neurodegenerative disorders, head trauma, coronary artery bypass graft (CABG) associated neurological damage, migraine with and without aura, migraine with allodynia, chronic tension type headache (CTTH), neuropathic pain, post-stroke pain, and chronic pain.

Nitric oxide (NO) has diverse roles both in normal and pathological processes, including the regulation of blood pressure, in neurotransmission, and in the macrophage defense systems (Snyder et al., *Scientific American*, May 1992:68). NO is synthesized by three isoforms of nitric oxide synthase, a constitutive form in endothelial cells (eNOS), a constitutive form in neuronal cells (nNOS), and an inducible form found in macrophage cells (iNOS). These enzymes are homodimeric proteins that catalyze a five-electron oxidation of L-arginine, yielding NO and citrulline. The role of NO produced by each of the NOS isoforms is quite unique. Overstimulation or overproduction of individual NOS isoforms, especially nNOS and iNOS, plays a role in several disorders, including septic shock, arthritis, diabetes, ischemia-reperfusion injury, pain, and various neurodegenerative diseases (Kerwin, et al., *J. Med. Chem.* 38:4343, 1995), while m inhibition of eNOS function leads to unwanted effects such as enhanced white cell and platelet activation, hypertension and increased atherogenesis (Valance and Leiper, *Nature Rev. Drug Disc.* 2002, 1, 939).

NOS inhibitors have the potential to be used as therapeutice agents in many disorders. However, the preservation of physiologically important nitric oxide synthase function suggests the desirability of the development of isoform-selective inhibitors that preferentially inhibit nNOS over eNOS.

SUMMARY OF THE INVENTION

It has been found that certain 5- and 6-amidine substituted indole compounds are nitric oxide synthase (NOS) inhibitors, and are particularly inhibitory for the nNOS isoform.

The invention features a compound having the formula:

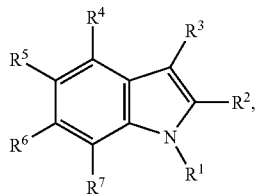

(I)

or a pharmaceutically acceptable salt or prodrug thereof, wherein, $R^1$ is H, optionally substituted $C_{1-6}$ alkyl, optionally substituted $C_{1-4}$ alkaryl, or optionally substituted $C_{1-4}$ alkheterocyclyl; each of $R^2$ and $R^3$ is, independently, H, Hal, optionally substituted $C_{1-6}$ alkyl, optionally substituted $C_{6-10}$ aryl, optionally substituted $C_{1-4}$ alkaryl, optionally substituted $C_{2-9}$ bridged heterocyclyl, optionally substituted $C_{1-4}$ bridged alkheterocyclyl, optionally substituted $C_{2-9}$ heterocyclyl, or optionally substituted $C_{1-4}$ alkheterocyclyl; each of $R^4$ and $R^7$ is, independently, H, F, $C_{1-6}$ alkyl, or $C_{1-6}$ alkoxy; $R^5$ is H, $R^{5A}C(NH)NH(CH_2)_{r5}$ or $R^{5A}NHC(S)NH(CH_2)_{r5}$, wherein r5 is an integer from 0 to 2, $R^{5A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl; and $R^6$ is H or $R^{6A}C(NH)(CH_2)_{r6}$ or $R^{6A}NHC(S)NH(CH_2)_{r6}$, wherein r6 is an integer from 0 to 2, $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl; wherein one, but not both, of $R^5$ and $R^6$ is H.

In certain embodiments, $R^1$ is H, optionally substituted $C_{1-6}$ alkyl, optionally substituted $C_{1-4}$ alkaryl, or optionally substituted $C_{1-4}$ alkheterocyclyl; each of $R^2$ and $R^3$ is, independently, H, Hal, optionally substituted $C_{1-6}$ alkyl, optionally substituted $C_{6-10}$ aryl, optionally substituted $C_{1-4}$ alkaryl, optionally substituted $C_{2-9}$ heterocyclyl, or optionally substituted $C_{1-4}$ alkheterocyclyl; each of $R^4$ and $R^7$ is, independently, H, F, $C_{1-6}$ alkyl, or $C_{1-6}$ alkoxy; $R^5$ is H or $R^{5A}C(NH)NH(CH_2)_{r5}$, wherein r5 is an integer from 0 to 2, $R^{5A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted $C_{1-4}$ thioalkheterocyclyl; and $R^6$ is H or $R^{6A}C(NH)(CH_2)_{r6}$, wherein r6 is an integer from 0 to 2, $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted $C_{1-4}$ thioalkheterocyclyl.

$R^{5A}$ or $R^{6A}$ is, for example, methyl, fluoromethyl, ethyl, n-propyl, i-propyl, n-butyl, i-butyl, t-butyl, thiomethoxy, thioethoxy, thio-n-propyloxy, thio-i-propyloxy, thio-n-butyloxy, thio-i-butyloxy, thio-t-butyloxy, phenyl, benzyl, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, and 4-isothiazole.

In certain embodiments, one or more of $R^1$, $R^2$, and $R^3$ is not H. For example, $R^1$, $R^2$, or $R^3$ is $(CH_2)_{m1}X^1$, wherein $X^1$ is selected from the group consisting of:

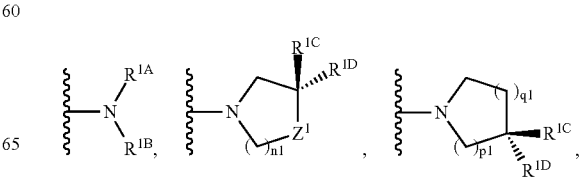

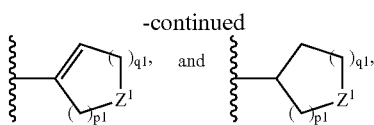

wherein
each of $R^{1A}$ and $R^{1B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl; each of $R^{1C}$ and $R^{1D}$ is, independently, H, OH, $CO_2R^{1E}$, or $NR^{1F}R^{1G}$, wherein each of $R^{1E}$, $R^{1F}$, and $R^{1G}$ is, independently, H, optionally substituted $C_{1-6}$ alkyl optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{1C}$ and $R^{1D}$ together with the carbon they are bonded to are C=O; $Z^1$ is $NR^{1H}$, $NC(O)R^{1H}$, $NC(O)OR^{1H}$, $NC(O)NHR^{1H}$, $NC(S)R^{1H}$, $NC(S)NHR^{1H}$, $NS(O)_2R^{1H}$, O, S, S(O), or $S(O)_2$, wherein $R^{1H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl; m1 is an integer of 2 to 6; n1 is an integer of 1 to 4; p1 is an integer of 0 to 2; and q1 is an integer of 0 to 5. In another example, $R^1$, $R^2$, and $R^3$ is $(CH_2)_mX^1$, wherein $X^1$ is selected from the group consisting of:

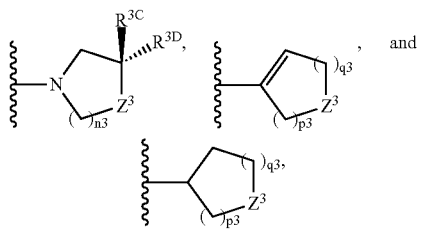

wherein
each of $R^{3C}$ and $R^{3D}$ is, independently, H, OH, $CO_2R^{3E}$, or $NR^{3F}R^{3G}$, wherein each of $R^{3E}$, $R^{3F}$, and $R^{3G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{3C}$ and $R^{3D}$ together with the carbon they are bonded to are C=O; $Z^3$ is $NC(NH)R^{3H}$, wherein $R^{3H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl; m3 is an integer of 0 to 6; n3 is an integer of 1 to 4; p3 is an integer of 0 to 2; and q3 is an integer of 0 to 5. $R^2$ or $R^3$ may also have the formula

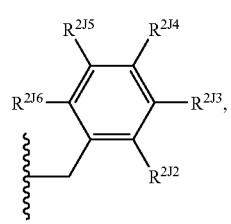

wherein each of $R^{2J2}$, $R^{2J3}$, $R^{2J4}$, $R^{2J5}$, $R^{2J6}$, and $R^{2J7}$ is, independently, $C_{1-6}$ alkyl; OH; $C_{1-6}$ alkoxy; SH; $C_{1-6}$ thioalkoxy; Halo; $NO_2$; CN; $CF_3$; $OCF_3$; $NR^{2Ja}R^{2Jb}$, where each of $R^{2Ja}$ and $R^{2Jb}$ is, independently, H or $C_{1-6}$ alkyl; $C(O)R^{2Jc}$, where $R^{2Jc}$ is H or $C_{1-6}$ alkyl; $CO_2R^{2Jd}$, where $R^{2Jd}$ is H or $C_{1-6}$ alkyl; tetrazolyl; $C(O)N^{2Je}R^{2Jf}$, where each of $R^{2Je}$ and $R^{2Jf}$ is, independently, H or $C_{1-6}$ alkyl; $OC(O)R^{2Jg}$, where $R^{2Jg}$ is $C_{1-6}$ alkyl; $NHC(O)R^{2Jh}$, where $R^{2Jh}$ is H or $C_{1-6}$ alkyl; $SO_3H$; $S(O)_2NR^{2Ji}R^{2Jj}$, where each of $R^{2Ji}$ and $R^{2Jj}$ is, independently, H or $C_{1-6}$ alkyl; $S(O)R^{2Jk}$, where $R^{2Jk}$ is $C_{1-6}$ alkyl; and $S(O)_2R^{2Jl}$, where $R^{2Jl}$ is $C_{1-6}$ alkyl. $R^1$ or $R^3$ may have the formula

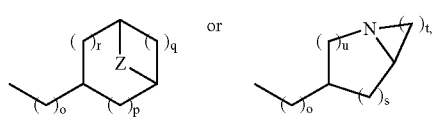

wherein Z is $NR^X$, o is an integer from 0-3, p is an integer from 1 to 2, q is an integer from 0 to 2, r is an integer from 0 to 1, s is an integer from 1 to 3, u is an integer from 0 to 1, and t is an integer from 5 to 7, and wherein said $R^1$ or $R^3$ substituent includes 0 to 6 carbon-carbon double bonds or 0 or 1 carbon-nitrogen double bonds.

The compounds of the invention may have the formula:

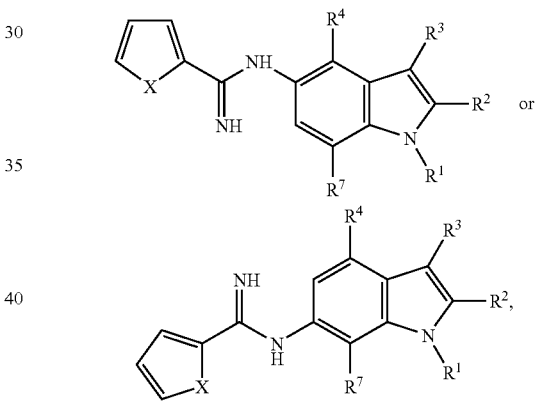

wherein X is O or S.

Preferably, a compound of the invention selectively inhibits neuronal nitric oxide synthase (nNOS) over endothelial nitric oxide synthase (eNOS) or inducible nitric oxide synthase (iNOS) or both in an in vitro assay. Preferably, the $IC_{50}$ or $K_i$ value observed for the compound when tested is at least 2 times lower in the nNOS assay than in the eNOS and/or iNOS assays. More preferably, the $IC_{50}$ or $K_i$ value is at least 5 times lower. Most preferably, the $IC_{50}$ or $K_i$ value is 20, or even 50 times lower. In one embodiment, the $IC_{50}$ or $K_i$ value is between 2 times and 50 times lower.

In another embodiment of the invention, compounds of formula I wherein $R^5$ is $R^{5A}C(NH)NH(CH_2)_{r5}$ or $R^{5A}NHC(S)NH(CH_2)_{r5}$, $R^6$, $R^2$, and $R^1$ are H, and $R^3$ is $(CH_2)_{m3}X^1$ also bind to the serotonin 5HT1D/1B receptors. Preferably the $IC_{50}$ or $K_i$ value is between 10 and 0.001 micromolar. More preferably, the $IC_{50}$ or $K_i$ is less than 1 micromolar. Most preferably, the $IC_{50}$ or $K_i$ is less than 0.1.

Specific exemplary compounds are described herein.

The invention further features pharmaceutical compositions including a compound of the invention and a pharmaceutically acceptable excipient.

In another aspect, the invention features a method of treating a condition in a mammal, such as, for example, a human, caused by the action of nitric oxide synthase (NOS), and particularly nNOS, that includes administering an effective amount of a compound of the invention to the mammal. Examples of conditions that can be prevented or treated include migraine headache (with or without aura), chronic tension type headache (CTTH), migraine with allodynia, neuropathic pain, post-stroke pain, chronic headache, chronic pain, acute spinal cord injury, diabetic neuropathy, trigeminal neuralgia, diabetic nephropathy, an inflammatory disease, stroke, reperfusion injury, head trauma, cardiogenic shock, CABG associated neurological damage, HCA, AIDS associated dementia, neurotoxicity, Parkinson's disease, Alzheimer's disease, ALS, Huntington's disease, multiple sclerosis, metamphetamine-induced neurotoxicity, drug addiction, morphine/opioid induced tolerance, dependence, hyperalgesia, or withdrawal, ethanol tolerance, dependence, or withdrawal, epilepsy, anxiety, depression, attention deficit hyperactivity disorder, and psychosis. Compounds of the invention are particularly useful for treating stroke, reperfusion injury, neurodegeneration, head trauma, CABG associated neurological damage, migraine headache (with or without aura), migraine with allodynia, chronic tension type headache, neuropathic pain, post-stroke pain, opioid induced hyperalgesia, or chronic pain. In particular, 3,5-substituted indole compounds are useful for treating migraine, with or without aura, and CTTH.

A compound of the invention can also be used in combination with one or more other therapeutic agents for the prevention or treatment of one of the aforementioned conditions. Examples of classes of therapeutic agents and some specific examples that are useful in combination with a compound of the invention are listed in Table 1.

Other agents useful in combination with a compound of the invention, include antiarrhythmics; DHP-sensitive L-type calcium channel antagonists; omega-conotoxin (Ziconotide)-sensitive N-type calcium channel antagonists; P/Q-type calcium channel antagonists; adenosine kinase antagonists; adenosine receptor $A_1$ agonists; adenosine receptor $A_{2a}$ antagonists; adenosine receptor $A_3$ agonists; adenosine deaminase inhibitors; adenosine nucleoside transport inhibitors; vanilloid VR1 receptor agonists; Substance P/$NK_1$ antagonists; cannabinoid CB1/CB2 agonists; GABA-B antagonists; AMPA and kainate antagonists, metabotropic glutamate receptor antagonists; alpha-2-adrenergic receptor agonists; nicotinic acetylcholine receptor agonists (nAChRs); cholecystokinin B antagonists; sodium channel blockers; a $K_{ATP}$ potassium channel, $K_{v1.4}$ potassium channel, $Ca^{2+}$-activated potassium channel, SK potassium channel, BK potassium channel, IK potassium channel, or KCNQ2/3 potassium channel opening agent (eg. retigabine); $5HT_{1A}$ agonists; muscarinic M3 antagonists, M1 agonists, M2/M3 partial agonist/antagonists; and antioxidants.

TABLE 1

Therapeutic agents useful in combination with compounds of the invention

| Class | Examples |
|---|---|
| Opioid | alfentanil, butorphanol, buprenorphine, codeine, dextromoramide, dextropropoxyphene, dezocine, dihydrocodeine, diphenoxylate, etorphine, fentanyl, hydrocodone, hydromorphone, ketobemidone, levorphanol, levomethadone, methadone, meptazinol, morphine, morphine-6-glucuronide, nalbuphine, naloxone, oxycodone, oxymorphone, pentazocine, pethidine, piritramide, remifentanil, sulfentanyl, tilidine, or tramadol |
| Antidepressant (selective serotonin reuptake inhibitor) | citalopram, escitalopram, fluoxetine, fluvoxamine, paroxetine, or sertraline |
| Antidepressant (norepinephrine-reuptake inhibitor) | amitriptyline, desmethylamitriptyline, clomipramine, doxepin, imipramine, imipramine oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, or tianeptine |
| Antidepressant (noradrenaline/norepinephrine reuptake inhibitor) | atomoxetine, bupropion, reboxetine, or tomoxetine |
| Antidepressant (dual serotonin/norepinephrine reuptake inhibitor) | duloxetine, milnacipran, mirtazapine, nefazodone, or venlafaxine |
| Antidepressant (monoamine oxidase inhibitor) | amiflamine, iproniazid, isocarboxazid, M-3-PPC (Draxis), moclobemide, pargyline, phenelzine, tranylcypromine, or vanoxerine |
| Antidepressant (reversible monoamine oxidase type A inhibitor) | bazinaprine, befloxatone, brofaromine, cimoxatone, or clorgyline |
| Antidepressant (tricyclic) | amitriptyline, clomipramine, desipramine, doxepin, imipramine, maprotiline, nortryptyline, protriptyline, or trimipramine |

TABLE 1-continued

Therapeutic agents useful in combination with compounds of the invention

| Class | Examples |
|---|---|
| Antidepressant (other) | adinazolam, alaproclate, amineptine, amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, lithium, litoxetine; lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, trazodone, tofenacin, tofisopam, toloxatone, tomoxetine, veralipride, viloxazine, viqualine, zimelidine, or zometapine |
| Antiepileptic | carbamazepine, flupirtine, gabapentin, lamotrigine, oxcarbazepine, phenyloin, retigabine, topiramate, or valproate |
| Non-steroidal anti-inflammatory drug (NSAID) | acemetacin, aspirin, celecoxib, deracoxib, diclofenac, diflunisal, ethenzamide, etofenamate, etoricoxib, fenoprofen, flufenamic acid, flurbiprofen, lonazolac, lornoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, or 2-(3,5-difluorophenyl)-3-[4-(methylsulfonyl)phenyl]-2-cyclopenten-1-one). |
| $5HT_{1B/1D}$ agonist | eletriptan, frovatriptan, naratriptan, rizatriptan, sumatriptan, or zolmitriptan |
| Anti-inflammatory compounds | aspirin, celecoxib, cortisone, deracoxib, diflunisal, etoricoxib, fenoprofen, ibuprofen, ketoprofen, naproxen, prednisolone, sulindac, tolmetin, piroxicam, mefenamic acid, meloxicam, phenylbutazone, rofecoxib, suprofen, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, or 2-(3,5-difluorophenyl)-3-[4-(methylsulfonyl)phenyl]-2-cyclopenten-1-one |
| N-methyl-D-aspartate antagonist | amantadine; aptiganel; besonprodil; budipine; conantokin G; delucemine; dexanabinol; dextromethorphan; dextropropoxyphen; felbamate; fluorofelbamate; gacyclidine; glycine; ipenoxazone; kaitocephalin; ketamine; ketobemidone; lanicemine; licostinel; midafotel; memantine; D-methadone; D-morphine; milnacipran; neramexane; orphenadrine; remacemide; sulfazocine; FPL-12,495 (racemide metabolite); topiramate; (αR)-α-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H-,5H-pyrido[1,2,3-de]quinoxalin-5-yl]acetyl]amino]phenoxy]-acetic acid; α-amino-2-(2-phosphonoethyl)-cyclohexanepropanoic acid; α-amino-4-(phosphonomethyl)-benzeneacetic acid; (3E)-2-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino[4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid; 7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene)methyl]-1H-indole-2-carboxylic acid; (2R,4S)-rel-5,7-dichloro-1,2,3,4-tetrahydro-4-[[(phenylamino)carbonyl]amino]-2-quinolinecarboxylic acid; (3R,4S)-rel-3,4-dihydro-3-[4-hydroxy-4-(phenylmethyl)-1-piperidinyl]-2H-1-benzopyran-4,7-diol; 2-[(2,3-dihydro-1H-inden-2-yl)amino]-acetamide; 1,4-dihydro-6-methyl-5-[(methylamino)methyl]-7-nitro-2,3-quinoxalinedione; [2-(8,9-dioxo-2,6-diazabicyclo[5.2.0]non-1(7)-en-2-yl)ethyl]-phosphonic acid; |

TABLE 1-continued

Therapeutic agents useful in combination with compounds of the invention

| Class | Examples |
|---|---|
| | (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[(pentafluorophenyl)methyl]amino]-benzoic acid; 1-[2-(4-hydroxyphenoxy)ethyl]-4-[(4-methylphenyl)methyl]-4-piperidinol; 1-[4-(1H-imidazol-4-yl)-3-butynyl]-4-(phenylmethyl)-piperidine; 2-methyl-6-(phenylethynyl)-pyridine; 3-(phosphonomethyl)-L-phenylalanine; or 3,6,7-tetrahydro-2,3-dioxo-N-phenyl-1H,5H-pyrido[1,2,3-de]quinoxaline-5-acetamide |

Asymmetric or chiral centers may exist in any of the compounds of the present invention. The present invention contemplates the various stereoisomers and mixtures thereof. Individual stereoisomers of compounds of the present invention are prepared synthetically from commercially available starting materials which contain asymmetric or chiral centers or by preparation of mixtures of enantiometic compounds followed by resolution well-known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns. Enantiomers are designated herein by the symbols "R," or "S," depending on the configuration of substituents around the chiral carbon atom. Alternatively, enantiomers are designated as (+) or (−) depending on whether a solution of the enantiomer rotates the plane of polarized light clockwise or counterclockwise, respectively.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, where the term "Z" represents substituents on the same side of the carbon-carbon double bond and the term "E" represents substituents on opposite sides of the carbon-carbon double bond. It is also recognized that for structures in which tautomeric forms are possible, the description of one tautomeric form is equivalent to the description of both, unless otherwise specified. For example, amidine structures of the formula —C(=NR$^Q$)NHR$^T$ and —C(NHR$^Q$)=NR$^T$, where R$^T$ and R$^Q$ are different, are equivalent tautomeric structures and the description of one inherently includes the other.

It is understood that substituents and substitution patterns on the compounds of the invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

Other features and advantages of the invention will be apparent from the following description and the claims.

DEFINITIONS

The terms "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups include from 2 to 7 carbons.

The terms "C$_{x-y}$ alkaryl" or "C$_{x-y}$ alkylenearyl," as used herein, represent a chemical substituent of formula —RR', where R is an alkylene group of x to y carbons and R' is an aryl group as defined elsewhere herein. Similarly, by the terms "C$_{x-y}$ alkheteroaryl" "C$_{x-y}$ alkyleneheteroaryl," is meant a chemical substituent of formula —RR", where R is an alkylene group of x to y carbons and R" is a heteroaryl group as defined elsewhere herein. Other groups preceded by the prefix "alk-" or "alkylene-" are defined in the same manner. Exemplary unsubstituted alkaryl groups are of from 7 to 16 carbons.

The term "alkcycloalkyl" represents a cycloalkyl group attached to the parent molecular group through an alkylene group.

The term "alkenyl," as used herein, represents monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl, and the like.

The term "alkheterocyclyl" represents a heterocyclic group attached to the parent molecular group through an alkylene group. Exemplary unsubstituted alkheterocyclyl groups are of from 3 to 14 carbons.

The term "alkoxy" represents a chemical substituent of formula —OR, where R is an alkyl group of 1 to 6 carbons, unless otherwise specified.

The term "alkoxyalkyl" represents an alkyl group which is substituted with an alkoxy group. Exemplary unsubstituted alkoxyalkyl groups include between 2 to 12 carbons.

The terms "alkyl" and the prefix "alk-," as used herein, are inclusive of both straight chain and branched chain saturated groups of from 1 to 6 carbons, unless otherwise specified. Alkyl groups are exemplified by methyl, ethyl, n- and isopropyl, n-, sec-, iso- and tert-butyl, neopentyl, and the like, and may be optionally substituted with one, two, three or, in the case of alkyl groups of two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) arylalkoxy; (7) aryloyl; (8) azido; (9) carboxaldehyde; (10) cycloalkyl of three to eight carbon atoms; (11) halo; (12) heterocyclyl; (13) (heterocycle) oxy; (14) (heterocycle)oyl; (15) hydroxyl; (16) N-protected amino; (17) nitro; (18) oxo; (19) spiroalkyl of three to eight carbon atoms; (20) thioalkoxy of one to six carbon atoms; (21) thiol; (22) —CO$_2$R$^A$, where R$^A$ is selected from the group consisting of (a) alkyl, (b) aryl and (c) alkaryl, where the alkylene group is of one to six carbon atoms; (23) —C(O) NR$^B$R$^C$, where each of R$^B$ and R$^C$ is, independently, selected from the group consisting of (a) hydrogen, (b) alkyl, (c) aryl and (d) alkaryl, where the alkylene group is of one to six carbon atoms; (24) —SO$_2$R$^D$, where R$^D$ is selected from the group consisting of (a) alkyl, (b) aryl and (c) alkaryl, where the alkylene group is of one to six carbon atoms; (25) —SO$_2$NR$^E$R$^F$, where each of R$^E$ and R$^F$ is, independently, selected from the group consisting of (a) hydrogen, (b) alkyl, (c) aryl and (d) alkaryl, where the alkylene group is of one to six carbon atoms; and (26) —NR$^G$R$^H$, where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkylsulfinyl," as used herein, represents an alkyl group attached to the parent molecular group through an —S(O)— group. Exemplary unsubstituted alkylsulfinyl groups are of from 1 to 6 carbons.

The term "alkylsulfonyl," as used herein, represents an alkyl group attached to the parent molecular group through an —SO$_2$— group. Exemplary unsubstituted alkylsulfonyl groups are of from 1 to 6 carbons.

The term "alkylsulfinylalkyl," as used herein, represents an alkyl group, as defined herein, substituted by an alkylsulfinyl group. Exemplary unsubstituted alkylsulfinylalkyl groups are of from 2 to 12 carbons.

The term "alkylsulfonylalkyl," as used herein, represents an alkyl group, as defined herein, substituted by an alkylsulfonyl group. Exemplary unsubstituted alkylsulfonylalkyl groups are of from 2 to 12 carbons.

The term "alkynyl," as used herein, represents monovalent straight or branched chain groups of from two to six carbon atoms containing a carbon-carbon triple bond and is exemplified by ethynyl, 1-propynyl, and the like.

The term "amidine," as used herein, represents a —C(=NH)NH$_2$ group.

The term "amino," as used herein, represents an —NH$_2$ group.

The term "aminoalkyl," as used herein, represents an alkyl group, as defined herein, substituted by an amino group.

The term "aryl," as used herein, represents a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, and (c) alkaryl, where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and R$^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The term "arylalkoxy," as used herein, represents an alkaryl group attached to the parent molecular group through an oxygen atom. Exemplary unsubstituted arylalkoxy groups are of from 7 to 16 carbons.

The term "aryloxy" represents a chemical substituent of formula —OR', where R' is an aryl group of 6 to 18 carbons, unless otherwise specified.

The terms "aryloyl" and "aroyl" as used interchangeably herein, represent an aryl group that is attached to the parent molecular group through a carbonyl group. Exemplary unsubstituted aryloyl groups are of 7 or 11 carbons.

The term "azido" represents an N$_3$ group, which can also be represented as N=N=N.

The term "azidoalkyl" represents an azido group attached to the parent molecular group through an alkyl group.

The term "bridged heterocyclyl" represents a heterocyclic compound, as otherwise described herein, having a bridged multicyclic structure in which one or more carbon atoms and/or heteroatoms bridges two non-adjacent members of a monocyclic ring. An exemplary bridged heterocyclyl group is a quinuclidinyl group.

The term "bridged alkheterocyclyl" represents a bridged heterocyclic compound, as otherwise described herein, attached to the parent molecular group through an alkylene group.

The term "carbonyl," as used herein, represents a C(O) group, which can also be represented as C=O.

The term "carboxyaldehyde" represents a CHO group.

The term "carboxaldehydealkyl" represents a carboxyaldehyde group attached to the parent molecular group through an alkylene group.

The term "cycloalkyl," as used herein represents a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl groups of this invention can be optionally substituted with (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, and (c) alkaryl, where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and where R$^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The terms "cycloalkyloxy" or "cycloalkoxy", as used interchangeably herein, represent a cycloalkyl group, as defined herein, attached to the parent molecular group through an oxygen atom. Exemplary unsubstituted cycloalkyloxy groups are of from 3 to 8 carbons.

The term an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an inhibitor of NOS, an effective amount of an agent is, for example, an amount sufficient to achieve a reduction in NOS activity as compared to the response obtained without administration of the agent.

The terms "halide" or "halogen" or "Hal" or "halo," as used herein, represent bromine, chlorine, iodine, or fluorine.

The term "heteroaryl," as used herein, represents that subset of heterocycles, as defined herein, which are aromatic: i.e., they contain 4n+2 pi electrons within the mono- or multicyclic ring system.

The terms "heterocycle" or "heterocyclyl," as used interchangeably herein represent a 5-, 6- or 7-membered ring, unless otherwise specified, containing one, two, three, or four heteroatoms independently selected from the group consisting of nitrogen, oxygen and sulfur. The 5-membered ring has zero to two double bonds and the 6- and 7-membered rings have zero to three double bonds. The term "heterocycle" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring and another monocyclic heterocyclic ring, such as indolyl, quinolyl, isoquinolyl, tetrahydroquinolyl, benzofuryl, benzothienyl and the like. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Heterocyclic groups also include compounds of the formula

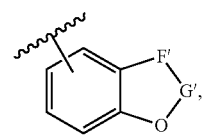

where

F' is selected from the group consisting of —CH$_2$—, —CH$_2$O— and —O—, and G' is selected from the group consisting of —C(O)— and —(C(R')(R"))$_v$—, where each of R' and R" is, independently, selected from the group consisting of hydrogen or alkyl of one to four carbon atoms, and v is one to three and includes groups, such as 1,3-benzodioxolyl, 1,4-benzodioxanyl, and the like. Any of the heterocycle groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —$(CH_2)_q CO_2 R^A$, where q is an integer of from zero to four, and $R^A$ is selected from the group consisting of (a) alkyl, (b) aryl, and (c) alkaryl, where the alkylene group is of one to six carbon atoms; (36) —$(CH_2)_q CONR^B R^C$, where q is an integer of from zero to four and where $R^B$ and $R^C$ are independently selected from the group consisting of (a) hydrogen, (b) alkyl, (c) aryl, and (d) alkaryl, where the alkylene group is of one to six carbon atoms; (37) —$(CH_2)_q SO_2 R^D$, where q is an integer of from zero to four and where $R^D$ is selected from the group consisting of (a) alkyl, (b) aryl, and (c) alkaryl, where the alkylene group is of one to six carbon atoms; (38) —$(CH_2)_q SO_2 NR^E R^F$, where q is an integer of from zero to four and where each of $R^E$ and $R^F$ is, independently, selected from the group consisting of (a) hydrogen, (b) alkyl, (c) aryl, and (d) alkaryl, where the alkylene group is of one to six carbon atoms; (39) —$(CH_2)_q NR^G R^H$, where q is an integer of from zero to four and where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The terms "heterocyclyloxy" and "(heterocycle)oxy," as used interchangeably herein, represent a heterocycle group, as defined herein, attached to the parent molecular group through an oxygen atom.

The terms "heterocyclyloyl" and "(heterocycle)oyl," as used interchangeably herein, represent a heterocycle group, as defined herein, attached to the parent molecular group through a carbonyl group.

The term "hydroxy" or "hydroxyl," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group and is exemplified by hydroxymethyl, dihydroxypropyl, and the like.

The terms "inhibit" or "suppress" or "reduce," as relates to a function or activity, such as NOS activity, means to reduce the function or activity when compared to otherwise same conditions except for a condition or parameter of interest, or alternatively, as compared to another condition.

The term "N-protected amino," as used herein, refers to an amino group, as defined herein, to which is attached an N-protecting or nitrogen-protecting group, as defined herein.

The terms "N-protecting group" and "nitrogen protecting group," as used herein, represent those groups intended to protect an amino group against undesirable reactions during synthetic procedures. Commonly used N-protecting groups are disclosed in Greene, "Protective Groups In Organic Synthesis," $3^{rd}$ Edition (John Wiley & Sons, New York, 1999), which is incorporated herein by reference. N-protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M Berge et al. describe pharmaceutically acceptable salts in detail in *J. Pharmaceutical Sciences* 66:1-19, 1977. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "Ph" as used herein means phenyl.

The term "prodrug," as used herein, represents compounds which are rapidly transformed in vivo to the parent compound of the above formula, for example, by hydrolysis in blood. Prodrugs of the compounds of the invention may be conventional esters. Some common esters which have been utilized as prodrugs are phenyl esters, aliphatic ($C_8$-$C_{24}$) esters, acyloxymethyl esters, carbamates, and amino acid esters. For example, a compound of the invention that contains an OH group may be acylated at this position in its prodrug form. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins et al., *Synthetic Communications* 26(23):4351-4367, 1996, each of which is incorporated herein by reference.

Each of the terms "selectively inhibits nNOS" or "a selective nNOS inhibitor" refers to a substance, such as, for example, a compound of the invention, that inhibits or binds the nNOS isoform more effectively than the eNOS and/or iNOS isoform by an in vitro assay, such as, for example, those assays described herein. Selective inhibition can be expressed in terms of an $IC_{50}$ value, a $K_i$ value, or the inverse of a percent inhibition value which is lower when the substance is tested in an nNOS assay than when tested in an eNOS and/or iNOS assay. Preferably, the $IC_{50}$ or $K_i$ value is 2 times lower. More preferably, the $IC_{50}$ or $K_i$ value is 5 times lower. Most preferably, the $IC_{50}$ or $K_i$ value is 10, or even 50 times lower.

The term "solvate" as used herein means a compound of the invention wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

The term "spiroalkyl," as used herein, represents an alkylene diradical, both ends of which are bonded to the same carbon atom of the parent group to form a spirocyclic group.

The term "sulfonyl," as used herein, represents an —S(O)$_2$— group.

The term "thioalkheterocyclyl," as used herein, represents a thioalkoxy group substituted with a heterocyclyl group.

The term "thioalkoxy," as used herein, represents an alkyl group attached to the parent molecular group through a sulfur atom. Exemplary unsubstituted alkylthio groups are of from 1 to 6 carbons.

The term "thiol" represents an —SH group.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. The term also includes prophylactic treatment.

DETAILED DESCRIPTION

Figure 1:
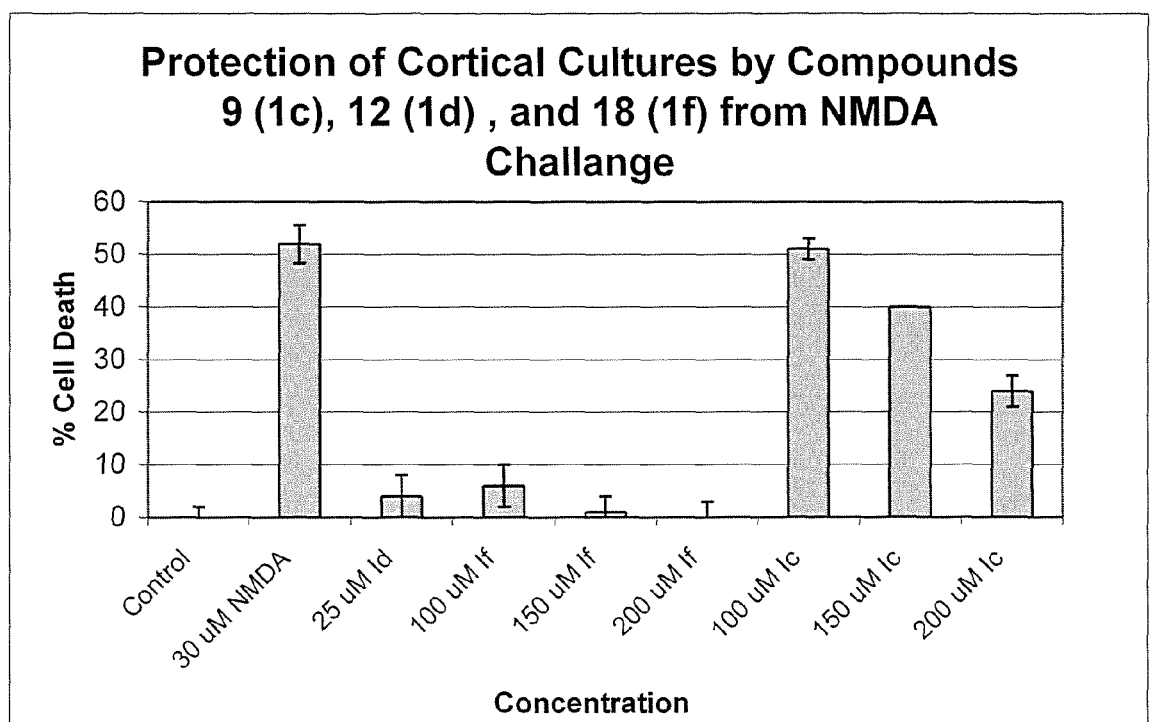
FIG. 1 is a bar graph showing the neuroprotective effect of compounds 9, 12, and 18 after NMDA challenge of rat cortical cells.

The invention features substituted indole compounds having nitric oxide synthase (NOS) inhibitory activity, pharmaceutical and diagnostic compositions containing them, and their medical use, particularly as compounds for the treatment of stroke, reperfusion injury, neurodegenerative disorders, head trauma, coronary artery bypass graft (CABG) associated neurological damage, migraine, migraine with allodynia, neuropathic pain, post-stroke pain, and chronic pain.

Exemplary 3,5-substituted indole compounds of the invention are provided in the following table.

TABLE I

Compounds of the invention with human NOS inhibition and selected $5HT_{1D}$ (bovine caudate) and $5HT_{1B}$ (rat cerebral cortex) inhibition constants ($IC_{50}$ values are in µM concentrations). All compounds tested are dihydrochloride or monohydrochloride salts. Compounds with a lower $IC_{50}$ are more potent at the NOS enzyme or 5HT1 receptors.

| Compound | nNOSh | eNOSh | iNOSh | e/n | 5HT1D | 5HT1B |
|---|---|---|---|---|---|---|
| 18 | 2.6 | 26 | 12 | 10 | 0.36 | |

TABLE I-continued

Compounds of the invention with human NOS inhibition and selected 5HT$_{1D}$ (bovine caudate) and 5HT$_{1B}$ (rat cerebral cortex) inhibition constants (IC$_{50}$ values are in μM concentrations). All compounds tested are dihydrochloride or monohydrochloride salts. Compounds with a lower IC$_{50}$ are more potent at the NOS enzyme or 5HT1 receptors.

| Compound | nNOSh | eNOSh | iNOSh | e/n | 5HT1D | 5HT1B |
|---|---|---|---|---|---|---|
| 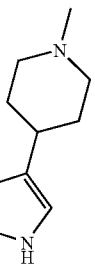 43 | 1.88 | 32.6 | 58 | 17 | 0.57 | |
| 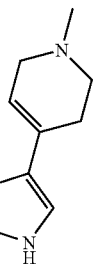 42 | 0.92 | 51.1 | 20 | 53 | 0.051 | 0.16 |
| 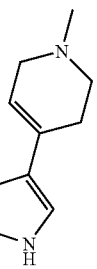 46 | 1.78 | 54 | 58 | 31 | 0.050 | |
|  47 | 2.24 | 97.4 | 55 | 43 | 0.28 | |

TABLE I-continued

Compounds of the invention with human NOS inhibition and selected 5HT$_{1D}$ (bovine caudate) and 5HT$_{1B}$ (rat cerebral cortex) inhibition constants (IC$_{50}$ values are in μM concentrations). All compounds tested are dihydrochloride or monohydrochloride salts. Compounds with a lower IC$_{50}$ are more potent at the NOS enzyme or 5HT1 receptors.

| Compound | nNOSh | eNOSh | iNOSh | e/n | 5HT1D | 5HT1B |
|---|---|---|---|---|---|---|
| 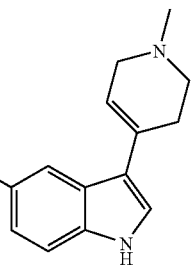 51 | 1.19 | 49.7 | 85 | 42 | 0.22 | |
| 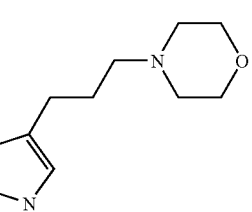 181 | 2 | 31 | 9.9 | 9.9 | | |
| 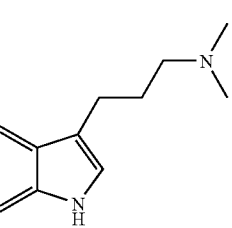 56 | 0.41 | 15.1 | 5.6 | 37 | 0.87 | |
| 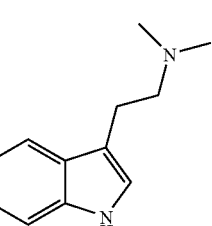 59 | 12.8 | 86.2 | | 7 | 0.29 | |
| 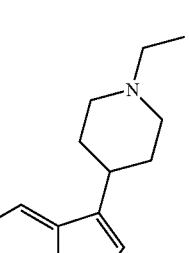 62 | 2.43 | 57.3 | | 24 | 0.68 | |

TABLE I-continued

Compounds of the invention with human NOS inhibition and selected 5HT$_{1D}$ (bovine caudate) and 5HT$_{1B}$ (rat cerebral cortex) inhibition constants (IC$_{50}$ values are in μM concentrations). All compounds tested are dihydrochloride or monohydrochloride salts. Compounds with a lower IC$_{50}$ are more potent at the NOS enzyme or 5HT1 receptors.

| Compound | nNOSh | eNOSh | iNOSh | e/n | 5HT1D | 5HT1B |
|---|---|---|---|---|---|---|
| 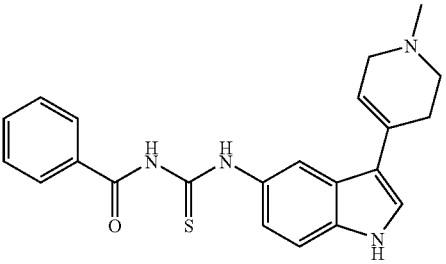 64 | 14 | 43 | | 3 | 0.056 | |
| 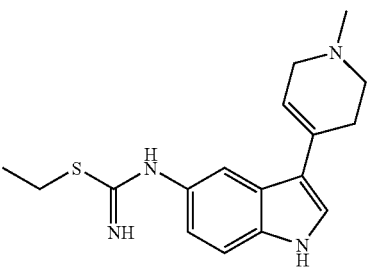 67 | 4.8 | 105 | | 22 | 0.048 | |
| 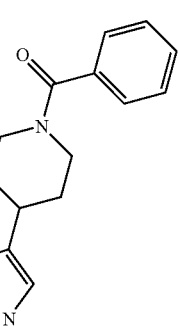 70 | 5.62 | 50.9 | | 9.06 | | |
| 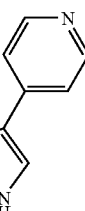 73 | 2.20 | 43.4 | | 19.7 | | |

TABLE I-continued

Compounds of the invention with human NOS inhibition and selected 5HT$_{1D}$ (bovine caudate) and 5HT$_{1B}$ (rat cerebral cortex) inhibition constants (IC$_{50}$ values are in μM concentrations). All compounds tested are dihydrochloride or monohydrochloride salts. Compounds with a lower IC$_{50}$ are more potent at the NOS enzyme or 5HT1 receptors.

| Compound | nNOSh | eNOSh | iNOSh | e/n | 5HT1D | 5HT1B |
|---|---|---|---|---|---|---|
| 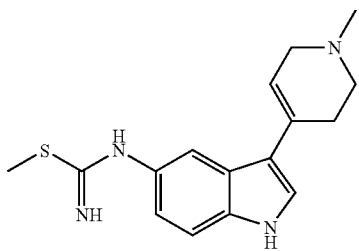 75 | 2.25 | 36.1 | | 16.0 | | |
| 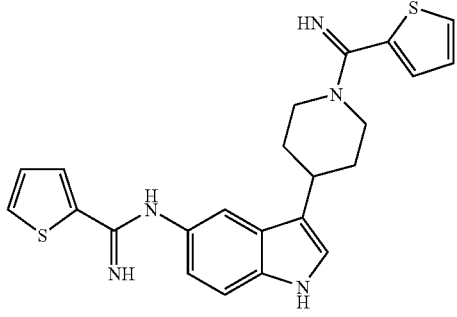 77 | 0.717 | 4.44 | | 6.19 | | |
| 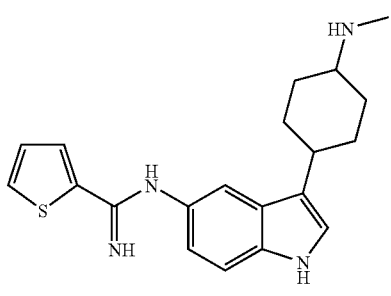 84 | 0.49 | 26.9 | | 55 | | |
| 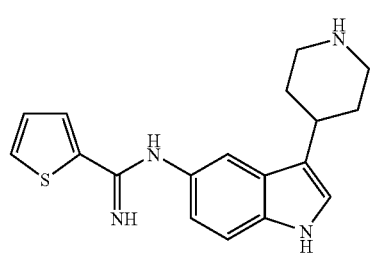 88 | 9.23 | 78.1 | | 8.5 | | |

TABLE I-continued

Compounds of the invention with human NOS inhibition and selected 5HT$_{1D}$ (bovine caudate) and 5HT$_{1B}$ (rat cerebral cortex) inhibition constants (IC$_{50}$ values are in μM concentrations). All compounds tested are dihydrochloride or monohydrochloride salts. Compounds with a lower IC$_{50}$ are more potent at the NOS enzyme or 5HT1 receptors.

| Compound | nNOSh | eNOSh | iNOSh | e/n | 5HT1D | 5HT1B |
|---|---|---|---|---|---|---|
| 90  | 3.35 | 67.9 | | 20.3 | | |
| 97 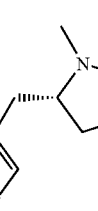 | 0.84 | 34.5 | | 41 | 0.13 | 0.31 |
| 100 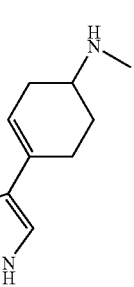 | 1.73 | 32 | | 18.5 | | |
| 105 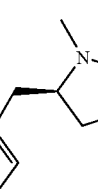 | 0.82 | 23 | | 29 | 1.1 | 0.29 |
| 106 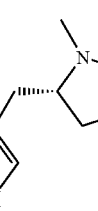 | 2.08 | 27.1 | | 13.0 | | |

TABLE I-continued

Compounds of the invention with human NOS inhibition and selected $5HT_{1D}$ (bovine caudate) and $5HT_{1B}$ (rat cerebral cortex) inhibition constants ($IC_{50}$ values are in μM concentrations). All compounds tested are dihydrochloride or monohydrochloride salts. Compounds with a lower $IC_{50}$ are more potent at the NOS enzyme or 5HT1 receptors.

| Compound | nNOSh | eNOSh | iNOSh | e/n | 5HT1D | 5HT1B |
|---|---|---|---|---|---|---|
| 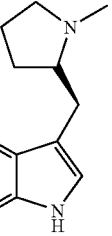 107 | 2.52 | 24.9 | | 9.9 | | |
| 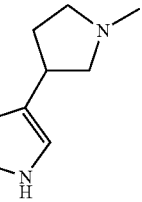 110 | 0.43 | 39 | | 90 | 0.35 | 0.49 |
| 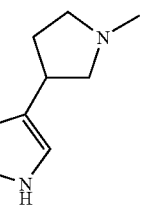 111 | 1.24 | 33.8 | | | 0.56 | 1.1 |
| 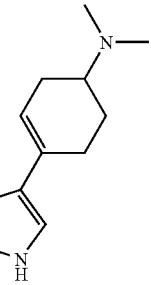 114 | 3 | 51.4 | | 17.1 | | |
| 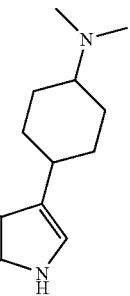 116 | 3.44 | 31.8 | | 9.2 | | |

TABLE I-continued

Compounds of the invention with human NOS inhibition and selected 5HT$_{1D}$ (bovine caudate) and 5HT$_{1B}$ (rat cerebral cortex) inhibition constants (IC$_{50}$ values are in µM concentrations). All compounds tested are dihydrochloride or monohydrochloride salts. Compounds with a lower IC$_{50}$ are more potent at the NOS enzyme or 5HT1 receptors.

| Compound | nNOSh | eNOSh | iNOSh | e/n | 5HT1D | 5HT1B |
|---|---|---|---|---|---|---|
| 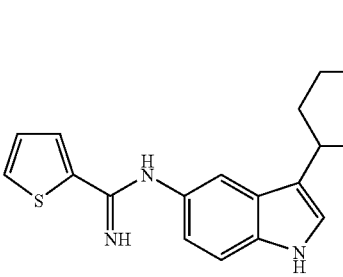 121 | 0.7 | 40.8 |  | 58.4 |  |  |
| 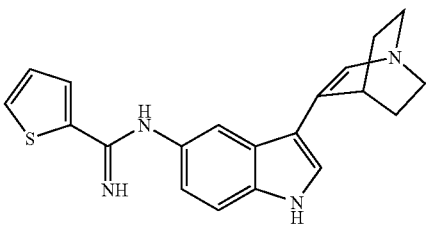 125 | 0.97 | 105 |  | 126 |  |  |
| 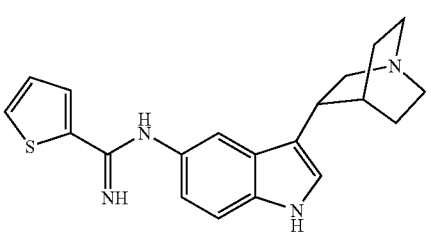 126 | 1.04 | 32.1 |  | 30.9 |  |  |
| 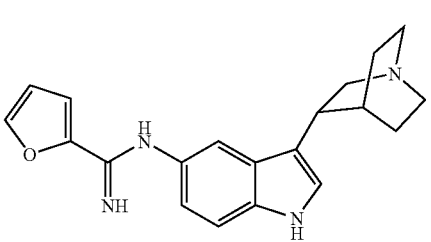 127 | 2.6 | 66 |  | 25.3 |  |  |

TABLE I-continued

Compounds of the invention with human NOS inhibition and selected 5HT$_{1D}$ (bovine caudate) and 5HT$_{1B}$ (rat cerebral cortex) inhibition constants (IC$_{50}$ values are in μM concentrations). All compounds tested are dihydrochloride or monohydrochloride salts. Compounds with a lower IC$_{50}$ are more potent at the NOS enzyme or 5HT1 receptors.

| Compound | nNOSh | eNOSh | iNOSh | e/n | 5HT1D | 5HT1B |
|---|---|---|---|---|---|---|
| 134 | 2.78 | 143 | | 51.4 | | |
| 137 | 4.78 | 40.1 | | | | |
| 142 | | | | | | |
| 147 | | | | | | |
| Sumatriptan | — | — | — | — | 0.059 | 0.11 |

Exemplary 1,6-substituted indole compounds of the invention are provided in the following table.

TABLE II

Compounds of the invention with human NOS inhibition constants and (IC$_{50}$ values are in μM concentrations). All compounds tested are dihydrochloride or monohydrochloride salts. Compounds with a lower IC$_{50}$ are more potent at the NOS enzyme.

| Compound | nNOSh | eNOSh | e/n |
|---|---|---|---|
| 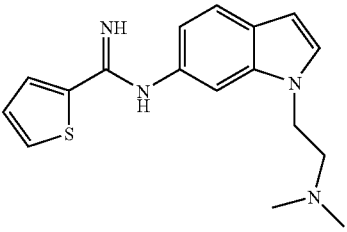<br>12 | 1.2 | 15.0 | 12.5 |
| 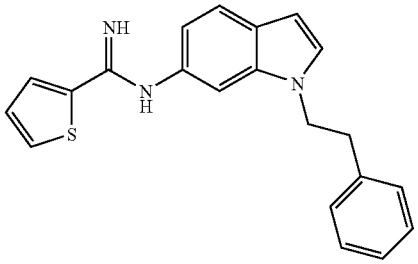<br>27 | 12 | >100 | >8.3 |
| 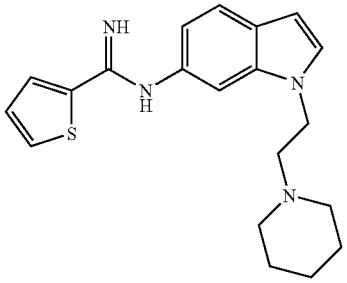<br>37 | 0.49 | 3.8 | 7.8 |
| 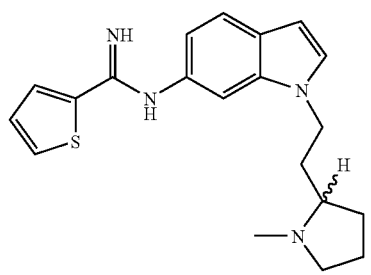<br>32 | 0.22 | 19 | 86.4 |

TABLE II-continued
Compounds of the invention with human NOS inhibition constants and (IC$_{50}$ values are in μM concentrations). All compounds tested are dihydrochloride or monohydrochloride salts. Compounds with a lower IC$_{50}$ are more potent at the NOS enzyme.
| Compound | nNOSh | eNOSh | e/n |
|---|---|---|---|
| 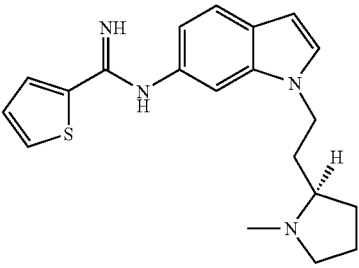<br>32 | 0.32 | 16 | 50 |
| 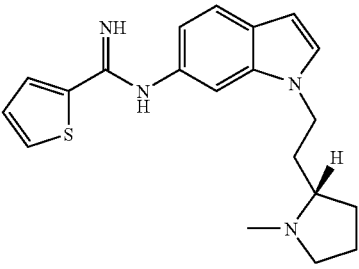<br>32 | 0.2 | 24 | 120 |
| 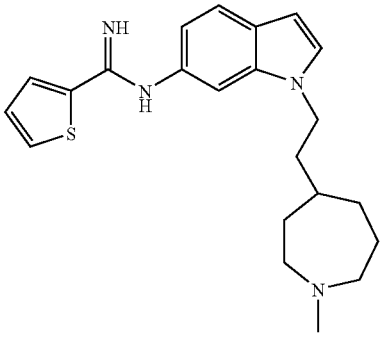<br>33 | 0.87 | 37 | 42.5 |

TABLE II-continued
Compounds of the invention with human NOS inhibition constants and ($IC_{50}$ values are in μM concentrations). All compounds tested are dihydrochloride or monohydrochloride salts. Compounds with a lower $IC_{50}$ are more potent at the NOS enzyme.
| Compound | nNOSh | eNOSh | e/n |
|---|---|---|---|
| 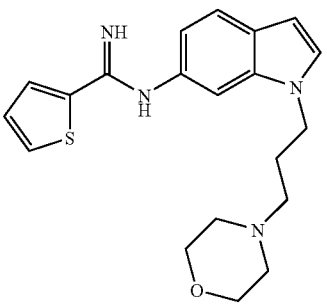 151 | 0.7 | 28.3 | 41.1 |
| 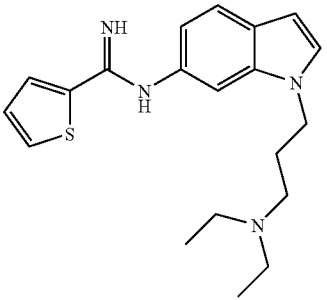 153 | 0.59 | 10.2 | 17.2 |
| 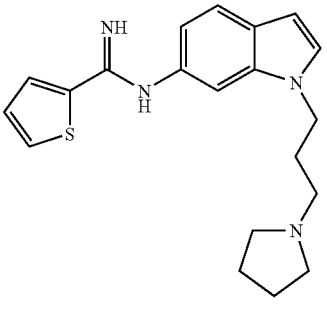 155 | 1.97 | 11.2 | 5.7 |
| 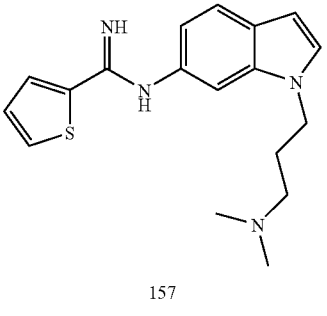 157 | 2.73 | 5.77 | 2.11 |

TABLE II-continued
Compounds of the invention with human NOS inhibition constants and ($IC_{50}$ values are in μM concentrations). All compounds tested are dihydrochloride or monohydrochloride salts. Compounds with a lower $IC_{50}$ are more potent at the NOS enzyme.
| Compound | nNOSh | eNOSh | e/n |
|---|---|---|---|
| 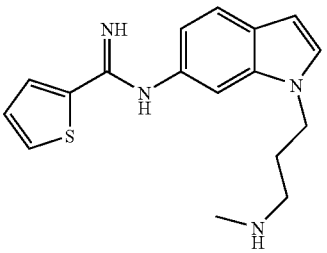 159 | 1.78 | 9.91 | 5.57 |
| 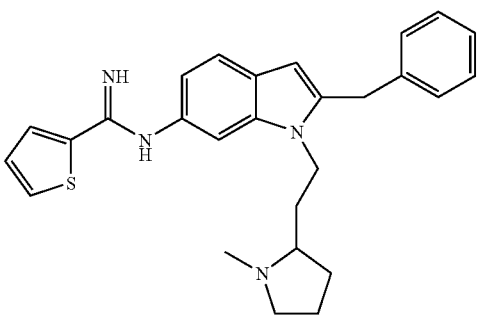 164 | 2.3 | 33 | 14.3 |
| 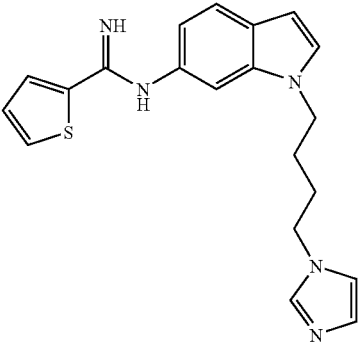 168 | 1.22 | 4.56 | 3.74 |
| 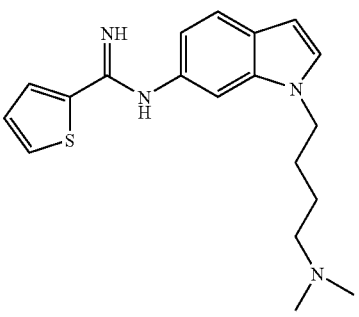 171 | 0.26 | 2.53 | 9.6 |

TABLE II-continued

Compounds of the invention with human NOS inhibition constants and ($IC_{50}$ values are in μM concentrations). All compounds tested are dihydrochloride or monohydrochloride salts. Compounds with a lower $IC_{50}$ are more potent at the NOS enzyme.

| Compound | nNOSh | eNOSh | e/n |
|---|---|---|---|
| 173 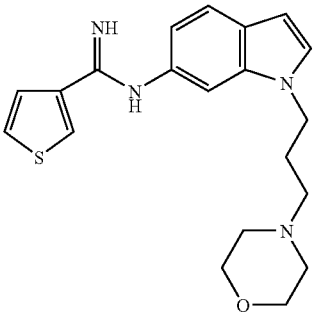 | 1.4 | 17 | 12.1 |
| 175 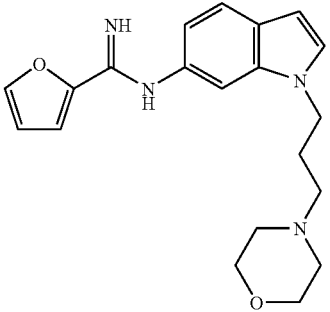 | 2.4 | 34 | 14.2 |
| 177 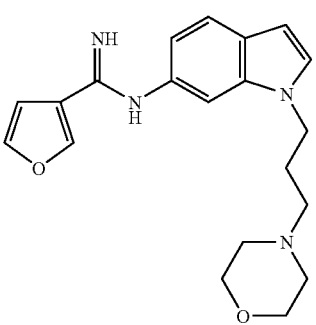 | 1 | 19 | 19 |

Methods of Preparing Compounds of the Invention

The compounds of the invention can be prepared by processes analogous to those established in the art, for example, by the reaction sequences shown in Schemes 1-12.

A compound of formula IVa or IVb, where $R^1$, $R^2$, $R^3$, $R^4$, and $R^7$ are as defined elsewhere herein, can be prepared under standard alkylating conditions by treating a compound of formula IIa or IIb, respectively, with a compound of formula III, or a suitably protected derivative thereof, where $R^1$ is as defined above, with the exception that $R^1$ is not H, and "LG" is a leaving group, such as, for example, chloro, bromo, iodo, or sulfonate (e.g., mesylate, tosylate, or triflate). Conditions to effect the alkylation of a compound of formula IIa or IIb with a compound of formula III may include, for example, heating a compound of formula II and a compound of formula III, with or without a solvent, optionally in the presence of a suitable base (see Scheme 1).

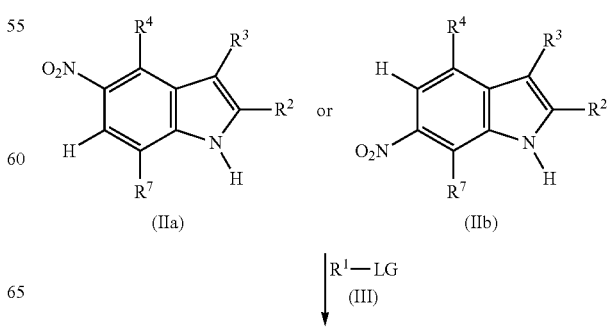

Scheme 1

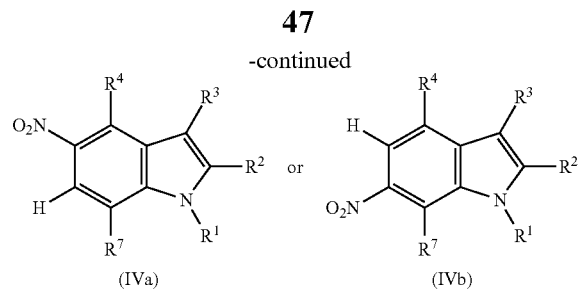

(IVa)     (IVb)

Alternatively, production of a compound of formula IVa or IVb, or a suitably protected derivative thereof, where $R^2$, $R^3$, $R^4$, and $R^7$ are as defined herein for a compound formula I and $R^1$ is $(CH_2)_m X^1$, where $X^1$ is

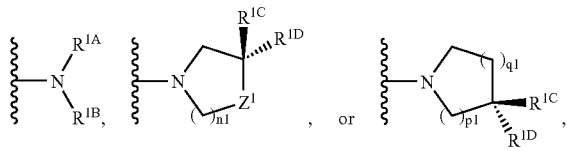

with $R^{1A}$, $R^{1B}$, $R^{1C}$, $R^{1D}$, $Z^1$, n1, p1, and q1 defined as for a compound of formula I involves the reaction of a compound of formula Va or Vb, wherein m1 is as defined in for a compound of formula I and LG is a suitable leaving group, such as, for example, chloro, bromo, iodo, or sulfonate (e.g., mesylate, tosylate, or triflate), with compounds of formula VI, where $X^1$ is as defined above, under standard alkylation conditions as shown in Scheme 2. Alternatively, a compound of formula Va or Vb, where LG represents an aldehyde, ester, or acylchloride group, may be reacted with a compound of formula VI. When LG is an aldehyde group, standard reductive amination conditions may be employed using a suitable reducing agent, such as $NaBH_4$, $NaBH(OAc)_3$, $NaCNBH_4$, and the like, in an alcoholic solvent, such as ethanol, to produce a compound of formula VIIIa or VIIIb, respectively. The reductive amination may be performed in one reaction or the imine resulting from mixing a compound of formula Va or Vb with a compound of formula VI can be preformed in situ, followed by sequential reduction with a suitable reducing agent. When LG is an acyl chloride or an ester group, preferably an active ester, such as, for example, pentafluorophenyl ester or hydroxysuccinimide ester, the reaction of a compound of formula Va or Vb with a compound of formula $X^1$—H, or a suitably protected derivative thereof, is followed by reduction of the resulting amide using a suitable reducing agent, such as, for example, $BH_3$. Compounds of formulas Va or Vb may be prepared using standard methodologies, as described in WO 00/38677.

Scheme 2

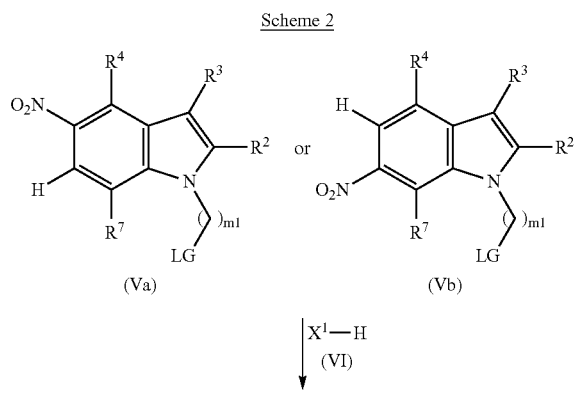

(Va)     (Vb)

$X^1$—H
(VI)

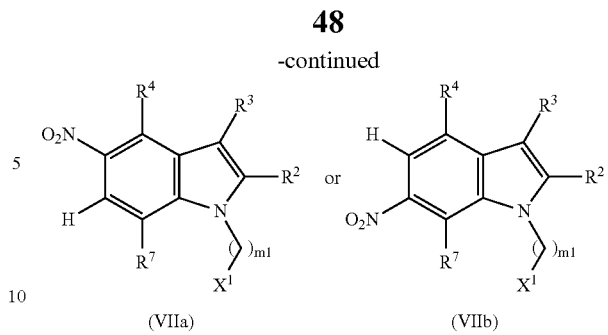

(VIIa)     (VIIb)

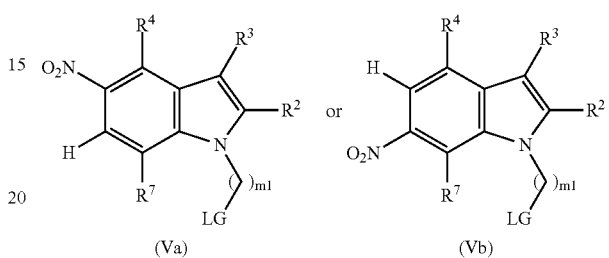

(Va)     (Vb)

$X^1$—H
(VI)

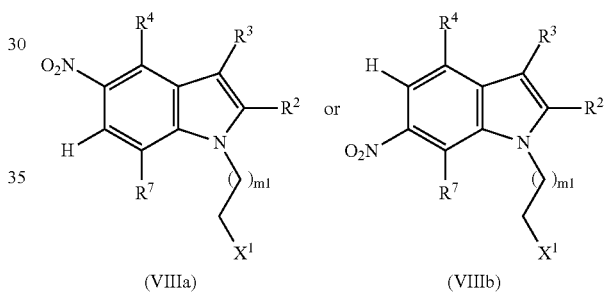

(VIIIa)     (VIIIb)

A compound of formula IVa or IVb, or a suitably protected derivative thereof, where $R^2$, $R^3$, $R^4$, and $R^7$ are as defined herein for a compound formula I; LG is a suitable leaving group, such as, for example, chloro, bromo, iodo, or a sulfonate (e.g., mesylate, tosylate, or triflate); and $X^3$ is

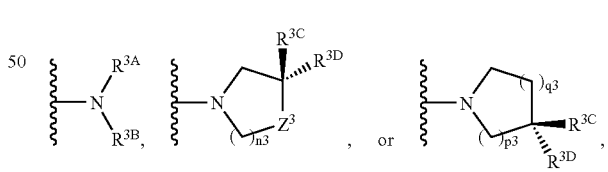

where $R^{3A}$, $R^{3B}$, $R^{3C}$, $R^{3D}$, $Z^3$, n3, p3, and q3 are defined as for a compound of formula I can be prepared according to Scheme 3, for example, by treating a compound of Formula IXa or IXb with oxalyl chloride in a suitable solvent, such as, for example, ether, to produce a compound of formula Xa or Xb, respectively. Subsequent reaction with amine $X^3$—H, followed by reduction with a reducing agent, such as $LiAlH_4$, according to standard procedures (Blair et. al., *J. Med. Chem.* 43:4701-4710, 2000; Speeter and Anthony, *J. Am. Chem. Soc.* 76:6208-6210, 1954) produces a compound of formula XIa or XIb.

Scheme 3

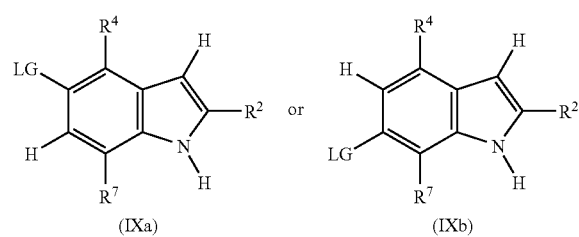

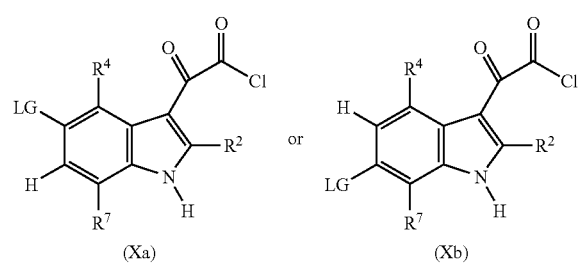

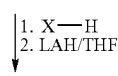

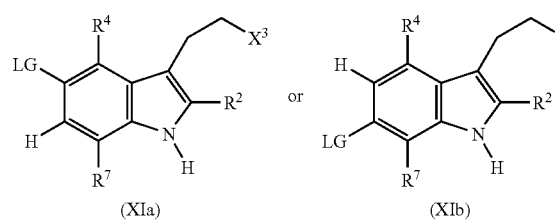

Using standard methodologies as described in the literature (Russell et al., *J. Med. Chem.* 42:4981-5001, 1999; Cooper et al., *Bioorg. Med. Chem. Lett.* 11:1233-1236, 2001; Sternfeld et al., *J. Med. Chem.* 42:677-690, 1999), a compound of formula XIVa, XIVb, XVa, or XVb, or a suitably protected derivative thereof, where $R^4$ and $R^7$ are as defined elsewhere herein; $X^3$ is

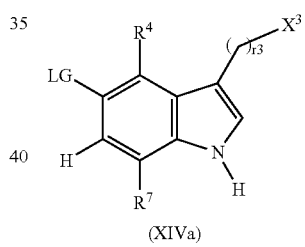

where $R^{3A}$, $R^{3B}$, $R^{3C}$, $R^{3D}$, $Z^3$, n3, p3, and q3 are as defined elsewhere herein; $X^2$ is

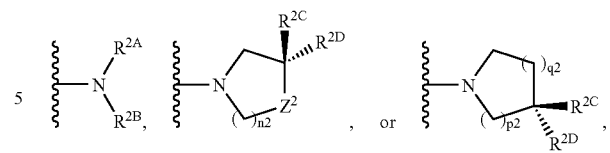

where $R^{2A}$, $R^{2B}$, $R^{2C}$, $R^{2D}$, $Z^2$, n2, p2, and q2 are as defined elsewhere herein; and LG is a suitable leaving group, such as, for example, chloro, bromo, iodo, or triflate, can be prepared according to Scheme 4 by treating amine $X^3$—H or $X^2$—H with a compound of formula XIIa or XIIb; or XIIIa or XIIIb, respectively, where Y is a suitable leaving group, such as, for example, chloro, bromo, iodo, or sulfonate (e.g., mesylate or tosylate). The Y group can be prepared from the appropriate alcohol (i.e., Y=OH) using standard techniques.

Scheme 4

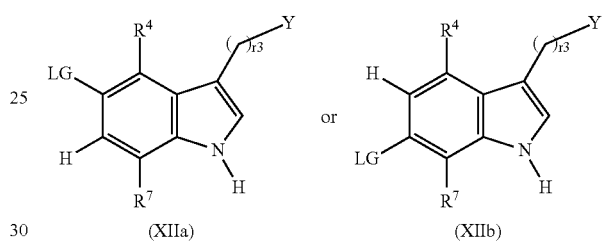

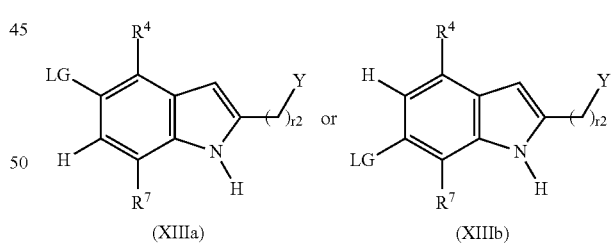

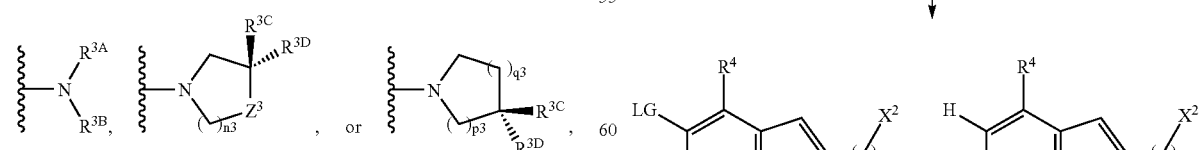

A compound of formula XXIa or XXIb, where LG, $R^4$, $R^7$, $Z^1$, p1, and q1 are as defined elsewhere herein, can be prepared as shown in Scheme 5 by procedures analogous to those previously described (see, for example, Coe et al., *Tett. Lett.* 37(34):6045-6048, 1996).
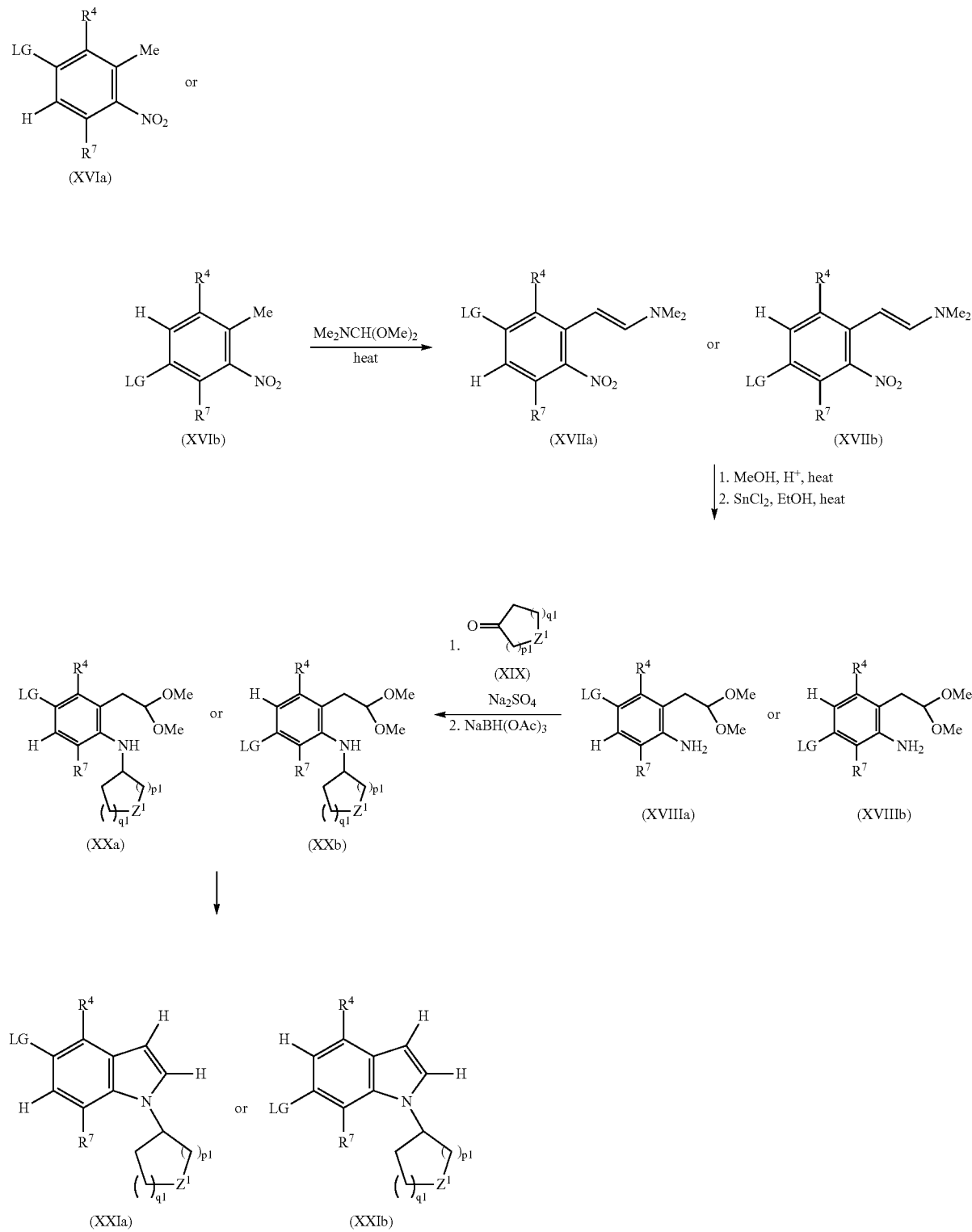
Scheme 5

Accordingly, a compound of formula XXIIIa or XXIIIb, where LG, $R^4$, $R^7$, $Z^3$, p3, and q3 are as defined elsewhere herein can be prepared from a compound of formula XXIIa or XXIIIb, as shown in Scheme 6, by procedures analogous to those previously described (see, for example, Perregaard et al., *J. Med. Chem.* 35:4813-4822, 1992; Rowley et al., *J. Med. Chem.* 44:1603-1614, 2001).

Scheme 6

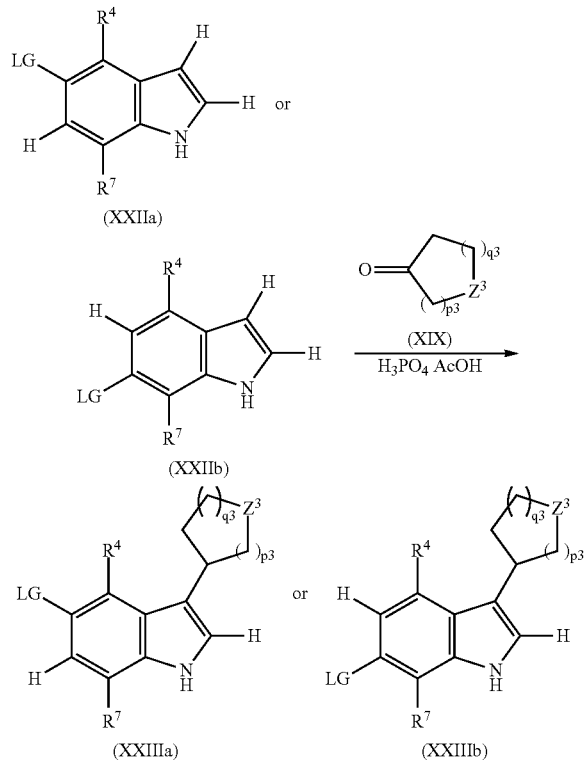

A compound of formula XXVa or XXVb, where $R^1$, $R^2$, $R^3$, $R^4$, and $R^7$ are as defined in formula I, can be prepared by reduction of the nitro group of a compound of formula XXIVa or XXIVb, respectively, or a suitably protected derivative, under standard conditions as shown in Scheme 7. In one example, standard reduction conditions include the use of $SnCl_2$ in a polar solvent, such as, for example, ethanol at refluxing temperatures. Alternatively, a compound of formula XXVa or XXVb can be prepared by the hydrogenation of a compound of formula XXIVa or XXIVb, respectively, using a suitable catalyst, such as palladium on charcoal in ethanol or another solvent or combinations of solvents.

Scheme 7

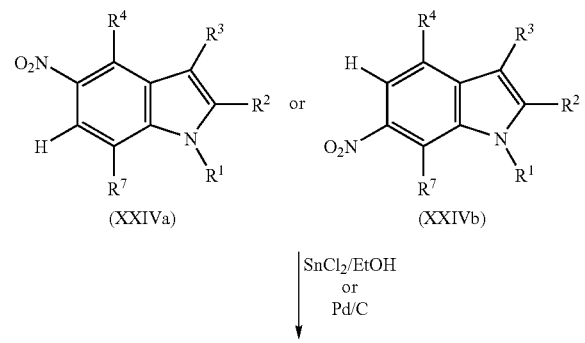

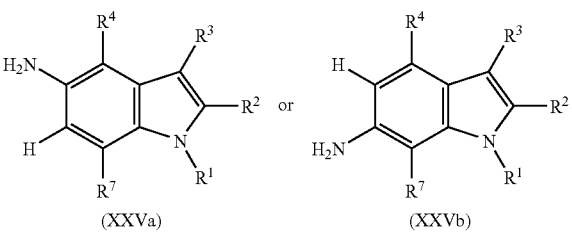

As shown in Scheme 8, a compound of formula XXVa or XXVb can also be prepared by metal catalyzed amination of compounds of a compound of formula XXVIa or XXVIb, respectively, where LG is chloro, bromo, iodo, or triflate (Wolfe, et al. *J. Org. Chem.* 65:1158-1174, 2000) in the presence of a suitable ammonia equivalent, such as benzophenone imine, $LiN(SiMe_3)_2$, $Ph_3SiNH_2$, $NaN(SiMe_3)_2$, or lithium amide (Huang and Buchwald, *Org. Lett.* 3(21):3417-3419, 2001). Examples of suitable metal catalysts include, for example, a palladium catalyst coordinated to suitable ligands. Alternatively a suitable leaving group for palladium catalyzed amination may be nonaflate (Anderson, et al., *J. Org. Chem.* 68:9563-9573, 2003) or boronic acid (Antilla and Buchwald, *Org. Lett.* 3(13):2077-2079, 2001) when the metal is a copper salt, such as Cu(II) acetate, in the presence of suitable additives, such as 2,6-lutidine. A preferred leaving group is bromo in the presence of palladium (0) or palladium (II) catalyst. Suitable palladium catalysts include tris-dibenzylideneacetone dipalladium ($Pd_2$ $dba_3$) and palladium acetate ($PdOAc_2$), preferably $Pd_2dba_3$. Suitable ligands for palladium can vary greatly and may include, for example, XantPhos, BINAP, DPEphos, dppf, dppb, DPPP, (o-biphenyl)-P(t-Bu)$_2$, (o-biphenyl)-P(Cy)$_2$, P($_t$-Bu)3, P(Cy)$_3$, and others (Huang and Buchwald, *Org. Lett.* 3(21):3417-3419, 2001). Preferably the ligand is P(t-Bu)$_3$. The Pd-catalyzed amination is performed in a suitable solvent, such as THF, dioxane, toluene, xylene, DME, and the like, at temperatures between room temperature and reflux.

Scheme 8

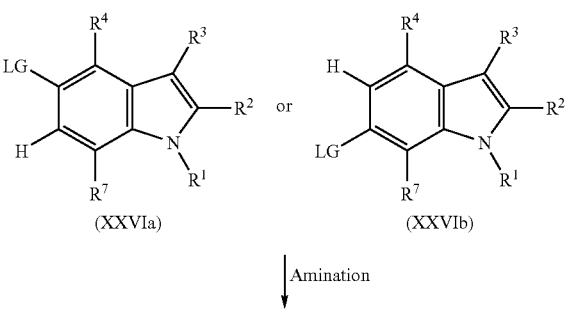

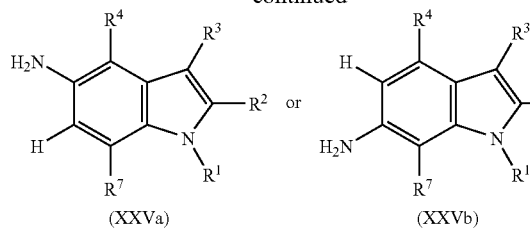

(XXVa)  (XXVb)

Compounds of formula XXIXa or XXIXb, where each of $R^{5A}$ or $R^{6A}$ is as defined elsewhere herein and Q is an aryl group (e.g., a phenyl group), a $C_1$ alkaryl group (e.g., a naphthylmethyl group), or an alkyl group (e.g., a methyl group) are either commercially available or may be prepared by reacting a cyano compound of formula XXVIIIa or XXVIIIb with thiol-containing compounds of formula XXVII. Other examples of this transformation are described the art (see, for example, Baati et al., *Synlett* 6:927-9, 1999; EP 262873 1988, Collins et al., *J. Med. Chem.* 41:15, 1998).

Scheme 9

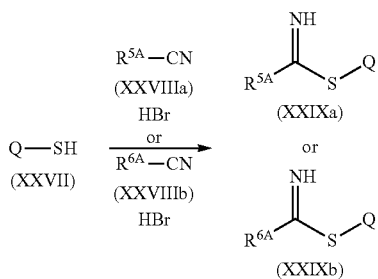

As shown in Scheme 10, a compound of formula XXXa or XXXb, where $R^1$, $R^2$, $R^3$, $R^4$, $R^{5A}$, $R^{6A}$, or $R^7$ are as defined elsewhere herein, can be prepared by reacting a compound of formula XXVa or XXVb with a compound of formula XXIXa or XXIXb, respectively, where Q is defined as above.

Scheme 10

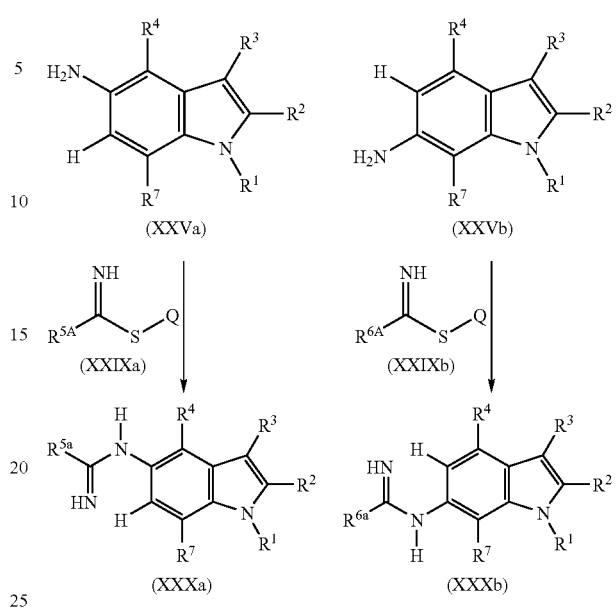

As shown in Scheme 11, a compound of formula XXXIIa or XXXIIb, where $R^1$, $R^2$, $R^3$, $R^4$ or $R^7$ are as defined elsewhere herein, can be prepared by reacting a compound of formula XXVa or XXVb with a compound of formula XXXIa or XXXIb, respectively, where $R^{5B}$ or $R^{6B}$ are $C_{1-6}$ alkyl, $C_{6-10}$ aryl, $C_{1-4}$ alkaryl, $C_{2-9}$ heterocyclyl, $C_{1-4}$ alkheterocyclyl, —C(O)$C_{1-6}$ alkyl, —C(O)$C_{6-10}$aryl, —C(O)$C_{1-4}$ alkaryl, —C(O)$C_{2-9}$ heterocyclyl, or —C(O)$C_{1-4}$ alkheterocyclyl. The reaction can be performed in an inert solvent, such as tetrahydrofuran, at ambient temperature or with heating. To prepare a compound of XXXIIIa or XXXIIIb, a compound of formula XXXIIa or XXXIIb, where the thiourea is bonded to a carbonyl moiety, is hydrolyzed under standard conditions, such as, for example, aqueous sodium hydroxide in tetrahydrofuran.

Scheme 11

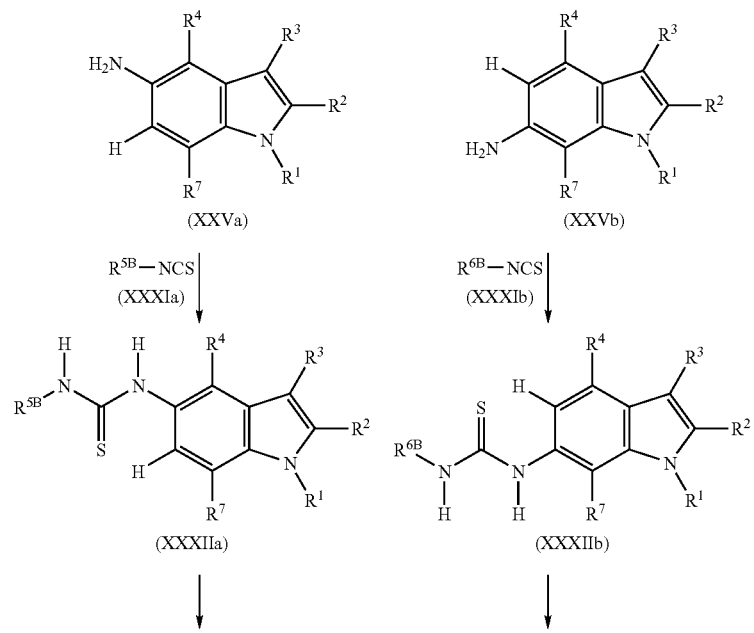

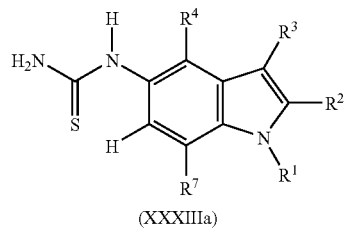

(XXXIIIa)

-continued

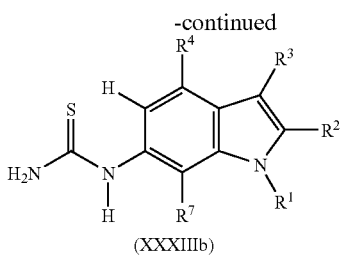

(XXXIIIb)

As shown in Scheme 12, a compound of formula XXXIIIa or XXXIIIb may be further reacted with an alkylating agent, such as, for example, $R^{5C}$-LG or $R^{6C}$-LG, where, $R^{5C}$ or $R^{6C}$ can be $C_{1-6}$ alkyl, $C_{1-4}$ alkaryl, or $C_{1-4}$ alkheterocyclyl and LG is a suitable leaving group, such as, for example, chloro, bromo, iodo, or sulfonate (e.g., mesylate or tosylate).

Scheme 12

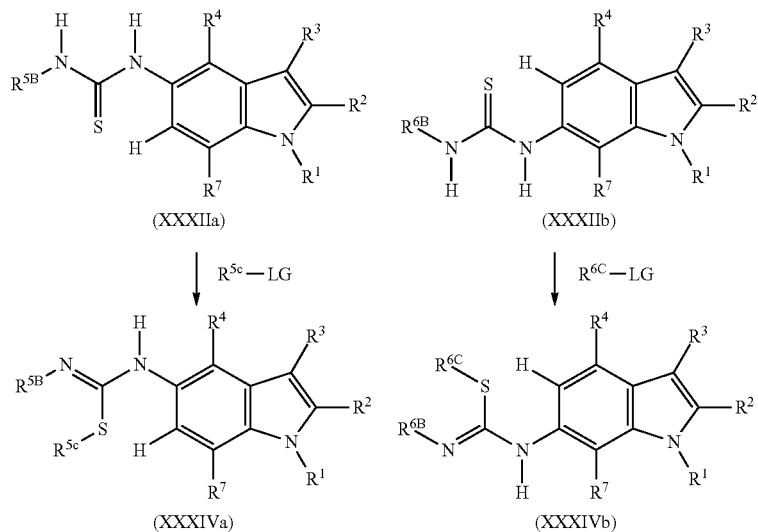

In some cases the chemistries outlined above may have to be modified, for instance, by the use of protective groups to prevent side reactions due to reactive groups, such as reactive groups attached as substituents. This may be achieved by means of conventional protecting groups as described in "Protective Groups in Organic Chemistry," McOmie, Ed., Plenum Press, 1973 and in Greene and Wuts. "Protective Groups in Organic Synthesis," John Wiley & Sons, $3^{rd}$ Edition, 1999.

The compounds of the invention, and intermediates in the preparation of the compounds of the invention, may be isolated from their reaction mixtures and purified (if necessary) using conventional techniques, including extraction, chromatography, distillation and recrystallization.

The formation of a desired compound salt is achieved using standard techniques. For example, the neutral compound is treated with an acid in a suitable solvent and the formed salt is isolated by filtration, extraction, or any other suitable method.

The formation of solvates of the compounds of the invention will vary depending on the compound and the solvate. In general, solvates are formed by dissolving the compound in the appropriate solvent and isolating the solvate by cooling or adding an antisolvent. The solvate is typically dried or azeotroped under ambient conditions.

Preparation of an optical isomer of a compound of the invention may be performed by reaction of the appropriate optically active starting materials under reaction conditions which will not cause racemization. Alternatively, the individual enantiomers may be isolated by separation of a racemic mixture using standard techniques, such as, for example, fractional crystallization or chiral HPLC.

A radiolabeled compound of the invention may be prepared using standard methods known in the art. For example, tritium may be incorporated into a compound of the invention using standard techniques, such as, for example, by hydrogenation of a suitable precursor to a compound of the invention using tritium gas and a catalyst. Alternatively, a compound of the invention containing radioactive iodine may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, such as, for example, hexamethylditin in the presence of tetrakis(triphenylphosphine) palladium (0) in an inert solvent, such as dioxane, and at elevated temperatures, suitably 50-100° C.

Pharmaceutical Uses

The present invention features all uses for a compound of formula I, including their use in therapeutic methods, whether alone or in combination with another therapeutic substance, their use in compositions for inhibiting NOS activity, their use in diagnostic assays, and their use as research tools.

The compounds of the invention have useful NOS inhibiting activity, and therefore are useful for treating, or reducing the risk of, diseases or conditions that are ameliorated by a reduction in NOS activity. Such diseases or conditions include those in which the synthesis or oversynthesis of nitric oxide plays a contributory part.

Accordingly, the present invention features a method of treating, or reducing the risk of, a disease or condition caused by NOS activity that includes administering an effective amount of a compound of the invention to a cell or animal in need thereof. Such diseases or conditions include, for example, migraine headache with and without aura, neuropathic pain, chronic tension type headache, chronic pain, acute spinal cord injury, diabetic neuropathy, diabetic nephropathy, an inflammatory disease, stroke, reperfusion injury, head trauma, cardiogenic shock, CABG associated neurological damage, HCA, AIDS associated dementia, neurotoxicity, Parkinson's disease, Alzheimer's disease, ALS, Huntington's disease, multiple sclerosis, metamphetamine-induced neurotoxicity, drug addiction, morphine/opioid induced tolerance, dependence, hyperalgesia or withdrawal, ethanol tolerance, dependence, or withdrawal, epilepsy, anxiety, depression, attention deficit hyperactivity disorder, and psychosis. In particular, 3,5-substituted indoles of the invention are particularly useful to treat migraine, with or without aura and chronic tension type headache (CTTH) and for migraine prophylaxis.

Following is a summary and a basis for the link between NOS inhibition and some of these conditions.

Migraine

The first observation by Asciano Sobrero in 1847 that small quantities of nitroglycerine, an NO releasing agent, causes severe headache lead to the nitric oxide hypothesis of migraine (Olesen et al., *Cephalagia* 15:94-100, 1995). Serotonergic $5HT_{1D/1B}$ agonists, such as sumatriptan, which are used clinically in the treatment of migraine, are known to prevent the cortical spreading depression in the lissencephalic and gyrencephalic brain during migraine attack, a process resulting in widespread release of NO. Indeed, it has been shown that sumatriptan modifies the artificially enhanced cortical NO levels following infusion of glyceryl trinitate in rats (Read et al., *Brain Res.* 847:1-8, 1999; ibid, 870(1-2):44-53, 2000). In a human randomized double-blinded clinical trial for migraine, a 67% response rate after single i.v. administration of $L-N^G$ methylarginine hydrochloride (L-NMMA, an NOS inhibitor) was observed. The effect was not attributed to a simple vasoconstriction since no effect was observed on transcranial doppler determined velocity in the middle cerbral artery (Lassen et al., *Lancet* 349:401-402, 1997). In an open pilot study using the NO scavenger hydroxycobalamin, a reduction in the frequency of migraine attack of 50% was observed in 53% of the patients and a reduction in the total duration of migraine attacks was also observed (van der Kuy et al., *Cephalgia* 22(7):513-519, 2002).

Migraine with Allodynia

Clinical studies have shown that as many as 75% of patients develop cutaneous allodynia (exaggerated skin sensitivity) during migraine attacks and that its development during migraine is detrimental to the anti-migraine action of triptan $5HT_{1B/1D}$ agonists (Burstein et al., *Ann. Neurol.* 47:614-624, 2000; Burstein et al., *Brain,* 123:1703-1709, 2000). While the early administration of triptans such as sumatriptan can terminate migraine pain, late sumatriptan intervention is unable to terminate migraine pain or reverse the exaggerated skin sensitivity in migraine patients already associated with allodynia (Burstein et al., *Ann. Neurol.* DOI: 10.1002/ana. 10785, 2003; Burstein and Jakubowski, *Ann. Neurol.,* 55:27-36, 2004). The development of peripheral and central sensitization correlates with the clinical manifestations of migraine. In migraine patients, throbbing occurs 5-20 minutes after the onset of headache, whereas cutaneous allodynia starts between 20-120 minutes (Burstein et al., *Brain,* 123:1703-1709, 2000). In the rat, experimentally induced peripheral sensitization of meningeal nociceptors occurs within 5-20 minutes after applying an inflammatory soup (I.S.) to the dura (Levy and Strassman, *J. Physiol.,* 538:483-493, 2002), whereas central sensitization of trigeminovascular neurons develops between 20-120 minutes (Burstein et al., *J. Neurophysiol.* 79:964-982, 1998) after I.S. administration. Parallel effects on the early or late administration of antimigraine triptans like sumatriptan on the development of central sensitization have been demonstrated in the rat (Burstein and Jakubowski, vide supra). Thus, early but not late sumatriptan prevents the long-term increase in I.S.-induced spontaneous activity seen in central trigeminovascular neurons (a clinical correlate of migraine pain intensity). In addition, late sumatriptan intervention in rats did not prevent I.S.-induced neuronal sensitivity to mechanical stimulation at the periorbital skin, nor decreased the threshold to heat (a clinical correlate of patients with mechanical and thermal allodynia in the periorbital area). In contrast, early sumatriptan prevented I.S. from inducing both thermal and mechanical hypersensitivity. After the development of central sensitization, late sumatriptan intervention reverses the enlargement of dural receptive fields and increases in sensitivity to dural indentation (a clinical correlate of pain throbbing exacerbated by bending over) while early intervention prevents its development.

Previous studies on migraine compounds such as sumatriptan (Kaube et al., *Br. J. Pharmacol.* 109:788-792, 1993), zolmitriptan (Goadsby et al., *Pain* 67:355-359, 1996), naratriptan (Goadsby et al., *Br. J. Pharmacol.,* 328:37-40, 1997), rizatriptan (Cumberbatch et al., *Eur. J. Pharmacol.,* 362:43-46, 1998), or L-471-604 (Cumberbatch et al., *Br. J. Pharmacol.* 126:1478-1486, 1999) examined their effects on nonsensitized central trigeminovascular neurons (under normal conditions) and thus do not reflect on their effects under the pathophysiolocal conditions of migraine. While triptans are effective in terminating the throbbing of migraine whether administered early or late, the peripheral action of sumatriptan is unable to terminate migraine pain with allodynia following late intervention via the effects of central sensitization of trigeminovascular neurons. The limitations of triptans suggest that improvement in the treatment of migraine pain can be achieved by utilizing drugs that can abort ongoing central sensitization, such as the compounds of the present invention.

It has been shown that systemic nitroglycerin increases nNOS levels and c-Fos-immunoreactive neurons (a marker neuronal activation) in rat trigeminal nucleus caudalis after 4 hours, suggesting NO likely mediates central sensitization of trigeminal neurons (Pardutz et al., *Neuroreport* 11(14):3071-3075, 2000). In addition, L-NAME can attenuate Fos expression in the trigeminal nucleus caudalis after prolonged (2 hrs) electrical stimulation of the superior sagittal sinus (Hoskin et al. *Neurosci. Lett.* 266(3): 173-6, 1999). Taken together with ability of NOS inhibitors to abort acute migraine attack (Lassen et al., *Cephalalgia* 18(1):27-32, 1998), the compounds of the invention, alone or in combination with other antinociceptive agents, represent excellent candidate therapeutics for aborting migraine in patients after the development of allodynia.

Chronic Headache (CTTH)

NO contributes to the sensory transmission in the peripheral (Aley et al., *J. Neurosci.* 1:7008-7014, 1998) and central nervous system (Meller and Gebhart, *Pain* 52:127-136, 1993). Substantial experimental evidence indicates that central sensitization, generated by prolonged nociceptive input from the periphery, increases excitability of neurons in the CNS and is caused by, or associated with, an increase in NOS activation and NO synthesis (Bendtsen, *Cephalagia* 20:486-508, 2000; Woolf and Salter, *Science* 288:1765-1769, 2000). It has been shown that experimental infusion of the NO donor, glyceryl trinitrate, induces headache in patients. In a double-blinded study, patients with chronic tension-type headache receiving L-NMMA (an NOS inhibitor) had a significant reduction in headache intensity (Ashina and Bendtsen, *J. Headache Pain* 2:21-24, 2001; Ashina et al., *Lancet* 243 (9149):287-9, 1999). Thus the NOS inhibitors of the present invention may be useful for the treatment of chronic tension-type headache.

Acute Spinal Cord Injury, Chronic or Neuropathic Pain

In humans, NO evokes pain on intracutaneous injection (Holthusen and Arndt, *Neurosci. Lett.* 165:71-74, 1994), thus showing a direct involvement of NO in pain. Furthermore, NOS inhibitors have little or no effect on nociceptive transmission under normal conditions (Meller and Gebhart, *Pain* 52:127-136, 1993). NO is involved in the transmission and modulation of nociceptive information at the periphery, spinal cord and supraspinal level (Duarte et al., *Eur. J. Pharmacol.* 217:225-227, 1992; Haley et al., *Neuroscience* 31:251-258, 1992). Lesions or dysfunctions in the CNS may lead to the development of chronic pain symptoms, known as central pain, and includes spontaneous pain, hyperalgesia, and mechanical and cold allodynia (Pagni, *Textbook of Pain*, Churchill Livingstone, Edinburgh, 1989, pp. 634-655; Tasker In: *The Management of Pain*, pp. 264-283, J. J. Bonica (Ed.), Lea and Febiger, Philadelphia, Pa., 1990; Casey, Pain and Central Nervous System Disease: The Central Pain Syndromes, pp. 1-11 K. L. Casey (Ed.), Raven Press, New York, 1991). It has been demonstrated that systemic administration (i.p.) of the NOS inhibitors 7-NI and L-NAME relieve chronic allodynia-like symptoms in rats with spinal cord injury (Hao and Xu, *Pain* 66:313-319, 1996). The effects of 7-NI were not associated with a significant sedative effect and were reversed by L-arginine (NO precursor). The maintenance of thermal hyperalgesia is believed to be mediated by nitric oxide in the lumbar spinal cord and can be blocked by intrathecal administration of a nitric oxide synthase inhibitor like L-NAME or soluble guanylate cyclase inhibitor methylene blue (*Neuroscience* 50(1):7-10, 1992). Thus the NOS inhibitors of the present invention may be useful for the treatment of chronic or neuropathic pain.

Diabetic Neuropathy

The endogenous polyamine metabolite agmatine is a metabolite of arginine that is both an NOS inhibitor and N-methyl-D-aspartate (NMDA) channel antagonist. Agmatine is effective in both the spinal nerve ligation (SNL) model of neuropathic pain as well as the streptozotocin model of diabetic neuropathy (Karadag et al., *Neurosci. Lett.* 339(1): 88-90, 2003). Thus compounds possessing NOS inhibitory activity, such as, for example, a compound of formula I, a combination of an NOS inhibitor and an NMDA antagonist should be effective in treating diabetic neuropathy and other neuropathic pain conditions.

Inflammatory Diseases and Neuroinflammation

LPS, a well known pharmacological tool, induces inflammation in many tissues and activates NFκB in all brain regions when administered intravenously. It also activates pro-inflammatory genes when injected locally into the striaitum (Stern et al., *J. Neuroimmunology*, 109:245-260, 2000). Recently it has been shown that both the NMDA receptor antagonist MK801 and the brain selective nNOS inhibitor 7-NI both reduce NFκB activation in the brain and thus reveal a clear role for glutamate and NO pathway in neuroinflammation (Glezer et al., *Neuropharmacology* 45(8):1120-1129, 2003). Thus, the administration of a compound of the invention, either alone or in combination with an NMDA antagonist, should be effective in treating diseases arising from neuroinflammation.

Stroke and Reperfusion Injury

The role of NO in cerebral ischemia can be protective or destructive depending on the stage of evolution of the ischemic process and on the cellular compartment producing NO (Dalkara et al., *Brain Pathology* 4:49, 1994). While the NO produced by eNOS is likely beneficial by acting as a vasodilator to improve blood flow to the affected area (Huang et al., *J. Cereb. Blood Flow Metab.* 16:981, 1996), NO produced by nNOS contributes to the initial metabolic deterioration of the ischemic penumbra, resulting in larger infarcts (Hara et al., *J. Cereb. Blood Flow Metab.* 16:605, 1996). The metabolic derangement that occurs during ischemia and subsequent reperfusion results in the expression and release of several cytokines that activate iNOS in several cell types including some of the central nervous system. NO can be produced at cytotoxic levels by iNOS, and increased levels of iNOS contribute to progressive tissue damage in the penumbra, leading to larger infarcts (Parmentier et al., *Br. J. Pharmacol.* 127:546, 1999). Inhibition of i-NOS has been shown to ameliorate cerebral ischemic damage in rats (*Am. J. Physiol.* 268:R286, 1995).

It has been shown that a synergistic neuroprotective effect is observed upon the combined administration of an NMDA antagonist (eg MK-801 or LY293558) with nNOS selective inhibitors (7-NI or ARL17477) in global cerebral ischemia (Hicks et al., *Eur. J. Pharmacol.* 381:113-119, 1999). Thus the compounds of the invention, administered either alone or in combination with NMDA antagonists, or compounds possessing mixed nNOS/NMDA activity, may be effective in treating conditions of stroke and other neurodegenerative disorders.

Complications Resulting from Coronary Artery Bypass Surgery

Cerebral damage and cognitive dysfunction still remains as a major complication of patients undergoing coronary artery bypass surgery (CABG) (Roch et al., *N. Eng. J. Med.* 335: 1857-1864, 1996; Shaw et al., *Q. J. Med.* 58:59-68, 1986). This cerebral impairment following surgery is a result of ischemia from preoperative cerebral microembolism. In a randomized trial of the NMDA antagonist remacemide, patients showed a significant overall postoperative improvement in learning ability in addition to reduced deficits (Arrowsmith et al., *Stroke* 29:2357-2362, 1998). Given the involvement of excitotoxicity produced by excessive release of glutamate and calcium influx, it is expected that a neuroprotective agent, such as a compound of the invention or an NMDA antagonist, either alone or in combination, may have a beneficial effect improving neurological outcomes after CABG.

AIDS-associated Dementia

HIV-1 infection can give rise to dementia. The HIV-1 coat protein gp-120 kills neurons in primary cortical cultures at low picomolar levels and requires external glutamate and calcium (Dawson et al., 90(8):3256-3259, 1993). This toxicity can be attenuated by administration of a compound of the invention, either alone or in combination with another therapeutic agent, such as, for example, an NMDA antagonist.

Examples of NMDA antagonist useful for any of the combinations of the invention include aptiganel; besonprodil; budipine; conantokin G; delucemine; dexanabinol; felbamate; fluorofelbamate; gacyclidine; glycine; ipenoxazone; kaitocephalin; lanicemine; licostinel; midafotel; milnacipran; neramexane; orphenadrine; remacemide; topiramate; (αR)-α-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H-,5H-pyrido[1,2,3-de]quinoxalin-5-yl]acetyl]amino]phenoxy]-acetic acid; α-amino-2-(2-phosphonoethyl)-cyclohexanepropanoic acid; α-amino-4-(phosphonomethyl)-benzeneacetic acid; (3E)-2-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino[4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid-7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene)methyl]-1H-indole-2-carboxylic acid; (2R,4S)-rel-5,7-dichloro-1,2,3,4-tetrahydro-4-[[(phenylamino)carbonyl]amino]-2-quinolinecarboxylic acid; (3R,4S)-rel-3,4-dihydro-3-[4-hydroxy-4-(phenylmethyl)-1-piperidinyl-]-2H-1-benzopyran-4,7-diol; 2-[(2,3-dihydro-1H-inden-2-yl)amino]-acetamide; 1,4-dihydro-6-methyl-5-[(methylamino)methyl]-7-nitro-2,3-quinoxalinedione; [2-(8,9-dioxo-2,6-diazabicyclo[5.2.0]non-1(7)-en-2-yl)ethyl]-phosphonic acid; (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[[(pentafluorophenyl)methyl]amino]-benzoic acid; 1-[2-(4-hydroxyphenoxy)ethyl]-4-[(4-methylphenyl)methyl]-4-piperidinol; 1-[4-(1H-imidazol-4-yl)-3-butynyl]-4-(phenylmethyl)-piperidine; 2-methyl-6-(phenylethynyl)-pyridine; 3-(phosphonomethyl)-L-phenylalanine; and 3,6,7-tetrahydro-2,3-dioxo-N-phenyl-1H,5H-pyrido[1,2,3-de]quinoxaline-5-acetamide or those described in U.S. Pat. Nos. 6,071,966; 6,034,134; and 5,061,703.

Cardiogenic Shock

Cardiogenic shock (CS) is the leading cause of death for patients with acute myocardial infarction that is consistent with increased levels of NO and inflammatory cytokines. High levels of NO and peroxynitrite have many effects, including a direct inhibition on myocardial contractability, suppression of mitochondrial respiration in myocardium, alteration in glucose metabolism, reduced catacholamine responsivity, and induction of systemic vasodilation (Hochman, *Circulation* 107:2998, 2003). In a clinical study in 11 patients with persistent shock, administration of the NOS inhibitor L-NMMA resulted in increases in urine output and blood pressure and survival rate of 72% up to 30 days (Cotter et al., *Circulation* 101:1258-1361, 2000). In a randomized trial of 30 patients, it was reported that L-NAME reduced patient mortality from 67% to 27% (Cotter et al., *Eur. Heart. J.* 24(14):1287-95, 2003). Similarly, administration of a compound of the invention, either alone or in combination with another therapeutic agent, may be useful for the treatment of cardiogenic shock.

Anxiety and Depression

Recent studies of rats and mice in the forced swimming test (FST) indicate that NOS inhibitors have antidepressant activity in mice (Harkin et al. *Eur. J. Pharm.* 372:207-213, 1999) and that their effect is mediated by a serotonin dependent mechanism (Harkin et al., *Neuropharmacology* 44(5):616-623, 1993). 7-NI demonstrates anxiolytic activity in the rat plus-maze test (Yildiz et al., *Pharmacology, Biochemistry and Behavior* 65:199-202, 2000), whereas the selective nNOS inhibitor TRIM is effective in both the FST model of depression and anxiety in the light-dark compartment test (Volke et al., *Behavioral Brain Research* 140(1-2):141-7, 2003). Administration of a compound of the invention to an afflicted individual, either alone or in combination with another therapeutic agent, such as, for example, an antidepressant, may be useful for the treatment of anxiety or depression.

Attention Deficit Hyperactivity Disorder

Non-selective attention (NSA) to environmental stimuli in Spontaneously Hypertensive (SHR) and Naples Low-Excitability (NHE) rats has been used as an animal model of Attention-Deficit Hyperactivity Disorder (ADHD) (Aspide et al., *Behav. Brain Res.* 95(1):23-33, 1998). These genetically altered animals show increased episodes of rearing that have a shorter duration than observed in normal animals. A single injection of L-NAME at 10 mg/kg produced an increase in rearing duration. Similarly, using the more neuronally selective 7-NINA, an increase in the rearing duration was observed after rapid administration (i.p.), while a slow release single release dose or a slow multiple release dose (s.c. in DMSO) resulted in the opposite effect. Thus, administration of a compound of the invention may be useful for the treatment of ADHD.

Psychosis

Phencyclidine (PCP) is a non-competitive NMDA channel blocker that produces behavioral side effects in human and mammals consistent with those observed in patients with psychosis. In two animal models of psychosis, the nNOS selective inhibitor AR-R17477 antagonized PCP-induced hyperlocomotion and PCP-induced deficit in prepulse inhibition of the acoustic response startle (Johansson et al., *Pharmacol. Toxicol.* 84(5):226-33, 1999). These results suggest the involvement of nNOS in psychosis. Therefore, administration of a compound of the invention to an afflicted individual may be useful for the treatment of this or related diseases or disorders.

Head Trauma

The mechanism of neurological damage in patients with head trauma parallels that of stroke and is related to excitotoxic calcium influx from excessive glutamate release, oxidative stress and free radical production from mitochondrial dysfunction and inflammation (*Drug & Market Development* 9(3):60-63, 1998). Animals treated with nitric oxide synthase inhibitors, such as 7-NI and 3-bromo-7-nitroindazole, have shown an improvement in neurological deficits after experimental traumatic brain injury (TBI) (Mesenge et al., *J. Neurotrauma* 13:209-14, 1996). Administration of a compound of the invention to an afflicted individual may also be useful for the treatment of neurological damage in head trauma injuries.

Hypothermic Cardiac Arrest

Hypothermic cardiac arrest (HCA) is a technique used to protect from ischemic damage during cardiac surgery when the brain is sensitive to damage during the period of blood flow interruption. Various neuroprotective agents have been used as adjunct agents during HCA and reducing nitric oxide production during HCA is predicted to result in improvements in neurological function. This is based on previous studies that showed glutamate excitotoxicity plays a role in HCA-induced neurologic damage (Redmond et al., *J. Thorac. Cardiovasc. Surg.* 107:776-87, 1994; Redmond et al., *Ann. Thorac. Surg.* 59:579-84, 1995) and that NO mediates glutamate excitotoxicity (Dawson and Snyder, *J. Neurosci.* 14:5147-59, 1994). In a study of 32 dogs undergoing 2 hours of HCA at 18° C., a neuronal NOS inhibitor was shown to reduce cerebral NO production, significantly reduce neuronal necrosis, and resulted in superior neurologic function relative to controls (Tseng et al., *Ann. Thorac. Surg.* 67:65-71, 1999). Administration of a compound of the invention may also be useful for protecting patients from ischemic damage during cardiac surgery.

Neurotoxicity and Neurodegenerative Diseases

Mitochondrial dysfunction, glutamate excitotoxicity, and free radical induced oxidative damage appear to be the underlying pathogenesis of many neurodegenerative diseases, including amyotrophic lateral sclerosis (ALS), Parkinson's disease (PD), Alzheimer's disease (AD), and Huntington's disease (HD) (Schulz et al., *Mol. Cell. Biochem.* 174(1-2): 193-197, 1997; Beal, *Ann. Neurol.* 38:357-366, 1995), and NO is a primary mediator in these mechanisms. For example, it was shown by Dawson et al., in *PNAS* 88(14):6368-6371, 1991, that NOS inhibitors like 7-NI and L-NAME prevent neurotoxicity elicited by N-methyl-D-aspartate and related excitatory amino acids.

(a) Parkinson's Disease

Studies have also shown that NO plays an important role in 1-methyl-4-phenyl-1,2,3,6-tetrahydropyridine (MPTP) neurotoxicity, a commonly used animal model of Parkinson's disease (Matthews et al., *Neurobiology of Disease* 4:114-121, 1997). MPTP is converted to MPP+ by MAO-B and is rapidly taken up by the dopamine transporter into the mitochondria of dopamine containing neurons with subsequent activation of nNOS resulting in neuronal death. Mutant mice lacking the nNOS gene, but not the eNOS gene, have reduced lesions in the substantia nigra after MPP+ injection into the striatum. In primate studies, 7-NI exerts a profound neuroprotective and antiparkinsonium effect after MPTP challenge (Hantraye et al., *Nature Med.* 2:1017-1021, 1996) as did the non-specific inhibitor L-NAME (T. S. Smith et. al. Neuroreport 1994, 5, 2598-2600).

(b) Alzheimer's Disease (AD)

The pathology of AD is associated with β-amyloid plaques infiltrated with activated microglia and astrocytes. When cultured rat microglia are exposed to beta-amyloid, there is a prominent microglial release of nitric oxide, especially in the presence of gamma-interferon (Goodwin et al., *Brain Research* 692(1-2):207-14, 1995). In cortical neuronal cultures, treatment with nitric oxide synthase inhibitors provides neuroprotection against toxicity elicited by human beta-amyloid (Resink et al., *Neurosci. Abstr.* 21:1010, 1995). Consistent with the glutamate hypothesis of excitotoxicity in neurodegerative disorders, the weak NMDA antagonist amantadine increases the life expectancy of PD patients (Uitti et al., *Neurology* 46(6):1551-6, 1996). In a preliminary, placebo-controlled study of patients with vascular- or Alzheimer's-type dementia, the NMDA antagonist memantine was associated with improved Clinical Global Impression of Change and Behavioral Rating Scale for Geriatric Patients scores (Winblad and Poritis, *Int. J. Geriatr. Psychiatry* 14:135-46, 1999).

(c) Amyotrophic Lateral Sclerosis

Amyotrophic lateral sclerosis (ALS) is a fatal neurodegenerative disease characterized by selective motor neuronal death. Accumulating, evidence suggests that the pathogenesis of ALS is the insufficient clearance of glutamate through the glutamate transporter, and the specific distribution of $Ca^{2+}$-permeable AMPA receptors in spinal motor neurons, indicates a glutamate-induced neurotoxicity. Increased nNOS immunoreactivity is found in the spinal cords (Sasaki et al., *Acta Neuropathol.* (*Berl*) 101(4):351-7, 2001) and glial cells (Anneser et al., *Exp. Neurol.* 171(2):418-21, 2001) of ALS patients, implicating NO as an important factor in the pathogenesis of ALS.

(d) Huntington's Disease

The pathogenesis of Huntington's disease (HD) arising from a mutation in the Htt protein is linked to excitotoxicity, oxidative stress and apoptosis, in all of which excessive NO has a clear role (Peterson et al., *Exp. Neurol.* 157:1-18, 1999). Oxidative damage is one of the major consequences of defects in energy metabolism and is present in HD models after injection of excitotoxins and mitochondrial inhibitors (A. Petersen et. al., *Exp. Neurol.* 157:1-18, 1999). This mitochrondrial dysfunction is associated with the selective and progressive neuronal loss in HD (Brown et al., *Ann. Neurol.* 41:646-653, 1997). NO can directly impair the mitochondrial respiratory chain complex IV (Calabrese et al., *Neurochem. Res.* 25:1215-41, 2000). Striatal medium spiny neurons appear to be the primary target for the generation of motor dysfunction in HD. Hyperphosphorylation and activation of NMDA receptors on these neurons likely participates in the generation of motor dysfunction. It has been shown clinically that the NMDA antagonist amantadine improve choreiform dyskinesias in HD (Verhagen Metman et al., *Neurology* 59:694-699, 2002). Given the role of nNOS in NMDA mediated neurotoxicity, it is expected that nNOS inhibitors, especially those with mixed nNOS/NMDA, or combinations of drugs with nNOS and NMDA activity will also be useful in ameliorating the effects and or progression of HD. For example, pretreatment of rats with 7-nitroindazole attenuates the striatal lesions elicited by stereotaxic injections of malonate, an injury that leads to a condition resembling Huntington's disease (Hobbs et. al., *Ann. Rev. Pharm. Tox.* 39:191-220, 1999). In a R6/1 transgenic mouse model of HD expressing a human mutated htt exon1, a 116 CAG repeat, mice at 11, 19 and 35 weeks show a progressive increase in lipid peroxidation with normal levels of superoxide dismutase (SOD) at 11 weeks similar to wild type (WT) mice; a maximum level at 19 weeks, above that observed in WT mice and corresponding to the early phase of disease progression; and finally, decreasing levels at 35 weeks below that observed in WT mice (Pérez-Sevriano et al., *Brain Res.* 951:36-42, 2002). The increase in SOD activity is attributable to a compensatory neuroprotective mechanism, with decreased levels at 35 weeks corresponding to a failed protective mechanism. Concomitant with the levels of SOD, levels of calcium dependent NOS was the same for 11 week mice in both WT and R6/1 mice, but increased significantly at 19 weeks and decreased at 35 weeks relative to WT control mice. Levels of nNOS expression also increased dramatically relative to controls at 19 weeks but were decreased significantly relative to controls at 35 weeks. No significant differences were observed in levels of eNOS expression, nor could iNOS protein be detected during progression of the disease. The progressive phenotypic expression of the disease, as measured by increased weight loss, feet clasping behavior, and horizontal and vertical movements, are consistent with changes in NOS activity and nNOS expression. Finally, the effects of L-NAME administration to both R6/2 transgenic HD mice and WT mice showed improved levels of clasping behavior at a 10 mg/kg dose similar to controls, which worsened at the highest dose of 500 mg/kg (Deckel et al., *Brain Res.* 919

(1):70-81, 2001). An improvement in weight increase in HD mice was also significant at the 10 mg/kg dose, but decreased relative to controls at high dose levels of L-NAME. These results demonstrate that administration of an appropriate dose of an NOS inhibitor, such as, for example, a compound of the invention, can be beneficial in the treatment of HD.
(e) Multiple Sclerosis (MS)

MS is in an inflammatory demyelinating disease of the CNS involving cytokines and other inflammatory mediators. Many studies suggest that NO and its reactive derivative peroxynitrite are implicated in the pathogenesis of MS (Acar et al. *J. Neurol.* 250(5):588-92, 2003; Calabrese et al., *Neurochem. Res.* 28(9):1321-8, 2003). In experimental autoimmune encephalomyelitis (EAE), a model of MS, nNOS levels are slightly increased in the spinal cord of EAE rats and treatment with 7-nitroindazole results in a significant delay in the onset of EAE paralysis (Shin, *J. Vet. Sci.* 2(3):195-9, 2001).

(f) Methamphetamine-Induced Neurotoxicity

Methamphetamine is neurotoxic by destroying dopamine nerve terminals in vivo. It has been shown that methamphetamine-induced neurotoxicity can be attenuated by treatment with NOS inhibitors in vitro (Sheng et al., *Ann. N.Y. Acad. Sci.* 801:174-186. 1996) and in in vivo animal models (Itzhak et al., *Neuroreport* 11(13):2943-6, 2000). Similarly, the nNOS selective inhibitor AR-17477AR, at 5 mg/kg s.c in mice, was able to prevent the methamphetamine-induced loss of the neurofilament protein NF68 in mouse brain and prevent the loss of striaital dopamine and homovanillic acid (HVA) (Sanchez et al., *J. Neurochem.* 85(2):515-524, 2003).

Administration of a compound of the invention, either alone or in combination with another therapeutic agent, such as, for example, an NMDA antagonist, may be useful for the protection or treatment of any of the neurodegenerative diseases described herein. Further, the compounds of the invention may be tested in standard assays used to assess neuroprotection (see for example, *Am. J. Physiol.* 268:R286, 1995).
Chemical Dependencies and Drug Addictions (e.g., Dependencies on Drugs, Alcohol and Nicotine)

A key step in the process of drug-induced reward and dependence is the regulation of dopamine release from mesolimbic dopaminergic neurons. Chronic application of cocaine alters the expression of the key protein controlling the synaptic level of dopamine—the dopamine transporter (DAT).

(a) Cocaine Addiction

Studies have shown that animals reliably self-administer stimulants intravenously and that dopamine is critical in their reinforcing effects. Recently NO containing neurons have been shown to co-localize with dopamine in areas of the striatum and ventral tegmental area and that NO can modulate stimulant-evoked dopamine (DA) release. Administration of dopamine D1 receptor antagonists decrease the levels of straital NADPH-diaphorase staining, a marker for NOS activity, while D2 antagonists produce the opposite effect. L-Arginine, the substrate of NOS, is also a potent modulator of DA release. Also, multiple NO-generating agents increase DA efflux or inhibit reuptake both in vitro and in vivo. L-NAME has been shown to significantly alter cocaine reinforcement by decreasing the amount of self-administration and by increasing the inter-response time between successive cocaine injections (Pudiak and Bozarth, *Soc. Neurosci. Abs.* 22:703, 1996). This indicates that NOS inhibition may be useful in the treatment of cocaine addiction.

(b) Morphine/Opioid Induced Tolerance and Withdrawal Symptoms

There is much evidence supporting the role of both the NMDA and NO pathways in opioid dependence in adult and infant animals. Adult or neonatal rodents injected with morphine sulfate develop behavioral withdrawal after precipitation with naltrexone. The withdrawal symptoms after naltrexone initiation can be reduced by administration of NOS inhibitors, such as 7-NI or L-NAME (Zhu and Barr, *Psychopharmacology* 150(3):325-336, 2000). In a related study, it was shown that the more nNOS selective inhibitor 7-NI attenuated more of the morphine induced withdrawal symptoms including mastication, salivation and genital effects than the less selective compounds (Vaupel et al., *Psychopharmacology (Berl.)* 118(4):361-8, 1995).

(c) Ethanol Tolerance and Dependence

Among the factors that influence alcohol dependence, tolerance to the effects of ethanol is an important component because it favors the exaggerated drinking of alcoholic beverages (Lê and Kiianmaa, *Psychopharmacology (Berl.)* 94:479-483, 1988). In a study with rats, ethanol tolerance to motor incoordination and hypothermia develop rapidly and can be blocked by i.c.v administration of 7-NI without altering cerebral ethanol concentrations (Wazlawik and Morato, *Brain Res. Bull.* 57(2):165-70, 2002). In other studies, NOS inhibition with L-NAME (Rezvani et al., *Pharmacol. Biochem. Behav.* 50:265-270, 1995) or by i.c.v. injection of nNOS antisense (Naassila et. al., Pharmacol. Biochem. Behav. 67:629-36, 2000) reduced ethanol consumption in these animals.

Administration of a compound of the invention, either alone or in combination with another therapeutic agent, such as, for example, an NMDA antagonist, may be useful for the treatment of chemical dependencies and drug addictions.
Epilepsy Co-administration of 7-NI with certain anticonvulsants, such as carbamazepine, shows a synergistic protective effect against amygdala-kindled seizures in rats at concentrations that do not alter roto-rod performance (Borowicz et al., *Epilepsia* 41(9):112-8, 2000). Thus, an NOS inhibitor, such as, for example, a compound of the invention, either alone or in combination with another therapeutic agent, such as, for example, an antiepileptic agent, may be useful for the treatment of epilepsy or a similar disorder. Examples of antiepileptic agents useful in a combination of the invention include carbamazepine, gabapentin, lamotrigine, oxcarbazepine, phenyloin, topiramate, and valproate.
Diabetic Nephropathy Urinary excretion of NO byproducts is increased in diabetic rats after streptozotocin treatment and increased NO synthesis has been suggested to be involved in diabetic glomerular hyperfiltration. The neuronal isoform nNOS is expressed in the loop of Henle and mucula densa of the kidney and inhibition of this isoform using 7-NI reduces glomerular filtration without affecting renal arteriole pressure or renal blood flow (Sigmon et al., *Gen. Pharmacol.* 34(2):95-100, 2000). Both the non-selective NOS inhibitor L-NAME and the nNOS selective 7-NI normalize renal hyperfiltration in diabetic animals (Ito et al., *J. Lab Clin. Med.* 138(3):177-185, 2001). Therefore, administration of a compound of the invention may be useful for the treatment of diabetic nephropathy.
Combination Formulations, and Uses Thereof In addition to the formulations described above, one or more compounds of the invention can be used in combination with other therapeutic agents. For example, one or more compounds of the invention can be combined with another NOS inhibitor. Exemplary inhibitors useful for this purpose include, without limitation, those described in U.S. Pat. No. 6,235,747; U.S. patent application Ser. Nos. 09/127,158, 09/325,480, 09/403,177, 09/802,086, 09/826,132, 09/740, 385, 09/381,887, 10/476,958, 10/483,140, 10/484,960, 10/678,369, 10/819,853, 10/938,891; International Publication Nos. WO 97/36871, WO 98/24766, WO 98/34919, WO 99/10339, WO 99/11620, and WO 99/62883.

In another example, one or more compounds of the invention can be combined with an antiarrhythmic agent. Exemplary antiarrhythmic agents include, without limitation, lidocaine and mixiletine.

GABA-B agonists, alpha-2-adrenergic receptor agonists, cholecystokinin antagonists, $5HT_{1B/1D}$ agonists, or CGRP antagonists can also be used in combination with one or more compounds of the invention. Non-limiting examples of alpha-2-adrenergic receptor agonists include clonidine, lofexidine, and propanolol. Non-limiting examples of cholecystokinin antagonists include L-365,260; CI-988; LY262691; S0509, or those described in U.S. Pat. No. 5,618,811. Non-limiting examples of $5HT_{1B/1D}$ agonists that may be used in combination with a compound of the invention include dihydroergotamine, eletriptan, frovatriptan, naratriptan, rizatriptan, sumatriptan, or zolmitriptan. Non-limiting examples of CGRP antagonists that may be used in combination with a compound of the invention include quinine analogues as described in International Publication No. WO9709046, non-peptide antagonists as described in International Publication Nos. WO0132648, WO0132649, WO9811128, WO9809630, WO9856779, WO0018764, or other antagonists such as SB-(+)-273779 or BIBN-4096BS.

Substance P antagonists, also known as $NK_1$ receptor antagonists, are also useful in combination with one or more compounds of the invention. Exemplary inhibitors useful for this purpose include, without limitation, those compounds disclosed in U.S. Pat. Nos. 3,862,114, 3,912,711, 4,472,305, 4,481,139, 4,680,283, 4,839,465, 5,102,667, 5,162,339, 5,164,372, 5,166,136, 5,232,929, 5,242,944, 5,300,648, 5,310,743, 5,338,845, 5,340,822, 5,378,803, 5,410,019, 5,411,971, 5,420,297, 5,422,354, 5,446,052, 5,451,586, 5,525,712, 5,527,811, 5,536,737, 5,541,195, 5,594,022, 5,561,113, 5,576,317, 5,604,247, 5,624,950, and 5,635,510; International Publication Nos. WO 90/05525, WO 91/09844, WO 91/12266, WO 92/06079, WO 92/12151, WO 92/15585, WO 92/20661, WO 92/20676, WO 92/21677, WO 92/22569, WO 93/00330, WO 93/00331, WO 93/01159, WO 93/01160, WO 93/01165, WO 93/01169, WO 93/01170, WO 93/06099, WO 93/10073, WO 93/14084, WO 93/19064, WO 93/21155, WO 94/04496, WO 94/08997, WO 94/29309, WO 95/11895, WO 95/14017, WO 97/19942, WO 97/24356, WO 97/38692, WO 98/02158, and WO 98/07694. European Patent Publication Nos. 284942, 327009, 333174, 336230, 360390, 394989, 428434, 429366, 443132, 446706, 484719, 499313, 512901, 512902, 514273, 514275, 515240, 520555, 522808, 528495, 532456, and 591040.

Suitable classes of antidepressant agents that may be used in combination with a compound of the invention include, without limitation, norepinephrine re-uptake inhibitors, selective serotonin re-uptake inhibitors (SSRIs), selective noradrenaline/norepinephrine reuptake inhibitors (NARIs), monoamine oxidase inhibitors (MAOs), reversible inhibitors of monoamine oxidase (RIMAs), dual serotonin/noradrenaline re-uptake inhibitors (SNRIs), α-adrenoreceptor antagonists, noradrenergic and specific serotonergic antidepressants (NaSSAs), and atypical antidepressants.

Non-limiting examples of norepinephrine re-uptake inhibitors include tertiary amine tricyclics and secondary amine tricyclics, such as, for example, adinazolam, amineptine, amitriptyline, amoxapine, butriptyline, clomipramine, demexiptiline, desmethylamitriptyline, desipramine, dibenzepin, dimetacrine, doxepin, dothiepin, femoxetine, fluacizine, imipramine, imipramine oxide, iprindole, lofepramine, maprotiline, melitracen, metapramine, norclolipramine, nortriptyline, noxiptilin, opipramol, perlapine, pizotifen, pizotyline, propizepine, protriptyline, quinupramine, tianeptine, trimipramine, trimipramineamiltriptylinoxide, and pharmaceutically acceptable salts thereof.

Non-limiting examples of selective serotonin re-uptake inhibitors include, for example, fluoxetine, fluvoxamine, paroxetine, and sertraline, and pharmaceutically acceptable salts thereof.

Non-limiting examples of selective noradrenaline/norepinephrine reuptake inhibitors include, for example, atomoxetine, bupropion; reboxetine, and tomoxetine.

Non-limiting examples of selective monoamine oxidase inhibitors include, for example, isocarboxazid, phenezine, tranylcypromine and selegiline, and pharmaceutically acceptable salts thereof. Other monoamine oxidase inhibitors useful in a combination of the invention include clorgyline, cimoxatone, befloxatone, brofaromine, bazinaprine, BW-616U (Burroughs Wellcome), BW-1370U87 (Burroughs Wellcome), CS-722 (RS-722) (Sankyo), E-2011 (Eisai), harmine, harmaline, moclobemide, PharmaProjects 3975 (Hoechst), RO 41-1049 (Roche), RS-8359 (Sankyo), T-794 (Tanabe Seiyaku), toloxatone, K-Y 1349 (Kalir and Youdim), LY-51641 (Lilly), LY-121768 (Lilly), M&B 9303 (May & Baker), MDL 72394 (Marion Merrell), MDL 72392 (Marion Merrell), sercloremine, and MO 1671, and pharmaceutically acceptable salts thereof. Suitable reversible inhibitors of monoamine oxidase that may be used in the present invention include, for example, moclobemide, and pharmaceutically acceptable salts thereof.

Non-limiting examples of dual serotonin/norepinephrine reuptake blockers include, for example, duloxetine, milnacipran, mirtazapine, nefazodone, and venlafaxine.

Non-limiting examples of other antidepressants that may be used in a method of the present invention include adinazolam, alaproclate, amineptine, amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, fengabine, fezolamine, fluotracen, idazoxan, indalpine, indeloxazine, levoprotiline, litoxetine, medifoxamine, metralindole, mianserin, minaprine, montirelin, nebracetam, nefopam, nialamide, nomifensine, norfluoxetine, orotirelin, oxaflozane, pinazepam, pirlindone, ritanserin, rolipram, sercloremine, setiptiline, sibutramine, sulbutiamine, sulpiride, teniloxazine, thozalinone, thymoliberin, tiflucarbine, tofenacin, tofisopam, toloxatone, veralipride, viqualine, zimelidine, and zometrapine, and pharmaceutically acceptable salts thereof, and St. John's wort herb, or Hypencuin perforatum, or extracts thereof.

In another example, opioids can be used in combination with one or more compounds of the invention. Exemplary opioids useful for this purpose include, without limitation, alfentanil, butorphanol, buprenorphine, dextromoramide, dezocine, dextropropoxyphene, codeine, dihydrocodeine, diphenoxylate, etorphine, fentanyl, hydrocodone, hydromorphone, ketobemidone, loperamide, levorphanol, levomethadone, meperidine, meptazinol, methadone, morphine, morphine-6-glucuronide, nalbuphine, naloxone, oxycodone, oxymorphone, pentazocine, pethidine, piritramide, propoxylphene, remifentanil, sulfentanyl, tilidine, and tramadol.

In yet another example, anti-inflammatory compounds, such as steroidal agents or non-steroidal anti-inflammatory drugs (NSAIDs), can be used in combination with one or more compounds of the invention. Non-limiting examples of steroidal agents include prednisolone and cortisone. Non-limiting examples of NSAIDs include acemetacin, aspirin, celecoxib, deracoxib, diclofenac, diflunisal, ethenzamide, etofenamate, etoricoxib, fenoprofen, flufenamic acid, flurbiprofen, lonazolac, lornoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3 (2H)-pyridazinone, and 2-(3,5-difluorophenyl)-3-[4-(methylsulfonyl)phenyl]-2-cyclopenten-1-one). Compounds of the invention may also be use in combination with acetaminophen.

Any of the above combinations can be used to treat any appropriate disease, disorder, or condition. Exemplary uses for combinations of a compound of the invention and another therapeutic agent are described below.

Opioid-NOS Inhibitor Combinations in Chronic, Neuropathic Pain

Nerve injury can lead to abnormal pain states known as neuropathic pain. Some of the clinical symptoms include tactile allodynia (nociceptive responses to normally innocuous mechanical stimuli), hyperalgesia (augmented pain intensity in response to normally painful stimuli), and spontaneous pain. Spinal nerve ligation (SNL) in rats is an animal model of neuropathic pain that produces spontaneous pain, allodynia, and hyperalgesia, analogous to the clinical symptoms observed in human patients (Kim and Chung, *Pain* 50:355-363, 1992; Seltzer, *Neurosciences* 7:211-219, 1995).

Neuropathic pain can be particularly insensitive to opioid treatment (Benedetti et al., *Pain* 74:205-211, 1998) and is still considered to be relatively refractory to opioid analgesics (MacFarlane et al., *Pharmacol. Ther.* 75:1-19, 1997; Watson, *Clin. J. Pain* 16:S49-S55, 2000). While dose escalation can overcome reduced opioid effectiveness, it is limited by increased side effects and tolerance. Morphine administration is known to activate the NOS system, which limits the analgesic action of this drug (Machelska et al., *NeuroReport* 8:2743-2747, 1997; Wong et al., *Br. J. Anaesth.* 85:587, 2000; Xiangqi and Clark, *Mol. Brain. Res.* 95:96-102, 2001). However, it has been shown that the combined systemic administration of morphine and L-NAME can attenuate mechanical and cold allodynia at subthreshold doses at which neither drug administered alone was effective (Ulugol et al., *Neurosci. Res. Com.* 30(3):143-153, 2002). The effect of L-NAME co-administration on morphine analgesia appears to be mediated by nNOS, as L-NAME loses its ability to potentiate morphine analgesia in nNOS null-mutant mice (Clark and Xiangqi, *Mol. Brain. Res.* 95:96-102, 2001). Enhanced analgesia has been demonstrated in the tail-flick or paw pressure models using coadministration of L-NAME or 7-NI with either a mu-, delta-, or kappa-selective opioid agonist (Machelska et al., *J. Pharmacol. Exp. Ther.* 282:977-984, 1997).

While opioids are an important therapy for the treatment of moderate to severe pain, in addition to the usual side effects that limit their utility, the somewhat paradoxical appearance of opioid-induced hyperalgesia may actually render patients more sensitive to pain and potentially aggravate their pain (Angst and Clark, Anesthesiology, 2006, 104(3), 570-587; Chu et. al. J. Pain 2006, 7(1) 43-48). The development of tolerance and opioid induced hyperalgesia is consistent with increased levels of NO production in the brain. The reduced analgesic response to opioids is due to an NO-induced upregulated hyperalgesic response (Heinzen and Pollack, Brain Res. 2004, 1023, 175-184).

Thus, the combination of an nNOS inhibitor with an opioid (for example, those combinations described above) can enhance opioid analgesia in neuropathic pain and prevent the development of opioid tolerance and opioid-induced hyperalgesia.

Antidepressant-NOS Inhibitor Combinations for Chronic Pain, Neuropathic Pain, Chronic Headache or Migraine Many antidepressants are used for the treatment of neuropathic pain (McQuay et al., *Pain* 68:217-227, 1996) and migraine (Tomkins et al., *Am. J. Med.* 111:54-63, 2001), and act via the serotonergic or noradrenergic system. NO serves as a neuromodulator of these systems (Garthwaite and Boulton, *Annu. Rev. Physiol.* 57:683, 1995). 7-NI has been shown to potentiate the release of noradrenaline (NA) by the nicotinic acetylcholine receptor agonist DMPP via the NA transporter (Kiss et al., *Neuroscience Lett.* 215:115-118, 1996). It has been shown that local administration of antidepressants, such as paroxetine, tianeptine, and imipramine decrease levels of hippocampal NO (Wegener et al., *Brain Res.* 959:128-134, 2003). It is likely that NO is important in the mechanism by which antidepressants are effective for treating pain and depression, and that a combination of an nNOS inhibitor with an antidepressant, such as, for example, those combinations described above, will produce better treatments.

Serotonin $5HT_{1B/1D/1F}$ Agonist or CGRP Antagonist and NOS Inhibitor Combinations in Migraine Administration of Glyceryl trinitrate (GTN), an NO donor, induces immediate headaches in normal individuals and results in delayed migraine attacks in migraineurs with a 4-6 hour latency period (Iversen et al., *Pain* 38:17-24, 1989). In patients with migraine attack, levels of CGRP (Calcitonin Gene Related Peptide), a potent vasodilator, in the carotid artery correlate with the onset and ablation of migraine attack (Durham, *Curr Opin Investig Drugs* 5(7):731-5, 2004). Sumatriptan, an antimigraine drug having affinity at $5HT_{1B}$, $5HT_{1D}$, and $5HT_{1F}$ receptors, reduces GTN-induced immediate headache and in parallel contracts cerebral and extracerebral arteries (Iversen and Olesen, *Cephalagia* 13(Suppl 13):186, 1993). The antimigraine drug rizatriptan also reduces plasma levels of CGRP following migraine pain reduction (Stepien et al., *Neurol. Neurochir. Pol.* 37(5):1013-23, 2003). Both NO and CGRP have therefore been implicated as a cause for migraine. Serotonin $5HT_{1B/1D}$ agonists have been shown to block NMDA receptor-evoked NO signaling in brain cortex slices (Strosznajder et al., *Cephalalgia* 19(10):859, 1999). These results suggest that a combination of a compound of the invention and a selective or non-selective $5HT_{1B/1D/1F}$ agonist or a CGRP antagonist, such as those combinations described above, would be useful for the treatment of migraine.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent or carrier.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal alone or in combination with pharmaceutically acceptable carriers, as noted above, the proportion of which is determined by the solubility and chemical nature of the compound, chosen route of administration, and standard pharmaceutical practice.

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of between 0.05 mg and 3000 mg (measured as the solid form). A preferred dose ranges between 0.05-500 mg/kg, more preferably between 0.5-50 mg/kg.

A compound of the invention can be used alone or in combination with other agents that have NOS activity, or in combination with other types of treatment (which may or may not inhibit NOS) to treat, prevent, and/or reduce the risk of stroke, neuropathic or migraine pain, or other disorders that benefit from NOS inhibition. In combination treatments, the dosages of one or more of the therapeutic compounds may be reduced from standard dosages when administered alone. In this case, dosages of the compounds when combined should provide a therapeutic effect.

In addition to the above-mentioned therapeutic uses, a compound of the invention can also be used in diagnostic assays, screening assays, and as a research tool.

In diagnostic assays, a compound of the invention may be useful in identifying or detecting NOS activity. For such a use, the compound may be radiolabelled (as described elsewhere herein) and contacted with a population of cells of an organism. The presence of the radiolabel on the cells may indicate NOS activity.

In screening assays, a compound of the invention may be used to identify other compounds that inhibit NOS, for example, as first generation drugs. As research tools, the compounds of the invention may be used in enzyme assays and assays to study the localization of NOS activity. Such information may be useful, for example, for diagnosing or monitoring disease states or progression. In such assays, a compound of the invention may also be radiolabeled.

The following non-limiting examples are illustrative of the present invention:

EXAMPLE 1

The Preparation of Compound 4

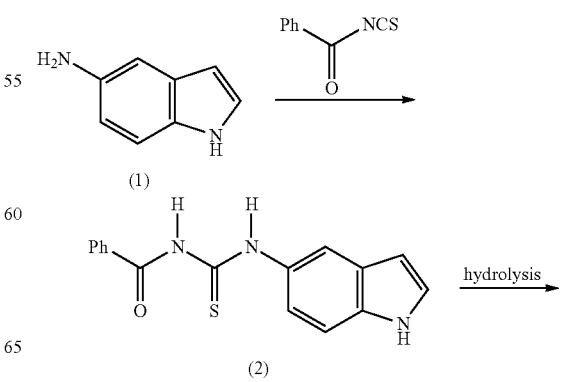

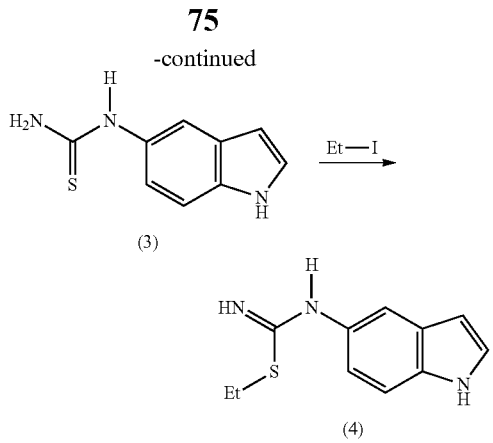

(a) Preparation of compound 2: 1H-Indol-5-ylamine (compound 1, 100 mg, 0.757 mmol) was dissolved in anhydrous tetrahydrofuran (4.5 mL) in a small argon purged flask. Benzoyl isothiocyanate (123 mg, 0.757 mmol) was added dropwise and the reaction was stirred at room temperature under argon for 60 hours. 3-(Diethylenetriamino)propyl-functionalized silica gel (0.5 g) was added, the mixture stirred for an additional 30 minutes, and the mixture filtered using 3:7 ethyl acetate/hexanes as the eluant. The product (compound 2, 90 mg, 40.3% yield) was obtained via purification by silica gel column chromatography (30% ethyl acetate/hexanes); $^1$H NMR (CDCl$_3$) δ: 6.59 (s, 1H), 7.25-7.26 (m, 2H), 7.51 (s, 1H), 7.54-7.66 (m, 3H), 7.93 (m, 3H), 8.32 (br s, 1H), 9.15 (s, 1H), 12.50 (s, 1H).

(b) Preparation of compound 3: 1-Benzoyl-3-(1H-indol-5-yl)-thiourea, (compound 2, 90 mg, 0.305 mmol) was dissolved in anhydrous tetrahydrofuran (5 mL) in a small argon purged flask. The reaction vessel was fitted with a condenser and placed in an oil bath preheated to 60° C. Aqueous 2M sodium hydroxide solution (0.6 mL) was added and the reaction was stirred under reflux for 4 hours. Workup gave compound 3 (22 mg, 38.0% yield).

(c) Preparation of compound 4: (1H-Indol-5-yl)-thiourea (compound 3, 22 mg, 0.116 mmol) was dissolved in DMF (2.5 mL). The solution was stirred under argon as ethyl iodide (18.1 mg, 0.116 mmol) was added dropwise. Potassium carbonate (48.01 mg, 0.347 mmol) was added and the reaction was stirred for 20 hours at room temperature. The reaction was treated with water (5 mL) and dichloromethane (20 mL) and transferred to a separatory funnel. The organic layer was dried (MgSO$_4$), filtered, and concentrated to give compound 4.

EXAMPLE 2

The Preparation of Compound 5

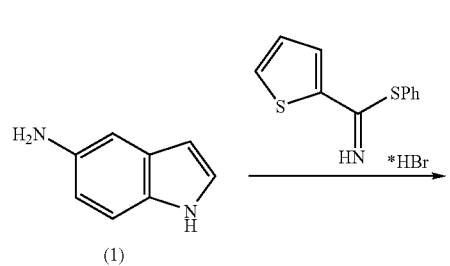

(a) Preparation of compound 5: 1H-Indol-5-ylamine (compound 1, 59 mg, 0.45 mmol) and thiophene-2-carboximidothioic acid phenyl ester hydrobromide (142.7 mg, 0.47 mmol) were dissolved in absolute ethanol (2.0 mL) in a dry, argon purged flask. The reaction was stirred under argon at ambient temperature for 17 hours. The solution was diluted with diethyl ether (20 mL), resulting in the formation of a tan precipitate, which was collected and washed with ether and dried under suction to provide compound 5 as a tan solid (121.4 mg, HBr salt, 84% yield); $^1$H NMR (DMSO-d6) δ: 10.9 (s, 1 H, NH), 7.74 (d, 1H, J=3.4), 7.63 (d, 1H, J=4.88), 7.35 (d, 1H, J=8.3), 7.29 (s, 1H), 7.12 (t, 1H, J=4.88), 7.03 (s, 1H), 6.69 (d, 1H, J=8.3), 6.35 (br s, 2H), 6.35 (s, 1H).

EXAMPLE 3

The Preparation of Compound 9

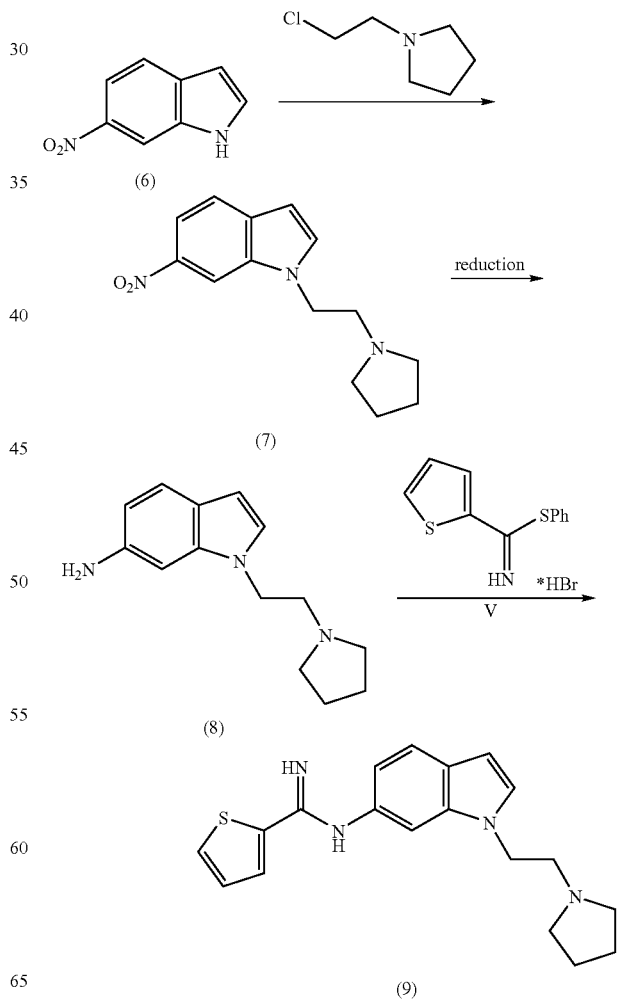

(a) Preparation of compound 7: 6-Nitroindole (compound 6, 95 mg, 0.59 mmol) and 1-(2-chloroethyl)pyrrolidine hydrochloride (100 mg, 0.59 mmol) were dissolved in DMF (3 ml) in an argon purged flask. The reaction was placed in an oil bath preheated to 50° C. and stirred under argon in the presence of potassium carbonate (244 mg, 1.77 mmol) for 24 hours. After cooling, the reaction vessel was placed in an ice bath and the reaction was diluted with ice water (10 mL) and ethyl acetate. The reaction was transferred to a separatory funnel and the organic layer collected. The organic layer was washed twice with brine, and the combined aqueous washes were re-extracted with ethyl acetate. The combined organic extracts were dried over sodium sulfate, filtered, and concentrated to afford a yellow oil. The product was taken up in methanol (2 mL) and acidified with 2N HCl (15 mL), followed by filtration to remove any insoluble material. The reaction was evaporated to dryness and the residual oil was placed under high vacuum overnight to give a yellow solid (compound 7, 63 mg, 41.2% yield); $^1$H NMR (CDCl$_3$; free base) δ: 8.37 (s, 1H), 8.02 (dd, 1H, J=2.0, 8.5), 7.64 (d, 1H, J=8.5), 7.46 (d, 1H, J=3.2), 6.59 (d, 1H, J=3.2), 4.34 (t, 2H, J=6.9), 2.92 (t, 2H, J=6.9), 2.56 (m, 4H), 1.82-1.74 (m, 4H); MS (APCI+) 260.0 (M+1).

(b) Preparation of compound 8: 6-Nitro-1-(2-pyrrolidin-1-yl-ethyl)-1H-indole (compound 7, 63 mg, 0.243 mmol) was placed in a small, argon purged flask fitted with a condenser and magnetic stirbar. Denatured absolute ethanol (5 mL) was added, followed by tin (II) chloride hydrate (202 mg, 1.07 mmol). The solution was heated to reflux in an oil bath for 1 hour. After cooling, the mixture was diluted with ethyl acetate (10 mL) and aqueous 3M sodium hydroxide solution (5 mL). The reaction was transferred to a separatory funnel and the organic layer was washed twice more with aqueous 3M sodium hydroxide solution, followed by washing with brine. The combined organic extracts were dried over sodium sulfate, filtered, and concentrated to afford a brown oil. The product was purified via silica gel column chromatography (5% 2M NH$_3$ in methanol/95% dichloromethane) to afford compound 8 as a brown oil (51.6 mg, 92.6% yield); $^1$H NMR (CDCl$_3$) δ: 7.34 (d, 1H, J=8.5), 6.93 (d, 1H, J=3.2), 6.66 (s, 1H), 6.56 (dd, 1H, J=8.5, 2.0), 4.17 (t, 2H, J=7.3), 2.90 (t, 2H, J=7.3), 2.57 (m, 4H), 1.83-1.76 (m, 4H); MS (ESI+): 230 (M+1).

(c) Preparation of compound 9: 1-(2-Pyrrolidin-1-yl-ethyl)-1H-indol-6-ylamine (compound 8, 51.6 mg, 0.225 mmol) and thiophene-2-carboximidothioic acid phenyl ester hydrobromide (68 mg, 0.225 mmol) were dissolved in methanol (4 mL) in a small, argon purged flask. The reaction was stirred under argon for 21 hours at ambient temperature. The solvent was evaporated and the product was purified via silica gel column chromatography (5% 2M NH$_3$ in Methanol/95% dichloromethane) to afford compound 9 as a brown oil (86 mg, >100% yield, note: the product is hydroscopic); $^1$H NMR (CDCl$_3$; 200 MHz) δ: 7.57 (d, 1H, J=8.5), 7.43-7.40 (m, 2H), 7.09-7.05 (m, 2H), 6.99 (s, 1H), 6.78 (dd, 1H, J=1.6, 8.1), 6.44 (d, 1H, J=3.2), 4.88 (br s, 2 H, NH2), 4.22 (t, 2H, J=7.7), 2.87 (t, 2H, J=7.7), 2.55 (br s, 4H), 1.78 (m, 4H).

EXAMPLE 4

Preparation of Compound 12

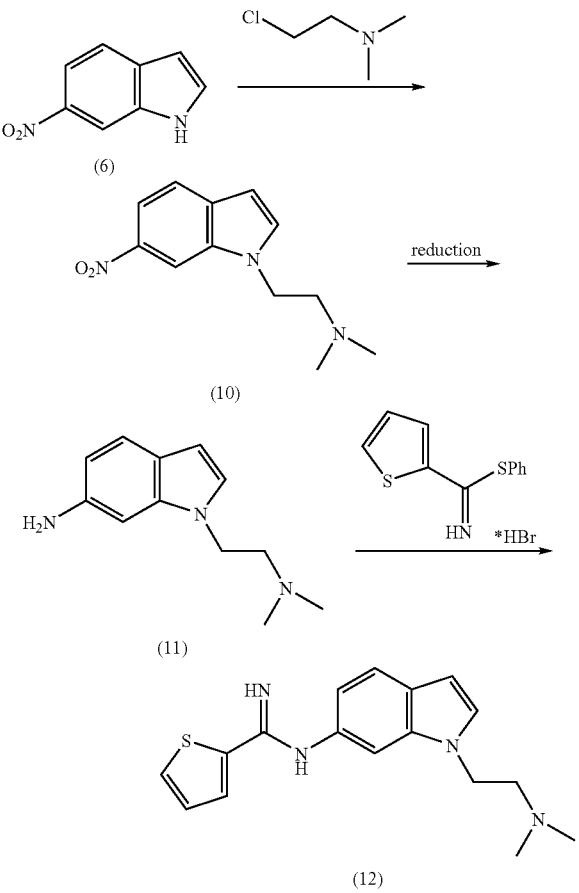

(a) Preparation of compound 10: 6-Nitroindole (compound 6, 315.3 mg, 1.94 mmol), potassium carbonate (804 mg, 5.82 mmol), and 2-dimethylaminoethyl chloride hydrochloride (363 mg, 2.52 mmol) were dissolved in DMF (4 mL) in an argon-purged flask. The reaction was placed in an oil bath preheated to 50° C. and stirred under argon for 21.5 hours. The mixture was transferred to a flask and an additional aliquot of 2-dimethylaminoethyl chloride hydrochloride was added (363 mg, 2.52 mmol). The flask was sealed and the mixture heated for an additional 24 hours. After cooling to room temperature the reaction was transferred to a separatory funnel and diluted with ethyl acetate (25 mL) and ice water (30 mL). The layers were separated and the organic layer was washed twice more with ice water (2×20 mL). The organic extracts were dried over sodium sulfate, filtered, and concentrated to afford a solid. The product was purified via silica gel column chromatography (1:1 ethyl acetate/hexanes to elute the starting material followed by 5% 2M NH$_{13}$ in methanol/ 95% dichloromethane) to afford compound 10 as a yellow oil (96.5 mg, 23% yield); $^1$H NMR (CDCl$_3$) δ: 8.35 (s, 1H), 7.99 (dd, 1H, J=1.6, 8.9), 7.64 (d, J=8.9), 7.46 (d, 1H, J=2.8), 6.59 (d, 1H, J=2.8); MS (APCI+) 234 (M+1).

(b) Preparation of compound 11: Dimethyl-[2-(6-nitro-indol-1-yl)-ethyl]-amine (compound 10, 74.3 mg, 0.339 mmol) and tin (II) chloride hydrate (267 mg, 1.41 mmol) were placed in a small, argon purged flask fitted with a condenser and magnetic stirbar. Denatured ethanol (5 mL) was added. The solution was heated to reflux in an oil bath for 3 hours. The mixture was diluted with ethyl acetate (20 mL) and aqueous 3M sodium hydroxide solution. The reaction was transferred to a separatory funnel and the organic layer collected. The organic layer was washed twice more with aqueous 3M sodium hydroxide solution (2×20 mL). The organic layer was dried over sodium sulfate, filtered, and concentrated. The product was purified via silica gel column chromatography to afford compound 11 as a black oil (33.5 mg, 48.6% yield); $^1$H NMR (CDCl$_3$) δ: 7.39 (d, 1H, J=8.5), 6.93 (d, 1H, J=3.2), 6.64 (s, 1H), 6.57 (d, 1H, J=8.5), 6.37 (d, 1H, J=3.2), 4.13 (t, 2H, J=7.3), 2.72 (t, 2H, J=7.3), 2.31 (s, 6H).

(c) Preparation of compound 12: 1-(2-Dimethylamino-ethyl)-1H-indol-6-ylamine (compound 11, 33 mg, 0.162 mmol) and thiophene-2-carboximidothioic acid phenyl ester hydrobromide (53 mg, 0.178 mmol) were dissolved in methanol in a small, argon purged flask. The reaction was stirred under argon for 27 hours at ambient temperature. The solvent was evaporated and the residue was purified via silica gel column chromatography (5% 2M NH$_3$ in methanol/95% dichloromethane) to afford a brown solid, which was recrystallized from ethyl acetate and hexanes to provide compound 12, 17.8 mg, 35.2% yield; $^1$H NMR (DMSO-d6) δ: 7.74 (d, 1H, J=3.1), 7.60 (d, 1H, J=5.0), 7.45 (d, 1H, J=8), 7.24 (d, 1H, J=2.7), 7.11 (t, 1H, J=3.9), 6.91 (s, 1H), 6.59 (d, 1H, J=8), 6.34 (m, 3H), 4.19 (t, 2H, J=6.7), 2.59 (t, 2H, J=6.7), 2.20 (s, 6H).

EXAMPLE 5

Preparation of Compound 15

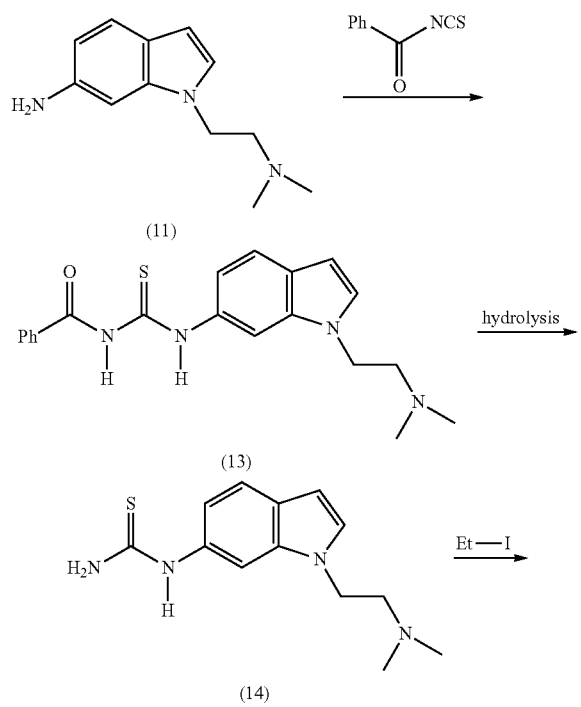

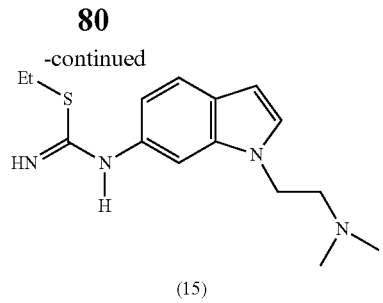

(a) Preparation of compound 13: 1-(2-Dimethylamino-ethyl)-1H-indol-6-ylamine (compound 11, 311.4 mg, 1.532 mmol) was suspended in anhydrous tetrahydrofuran (5 mL) in an argon purged flask. The addition of benzoyl isothiocyanate (0.25 mL, 1.84 mmol) caused the amine to dissolve completely. The resulting brown solution was stirred at room temperature under argon for 24 hours. The reaction was quenched with 3-(diethylenetriamino)propyl-functionalized silica gel (482 mg), stirred for 2 hours, filtered, and concentrated. The product was purified via silica gel column chromatography (3.5% 2M NH$_3$ in methanol/95% dichloromethane) to provide compound 13 (180.1 mg, 32.1% yield); $^1$H NMR (CDCl$_3$) δ: 2.31 (s, 6H), 2.70-2.77 (d, 2H), 4.20-4.27 (d, 2H), 6.49-6.50 (s, 1H), 7.19-7.26 (m, 1H), 7.54-7.63 (m, 5H), 7.89-7.93 (m, 2H), 8.14 (s, 1H).

(b) Preparation of compound 14: 1-Benzoyl-3-[1-(2-dimethylamino-ethyl)-1H-indol-6-yl]-thiourea (compound 13, 133.6 mg, 0.365 mmol) was dissolved in anhydrous tetrahydrofuran (3 mL). Aqueous 2N sodium hydroxide solution (0.37 mL) was added, the flask purged with argon, and the mixture was heated to reflux in an oil bath overnight. After cooling, the mixture was diluted with distilled water (20 mL) and ethyl acetate (50 mL) and transferred to a separatory funnel. The aqueous phase was removed and the organic phase collected. The aqueous phase was re-extracted with ethyl acetate three times (3×20 mL). The combined organic fractions were dried over sodium sulfate, filtered and concentrated to provide compound 14 (45.2 mg, 47.2% yield).

(c) Preparation of compound 15: [1-(2-Dimethylamino-ethyl)-1H-indol-6-yl]-thiourea (compound 14, 45.2 mg, 0.172 mmol) was dissolved in dry DMF (0.5 mL) and iodoethane (20 μL, 0.19 mmol) was added. The flask fitted with a plastic stopper, which was sealed with parafilm, and the reaction mixture stirred at room temperature for 26 hours. The solution was diluted with ethyl acetate (20 mL) resulting in a precipitate. Addition of 3N aqueous sodium hydroxide solution (2 mL) was followed by transfer of the mixture to a separatory funnel. The organic layer was collected and the aqueous layer was extracted with ethyl acetate (20 mL). The organic fractions were combined, dried over sodium sulfate, filtered, and condensed. The product was purified via silica gel column chromatography (5% 2M NH$_3$ in methanol/95% dichloromethane). The purified product was dissolved in methanol (2 mL) and 1M HCl (2 ml) was added. Evaporation of the solvent afforded compound 15 as a yellow oil (6.1 mg, 10.9% yield of the dihydrochloride salt).

EXAMPLE 6

Preparation of Compound 18

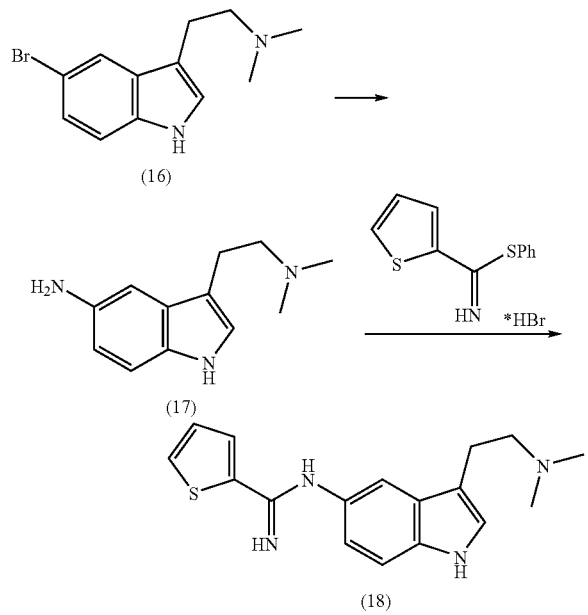

(a) Preparation of compound 17: [2-(5-Bromo-1H-indol-3-yl)-ethyl]-dimethylamine (compound 16, 372.4 mg, 1.394 mmol) (Slassi et al., U.S. Pat. No. 5,998,438) was placed in an argon purged flame dried flask fitted with a condenser and stirbar. Anhydrous tetrahydrofuran (10 mL) was added followed by tris(dibenzylideneacetone)dipalladium(0) (63.8 mg, 0.05 eq) and tributylphosphine (0.42 mL, 0.139 mmol). The mixture was stirred for 5 minutes at room temperature. Lithium bis(trimethylsilyl)amide (4.2 mL, 4.2 mmol) was added and the resultant solution refluxed for 6 hours and then stirred at room temperature for an additional 15 hours. The brown solution was quenched by adding 1M HCl (3 mL). The reaction was stirred for 15 minutes, followed by further addition of 1M HCl (3 mL) to ensure an acidic solution. The mixture was transferred into a separatory funnel and diluted with distilled water (20 mL). The aqueous phase was extracted with ethyl acetate (2×20 mL). The aqueous phase was made basic by adding aqueous 3M sodium hydroxide solution (3 mL) and extracted with ethyl acetate (3×20 mL). The combined organic extracts were dried over magnesium sulfate, filtered, and concentrated to provide compound 17 as a brownish oil (209.6 mg, 74.1% yield); $^1$H NMR (CD$_3$OD) δ: 2.52-2.55 (s, 6H), 2.86-2.89 (d, 2 H), 2.90-2.99 (d, 2H), 6.70-6.72 (d, 1H), 6.97 (s, 1H), 7.02 (s, 1H), 7.16-7.18 (d, 1H); MS: 204.0 (M+1).

(b) Preparation of compound 18: 3-(2-Dimethylaminoethyl)-1H-indol-5-ylamine (compound 17, 210 mg, 1.033 mmol) and thiophene-2-carboximidothioic acid phenyl ester hydrobromide (434 mg, 1.446 mmol) were dissolved in reagent grade ethanol (19 mL) in a small, argon purged flask. The reaction was stirred under argon for 21 hours at ambient temperature and placed in an ice-water bath to cool. Diethylether (50 mL) was added slowly while stirring vigorously to produce a light yellow precipitate. The mixture was stirred at 0° C. for 1 hour, followed by 4 hours of stirring at room temperature. The yellow precipitate was collected through vacuum filtration and washed with ether. The sample was dried under vacuum overnight at 110° C. to provide compound 18 as the hydrobromide salt (327.5 mg, 83% yield). To form the HCl salt, the hydrobromide was dissolved in water (20 mL) and transferred to a separatory funnel, where it was made basic through the addition of aqueous 2N sodium hydroxide solution (3 mL). The mixture was extracted with dichloromethane (3×20 mL). The combined organic extracts were dried over magnesium sulfate, filtered and concentrated. The residue was purified via silica gel column chromatography (5-10% 2M NH$_3$ in methanol/90-95% dichloromethane) to provide the free base as a brown oil. The oil was dissolved in methanol (5 mL) and 1M aqueous HCl (3 mL) was added. The solvent was removed and the oil dried under high vacuum to give compound 18 as the hydrochloride salt (87.5 mg, 30.2% yield); $^1$H NMR (free base, CDCl$_3$) δ: 2.31 (s, 6H), 2.57-2.65 (t, 2H), 2.85-2.92 (t, 2H), 6.79-6.85 (dd, 1H), 6.94-6.95 (d, 1H), 7.03-7.08 (t, 1H), 7.18 (s, 1H), 7.19-7.22 (d, 1H), 7.39-7.41 (t, 2H), 8.61 (s, 1H); MS: 313.0 (M+1).

EXAMPLE 7

Preparation of Compound 24

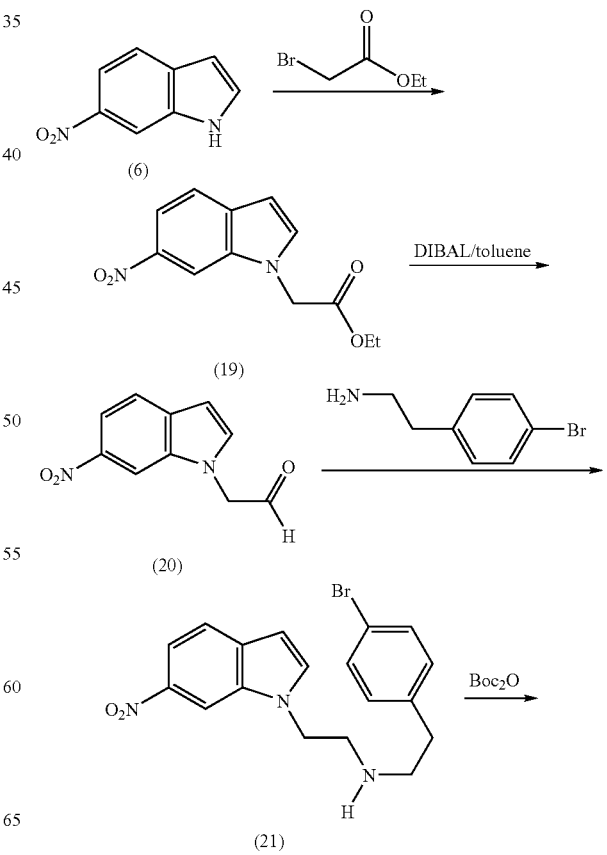

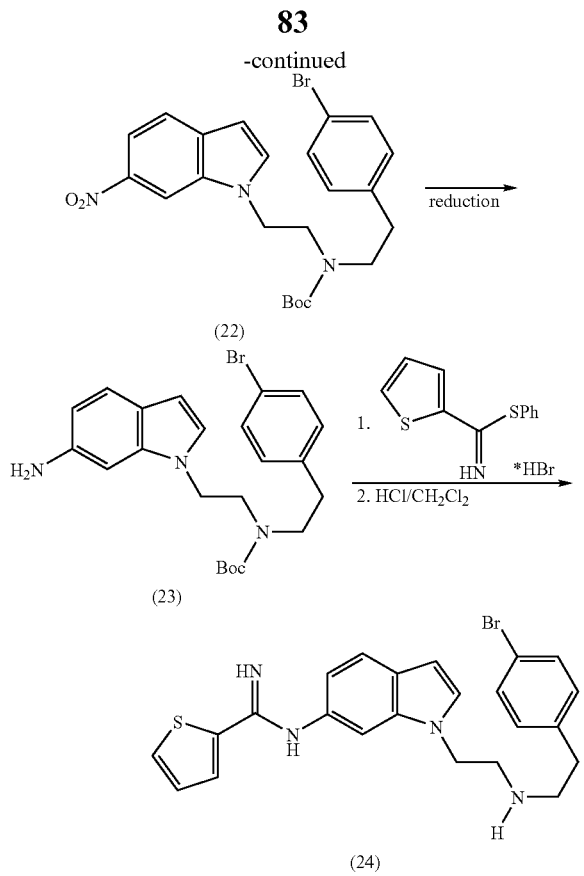

(a) Preparation of compound 19: Sodium hydride in oil (60% by wt., 1.088 g) was placed in a dry argon purged flask equipped with a septum and stirbar. DMF (Aldrich, dry sureseal™, 50 mL) was slowly added to the ice-chilled flask. After the addition of the solvent, 6-nitroindole (compound 6, 4.01 g, 24.7 mmol) was added in portions over a 10 minute period. Stirring was continued for an additional 15 minutes, followed by the addition of ethyl bromoacetate (3 mL, 27.2 mmol) via syringe. The solution was stirred at room temperature for 26 hours and then quenched with distilled water (200 mL). The yellow precipitate which formed was collected through filtration. The precipitate was washed with water (4×100 mL) and the solid dried under reduced pressure to provide compound 19 (5.94 g, 97% yield); $^1$H NMR (CDCl$_3$) δ: 8.25 (d, 1H, J=1.5), 8.05 (dd, 1H, J=1.5, 9), 7.70 (d, 1H, J=9), 7.38 (d, 1H, J=3.3), 6.68 (d, 1H, J=3.3), 4.93 (s, 2H), 4.26 (q, 2H, J=7.2), 1.30 (t, 1H, J=7.2).

(b) Preparation of compound 20: (6-Nitro-indol-1-yl)-acetic acid ethyl ester (compound 19, 503 mg, 2.026 mmol) was dissolved in dry toluene (30 mL). The mixture was cooled to −78° C. in an acetone-dry ice bath under argon and the starting material began to precipitate. A solution of DIBAL in toluene (1.5 mL, 1.1 eq) was added slowly down the side of the flask and the mixture became homogenous. Stirring was continued for 2 hours at −78° C. The reaction was quenched with methanol (1 mL) and then saturated potassium sodium tartrate (20 mL) was added. The mixture was transferred to a separatory funnel and diluted with ethyl acetate (20 mL) and water (10 mL). The organic phase was washed with potassium sodium tartrate (20 mL) and an additional 20 mL of brine and 20 mL of ethyl acetate were added to break up the emulsion. The layers were separated and the organic phase washed with brine (20 mL), dried over magnesium sulfate, filtered, and concentrated under reduced pressure to afford a yellow solid. The solid was dissolved in dichloromethane, preabsorbed onto silica gel (5 g), and purified via silica gel column chromatography, using a packed column of 10 cm (height) by 3 cm (diameter) using an eluant system of ethyl acetate and hexanes (30:70—2 column volumes, 1:1—2 column volumes) to provide compound 20, (366.5 mg, 88.6% yield); $^1$H NMR (CDCl$_3$) δ: 5.04 (s, 2H), 6.71-6.73 (d, 1H), 7.36-7.37 (d, 1H), 7.68-7.73 (d, 1H), 8.02-8.07 (d, 1H), 8.18 (s, 1H), 9.79 (s, 1H); MS (APCI negative mode): 203.2.

(c) Preparation of compound 21: (6-Nitro-indol-1-yl)-acetaldehyde (compound 20, 86.5 mg, 0.424 mmol) was placed in a small argon purged flask. A solution of 4-bromophenethylamine (127 mg, 0.636 mmol) in dry methanol (3 mL) was added. The solution was stirred for 4.5 hours, followed by the addition of sodium triacetoxyborohydride (179 mg, 0.848 mmol). The solution was stirred at room temperature for an additional 24 hours. The mixture was concentrated, the residue taken up in distilled water (5 mL) and ethyl acetate (15 mL), and the biphasic mixture transferred to a separatory funnel. The aqueous layer was washed with ethyl acetate (15 mL). The organic layers were combined, washed with brine (5 mL), dried over MgSO$_4$, filtered, and concentrated under reduced pressure. The product was dissolved in CH$_2$Cl$_2$ and absorbed onto silica, which was subsequently dried and placed at the top of a silica gel column. Elution of the column with 4:6 ethyl acetate/hexanes followed by 2.5% 2M NH$_3$ in methanol/97.5% dichloromethane provided compound 21 as a brown solid (129.9 mg, 79% yield); $^1$H NMR (CDCl$_3$) δ: 2.64-2.71 (t, 2H), 2.75-2.86 (t, 2H), 3.03-3.12 (t, 2H), 4.27-4.33 (t, 2H), 6.57-6.58 (d, 1H), 6.93-6.98 (d, 2H), 7.31-7.39 (t, 3H), 7.64-7.68 (d, 1 H), 8.00-8.05 (dd, 1H), 8.34 (s, 1H); MS: 388.0, 390.0 (M+1).

(d) Preparation of compound 22: [2-(4-Bromo-phenyl)-ethyl]-[2-(6-nitro-indol-1-yl)-ethyl]-amine (compound 21, 53.5 mg, 0.138 mmol) was dissolved in anhydrous THF (2 mL) and cooled in an ice bath. A solution of Boc$_2$O (90 mg, 0.41 mmol) in THF (2 mL) was added followed by aqueous 2N NaOH (0.41 mL). The solution was stirred at room temperature for 20.5 hours. The mixture was diluted with water (20 mL) and ethyl acetate (20 mL) and transferred to a separatory funnel. The aqueous layer was re-extracted with ethyl acetate (20 mL) and the combined organic extracts were dried over MgSO$_4$, filtered, and concentrated to afford compound 22 as a yellow oil (62.9 mg, 99% yield); $^1$H NMR (CDCl$_3$) δ: 8.28 (br s, 1H), 8.00 (d, 1H, J=2.0, 8.9), 7.65 (d, 1H, J=8.9), 7.38-7.25 (m, 3H), 7.0-6.8 (m, 2H), 6.6 (d, 1H, J=3.2), 4.36-4.24 (m, 2H), 3.44 (m, 2H), 3.20 (m, 1H), 2.91 (m, 1H), 2.68 (m, 1H), 2.47 (m, 1H), 1.40 (s, 4.5H), 1.30 (4.5H) [note: Boc conformational isomers were observed].

(e) Preparation of compound 23: [2-(4-Bromo-phenyl)-ethyl]-[2-(6-nitro-indol-1-yl)-ethyl]-carbamic acid tert-butyl ester (compound 22, 58.7 mg, 0.128 mmol) was placed in a small, argon purged flask fitted with a condenser and magnetic stirbar. Tin (II) chloride dihydrate (143.8 mg, 0.637 mmol) was added followed by absolute ethanol (10 mL). The solution was heated to reflux in an oil bath for 24 hours, followed by cooling to room temperature. The reaction was diluted with ethyl acetate (50 mL) and transferred to a separatory funnel. Aqueous 3N sodium hydroxide solution was added and the organic phase collected. The organic phase was washed with additional 3N NaOH (20 mL) followed by two brine washes (2×20 mL). The organic phase was dried over magnesium sulfate, filtered, and concentrated to afford a brown oil, which was purified using silica gel column chromatography to afford compound 23 as a light yellow oil (28.3 mg, 48% yield); H NMR (CDCl$_3$) δ: 7.40-7.37 (m, 3H), 6.95-6.7 (m, 3H), 6.6-6.5 (m, 2H), 6.35 (d, 1H, J=3.2), 4.18-3.95 (m, 2H), 3.61 (br s, 2H), 3.44-3.32 (m, 2H), 3.13-3.07 (m, 1H), 2.93-2.78 (m, 1H), 2.62 (m, 1H), 2.42 (m, 1H), 1.44 (s, 9H).

(f) Preparation of compound 24: [2-(6-Amino-indol-1-yl)-ethyl]-[2-(4-bromo-phenyl)-ethyl]-carbamic acid tert-butyl ester (compound 23, 24.5 mg, 0.053 mmol) and thiophene-2-carboximidothioic acid phenyl ester hydrobromide (24 mg, 0.080 mmol) were dissolved in ethanol (2 mL) in a small, argon purged flask. The reaction was stirred under argon for 20 hours at room temperature. Additional reagent was added (8 mg, 0.027 mmol) to ensure complete conversion of starting material and stirring was continued for 24 hours. The solvent was evaporated and the product was purified via silica gel column chromatography (2-5% 2M $NH_3$ in methanol/98-95% dichloromethane). The product was dissolved in $CH_2Cl_2$ (2 mL) and 1 M HCl in ether (2 mL) was added, followed by stirring at room temperature. The solvent was evaporated to afford compound 24 (5.7 mg, 21.4% yield).

EXAMPLE 8

Preparation of Compound 27

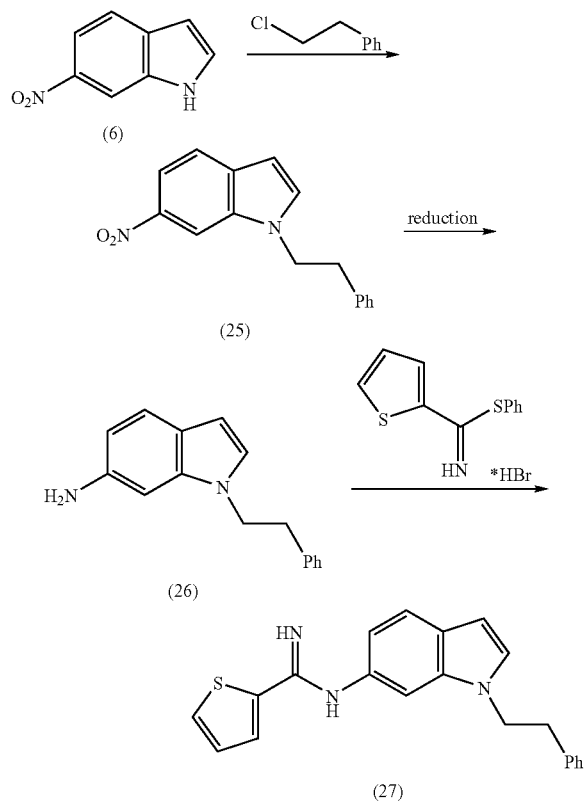

(a) Preparation of compound 25: To an ice cold solution of 6-nitroindole (250 mg, 1.54 mmol) in DMF (8 mL) was added sodium hydride (60% in oil suspension; 68 mg, 1.70 mmol) in one portion. The resulting dark red solution was stirred at this temperature for 30 minutes and then (2-chloro-ethyl)-benzene (0.60 mL, 2.31 mmol) was added. The reaction mixture was then heated to 110° C. for 5 hours. At this time, potassium carbonate (426 mg, 3.08 mmol) was added followed by additional 2-chloroethylbenzene (0.30 mL, 2.31 mmol) and the mixture heated at 110° C. for 17 hours. The mixture was then removed from the bath and diluted with water (20 mL) and extracted with ethyl acetate (100 mL). The organic layer was separated, washed with brine, and dried over magnesium sulfate, filtered, and concentrated to afford a brown residue. The residue was subjected to silica gel column chromatography using a ethyl acetate/hexanes (10%:90%) to provide compound 25 (310 mg, 76% yield); $^1$H NMR (DMSO $d_6$) δ: 8.42 (s, 1H), 7.88 (dd, 1H, J=1.5, 8.9), 7.71-7.69 (m, 2H), 7.24-7.16 (m, 5H), 6.61 (d, 1H, J=2.8), 4.60 (t, 2H, J=7.0), 3.10 (t, 2H, J=7.0).

(b) Preparation of compound 26: A solution of 6-nitro-1-phenethyl-1H-indole (compound 25, 235 mg, 0.88 mmol) and tin (II) chloride dihydrate (995 mg, 4.41 mmol) in absolute ethanol (10 mL) was heated to reflux in a small, argon purged flask fitted with a condenser and magnetic stirbar. The solution was stirred for 6 hours, and then cooled to room temperature. The reaction was diluted with aqueous 1N sodium hydroxide solution (50 mL) and transferred to a separatory funnel. Ethyl acetate (100 mL) was added and the organic phase washed with brine, dried over magnesium sulfate, and filtered through a pad of silica gel. The filtrate was concentrated and purified via silica gel column chromatography (1:1 ethyl acetate:hexanes) to provide compound 26 (180 mg, 86.6%); $^1$H NMR (DMSO $d_6$) δ: 7.32-7.17 (m, 6H), 6.90 (d, 1H, J=3), 6.63 (s, 1H), 6.42 (dd, 1H, J=1.1, 8.5), 6.14 (d, 1H, J=3), 4.19 (t, 2H, J=7.3), 3.01 (t, 2H, J=7.3); MS (APCI+): 237.0 (M+1).

(c) Preparation of compound 27: A mixture of 1-phenethyl-1H-indol-6-ylamine (compound 26, 100 mg, 0.42 mmol) and thiophene-2-carboximidothioic acid phenyl ester hydrobromide (254 mg, 0.85 mmol) was dissolved in anhydrous ethanol (4 mL) and stirred under argon for 66 hours at room temperature. The reaction mixture was concentrated, diluted with ethyl acetate (50 mL), and treated with saturated aqueous sodium bicarbonate (10 mL) and water (20 mL). The organic layer was separated, washed with brine, dried over magnesium sulfate, filtered, and concentrated to give a brown residue, which was purified via silica gel column chromatography (5% 2M $NH_3$ in methanol/95% dichloromethane). The product was dissolved in methanol (10 mL) and 1 M aqueous HCl (2 mL) was added and stirred at room temperature. The solvent was evaporated to provide compound 27 as a yellow solid (65 mg, 40.5% yield); $^1$H NMR (free base in $CD_3OD$) δ: 7.66 (d, 1H, J=3.8), 7.58 (d, 1H, J=4.8), 7.53 (d, 1H, J=8.3), 7.20-7.13 (m, 4H), 7.08-7.06 (m, 2H), 6.99 (d, 1H, J=3.0), 6.73 (dd, 1H), 6.36 (d, 1H, 3.0), 4.36 (t, 2H, J=7.0), 3.09 (t, 2H, J=7.0); MS (APCI+): 346.4 (M+1).

EXAMPLE 9

Preparation of Compounds 32 and 33

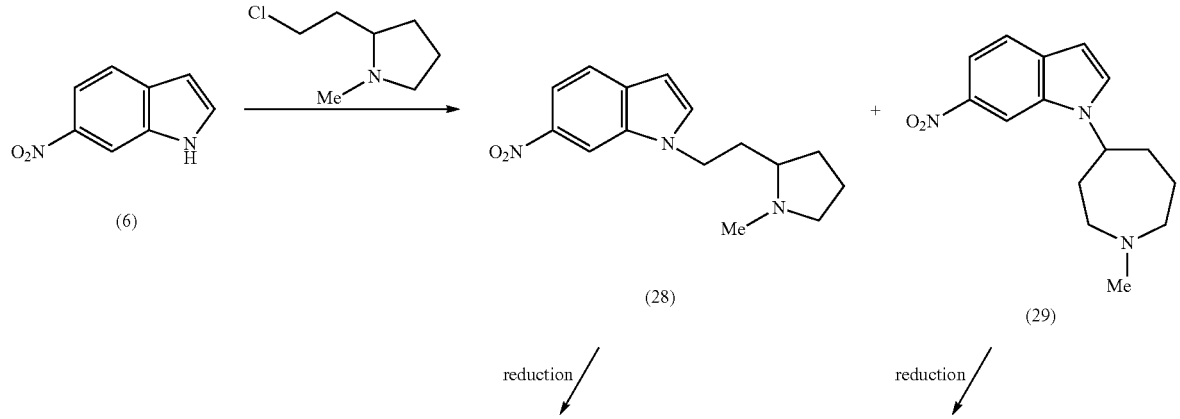

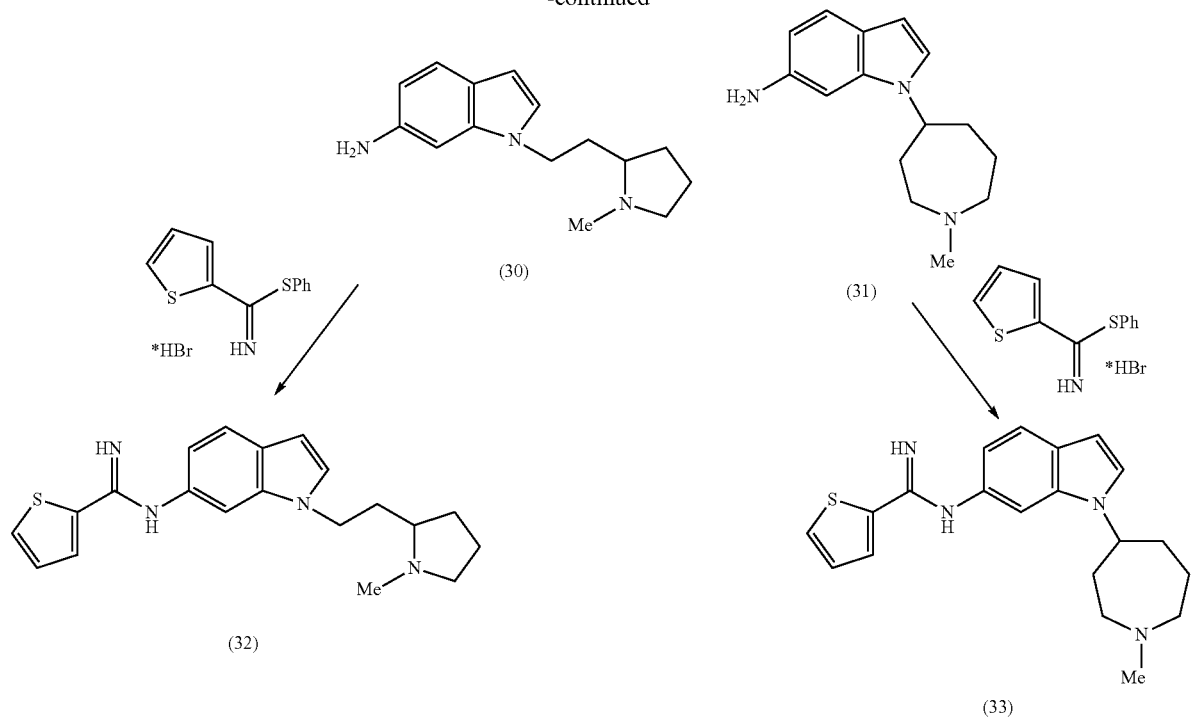

(a) Preparation of compounds 28 and 29: 6-Nitroindole (1.545 g, 9.52 mmol), 2-(2-chloroethyl)-1-methylpyrrolidine hydrochloride (2.28 g, 12.4 mmol), and powdered potassium carbonate (2.55 g, 18.5 mmol) were placed in an argon-purged two neck flask. DMF (20 mL, Aldrich sure seal™) was added and the mixture heated to 65° C. in an oil bath for 46 hours. An additional amount of the 2-(2-chloroethyl)-1-methylpyrrolidine hydrochloride (0.3 eq) was added and heating continued for an additional hour. The solution was cooled to room temperature and diluted with water (50 mL) and ethyl acetate (50 mL). The layers were separated and the aqueous phase extracted with ethyl acetate (2×50 mL). The organic extracts were combined, washed with brine (2×50 mL), and extracted with 1M HCl solution (20 mL, 15 mL, then 10 mL). The acidic fractions were combined, made basic with 1N NaOH, extracted with ethyl acetate, washed with brine, and dried over magnesium sulfate. The sample was filtered, concentrated, and the resultant yellow oil purified via chromatography on silica (5% 2M ammonia/methanol in dichloromethane) to give two compounds, compound 28 (1.087 g, 4.16 mmol, 43.7% yield); $^1$H NMR (CDCl$_3$) δ: 1.43-1.67 (m, 1H), 1.71-1.97 (m, 4H), 2.12-2.32 (m, 6H), 3.06-3.10 (m, 1H), 4.24-4.32 (m, 2H), 6.62-6.63 (d, 1H), 7.42-7.43 (d, 1H), 7.66-7.68 (d, 1H), 8.01-8.04 (dd, 1H), 8.36-8.37 (d, 1H); MS (positive): 274.0 (M+1); and a rearranged product (compound 29, brown oil, 255 mg); $^1$H NMR (CDCl$_3$) δ: 8.39 (s, 1H), 8.02 (dd, 1H, J=1.5, 6.6), 7.66 (d, 1H, J=6.6), 7.55 (d, 1H, J=2.3), 6.62 (d, 1H, J=2.3), 4.72-4.65 (heptet, 1H), 2.83-2.66 (m, 4H), 2.46 (s, 3H), 2.32-2.15 (m, 5 H), 2.03-1.95 (m, 1H), 1.90-1.80 (m, 1 H); MS (positive): 274.5 (M+1).

Resolution of enantiomers: To a solution of the racemic compound 28 (3.76 g, 13.76 mmol) in anhydrous ethanol (60 mL) was added a solution of dibenzoyl-L-tartaric acid (2.46 g, 0.5 eq) in anhydrous ethanol (60 mL) with swirling. The resulting faintly cloudy yellow solution was cooled for 24 hrs at 1° C. The yellow precipitate was collected through vacuum filtration, washed with cold ethanol and ether, and dried under high vacuum overnight to yield 4.1 g of a granular yellow solid. The filtrate was concentrated to afford a residue. Both the precipitate and the filtrate residue were converted to free base in parallel as follows: The crude enantiomer was partitioned between ethyl acetate and water and the pH adjusted to 8 with saturated sodium hydrogen carbonate. The aqueous phase was extracted twice more with ethyl acetate. The combined organics were washed with brine, dried over magnesium sulfate, filtered, and concentrated. The residue was dried under high vacuum at for 3 hours at 75° C., followed by further drying overnight at room temperature. Both enantiomers were brown oils; L-enantiomer, compound 28(−) (2.42 g from the crystalline fraction using L-dibenzoyltartaric acid): [α$_d$]$_{20}$ (methanol)=−12.950°; and D-enantiomer, compound 28(+) (filtrate residue, 1.229 g, [α$_d$]$_{20}$ (methanol)=+25.416°.

L-enantiomer enrichment: The enriched L-enantiomer (compound 28(−), 2.42 g, 6.88 mmol) was dissolved in ethanol (37 mL) and a solution of dibenzoyl-L-tartaric acid (1.232 g, 3.44 mmol) in ethanol (37 mL) added with swirling, resulting in a faintly cloudy orange-yellow solution. The solution was kept at room temperature for 1 hr and then overnight at 1° C. The solid was collected by filtration, washed with ethanol, followed by washing with ether, and the solid dried under high vacuum at room temperature for 3 hrs to yield 2.75 g of a yellow solid, mp 99-110° C. The solid was recrystallized from hot ethanol (70 mL total volume) and allowed to cool to room temperature followed by cooling to 1° C. for 44 hrs. The solid was collected by filtration, washed with cold ethanol and then cold diethylether, dried under high vacuum to yield a yellow solid (1.55 g, mp 99-110° C.). The solid was partitioned between ethyl acetate (100 mL) and water (50 mL) and the pH adjusted to 8-9 using saturated sodium bicarbonate solution. The layers were separated and the aqueous layer extracted with ethyl acetate (twice). The combined organic layers were washed with brine, dried over magnesium sulfate and concentrated to yield a brown oil. The oil was dried under high vacuum at room temperature overnight to provide compound 28(−) enantiomer (0.969 g); $[\alpha_d]_{20}$ (methanol)=−38.64°; $^1$H NMR (CDCl$_3$) δ: 1.59-1.47 (m, 1H), 2.00-1.79 (m, 4H), 2.24-2.15 (m 3H), 2.31 (s, 3H), 3.13-3.08 (m, 1H), 4.35-4.19 (m, 2H), 6.60 (d, 1H, J=3.0), 7.41 (d, 1H, J=3.2), 7.65 (d, 1H, J=8.8), 7.99 (dd, 1H, J=8.93, 1.91), 8.35 (s, 1H).

D-enantiomer enrichment: In a manner similar to the enrichment of the L-enantiomer, compound 28(+) was prepared using D-(+)-dibenzoyltartaric acid to yield 0.898 g of a brown oil; $[\alpha_d]20$ (methanol)=+40.52°; $^1$H NMR (CDCL$_3$) δ: 8.34 (d, 1H, J=1.5), 8.1 (1H, dd, J=1.8, 8.4), 7.66 (d, 1H, J=8.7), 7.40 (d, 1H, J=3), 6.60 (d, 1H, J=3), 4.37-4.19 (m, 2H), 3.12-3.07 (m, 1H), 2.31 (s, 3H), 2.28-2.15 (m, 3H), 2.02-1.70 (m, 4H), 1.59-1.51 (m, 1H).

(b) Preparation of compound 30: Racemic 1-[2-(1-Methyl-pyrrolidin-2-yl)-ethyl]-6-nitro-1H-indole (compound 28, 727 mg, 2.66 mmol) and tin (II) chloride dihydrate (2.017 g, 10.67 mmol) were placed in a small flask fitted with a condenser and magnetic stirbar. Absolute ethanol (10 mL) was added and the solution was heated to reflux in an oil bath for 24 hours, followed by cooling to room temperature. The mixture was diluted with ethyl acetate (50 mL) and transferred to a separatory funnel. An aqueous 3N sodium hydroxide solution (50 mL) was added and the organic fraction collected. Precipitate present in the funnel was removed with the aqueous layer. The organic phase was washed twice with additional 3N NaOH (20 mL), followed by two brine washes (2×20 mL). The organic phase was dried over sodium sulfate, filtered, and concentrated to give a black oil, which was purified via silica gel column chromatography (5% 2M NH$_3$ in Methanol/95% dichloromethane) to afford racemic compound 30 (472.3 mg, 73% yield) as a brownish oil; $^1$H NMR (CDCl$_3$) δ: 1.41-1.59 (m, 1H), 1.71-1.79 (m, 3H), 1.86-1.98 (m, 1H), 2.05-2.16 (m, 3H), 2.29 (s, 3H), 3.03-3.06 (t, 1H), 3.63 (bs, 2H, —NH$_2$), 4.00-4.08 (m, 2H), 6.35-6.36 (d, 1H), 6.54-6.55 (d, 1H) 6.56-6.57 (d, 1H), 6.90-6.91 (d, 1H), 7.38-7.40 (d, 1H).

Preparation of compound 30(−): To an argon purged flask containing the enantiomerically resolved 1-[2-(1-methyl-pyrrolidin-2-yl)-ethyl]-6-nitro-1H-indole (compound 28(−), 969 mg, 3.545 mmol) and a magnetic stir bar was added anhydrous ethanol (75 mL). While stirring, palladium on carbon (10%, 283 mg, 0.266 mmol) was added quickly in portions and the atmosphere evacuated and replaced with hydrogen using a balloon/aspirator system. The system was evacuated a total of 3 times to ensure that no residual oxygen remained. The mixture was stirred at room temperature for 3 hrs. The hydrogen atmosphere replaced with argon via a purge/fill operation, the mixture filtered through celite, and the solid washed with absolute ethanol (25 mL). The collection flask was sealed and purged with argon and used crude in the next reaction for the synthesis of compound 32(−).

Preparation of compound 30(+): In a manner similar to the preparation of compound 30(−) from compound 28(−), compound 28(+) (870 mg, 3.183 mmol) was used to prepare compound 30(+). After filtration through celite, the crude solution of compound 30(+) in ethanol was used for the preparation of optically pure compound 32(+).

Preparation of compound 31: In a manner similar to the preparation of compound 30 from compound 28, compound 31 was synthesized from compound 29 (190 mg, 0.695 mmol). After filtration through celite, the crude solution of compound 31 was used directly in the preparation of compound 33.

(c) Preparation of racemic compound 32: 1-[2-(1-Methyl-pyrrolidin-2-yl)-ethyl]-1H-indol-6-ylamine (compound 30, 47.9 mg, 0.197 mmol) was dissolved in ethanol (3 mL) in a small, argon purged flask. Thiophene-2-carboximidothioic acid phenyl ester hydrobromide (76.9 mg, 0.256 mmol) was added and the solution was stirred at room temperature for 48 hours. The solvent was evaporated and the product was purified via silica gel column chromatography (5% 2M NH$_3$ in methanol/95% dichloromethane) to afford the free base of compound 32 as a yellow oil (52.5 mg, 75% yield). The free base was dissolved in methanol (2 mL), treated with 1M HCl, followed by evaporation to dryness to provide the HCl salt of compound 32 as a reddish (salmon) coloured solid (54.8, 95.1% yield); $^1$H NMR (free base, CDCl$_3$) δ: 1.67-1.78 (m, 1H), 1.93-1.98 (m, 2H), 2.04-2.19 (m, 4H), 2.26 (s, 3H), 3.00-3.05 (t, 1H), 4.05-4.12 (m, 2H), 4.86 (s, 2H), 6.43-6.44 (d, 1H), 6.76-6.78 (d, 1H), 6.96 (s, 1H), 7.02-7.03 (d, 1H), 7.05-7.07 (t, 1H), 7.40-7.41 (d, 2H), 7.52-7.57 (d, 1H); MS (positive): 353.2 (M+1).

Preparation of compound 32(−): To an argon purged flask containing crude enantiomerically-resolved 1-[2-(1-methyl-pyrrolidin-2-yl)-ethyl]-1H-indol-6-ylamine (compound 30(−), 3.545 mmol) in anhydrous ethanol (100 mL) was added a magnetic stirbar, followed by the addition of thiophene-2-carboximidothioic acid methyl ester hydroiodide (1.213 g, 1.2 eq). After stirring at room temperature for 24 hours, additional thiophene reagent (0.202 g, 0.2 eq) was added. After an additional 18 hours, the reaction was concentrated and the residue partitioned between ethyl acetate (100 mL), water (50 mL), and saturated sodium hydrogen carbonate (50 mL). The aqueous layer was checked and found to be a pH of 8. The aqueous layer was extracted twice more with ethyl acetate and the combined organics were washed successively with saturated sodium hydrogen carbonate and brine, filtered, and concentrated to yield an orange-brown oil (1.56 g). The crude product was purified via dry column chromatography (5% 2M NH$_3$ in methanol/95% dichloromethane) with 17×100 mL aliquots to yield compound 32(−) as a yellow oil (0.63 g). The HCl salt was formed by dissolving the product in anhydrous dichloromethane (10 mL) and adding 1M HCl in ether (5.36 mL, 3 eq) under argon; $^1$H NMR (free base, CDCl$_3$) δ: 1.50-1.52 (m, 1H), 1.67-1.82 (m, 4H), 1.92-1.95 (m, 1H), 2.07-2.15 (m, 3H), 2.28 (s, 3H), 3.06 (t, 1H), 4.02-4.12 (m, 2H), 4.87 (s, 2H), 6.45-6.46 (d, 1H), 6.78-6.81 (d, 1H), 6.98 (s, 1H), 7.04-7.05 (d, 2H), 7.43-7.45 (d, 2H), 7.57-7.59 (d, 1H); MS (positive): 353.5 (M+1).

Preparation of compound 32(+): Similar to the preparation of compound 32(−) from compound 30(−), compound 30(+) was used to prepare compound 32(+) as a yellow oil (0.715 g) which was converted to a hydrochloride salt with excess 1M HCl in ether; $^1$H NMR (free base, CDCl$_3$) δ: 1.49-1.57 (m, 1H), 1.71-1.82 (m, 4H), 1.89-1.95 (m, 1H), 2.07-2.15 (m, 3H), 2.29 (s, 3 H), 3.04-3.06 (t, 1H), 4.07-4.15 (m, 1H), 4.87 (s, 2H), 6.45-6.46 (d, 1H), 6.78-6.81 (d, 1H), 6.98 (s, 1H), 7.04-7.09 (m, 2 H), 7.43-7.45 (d, 2H), 7.57-7.59 (d, 1H); MS (positive): 353.5 (M+1).

Preparation of compound 33: In a manner similar to the preparation of compound 32 from compound 30, compound 31 was used to prepare the free base of compound 33 as a pale pink solid (107 mg, 0.304 mmol). The hydrochloride salt was prepared by dissolving the crude solid (107 mg) in anhydrous dichloromethane (5 mL) followed by the addition of 1M HCl in ether (3 eq. 0.91 mL). The pale green/beige solid which precipitated immediately was collected and washed with a small amount of dichloromethane and dried under high vacuum to yield the hydrochloride salt as a pale brown solid (92 mg as the dihydrochloride); $^1$H NMR(HCl salt, DMSO-d6) δ: 11.55 (br s, 1H), 11.18 (br s, 1H), 9.74 (br s, 1H), 8.74 (br s, 1H), 8.18 (m, 2H), 7.77-7.70 (m, 3H), 7.40 (3 line m, 1H), 7.06 (d, 1H, J=7.8 Hz), 6.62 (s, 1H), 4.94-4.77 (m, 1H), 3.48-3.17 (m, 4H), 2.78 (s, 3H), 2.26-1.95 (m, 6H); MS (pos): 353.5.

EXAMPLE 10

Preparation of Compound 37

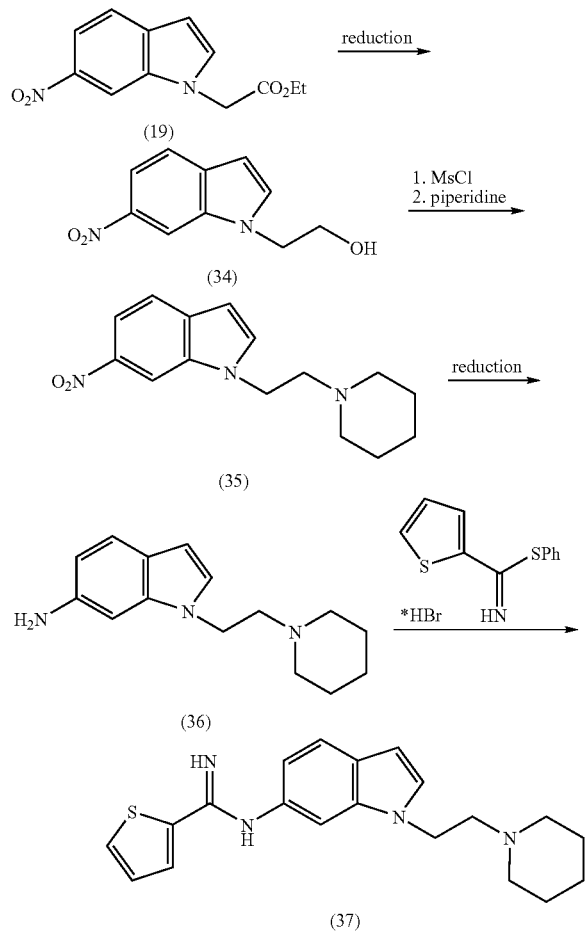

(a) Preparation of compound 34: (6-Nitro-indol-1-yl)-acetic acid ethyl ester (compound 19, 3.06 g, 12.3 mmol) was dissolved in THF (60 mL, Aldrich Sure Seal™). The solution was cooled to −78° C. in an acetone-dry ice bath under argon and a solution of DIBAL in toluene (18.9 mL, 2.3 eq) was added slowly down the side of the flask. The reaction was stirred for 44.5 hrs at room temperature, after which the brown solution was quenched with 3N sodium hydroxide (20 mL). The mixture was transferred to a separatory funnel and diluted with ethyl acetate (50 mL) and water (20 mL). The layers were shaken, separated, and the aqueous phase extracted with ethyl acetate (20 mL). The combined organics were washed with brine (20 mL), dried over magnesium sulfate, treated with charcoal, filtered, and concentrated to afford a brownish-yellow solid (2.10 g). The crude product was dissolved in ethyl acetate, pre-absorbed onto silica gel, and purified via silica gel column chromatography (3:7 ethyl acetate and hexanes) to provide compound 34 as a yellow solid (1.18 g, 61% yield).

(b) Preparation of compound 35: 2-(6-Nitro-indol-1-yl)-ethanol (compound 34, 1.1791 g, 5.72 mmol) was placed in a small argon purged flask and dissolved in dry THF (20 mL). Triethylamine (1.6 mL, 1.5 eq) was added, followed by the addition of methanesulfonyl chloride (0.63 mL, 1.43 eq). A precipitate began forming immediately. The mixture was stirred at room temperature under argon for 48 hrs. The reaction was concentrated to afford a yellow solid. DMF (15 mL) and piperidine (10 mL) were added and the solution was heated to 110° C. and stirred for 21 hrs. The dark yellow solution was cooled to room temperature, transferred to a separatory funnel, and diluted with water (75 mL) and ethyl acetate (25 mL). The aqueous layer was extracted with ethyl acetate (3×25 mL) and the combined organic layers were washed with brine (3×25 mL). The organic phase was then treated with 1M hydrochloric acid (50 mL), resulting in a yellow precipitate. The precipitate was removed through filtration and the filtrate treated with additional hydrochloric acid (25 mL). The layers were separated after shaking, and the aqueous phase made basic with 10% sodium hydroxide solution. The cloudy mixture was extracted with ethyl acetate (3×20 mL). The combined organics were washed with brine, dried over MgSO$_4$, filtered, and concentrated. The product was purified via silica gel column chromatography (2.5% 2M NH$_3$ in methanol/97.5% dichloromethane), followed by recrystallization from ethanol to give compound 35 as a yellow solid (1.029 g, 66% yield); $^1$H NMR (CDCl$_3$) δ: 8.37 (s, 1H), 7.98 (dd, 1H, J=1.67, 8.8), 7.62 (d, 1H, J=8.8), 7.44 (d, 1H, J=3.3), 7.25 (s, 1H), 6.56 (d, 1H, J=3.0), 4.28 (t, 2H, J=6.7), 2.70 (t, 2H, J=6.7), 2.43 (t, 4H, J=4.9), 1.59-1.55 (m, 4H), 1.45-1.40 (m, 2H).

(c) Preparation of compound 36: 6-Nitro-1-(2-piperidin-1-yl-ethyl)-1H-indole (compound 35, 1.029 g, 3.76 mmol) and 10% palladium on carbon (111 mg) were placed in a large, argon purged flask. Absolute ethanol (20 mL) was added, and the atmosphere was replaced with hydrogen using a balloon/aspirator system. The mixture was stirred at room temperature for 18.5 hrs. The solution was treated with charcoal and filtered through celite (2 cm pad) and washed through with absolute ethanol (30 mL). The flask was sealed and purged with argon and used crude in the next reaction.

(d) Preparation of compound 37: To the crude solution of 1-(1-(2-piperidin-1-yl-ethyl)-1H-indol-6-ylamine (compound 36, 3.76 mmol) in absolute ethanol (50 mL) was added thiophene-2-carboximidothioic acid phenyl ester hydrobromide (1.185 g, 1.05 eq). The reaction was stirred under argon for 24 hours at ambient temperature. An additional 0.1 eq of the thiophene reagent was added and the reaction stirred for a further 24 hours. The solvent was evaporated and the oil diluted with a small amount of ethanol (<5 mL) followed by diethyl ether to afford a yellow precipitate. The solid was isolated through filtration and washed with ether. The precipitate was dried under suction followed by additional drying under high vacuum to give compound 37 as the HBr salt (yield 983.2 mg). The free base was obtained by dissolving the solid in water (35 mL) and adding 1N sodium hydroxide (10 mL). The product was extracted into ethyl acetate (2×30 mL). The combined organics were dried over MgSO$_4$, filtered, and concentrated to afford compound 37 as a light yellow solid (708 mg); $^1$H NMR (CDCl$_3$) δ: 7.57 (d, 1H J=8.3), 7.43 (m, 2H), 7.09 (m, 2H), 6.99 (s, 1H), 6.79 (d, 1H, J=7.6), 6.44 (d, 1H, J=3.0), 4.87 (br s, 2H), 4.20, (t, 2H, J=7.5), 2.71 (t, 2H, J=7.6), 2.45 (br s, 4H), 1.62-1.58 (m, 6H) 1.46-1.40 (m, 2H).

EXAMPLE 11

Preparation of N-(3-(1-methyl-1,2,3,6-tetrahydropyridin-4-yl)-1H-indol-5-yl)thiophene-2-carboximidamide (42) and N-(3-(1-methylpiperidin-4-yl)-1H-indol-5-yl)thiophene-2-carboximidamide (43)

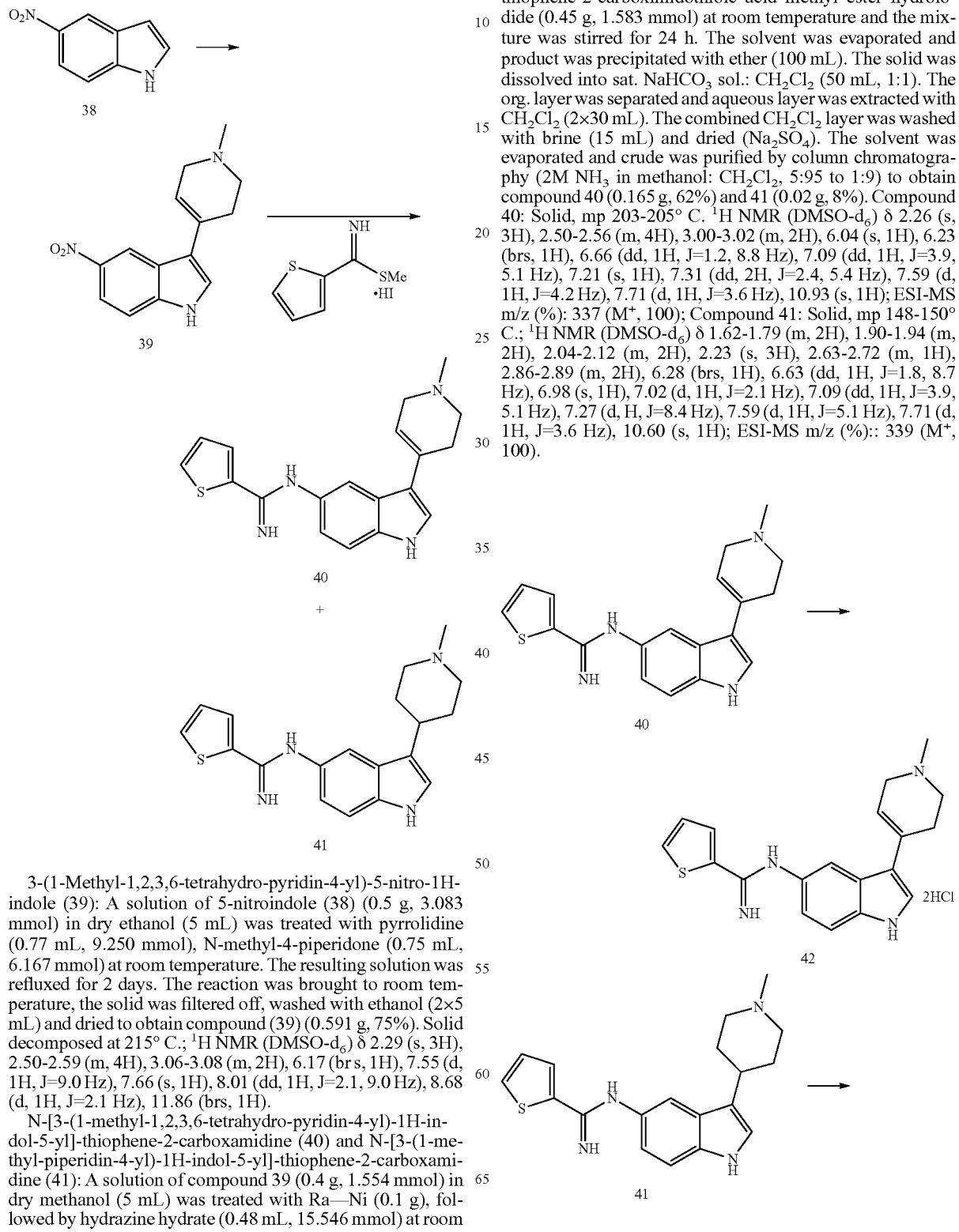

3-(1-Methyl-1,2,3,6-tetrahydro-pyridin-4-yl)-5-nitro-1H-indole (39): A solution of 5-nitroindole (38) (0.5 g, 3.083 mmol) in dry ethanol (5 mL) was treated with pyrrolidine (0.77 mL, 9.250 mmol), N-methyl-4-piperidone (0.75 mL, 6.167 mmol) at room temperature. The resulting solution was refluxed for 2 days. The reaction was brought to room temperature, the solid was filtered off, washed with ethanol (2×5 mL) and dried to obtain compound (39) (0.591 g, 75%). Solid decomposed at 215° C.; $^1$H NMR (DMSO-d$_6$) δ 2.29 (s, 3H), 2.50-2.59 (m, 4H), 3.06-3.08 (m, 2H), 6.17 (br s, 1H), 7.55 (d, 1H, J=9.0 Hz), 7.66 (s, 1H), 8.01 (dd, 1H, J=2.1, 9.0 Hz), 8.68 (d, 1H, J=2.1 Hz), 11.86 (brs, 1H).

N-[3-(1-methyl-1,2,3,6-tetrahydro-pyridin-4-yl)-1H-indol-5-yl]-thiophene-2-carboxamidine (40) and N-[3-(1-methyl-piperidin-4-yl)-1H-indol-5-yl]-thiophene-2-carboxamidine (41): A solution of compound 39 (0.4 g, 1.554 mmol) in dry methanol (5 mL) was treated with Ra—Ni (0.1 g), followed by hydrazine hydrate (0.48 mL, 15.546 mmol) at room temperature and the resulting solution was stirred at 65° C. for 3 h. The reaction was brought to room temperature, solid was filtered off though celite bed and washed with methanol: CH$_2$Cl$_2$ (1:1, 2×10 mL). The combined organic layer was evaporated and crude was purified by column chromatography (2 M NH$_3$ in methanol: CH$_2$Cl$_2$, 1:9) to obtain the free amine (0.35 g, quantitative) as a foam. A solution of the amine (0.18 g, 0.791 mmol) in dry ethanol (10 mL) was treated with thiophene-2-carboximidothioic acid methyl ester hydroiodide (0.45 g, 1.583 mmol) at room temperature and the mixture was stirred for 24 h. The solvent was evaporated and product was precipitated with ether (100 mL). The solid was dissolved into sat. NaHCO$_3$ sol.: CH$_2$Cl$_2$ (50 mL, 1:1). The org. layer was separated and aqueous layer was extracted with CH$_2$Cl$_2$ (2×30 mL). The combined CH$_2$Cl$_2$ layer was washed with brine (15 mL) and dried (Na$_2$SO$_4$). The solvent was evaporated and crude was purified by column chromatography (2M NH$_3$ in methanol: CH$_2$Cl$_2$, 5:95 to 1:9) to obtain compound 40 (0.165 g, 62%) and 41 (0.02 g, 8%). Compound 40: Solid, mp 203-205° C. $^1$H NMR (DMSO-d$_6$) δ 2.26 (s, 3H), 2.50-2.56 (m, 4H), 3.00-3.02 (m, 2H), 6.04 (s, 1H), 6.23 (brs, 1H), 6.66 (dd, 1H, J=1.2, 8.8 Hz), 7.09 (dd, 1H, J=3.9, 5.1 Hz), 7.21 (s, 1H), 7.31 (dd, 2H, J=2.4, 5.4 Hz), 7.59 (d, 1H, J=4.2 Hz), 7.71 (d, 1H, J=3.6 Hz), 10.93 (s, 1H); ESI-MS m/z (%): 337 (M$^+$, 100); Compound 41: Solid, mp 148-150° C.; $^1$H NMR (DMSO-d$_6$) δ 1.62-1.79 (m, 2H), 1.90-1.94 (m, 2H), 2.04-2.12 (m, 2H), 2.23 (s, 3H), 2.63-2.72 (m, 1H), 2.86-2.89 (m, 2H), 6.28 (brs, 1H), 6.63 (dd, 1H, J=1.8, 8.7 Hz), 6.98 (s, 1H), 7.02 (d, 1H, J=2.1 Hz), 7.09 (dd, 1H, J=3.9, 5.1 Hz), 7.27 (d, H, J=8.4 Hz), 7.59 (d, 1H, J=5.1 Hz), 7.71 (d, 1H, J=3.6 Hz), 10.60 (s, 1H); ESI-MS m/z (%):: 339 (M$^+$, 100).

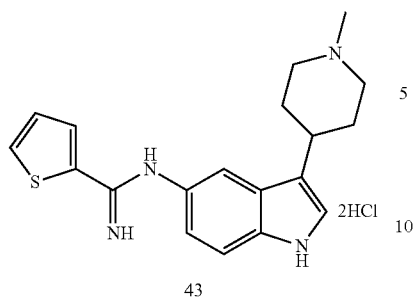

Dihydrochloride salt of N-[3-(1-methyl-1,2,3,6-tetrahydro-pyridin-4-yl)-1H-indol-5-yl]-thiophene-2-carboxamidine (42): A solution of compound 40 (0.155 g, 0.460 mmol) in ethanol (5 mL) was treated with 1 N HCl in ether (1.5 mL) at room temperature and stirred for 1 h. The product was recrystallized from ethanol/ether to obtain compound 42 (0.13 g, 69%) as a solid. mp 215-218° C.

Dihydrochloride salt of N-[3-(1-methyl-piperidin-4-yl)-1H-indol-5-yl]-thiophene-2-carboxamidine (43): A solution of compound 41 (0.015 g, 0.044 mmol) in ethanol (3 mL) was treated with 1 N HCl in ether (0.13 mL) at room temperature and stirred for 1 h. The product was recrystallized from ethanol/ether to obtain compound 43 (0.012 g, 67%) as a foam.

EXAMPLE 12

N-(3-(1-methyl-1,2,3,6-tetrahydropyridin-4-yl)-1H-indol-5-yl)furan-2-carboximidamide (46) and N-(3-(1-methylpiperidin-4-yl)-1H-indol-5-yl)furan-2-carboximidamide (47)

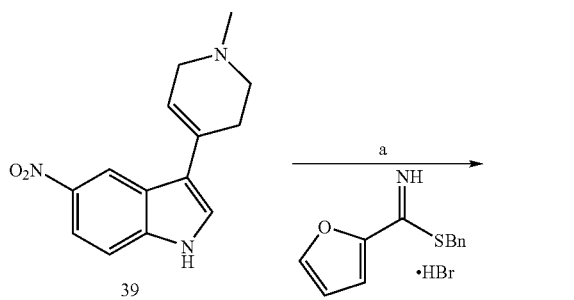

3-(1-Methyl-1,2,3,6-tetrahydro-pyridin-4-yl)-5-nitro-1H-indole (39): Please see Example 11 for experimental details.

N-[3-(1-Methyl-1,2,3,6-tetrahydro-pyridin-4-yl)-1H-indol-5-yl]-furan-2-carboxamidine (44) and N-[3-(1-methyl-piperidin-4-yl)-1H-indol-5-yl]-furan-2-carboxamidine (45): A solution of compound 39 (0.4 g, 1.554 mmol) in dry methanol (5 mL) was treated with Ra—Ni (0.1 g), followed by hydrazine hydrate (0.48 mL, 15.546 mmol) at room temperature and the resulting solution was stirred at 65° C. for 3 h. The reaction was brought to room temperature, solid was filtered off though celite bed and washed with methanol: $CH_2Cl_2$ (1:1, 2×10 mL). The combined organic layer was evaporated and crude was purified by column chromatography (2 M $NH_3$ in methanol: $CH_2Cl_2$, 1:9) to obtain the free amine (0.35 g, quantitative) as a solid. A solution of the amine (0.17 g, 0.747 mmol) in dry ethanol (10 mL) was treated with benzyl furan-2-carbimidothioate hydrobromide (0.44 g, 1.495 mmol) at room temperature and stirred for 24 h. The solvent was evaporated and product was precipitated with ether (100 mL). The solid was dissolved into sat. $NaHCO_3$ sol.: $CH_2Cl_2$ (50 mL, 1:1). The org. layer was separated and aqueous layer was extracted with $CH_2Cl_2$ (2×30 mL). The combined $CH_2Cl_2$ layer was washed with brine (15 mL) and dried ($Na_2SO_4$). The solvent was evaporated and crude was purified by column chromatography (2M $NH_3$ in methanol: $CH_2Cl_2$, 5:95 to 1:9) to obtain compound 44 (0.16 g, 67%) and 45 (0.02 g, 8%). Compound 44: Solid, mp 161-163° C.; $^1$H NMR (DMSO-$d_6$) δ 2.28 (s, 3H), 2.50-2.57 (m, 4H), 3.03-3.05 (m, 2H), 6.04 (s, 1H), 6.63 (s, 1H), 6.73 (d, 1H, J=8.1 Hz), 7.15 (s, 1H), 7.31-7.34 (m, 3H), 7.82 (s, 1H), 10.99 (s, 1H); ESI-MS i/z (%): 321 (M, 100). Compound 45: Solid, mp 85-87° C.; $^1$H NMR (DMSO-$d_6$) δ 1.81-1.90 (m, 2H), 1.99-2.03 (m, 2H), 2.40-2.60 (m, 5H), 2.81-2.88 (m, 1H), 3.12-3.15 (m, 2H), 6.81 (s, 1H), 6.93 (d, 1H, J=8.4 Hz), 7.20 (s, 1H), 7.41-7.47 (m, 3H), 7.58 (brs, 1H), 8.09 (s, 1H), 11.01 (s, 1H); ESI-MS m/z (%): 323 (M+, 100).

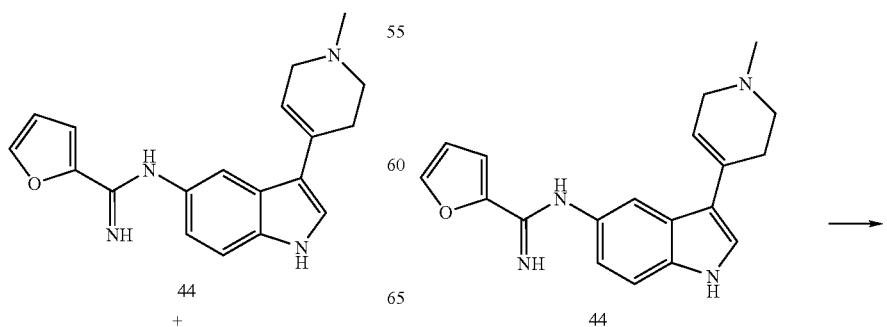

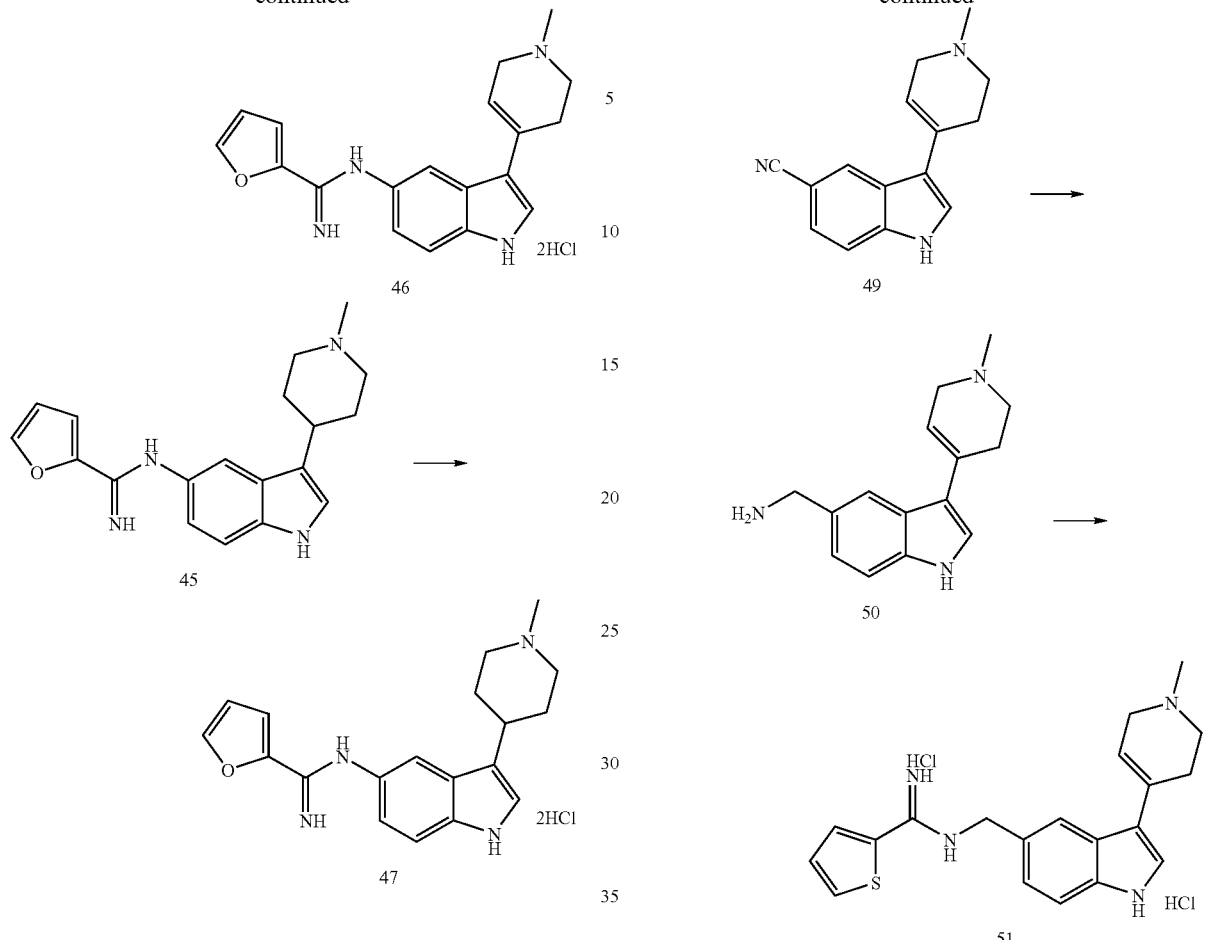

Dihydrochloride salt of N-[3-(1-methyl-1,2,3,6-tetrahydro-pyridin-4-yl)-1H-indol-5-yl]-furan-2-carboxamidine (46): A solution of compound 44 (0.145 g, 0.452 mmol) in ethanol (5 mL) was treated with 1 N HCl in ether (1.35 mL) at room temperature and stirred for 1 h. The product was recrystallized from ethanol/ether to obtain compound 46 (0.135 g, 76%) as a solid. mp 212-215° C.

Dihydrochloride salt of N-[3-(1-methyl-piperidin-4-yl)-1H-indol-5-yl]-furan-2-carboxamidine (47):A solution of compound 45 (0.015 g, 0.046 mmol) in ethanol (2 mL) was treated with 1 N HCl in ether (0.14 mL) at room temperature and stirred for 1 h. The product was recrystallized from ethanol/ether to obtain compound 47 (0.01 g, 56%) as a foam.

EXAMPLE 13

N-((3-(1-methyl-1,2,3,6-tetrahydropyridin-4-yl)-1H-indol-5-yl)methyl)thiophene-2-carboximidamide (51)

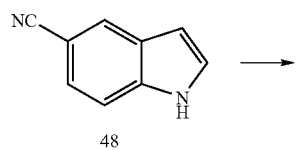

3-(1-Methyl-1,2,3,6-tetrahydropyridin-4-yl)-1H-indole-5-carbonitrile (49): To an argon-purged round bottom flask fitted with a magnetic stirbar containing an orange solution of 5-cyanoindole (48) (250 mg, 1.76 mmol) dissolved in absolute ethanol (10 mL) were added 1-methyl-4-piperidone (0.43 mL, 3.50 mmol) and pyrrolidine (0.44 mL, 5.27 mmol). The reaction vessel was fitted with a condenser and transferred to an oil bath preheated to 80° C. The reaction was stirred at this temperature for 44 hrs. As no starting material remained (TLC 5% 2M $NH_3$ in methanol/95% $CH_2Cl_2$) the reaction was cooled to room temperature followed by additional cooling in the fridge. As no precipitate formed, the reaction was concentrated under reduced pressure to afford an orange oil. The oil was redissolved in ethanol (20 mL) and the solvent removed under reduced pressure. This was repeated once more, and then the final residue was treated with ethanol and left in the fridge for 2 hrs. The precipitate which formed was collected by vacuum filtration and washed with hexanes (205 mg of pale yellow solid, compound 49, 48.7%) $^1$H NMR (DMSO) δ 11.90 (br s, NH), 8.51 (s, 1H), 7.80 (s, 1H), 7.77-7.74 (d, J=8.7 Hz, 1H), 7.68-7.65 (d, J=8.1 Hz, 1H), 6.41 (s, 1H), 3.53 (s, 2H), 3.27-3.26 (d, J=2.4 Hz, 2H), 2.79-2.77 (d, J=4.5 Hz, 2H), 2.72-2.71 (d, J=1.5 Hz, 3H).

(3-(1-Methyl-1,2,3,6-tetrahydropyridin-4-yl)-1H-indol-5-yl)methanamine (50): To an argon purged round bottom flask fitted with a condenser and magnetic stirbar containing 49 (105 mg, 0.442 mmol) was added lithium aluminum hydride (34 mg, 0.896 mmol) followed by absolute THF (5 mL). A small amount of gas was produced. Once no more bubbling occurred, the reaction was transferred to an oil bath heated to 75° C. The reaction was stirred at this temperature for 18 hrs. The reaction was then cooled to room temperature. The reaction was quenched with water (0.1 mL), 3N NaOH (0.1 mL) and water (0.3 mL) sequentially, followed by filtration through a celite plug. The plug was washed with THF and the filtrate concentrated to afford a yellow oil, compound 50 (106 mg, 99%). $^1$H NMR (DMSO) δ 10.95 (br s, NH), 7.74 (s, 1H), 7.32-7.31 (d, J=2.4 Hz, 1H), 7.30-7.27 (d, J=8.4 Hz, 1H), 7.08-7.05 (d, J=8.1 Hz, 1H), 6.14 (s, 1H), 3.77 (s, 2H), 3.29 (s, 2H), 3.06-3.05 (d, J=2.7 Hz, 2H), 2.57-2.56 (d, J=4.5 Hz, 2H), 2.51-2.50 (d, J=1.2 Hz, 2H), 2.29 (s, 3H), 1.75 (br s, 2NH).

N-((3-(1-methyl-1,2,3,6-tetrahydropyridin-4-yl)-1H-indol-5-yl)methyl)thiophene-2-carboximidamide dihydrochloride (51): An Ar purged 20 mL reaction vial fitted with a magnetic stirbar containing a solution of compound 50 (58 mg, 2.55 mmol) and thiophene-2-carboximidothioic acid methyl ester hydroiodide (145 mg, 5.08 mmol) in absolute ethanol (5 mL) was stirred at room temperature for 41 hrs. As all starting material had reacted (20% 2M NH$_3$ in methanol/ 80% CH$_2$Cl$_2$) the reaction was concentrated to dryness under reduced pressure. The residue was partitioned between ethyl acetate (10 mL) and 3N NaOH (10 mL) followed by transfer to a separatory funnel. The aqueous phase was extracted twice more with ethyl acetate (2×10 mL). The combined organics were washed with brine, dried over MgSO4, filtered and concentrated to afford a pale yellow solid (35 mg). The product was absorbed onto silica gel and purified by column chromatography (25-50% 2M NH$_3$ in methanol/CH$_2$Cl$_2$) to afford a pale yellow solid (23 mg) The product was taken up in methanol and treated with 1M HCl in ether. The reaction was stirred for 25 minutes and then concentrated to dryness under reduced pressure. The residue was taken up in ethanol (3 mL) and diluted with ether (35 mL) to afford a precipitate that was collected by filtration. The precipitate was washed with ether (2×10 mL) and dried under high vacuum. Yield: 17 mg of pale yellow solid, compound 51 (21%). $^1$H NMR (free base in DMSO-d$_6$) δ 11.04 (br s, NH), 7.86 (s, 1H), 7.68-7.67 (d, J=3.9 Hz, 1H), 7.64 (s, 1H), 7.36-7.35 (d, J=2.7 Hz, 1H), 7.32 (s, 1H), 7.15-7.14 (d, J=1.2, 1H), 7.13-7.11 (t, J=4.2, 1H), 6.13 (s, 1H), 4.47 (s, 2H), 3.31 (s, 2H), 3.05-3.04 (d, J=2.7 Hz, 2H), 2.58-2.56 (d, J=4.5 Hz, 2H), 2.29 (s, 3H); ESI-MS m/z (%): 351 (M+, 100).

EXAMPLE 14

N-(3-(3-(dimethylamino)propyl)-1H-indol-5-yl) thiophene-2-carboximidamide (56)

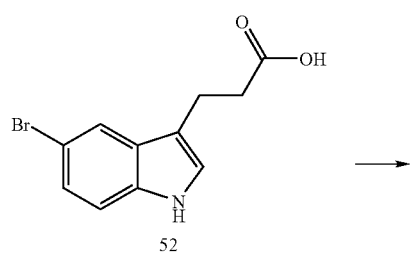
52

3-(5-Bromo-1H-indol-3-yl)-N,N-dimethylpropanamide (53): To a 250 mL argon purged round bottom flask fitted with a magnetic stirbar containing a yellow solution of 5-bromo-indol-3-propionic acid (52) (3.00 g, 11.19 mmol), 1-[3-(dimethylamino)propyl]-3-ethylcarbodiimide hydrochloride (2.36 g, 12.31 mmol), 1-hydroxybenzotriazole (1.51 g 11.17 mmol) and dimethylamine hydrochloride (912 mg, 11.19 mmol) in DMF (20 mL) was added triethylamine (4.7 mL, 25.83 mmol) resulting in the formation of a precipitate. The reaction was monitored by TLC (1:1 ethyl acetate, hexane). After 2 hours the argon purge needle was removed and additional dimethylamine hydrochloride added (0.3 eq). After a total of 20 hours, TLC revealed complete consumption of starting material. The reaction was diluted with water (40 mL) and ethyl acetate (40 mL). The reaction was transferred to a separatory funnel and the product was extracted into the organic layer. The organic layer was extracted again with water (20 mL) to remove the DMF, followed by 2 N NaOH (20 mL) and brine (15 mL). The yellow organic layer was dried over magnesium sulfate, filtered and concentrated to afford a white-pink solid. The product was purified by silica gel column chromatography (9:1 Ethyl acetate/hexanes) Yield: 1.407 g pure, compound 53, $^1$H NMR (DMSO) δ 11.00 (br s, NH), 7.68-7.67 (d, 1H, J=1.5), 7.31-7.28 (d, 1H, J=8.4 Hz), 7.72-7.14 (td, 2H, J=1.8, 8.4 Hz), 2.93-2.81 (m, 8 H), 2.64-2.59 (t, J=7.5 Hz, 2H).

3-(5-Bromo-1H-indol-3-yl)-N,N-dimethylpropan-1-amine (54): To an argon purged 250 mL round bottom flask fitted with condenser and magnetic stirbar containing 53 (1.283 g, 4.35 mmol) was added lithium aluminum hydride (412 mg, 10.86 mmol). Anhydrous tetrahydrofuran (15 mL) was added resulting in gas formation. The flask was placed in an oil bath and heated to 65° C. and stirred for 16 hours under argon. The reaction was cooled to room temperature and quenched with water (1.1 mL), 3N sodium hydroxide (1.7 mL) and water (3.3 mL) sequentially. The mixture was filtered to remove the white solid and the pale yellow filtrate concentrated to afford a pale yellow oil. Drying under high vacuum afforded a pale yellow solid, compound 54. Yield: 1.193 g of pale yellow solid (97.5%). $^1$H NMR (DMSO) δ 7.65-7.64 (d, 1H, J=1.5), 7.30-7.27 (d, 1H, J=8.7 Hz), 7.167 (s, 1 H), 7.14-7.09 (q, 1H, J=6.9, 8.4 Hz), 2.67-2.62 (t, J=7.5, 2H), 2.25-2.20 (t, J=7.5 Hz, 2H), 2.12 (s, 8 H).

3-(3-(Dimethylamino)propyl)-1H-indol-5-amine (55): To an argon purged vial fitted with a magnetic stirbar and containing 54 (324 mg, 1.15 mmol) was cannulated a solution of $Pd_2(dba)_3$ (53 mg, 0.058 mmol), and Tri-t-butyl phosphine solution (0.34 mL, 10%, 0.11 mmol) in dry THF (8 mL). The flask was fitted with a condenser and a 1M solution of lithium hexamethyldisilane in THF (3.45 mL, 3.45 mmol) was added. The reaction was placed in a metal heating block and heated to reflux. The reaction was stirred at this temperature for 16 hours. TLC (10% 2M ammonia in methanol, 90% dichloromethane) revealed all starting material had reacted. The reaction was cooled to room temperature and quenched with 1M aqueous hydrogen chloride (15 mL). The acidic reaction was extracted with ethyl acetate (3×10 mL). The aqueous phase was basified with 3N sodium hydroxide (8 mL) and partitioned into ethyl acetate (3×10 mL). The organics were washed with brine, dried over magnesium sulfate, and treated with charcoal. Filtration through celite, concentration and further drying under high vacuum afforded a dark yellow oil. Purification of the product was performed using silica gel column chromatography (5-10% 2M ammonia in methanol, 95-90% dichloromethane) Yield: 162 mg of brown oil, compound 55 (65%). $^1$H NMR (CDCl3) δ 7.76 (br s, NH), 7.17-7.14 (d, 1H, J=8.4 Hz), 6.92-6.90 (dd, 2H, J=2.1, 4.5 Hz), 6.67-6.64 (dd, 1H, J=2.1, 8.4 Hz), 2.73-2.68 (t, J=7.5, 2H), 2.41-2.36 (t, J=7.5 Hz, 2H), 2.26 (s, 8 H).

N-(3-(3-(dimethylamino)propyl)-1H-indol-5-yl) thiophene-2-carboximidamide (56): To an argon purged round bottom flask containing 55 (340 mg, 1.56 mmol) was added thiophene-2-carboximidothioic acid methyl ester hydroiodide (669 mg, 2.35 mmol). The two were suspended in absolute ethanol (10 mL) and stirred at room temperature for 16 hours. TLC (10% 2M ammonia in methanol, 90% dichloromethane) revealed all amine had reacted. The reaction was diluted with ether (80 mL) and the fluffy yellow precipitate collected by vacuum filtration. The precipitate was washed with ether (50 mL) and became an oil on the fritted filter. Ethanol was used to wash the product through the filter into a round bottom flask (50 mL). The flask was fitted with a stir bar and DOWEX-66 (5.5 g) was added. The reaction was stirred for 2 hours. The reaction was filtered and the filtrate concentrated to afford a yellow foam. The product was purified by silica gel column chromatography (5-10% 2M ammonia in methanol, 95-90% dichloromethane) to afford a yellow oil. The oil was taken up in methanol (5 mL) and stirred during the addition of 1M hydrogen chloride in ether (3 mL). After stirring for 2 hours the reaction was concentrated on the rotary evaporator. The resulting yellow foam was dried further on the high vacuum line. Yield: 347 mg of yellow foam, compound 56, $^1$H NMR (DMSO) δ 11.44 (br s, 1H), 11.26 (s, 1H), 10.62 (bs, 1H), 9.66 (bs, 1H), 8.61 (bs, 1H), 8.18-8.17 (d, 2H, J=4.2 Hz), 7.65 (s, 1H), 7.54-7.51 (d, J=8.7 Hz, 1H), 7.41-7.36 (q 2H, J=4.5 Hz), 7.13-7.09 (dd, J=1.2, 8.7 Hz, 1H), 3.10-3.04 (t J=7.5, 2H), 2.79-2.74 (t, J=7.5 Hz, 2H), 2.72 (s, 6H), 2.05 (m, 2H). ESI-MS m/z (%): 327 (M$^+$, 100).

EXAMPLE 15

Preparation of N-((3-(2-(dimethylamino)ethyl)-1H-indol-5-yl)methyl)thiophene-2-carboximidamide (59)

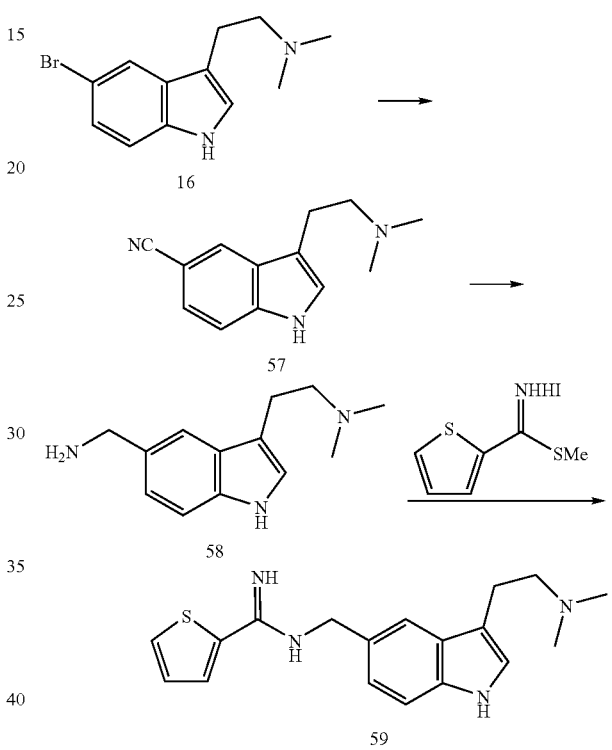

3-(2-(Dimethylamino)ethyl)-1H-indole-5-carbonitrile (57): [2-(5-Bromo-1H-indol-3-yl)-ethyl]-dimethylamine (16) (500.0 mg, 1.872 mmol) (U.S. Pat. No. 5,998,438) was placed in an argon purged oven dried flask fitted with a stirbar. Zinc cyanide (395.0 mg, 3.368 mmol, 1.8 equivalents); Zinc powder (14.7 mg. 0.225 mmol, 0.12 equivalents) and tris (dibenzylideneacetone)dipalladium(0) (42.9 mg, 0.0468 mmol, 0.025 equivalents) were added sequentially followed by anhydrous N,N-dimethylformamide (15 mL). A solution of tri-t-butylphosphine in hexanes (10 wt %, 189.0 mg, 280 µl, 0.05 equivalents) was added and the mixture was stirred for 15 minutes at room temperature and then heated in an oil bath at 60° C. for 30 minutes. After cooling to room temperature the mixture was transferred into a separatory funnel and diluted with distilled water (15 mL). The aqueous phase was extracted with ethyl acetate (3×30 mL). The combined organic extracts were dried over magnesium sulfate, filtered, and concentrated. The residue was purified via silica gel column chromatography (10% 2M NH$_3$ in methanol/90% dichloromethane) to provide 3-(2-(dimethylamino)ethyl)-1H-indole-5-carbonitrile (57) as a yellow residue (150 mg, 37.6% yield). $^1$H NMR (DMSO) δ: 2.21 (s, 6H), 2.54 (m, 2 H), 2.84 (t, 2H), 7.36-7.41 (m, 2H), 7.49 (d, 1H), 8.07 (s, 1H), 11.38 (br s, 1H).

2-(5-(Aminomethyl)-1H-indol-3-yl)-N,N-dimethylethanamine (58): Lithium aluminium hydride (40.0 mg, 1.055 mmol, 1.5 equivalents) was placed in an argon purged oven dried flask fitted with a stirbar and condenser. Anhydrous diethylether (5 mL) was added and stirring begun. 3-(2-Dimethylamino-ethyl)-1H-indole-5-carbonitrile (57) (150.0 mg, 0.703 mmol, 1.0 equivalent) was dissolved in a separate dry flask in a mixture of anhydrous diethylether (5 mL) and anhydrous tetrahydrofuran (5 mL) and this solution added dropwise to the solution of lithium aluminium hydride and the resulting mixture heated to reflux. After 30 minutes the reaction was cooled to room temperature and quenched with distilled water (50 μL), aqueous 3N sodium hydroxide solution (75 μL) and distilled water (150 μL) sequentially. The solution was filtered and concentrated. The residue was purified via silica gel column chromatography (10-15-20% 2M NH$_3$ in methanol/90-85-80% dichloromethane) to provide 2-(5-(aminomethyl)-1H-indol-3-yl)-N,N-dimethylethanamine (58) as a pale yellow residue (73 mg, 47.8% yield). $^1$H NMR (DMSO) δ: 2.21 (s, 6H), 2.53 (m, 2 H), 2.78 (t, 2H), 3.79 (s, 2H), 7.02-7.05 (d, 1H), 7.09 (s, 1H), 7.24 (d, 1H), 7.44 (s, 1H), 10.66 (br s, 1H). MS: 218 (M+1), 201 (M+1-NH$_3$).

N-((3-(2-(Dimethylamino)ethyl)-1H-indol-5-yl)methyl) thiophene-2-carboximidamide (59): [2-(5-Aminomethyl-1H-indol-3-yl)-ethyl]-dimethyl-amine (58) (70 mg, 0.322 mmol) and thiophene-2-carboximidothioic acid methyl ester hydroiodide (160.7 mg, 0.564 mmol, 1.75 equivalents) were dissolved in anhydrous ethanol (5 mL) in a small, argon purged flask. The reaction was stirred under argon for 20 hours at ambient temperature at which time the solvent was removed. The crude residue was dissolved in water (10 mL) and transferred to a separatory funnel, where it was made basic (pH 9-10) through the addition of aqueous 1N sodium hydroxide solution. The mixture was extracted with ethyl acetate (3×20 mL). The combined organic extracts were washed with distilled water, brine, dried over magnesium sulfate, filtered and concentrated to yield crude freebase. The residue was purified via silica gel column chromatography (10-25% 2M NH$_3$ in methanol/90-75% dichloromethane) to provide the freebase as a colorless/white residue (36 mg, 34.3% yield). The freebase was dissolved in methanol (5 mL) and 1M HCl in diethylether (3 equivalents) was added. The solvent was removed and the oil dried under high vacuum to give N-((3-(2-(dimethylamino)ethyl)-1H-indol-5-yl)methyl) thiophene-2-carboximidamide (59) as the dihydrochloride salt. $^1$H NMR (free base, DMSO-d6) δ: 2.21 (s, 6H), 2.53 (m, 2H), 2.79 (t, 2H), 4.39 (s, 2H), 7.06-7.10 (m, 3H), 7.26 (d, 1H), 7.51 (s, 1H), 7.52 (m, 1H), 7.60 (d, 1H), 10.65 (br s, 1H). MS: 327 (M+1).

EXAMPLE 16

N-(3-(1-ethylpiperidin-4-yl)-1H-indol-5-yl) thiophene-2-carboximidamide (62)

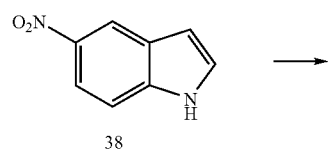

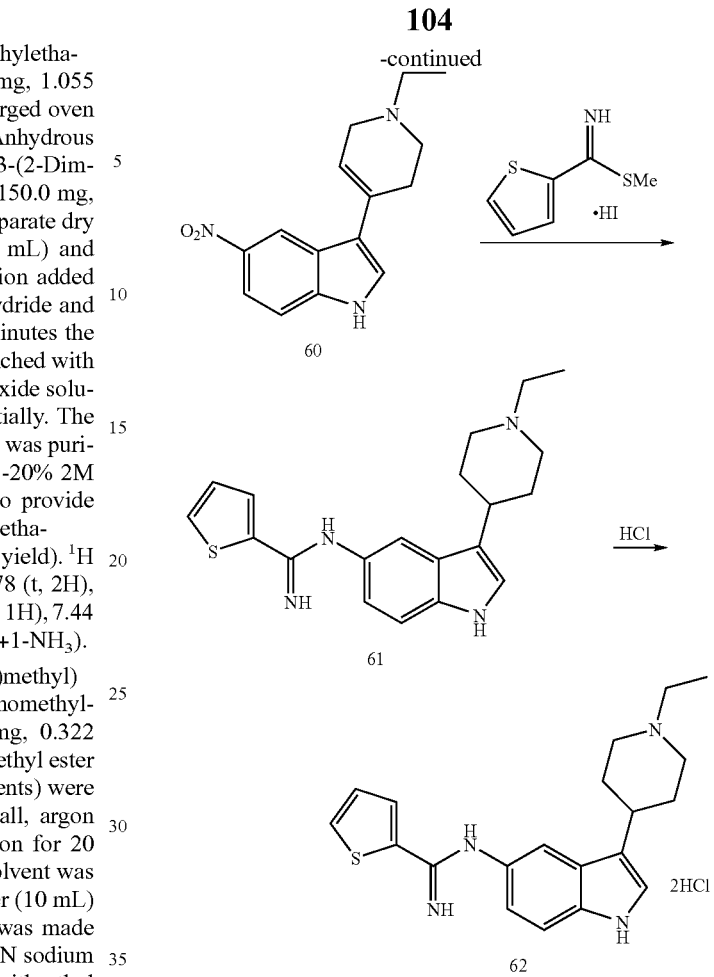

3-(1-Ethyl-1,2,3,6-tetrahydropyridin-4-yl)-5-nitro-1H-indole (60): A solution of 5-nitroindole (38) (0.5 g, 3.083 mmol) in dry ethanol (15 mL) was treated with pyrrolidine (0.65 mL, 9.250 mmol), N-ethyl-4-piperidone (0.8 mL, 6.167 mmol) at room temperature and the resulting solution was refluxed for 3 days. The reaction was brought to room temperature and solvent was evaporated. The crude was purified by column chromatography (2 M NH$_3$ in methanol: CH$_2$Cl$_2$, 5:95), and washed with ether (3×10 mL) to obtain compound 60 (0.35 g, 42%) as a solid. mp 188-190° C.; $^1$H NMR (DMSO-d6) δ: 1.07 (t, 3H, J=7.2 Hz), 2.41-2.50 (m, 4H), 2.63 (t, 2H, J=5.1 Hz), 3.10-3.15 (m, 2H), 6.18 (s, 1H), 7.55 (d, 1H, J=9.0 Hz), 7.65 (s, 1H), 8.01 (dd, 1H, J=2.1, 9.0 Hz), 8.69 (d, 1H, J=2.1 Hz), 11.86 (s, 1H)— ESI-MS m/z (%): 272 (M$^+$, 100).

N-(3-(1-ethylpiperidin-4-yl)-1H-indol-5-yl)thiophene-2-carboximidamide (61): A solution of 3-(1-ethyl-1,2,3,6-tetrahydropyridin-4-yl)-5-nitro-1H-indole (60) (0.1 g, 0.368 mmol) in dry ethanol (5 mL) was treated with 10% Pd—C (0.02 g), purged with hydrogen gas and stirred for 4 h under hydrogen atm. (balloon pressure). The solid was filtered off using celite bed and washed with dry ethanol (2×5 mL). The combined ethanol layer was treated with thiophene-2-carboximidothioic acid methyl ester hydroiodide (0.21 g, 0.737 mmol) and stirred for 24 h at room temperature. The solvent was evaporated and product was precipitated with ether (100 mL). The solid was filtered and dissolved into sat. NaHCO$_3$ sol.: CH$_2$Cl$_2$ (50 mL, 1:1). The org. layer was separated and aqueous layer was extracted with CH$_2$Cl$_2$ (2×20 mL). The combined CH$_2$Cl$_2$ layer was washed with brine (15 mL) and dried (Na$_2$SO$_4$). The solvent was evaporated and crude was purified by column chromatography (2M NH$_3$ in methanol: CH$_2$Cl$_2$, 5:95) to obtain N-(3-(1-ethylpiperidin-4-yl)-1H-indol-5-yl)thiophene-2-carboximidamide (61) (0.085 g, 66%) as a solid. mp 150-152° C.; $^1$H NMR (DMSO-d$_6$) δ 1.01 (t, 3H, J=6.9 Hz), 1.59-1.75 (m, 2H), 1.90-2.05 (m, 4H), 2.35 (q, 2H), 2.65-2.73 (m, 1H), 2.94-2.97 (m, 2H), 6.23 (brs, 1H), 6.62 (dd, 1H, J=1.2, 8.4 Hz), 6.97 (s, 1H), 7.02 (d, 1H, J=2.1 Hz), 7.09 (t, 1H, J=4.2 Hz), 7.26 (d, 1H, J=8.4 Hz), 7.58 (d, 1H, J=5.4 Hz), 7.70 (d, 1H, J=3.6 Hz), 10.59 (s, 1H); ESI-MS m/z (%): 353 (M$^+$, 100).

Dihydrochloride salt of N-(3-(1-ethylpiperidin-4-yl)-1H-indol-5-yl)thiophene-2-carboximidamide (62): A solution of N-(3-(1-ethylpiperidin-4-yl)-1H-indol-5-yl)thiophene-2-carboximidamide (61) (0.07 g, 0.198 mmol) in ethanol (2 mL) was treated with 1 N HCl in ether (0.59 mL, 0.595 mmol) at room temperature. The solvent was evaporated after stirring for 15 min. and the crude was recrystallised from ethanol/ether to obtain compound 62 (0.067 g, 80%) as a solid. mp 254-256° C.

EXAMPLE 17

N-(3-(1-methyl-1,2,3,6-tetrahydropyridin-4-yl)-1H-indol-5-ylcarbamothioyl)benzamide (64)

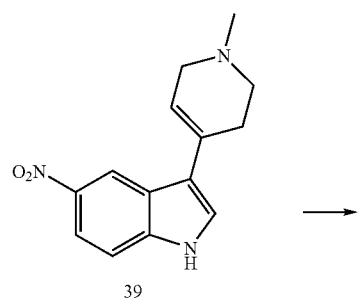

3-(1-Methyl-1,2,3,6-tetrahydropyridin-4-yl)-5-nitro-1H-indole (39): Experimental details were discussed in Example 11.

N-(3-(1-Methyl-1,2,3,6-tetrahydropyridin-4-yl)-1H-indol-5-ylcarbamothioyl)benzamide (63). A solution of compound 3-(1-Methyl-1,2,3,6-tetrahydropyridin-4-yl)-5-nitro-1H-indole (39) (1.0 g, 3.886 mmol) in dry methanol (20 mL) was treated with Raney-Ni (0.3 g), followed by hydrazine hydrate (1.21 mL, 38.866 mmol) at room temperature and the resulting solution was stirred at 65° C. for 2 h. The reaction was brought to room temperature and the mixture filtered through a celite bed to remove the solid. The celite bed was washed with methanol (2×10 mL). The combined organic fraction was evaporated and the crude material was purified by column chromatography (2 M NH$_3$ in methanol: CH$_2$Cl$_2$, 5:95) to obtain the free amine 3-(1-methyl-1,2,3,6-tetrahydropyridin-4-yl)-1H-indol-5-amine (0.78 g, 88%) as a solid. A solution of the amine (0.78 g, 3.431 mmol) in acetone (20 mL) was treated with benzoylisothiocyanate (0.53 mL, 3.946 mmol) at room temperature and the resulting mixture was stirred for overnight. The solvent was evaporated and the crude product was purified by column chromatography (2M ammonia in methanol: CH$_2$Cl$_2$, 5:95) to obtain compound 63 (1.23 cg, 92%) as a solid. mp 182-184° C.; $^1$H NMR (DMSO-d$_6$) δ 2.28 (s, 3H), 2.50-2.58 (m, 4H), 3.00-3.10 (m, 2H), 6.09 (s, 1H), 7.26 (d, 1H, J=7.8 Hz), 7.40 (d, 1H, J=8.7 Hz), 7.44 (d, 1H, J=2.1 Hz), 7.54 (t, 2H, J=7.5 Hz), 7.66 (t, 1H, J=7.2 Hz), 7.99 (d, 2H, J=7.5 Hz), 8.15 (s, 1H), 11.24 (s, 1H), 11.48 (s, 1H), 12.58 (s, 1H); ESI-MS m/z (%):: 391 (M$^+$, 76), 289 (74), 348 (100).

Hydrochloride salt of N-(3-(1-methyl-1,2,3,6-tetrahydropyridin-4-yl)-1H-indol-5-ylcarbamothioyl)benzamide (64): A solution of compound 63 (0.08 g, 0.204 mmol) in methanol (5 mL) was treated with 1 N HCl in ether (0.6 mL, 0.614 mmol) at room temperature. The solvent was evaporated under vacuum after stirring for 15 min. and the crude was recrystallised from ethanol/ether to obtain compound 64 (0.075 g, 80%) as a solid. mp 197-199° C.

EXAMPLE 18

Preparation of Ethyl 3-(1-methyl-1,2,3,6-tetrahydropyridin-4-yl)-1H-indol-5-ylcarbamimidothioate (67)

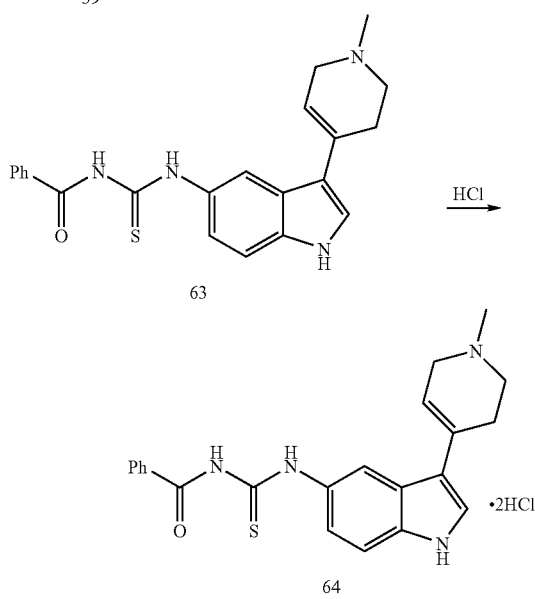

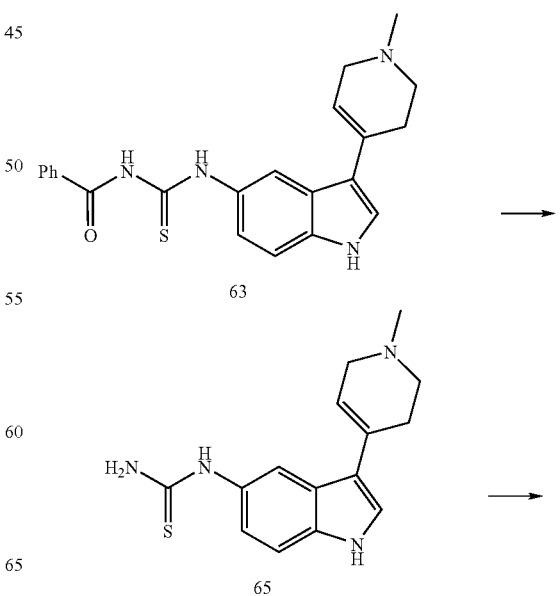

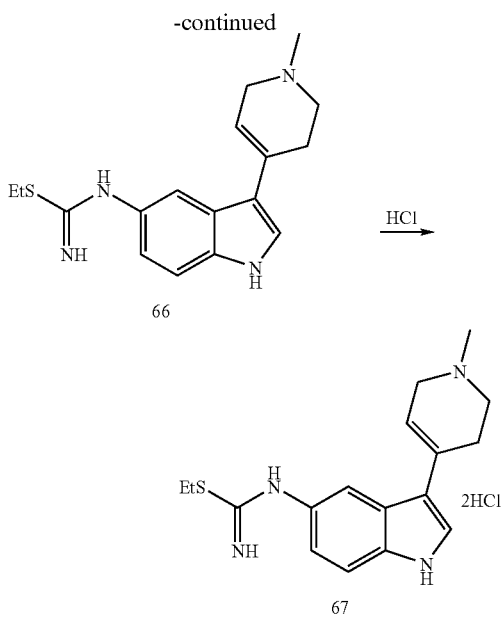

N-(3-(1-Methyl-1,2,3,6-tetrahydropyridin-4-yl)-1H-indol-5-ylcarbamothioyl)benzamide (63): Synthesis was described in Example 17.

1-(3-(1-Methyl-1,2,3,6-tetrahydropyridin-4-yl)-1H-indol-5-yl)thiourea (65): A solution of compound 63 (1.12 g, 2.868 mmol) in THF (20 mL) was treated with 2 N NaOH (3.1 mL, 6.309 mmol) at room temperature and the resulting solution was refluxed for 5 h. The reaction was brought to room temperature, solvent was evaporated. The crude was diluted with water (20 mL) and ethyl acetate (20 mL). The precipitated solid was filtered, washed with water (10 mL), EtOAc (10 mL) and ether (2×10 mL) and dried under vacuum to obtain compound 65 (0.65 g, 79%). mp 209-211° C.: $^1$H NMR (DMSO-d$_6$) δ 2.27 (s, 3H), 2.50-2.56 (m, 4H), 3.00-3.08 (m, 2H), 6.05 (s, 1H), 6.98 (d, 1H, J=8.4 Hz), 7.32-7.40 (m, 3H), 7.67 (s, 1H), 9.51 (s, 1H), 11.15 (s, 1H); ESI-MS m/z (%):: 287 (M+, 71), 249 (46), 244 (100).

Ethyl 3-(1-methyl-1,2,3,6-tetrahydropyridin-4-yl)-1H-indol-5-ylcarbamimidothioate (66): A solution of compound 65 (0.2 g, 0.698 mmol) in acetone (10 mL) was treated with iodoethane (0.33 mL, 4.189 mmol) at room temperature and the resulting solution was refluxed for 4 h. The reaction was brought to room temperature, and solvent was evaporated. The crude was diluted with sat. NaHCO$_3$ solution (20 mL) and compound was extracted into CH$_2$Cl$_2$ (3×20 mL). The combined CH$_2$Cl$_2$ layer was washed with brine (15 mL) and dried (Na$_2$SO$_4$). Evaporation of solvent and purification of crude by column chromatography (2 M NH$_3$ in methanol: CH$_2$Cl$_2$, 5:95) to obtain compound 66 (0.055 g, 25%) as a solid. mp 77-79° C.; $^1$H NMR (DMSO-d$_6$) δ 1.20-1.30 (m, 3H), 2.28 (s, 3H), 2.50-2.57 (m, 4H), 2.90-2.96 (m, 2H), 3.02-3.06 (m, 2H), 5.98-6.04 (m, 2H), 6.60-6.63 (m, 1H), 7.17-7.35 (m, 4H), 10.90 (s, 1H); ESI-MS m/z (%):: 315 (M+, 66), 311 (78), 249 (100).

Dihydrochloride salt of ethyl 3-(1-methyl-1,2,3,6-tetrahydropyridin-4-yl)-1H-indol-5-ylcarbamimidothioate (67): A solution of compound 66 (0.05 g, 0.159 mmol) in methanol (5 mL) was treated with 1 N HCl in ether (0.47 mL, 0.477 mmol) at room temperature. The solvent was evaporated under vacuum after stirring for 15 min. and the crude was recrystallised from ethanol/Ether to obtain compound 67 (0.04 g, 66%) as a solid. mp 190-192° C.

EXAMPLE 19

N-(3-(1-benzoylpiperidin-4-yl)-1H-indol-5-yl)thiophene-2-carboximidamide (70)

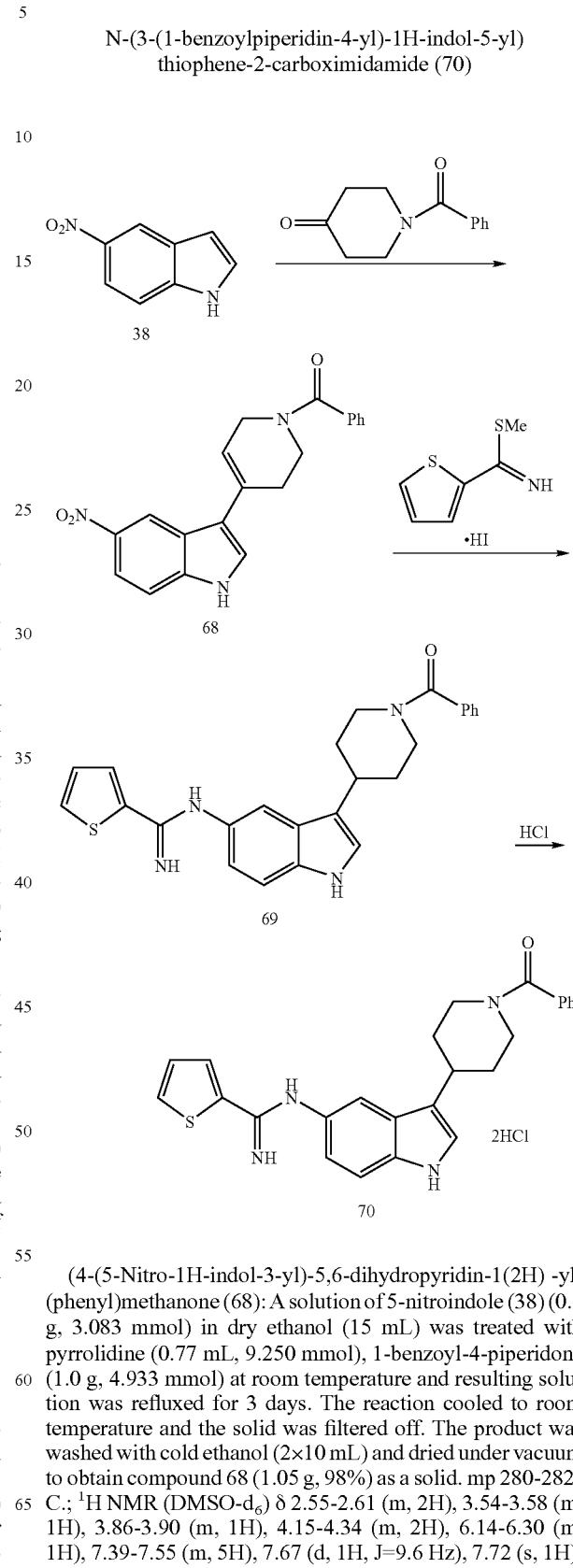

(4-(5-Nitro-1H-indol-3-yl)-5,6-dihydropyridin-1(2H)-yl)(phenyl)methanone (68): A solution of 5-nitroindole (38) (0.5 g, 3.083 mmol) in dry ethanol (15 mL) was treated with pyrrolidine (0.77 mL, 9.250 mmol), 1-benzoyl-4-piperidone (1.0 g, 4.933 mmol) at room temperature and resulting solution was refluxed for 3 days. The reaction cooled to room temperature and the solid was filtered off. The product was washed with cold ethanol (2×10 mL) and dried under vacuum to obtain compound 68 (1.05 g, 98%) as a solid. mp 280-282° C.; $^1$H NMR (DMSO-d$_6$) δ 2.55-2.61 (m, 2H), 3.54-3.58 (m, 1H), 3.86-3.90 (m, 1H), 4.15-4.34 (m, 2H), 6.14-6.30 (m, 1H), 7.39-7.55 (m, 5H), 7.67 (d, 1H, J=9.6 Hz), 7.72 (s, 1H), 8.03 (d, 1H, J=8.1 Hz), 8.70-8.78 (m, 1H), 11.94 (s, 1H); ESI-MS m/z (%): 348 (M+, 100), 276 (83), 244 (40).

Dihydrochloride salt of N-(3-(1-Benzoylpiperidin-4-yl)-1H-indol-5-yl)thiophene-2-carboximidamide (70): A solution of compound 1 (0.2 g, 0.575 mmol) in dry ethanol (5 mL) was treated with Pd—C (0.02 g), purged with hydrogen gas and stirred for overnight (14 h) under hydrogen atm. (balloon pressure). The reaction mixture was filtered through celite bed and washed with dry ethanol (2×5 mL). The combined ethanol layer was treated with thiophene-2-carboximidothioic acid methyl ester hydroiodide (0.32 g, 1.157 mmol) and the resulting mixture was stirred for 24 h at room temperature. The solvent was evaporated and product was precipitated with ether (50 mL). The solid was partitioned between sat. NaHCO$_3$ solution: CH$_2$Cl$_2$ (40 mL, 1:1). The organic layer was separated and aqueous layer was extracted with CH$_2$Cl$_2$ (2×20 mL). The combined CH$_2$Cl$_2$ layer was washed with brine (10 mL) and dried (Na$_2$SO$_4$). The solvent was evaporated and crude was product was purified by column chromatography (2M NH$_3$ in methanol: CH$_2$Cl$_2$, 5:95) to obtain compound 69 (0.07 g, 28%) as a free base. Solid, mp 135-137° C.; $^1$H NMR (DMSO-d$_6$) δ 1.57-1.65 (m, 2H), 1.89-2.06 (m, 2H), 2.92-3.08 (m, 2H), 3.18-3.25 (m, 1H), 3.64-3.69 (m, 1H), 4.58-4.64 (m, 1H), 6.22 (s, 1H), 6.63 (d, 1H, J=8.7 Hz), 7.01-7.10 (m, 3H), 7.27 (d, 1H, J=8.4 Hz), 7.40-7.45 (m, 6H), 7.58 (d, 1H, J=4.8 Hz), 7.70 (d, 1H, J=3.6 Hz), 10.65 (s, 1H); ESI-MS m/z (%): 429 (M+, 100), 412 (46). A solution of compound 69 (0.06 g, 0.140 mmol) in methanol (3 mL) was treated with 1 N HCl in ether (0.42 mL, 0.420 mmol) and stirred for 30 min at room temperature. The solvent was evaporated and crude was recrystallized from ethanol/ether to obtain compound 70 (0.053 g, 76%) as a solid. mp 180-183° C.

EXAMPLE 20

N-(3-(pyridin-4-yl)-1H-indol-5-yl)thiophene-2-carboximidamide (73)

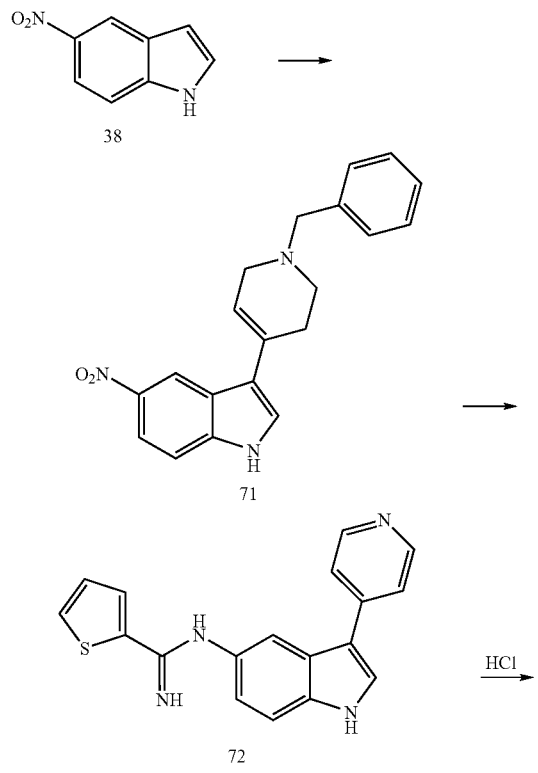

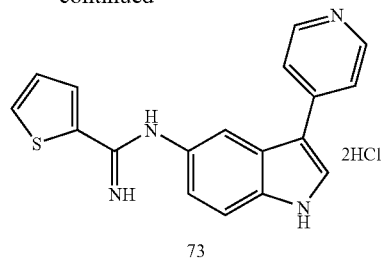

3-(1-Benzyl-1,2,3,6-tetrahydropyridin-4-yl)-5-nitro-1H-indole (71): A solution of 5-nitroindole (38) (1.0 g, 6.167 mmol) in dry ethanol (20 mL) was treated with pyrrolidine (1.54 mL, 18.501 mmol), N-benzyl-4-piperidone (2.2 mL, 12.3 mmol) at room temperature and the resulting solution was refluxed for 4 days. The reaction was brought to room temperature and solvent was evaporated. The crude product was purified by column chromatography (2 M NH$_3$ in methanol: CH$_2$Cl$_2$, 5:95) to obtain compound 71 (0.925 g, 45%) as a solid. mp 168-170° C.; $^1$H NMR (DMSO-d6) δ 2.51-2.55 (m, 2H), 2.66 (t, 2H, J=5.4 Hz), 3.12-3.18 (m, 2H), 3.60 (s, 2H), 6.17 (s, 1H), 7.23-7.38 (m, 5H), 7.55 (d, 1H, J=9.0 Hz), 7.65 (s, 1H), 8.01 (dd, 1H, J=2.1, 8.7 Hz), 8.68 (d, 1H, J=2.1 Hz), 11.87 (s, 1H); ESI-MS m/z (%): 334 (M+, 100).

Dihydrochloride salt of N-(3-(pyridin-4-yl)-1H-indol-5-yl) thiophene-2-carboximidamide (73): A solution of compound 71 (0.3 g, 0.899 mmol) in dry methanol (5 mL) was treated with Pd—C (0.03 g), HCO$_2$NH$_4$ (0.28 g, 4.499 mmol) at room temperature and the resulting solution was refluxed for 24 h. The reaction was brought to room temperature, filtered through celite bed and washed with methanol (2×15 mL). The combined methanol layer was evaporated and crude was purified by column chromatography (2 M NH$_3$ in methanol: CH$_2$Cl$_2$, 5:95) to obtain the amine intermediate. A solution of the amine in dry ethanol (10 mL) was treated with thiophene-2-carboximidothioic acid methyl ester hydroiodide (0.51 g, 1.799 mmol) and the resulting mixture was stirred for 24 h at room temperature. The solvent was evaporated and product was precipitated with ether (50 mL). The solid was dissolved into sat. NaHCO$_3$ sol.: CH$_2$Cl$_2$ (40 mL, 1:1). The organic layer was separated and aqueous layer was extracted with CH$_2$Cl$_2$ (2×20 mL). The combined CH$_2$Cl$_2$ layer was washed with brine (15 mL) and dried (Na$_2$SO$_4$). The solvent was evaporated and crude was purified by column chromatography (2M NH$_3$ in methanol: CH$_2$Cl$_2$, 5:95) to obtain compound 72 (0.04 g, 14%) as a solid. mp 112-115° C.; $^1$H NMR (DMSO-d$_6$) δ 6.39 (brs, 1H), 6.76 (d, 1H, J=8.4 Hz), 7.10 (dd, 1H, J=3.6, 4.9 Hz), 7.41-7.44 (m, 2H), 7.61 (d, 1H, J=4.8 Hz), 7.68 (d, 2H, J=6.3 Hz), 7.74 (d, 1H, J=2.7 Hz), 7.96 (d, 1H, J=2.7 Hz), 8.49 (d, 2H, J=6.0 Hz), 11.53 (s, 1H); ESI-MS m/z (%): 319 (M+, 100). A solution of free base of compound 72 (0.035 g, 0.109 mmol) in methanol (3 mL) was treated with 1 N HCl in ether (0.32 mL, 0.329 mmol) and stirred for 30 min. at room temperature. The solvent was evaporated and crude was recrystallized from ethanol/ether to obtain compound 73 (0.031 g, 72%) as a dihydrochloride salt. Solid, mp 183-185° C.

EXAMPLE 21

Methyl 3-(1-methyl-1,2,3,6-tetrahydropyridin-4-yl)-1H-indol-5-ylcarbamimidothioate (75)

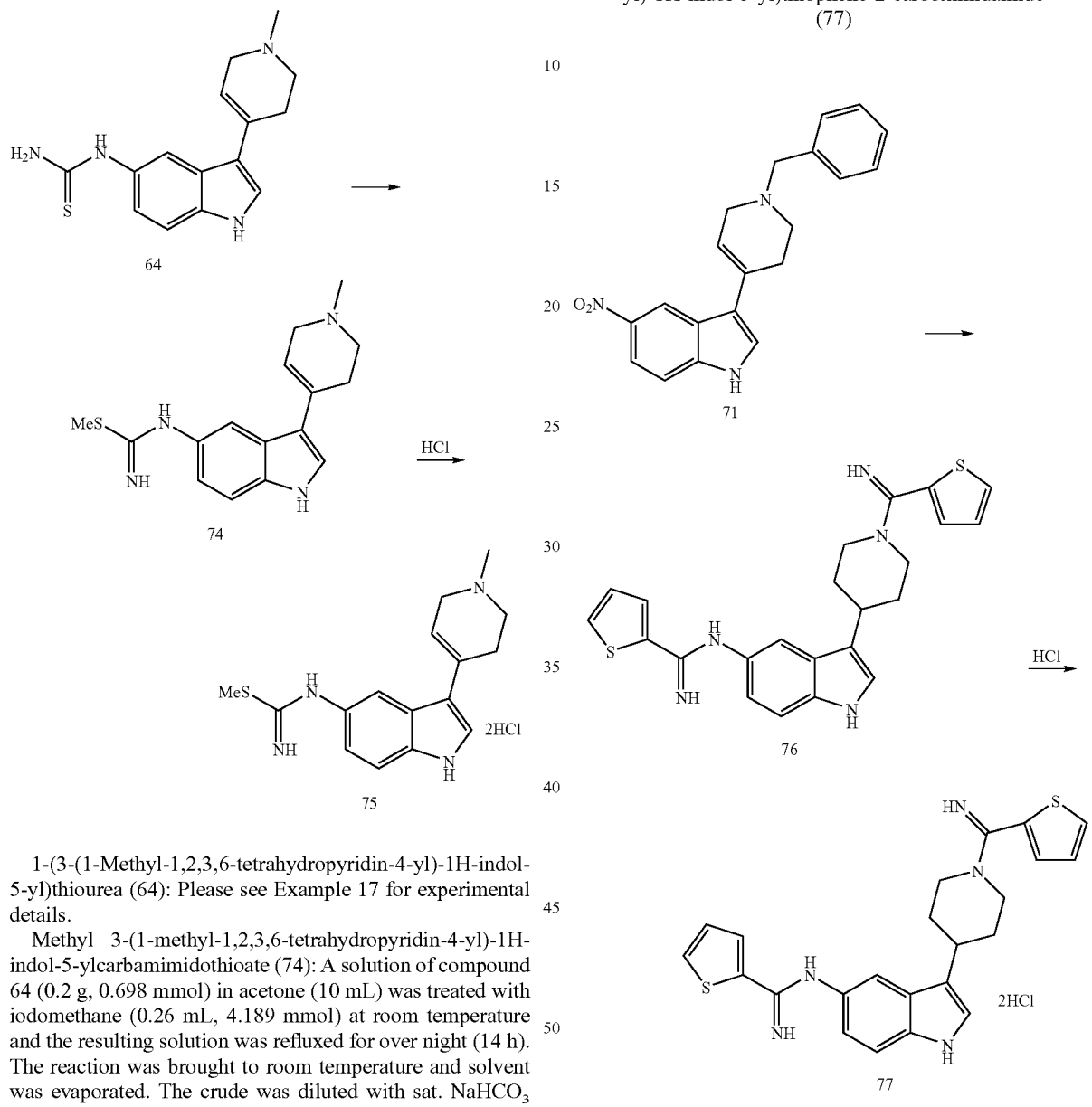

EXAMPLE 22

N-(3-(1-(imino(thiophen-2-yl)methyl)piperidin-4-yl)-1H-indol-5-yl)thiophene-2-carboximidamide (77)

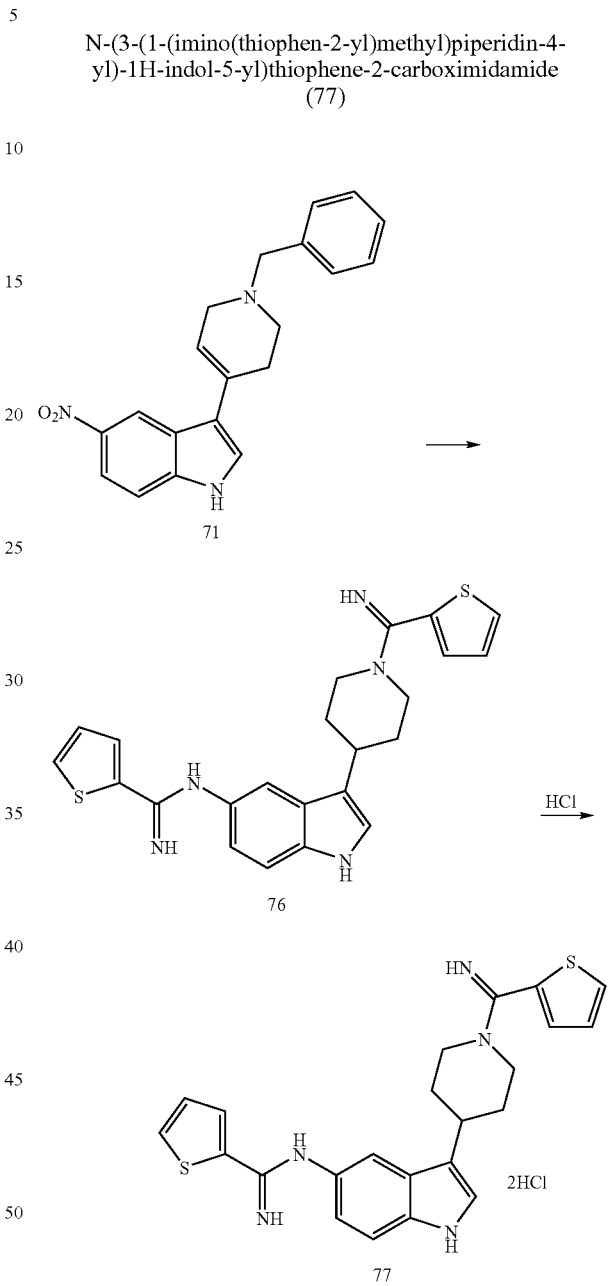

1-(3-(1-Methyl-1,2,3,6-tetrahydropyridin-4-yl)-1H-indol-5-yl)thiourea (64): Please see Example 17 for experimental details.

Methyl 3-(1-methyl-1,2,3,6-tetrahydropyridin-4-yl)-1H-indol-5-ylcarbamimidothioate (74): A solution of compound 64 (0.2 g, 0.698 mmol) in acetone (10 mL) was treated with iodomethane (0.26 mL, 4.189 mmol) at room temperature and the resulting solution was refluxed for over night (14 h). The reaction was brought to room temperature and solvent was evaporated. The crude was diluted with sat. NaHCO$_3$ solution (10 mL) and compound was extracted into CH$_2$Cl$_2$ (2×20 mL). The combined CH$_2$Cl$_2$ layer was washed with brine (10 mL) and dried (Na$_2$SO$_4$). Solvent was evaporated and crude was purified by column chromatography (2 M NH$_3$ in methanol: CH$_2$Cl$_2$, 5:95) to obtain compound 74 (0.04 g, 19%) as a solid. mp 260-162° C.; $^1$H NMR (DMSO-d$_6$) δ 2.29 (s, 3H), 2.33 (s, 3H), 2.50-2.59 (m, 4H), 3.06 (brs, 2H), 6.01 (s, 1H), 6.64 (brs, 1H), 7.22-7.30 (m, 3H), 10.91 (s, 1H); ESI-MS m/z (%): 301 (M$^+$, 36), 285 (55), 258 (66), 242 (100).

Dihydrochloride salt of Methyl 3-(1-methyl-1,2,3,6-tetrahydropyridin-4-yl)-1H-indol-5-ylcarbamimidothioate (75): A solution of compound 74 (0.035 g, 0.116 mmol) in methanol (3 mL) was treated with 1 N HCl in ether (0.34 mL, 0.349 mmol) at room temperature. The solvent was evaporated under vacuum after stirring for 15 min and dried to obtain compound 75 (0.03 g, 70%) as a semi-solid.

3-(1-Benzyl-1,2,3,6-tetrahydropyridin-4-yl)-5-nitro-1H-indole (71): Please see Example 20 for experimental details.

N-(3-(1-(imino(thiophen-2-yl)methyl)piperidin-4-yl)-1H-indol-5-yl)thiophene-2-carboximidamide (76): A solution of compound 71 (0.17 g, 0.509 mmol) in dry ethanol (5 mL) was treated with Pd—C (0.02 g), purged with hydrogen gas and stirred for overnight (14 h) under hydrogen atm. (balloon pressure). The reaction mixture was filtered through celite bed and washed with dry ethanol (2×5 mL). The combined ethanol layer was treated with thiophene-2-carboximidothioic acid methyl ester hydroiodide (0.32 g, 1.019 mmol) and the resulting mixture was stirred for 24 h at room temperature. The solvent was evaporated and product was precipitated with ether (50 mL). The solid was dissolved into a mixture of sat. NaHCO₃ sol. and CH₂Cl₂ (40 mL, 1:1). The org. layer was separated and aqueous layer was extracted with CH₂Cl₂ (2×20 mL). The combined CH₂Cl₂ layer was washed with brine (10 mL) and dried (Na₂SO₄). The solvent was evaporated and crude product was purified by column chromatography (2M NH₃ in methanol: CH₂Cl₂, 5:95) to obtain compound 77 (0.06 g, 27%) as a solid. mp 115-117° C.; $^1$H NMR (DMSO-$d_6$) δ 1.66-1.77 (m, 2H), 1.99-2.03 (m, 2H), 3.04-3.16 (m, 3H), 3.97-4.01 (m, 2H), 6.23 (brs, 1H), 6.64 (dd, 1H, J=1.2, 8.4 Hz), 7.03 (s, 1H), 7.07-7.10 (m, 2H), 7.17 (t, 1H, J=3.9 Hz), 7.28 (d, 1H, J=8.4 Hz), 7.43 (d, 1H, J=3.9 Hz), 7.58 (d, 1H, J=4.5 Hz), 7.71 (d, 1H, J=3.6 Hz), 7.78 (d, 1H, J=4.5 Hz), 10.65 (s, 1H); ESI-MS m/z (%): 434 (M+, 47), 325 (100), 242 (34).

Dihydrochloride salt of N-(3-(1-(imino(thiophen-2-yl)methyl)piperidin-4-yl)-1H-indol-5-yl)thiophene-2-carboximidamide (77): A solution of compound 76 (0.055 g, 0.115 mmol) in methanol (3 mL) was treated with 1 N HCl in ether (0.34 mL, 0.345 mmol) and stirred for 30 min at room temperature. The solvent was evaporated and crude was recrystallized from ethanol/ether to obtain compound 77 (0.051 g, 80%) as a solid. mp 123-125° C.

EXAMPLE 23

N-(3-(4-(methylamino)cyclohexyl)-1H-indol-5-yl)thiophene-2-carboximidamide (84)

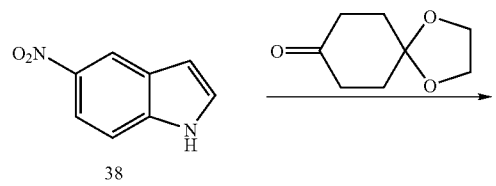

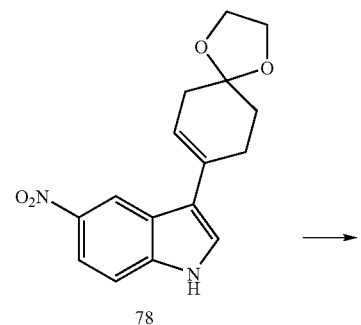

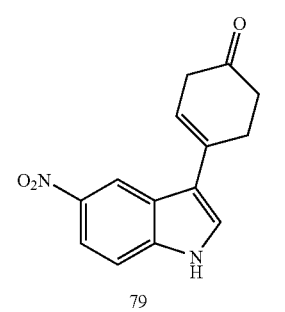

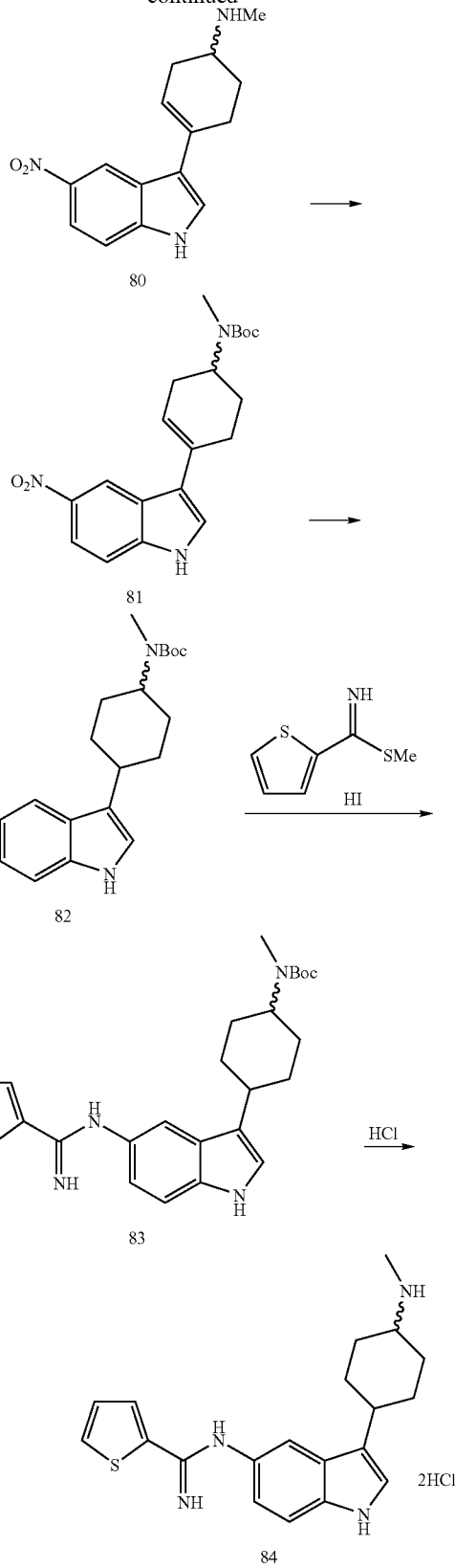

5-Nitro-3-(1,4-dioxaspiro[4.5]dec-7-en-8-yl)-1H-indole (78): A solution of 5-nitroindole (38) (0.2 g, 1.233 mmol) in dry methanol (5 mL) was treated with KOH (0.56 g) at room temperature. After stirring for 10 min., 1,4-cyclohexanedione monoethylene ketal (0.48 g, 3.083 mmol) was added and the resulting solution was refluxed for 36 h. The reaction was brought to room temperature and solvent was evaporated. The crude product was diluted with water (25 mL) and product was extracted into ethyl acetate (2×25 mL). The combined ethyl acetate layer was washed with brine (20 mL) and dried ($Na_2SO_4$). The solvent was evaporated and crude material was purified by flash-column chromatography (ethyla acetate) to obtain compound 78 (0.25 g, 68%) as a solid. mp 175-177° C.; $^1H$ NMR ($CDCl_3$) δ 1.91 (t, 2H, J=6.6 Hz), 2.49 (brs, 2H), 2.49-2.66 (m, 2H), 3.96-4.00 (m, 4H), 6.12 (t, 1H, J=3.9 Hz), 7.22 (d, 1H, J=2.4 Hz), 7.32 (d, 1H, J=8.7 Hz), 8.05 (dd, 1H, J=2.1, 9.0 Hz), 8.36 (brs, 1H), 8.78 (d, 1H, J=2.1 Hz); ESI-MS m/z (%): 301 ($M^+$, 100).

4-(5-Nitro-1H-indol-3-yl)cyclohex-3-enone (79): A solution of compound 78 (0.1 g, 0.332 mmol) in acetone (5 mL) was treated with 10% aq. HCl (5 mL) at room temperature and stirred for 6 h. Acetone was evaporated and crude was basified using $NH_4OH$ solution (20 mL). The product was extracted into $CH_2Cl_2$ (2×20 mL), washed with brine (10 mL) and dried ($Na_2SO_4$). The $CH_2Cl_2$ layer was evaporated to obtain compound 79 (0.075 g, 88%) as a solid. mp 210-212° C.; $^1H$ NMR (DMSO-$d_6$) δ 2.59 (t, 2H, J=6.9 Hz), 2.90 (t, 2H, J=6.6 Hz), 3.11-3.12 (m, 2H), 6.24 (t, 1H, J=3.6 Hz), 7.57 (d, 1H, J=9.0 Hz), 7.76 (d, 1H, J=2.1 Hz), 8.03 (dd, 1H, J=2.1, 9.0 Hz), 8.71 (d, 1H, J=2.1 Hz), 11.95 (s, 1H); ESI-MS m/z (%): 257 ($M^+$, 100).

N-Methyl-4-(5-nitro-1H-indol-3-yl)cyclohex-3-enamine (80): A solution of compound 79 (0.07 g, 0.273 mmol) in 1,2-dichloroethane (3 mL) was treated with AcOH (0.015 mL, 0.273 mmol), methylamine hydrochloride (0.018 g, 0.273 mmol), NaBH(OAc)$_3$ (0.086 g, 0.409 mmol) at room temperature and stirred for over night (14 h). The reaction was basified with 2 N NaOH (25 mL) and product was extracted into ethyl acetate (2×20 mL). The combined ethyl acetate layer was washed with brine (15 mL) and dried ($Na_2SO_4$). Solvent was evaporated and crude was purified by column chromatography (2 M $NH_3$ in methanol: $CH_2Cl_2$, 1:9) to obtain compound 80 (0.074 g, quantitative) as a solid. mp 208-210° C.; $^1H$ NMR (DMSO-$d_6$) δ 1.44-1.53 (m, 1H), 1.97-2.01 (m, 2H), 2.35 (s, 3H), 2.40-2.57 (m, 3H), 2.60-2.70 (m, 1H), 6.13 (brs, 1H), 7.54 (d, 1H, J=9.0 Hz), 7.63 (s, 1H), 8.00 (d, 1H, J=7.5 Hz), 8.67 (s, 1H), 11.85 (brs, 1H); ESI-MS m/z (%): 272 ($M^+$, 100).

tert-Butyl methyl(4-(5-nitro-1H-indol-3-yl)cyclohex-3-enyl)carbamate (81): A solution of compound 80 (0.1 g, 0.368 mmol) in dry 1,4-dioxane (3 mL) was treated with $Et_3N$ (0.1 mL, 0.737 mmol) followed by (Boc)$_2$O (0.084 g, 0.387 mmol) at room temperature and the resulting solution was stirred for over night (16 h). Solvent was evaporated and crude was purified by column chromatography (EtOAc: Hexanes, 1:1) to obtain compound 81 (0.135 g, quantitative) as a solid. mp 224-226° C.; $^1H$ NMR (DMSO-$d_6$) δ 1.42 (s, 9H), 1.81-1.87 (m, 2H), 2.29-2.45 (m, 2H), 2.60-2.70 (m, 2H), 2.74 (s, 3H), 4.10-4.16 (m, 1H), 6.17 (brs, 1H), 7.55 (d, 1H, J=9.0 Hz), 7.66 (s, 1H), 8.01 (dd, 1H, J=2.4, 9.0 Hz), 8.68 (d, 1H, J=2.1 Hz), 11.87 (s, 1H); ESI-MS m/z (%): 394 (M.Na$^+$, 100), 316 (44), 272 (82).

tert-Butyl 4-(5-amino-1H-indol-3-yl)cyclohex-3-enyl (methyl)carbamate (82): A solution of compound 81 (0.5 g, 1.364 mmol) in 2 M $NH_3$ in methanol (20 mL) was treated with Pd—C (0.05 g) and flushed with hydrogen gas. The reaction was stirred at room temperature for over night (16 h) under hydrogen atm. (balloon pressure). The solution was filtered using celite bed and washed with $CH_2Cl_2$:methanol (1:1, 3×20 mL). The solvent was evaporated and crude was purified by column chromatography (EtOAc: Hexanes, 1:1) to obtain compound 82 (0.46 g, quantitative) as a solid in 1:2 ratio of diastereomers. $^1H$ NMR (DMSO-$d_6$) δ 1.38, 1.41 (2s, 9H), 1.46-1.84 (m, 6H), 2.02-2.17 (m, 2H), 2.53-2.57 (m, 1H), 2.60-2.72 (2s, 3H), 3.82-3.85 (m, 1H), 4.41 (brs, 2H), 6.42-6.50 (m, 1H), 6.66-6.68 (m, 1H), 6.85-6.87, 6.99-7.06 (2m, 2H), 10.23, 10.28 (2s, 1H); ESI-MS m/z (%): 366 (M.Na$^+$, 8), 344 (MH$^+$, 10), 288 (100).

tert-Butyl methyl(4-(5-(thiophene-2-carboximidamido)-1H-indol-3-yl)cyclohexyl)carbamate (83): A solution of compound 82 (0.44 g, 1.281 mmol) in dry ethanol (20 mL) was treated with thiophene-2-carboximidothioic acid methyl ester hydroiodide (0.73 g, 2.562 mmol) at room temperature and stirred for 24 h. The solvent was evaporated and product was precipitated with ether (100 mL). The solid was dissolved into sat. $NaHCO_3$ sol.: $CH_2Cl_2$ (50 mL, 1:1). The org. layer was separated and aqueous layer was extracted with $CH_2Cl_2$ (2×25 mL). The combined $CH_2Cl_2$ layer was washed with brine (20 mL) and dried ($Na_2SO_4$). The solvent was evaporated and crude was purified by column chromatography (2M $NH_3$ in methanol: $CH_2Cl_2$, 5:95) to obtain compound 83 (0.425 g, 73%) as a foam in 1:2 ration of diastereomers. $^1H$ NMR (DMSO-$d_6$) δ 1.38-1.56 (m, 11H), 1.64-1.82 (m, 4H), 2.06-2.18 (m, 2H), 2.62-2.70 (m, 4H), 3.80-3.90 (m, 1H), 6.27 (brs, 1H), 6.62-6.66 (m, 1H), 6.95-7.11 (m, 3H), 7.22-7.29 (m, 1H), 7.59 (d, 1H, J=5.1 Hz), 7.71 (d, 1H, J=3.6 Hz), 10.59, 10.63 (2s, 1H); ESI-MS m/z (%): 453 (MH$^+$, 100).

Dihydrochloride salt of N-(3-(4-(methylamino)cyclohexyl)-1H-indol-5-yl)thiophene-2-carboximidamide (84): Compound 83 (0.2 g, 0.441 mmol) was treated with 1 N HCl solution at room temperature and the resulting solution was refluxed for 2 h. The reaction was brought to room temperature, filtered and washed with water (5 mL). The solvent was evaporated and crude was recrystallised from ethanol/ether to obtain compound 84 (0.175 g, 94%) as a solid in 1:2 ratio of diastereomers. $^1H$ NMR (DMSO-$d_6$) δ 1.52-1.56 (m, 2H), 1.81-2.16 (m, 6H), 2.50 (s, 3H), 2.75-2.80 (m, 1H), 3.00-3.05 (m, 1H), 7.08 (d, 1H, J=8.1 Hz), 7.24-7.40 (m, 2H), 7.50 (d, 1H, J=8.7 Hz), 7.70-7.72 (m, 1H), 8.15-8.19 (m, 2H), 8.58 (brs, 1H), 9.19 (brs, 2H), 9.65 (brs, 1H), 11.21, 11.26 (2s, 1H), 11.43 (s, 1H); ESI-MS m/z (%): 353 (MH$^+$ for free base, 100) 322 (85); ESI-HRMS calculated for $C_{20}H_{25}N_4S$ (MH$^+$ for free base), Calculated: 353.1808; Observed: 353.1794.

EXAMPLE 24

N-(3-(piperidin-4-yl)-1H-indol-5-yl)thiophene-2-carboximidamide (88)

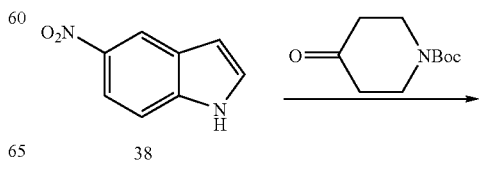

38

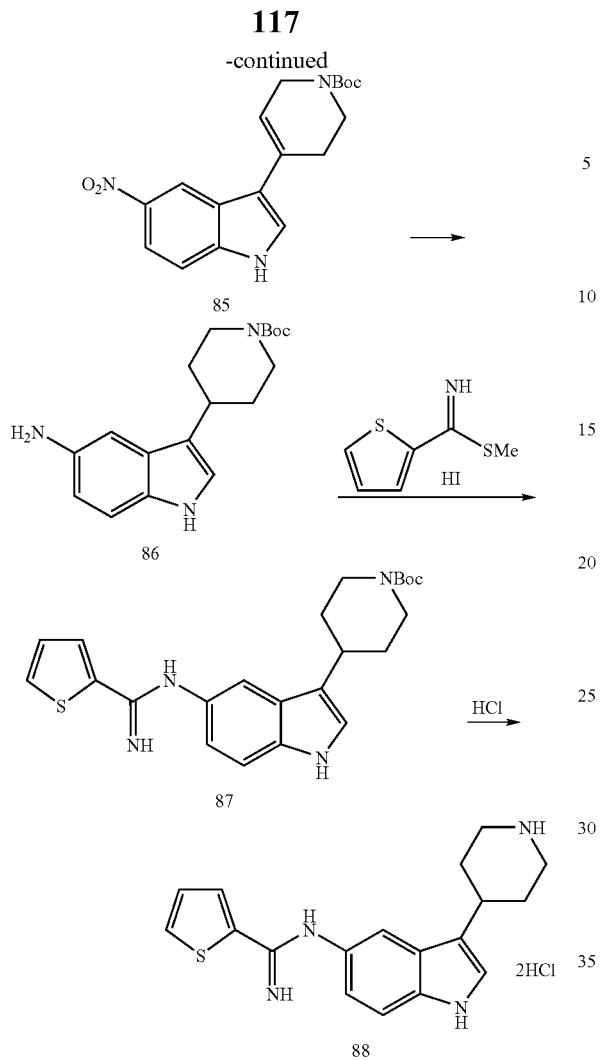

tert-Butyl 4-(5-nitro-1H-indol-3-yl)-5,6-dihydropyridine-1(2H)-carboxylate (85): A solution of 5-nitroindole (38) (2.0 g, 12.334 mmol) in dry ethanol (20 mL) was treated with pyrrolidine (3.08 mL, 37.002 mmol) followed by N-Boc-4-piperidone (4.91 g, 24.668 mmol) at room temperature and the resulting solution was refluxed for 3 days. The reaction was brought to room temperature, the solvent was evaporated and the crude product was purified by column chromatography (ethyl acetate:hexanes, 1:3) to obtain compound 85 (4.2 g, quantitative) as a solid. mp 210-212° C.; $^1$H NMR (DMSO-$d_6$) δ 1.36-1.43 (m, 11H), 3.57 (t, 2H, J=5.7 Hz), 4.08 (s, 2H), 6.20 (s, 1H), 7.56 (d, 1H, J=9.0 Hz), 7.71 (s, 1H), 8.02 (dd, 1H, J=2.1, 9.0 Hz), 8.71 (d, 1H, J=2.1, Hz), 11.93 (s, 1H); ESI-MS m/z (%): 366 (M.Na$^+$, 100), 288 (52).

tert-Butyl 4-(5-amino-1H-indol-3-yl)piperidine-1-carboxylate (86): A solution of compound 85 (0.5 g, 1.456 mmol) in 2 M NH$_3$ in methanol (15 mL) was treated with Pd—C (0.05 g) and purged with hydrogen gas. The reaction was stirred under hydrogen atm. for overnight. The solution was filtered through a celite bed and washed with methanol:CH$_2$Cl$_2$ (1:1, 2 20 mL). The combined organic layer was evaporated to obtain compound 86 (0.46 g, quantitative) as a solid. mp 205-207° C.; $^1$H NMR (DMSO-$d_6$) δ 1.41-1.53 (m, 11H), 1.87-1.91 (m, 2H), 2.73-2.85 (m, 3H), 4.03-4.07 (m, 2H), 4.43 (s, 2H), 6.45 (dd, 1H, J=1.8, 8.4 Hz), 6.69 (d, 1H, J=1.5 Hz), 6.90 (d, 1H, J=2.4 Hz), 7.01 (d, 1H, J=8.4 Hz), 10.28 (s, 1H); ESI-MS m/z (%): 338 (M.Na$^+$, 23), 316 (MH$^+$, 11), 216 (100).

tert-Butyl 4-(5-(thiophene-2-carboximidamido)-1H-indol-3-yl)piperidine-1-carboxylate (87): A solution of compound 86 (0.45 g, 1.426 mmol) in dry ethanol (25 mL) was treated with thiophene-2-carboximidothioic acid methyl ester hydroiodide (0.81 g, 2.853 mmol) at room temperature and resulting solution was stirred for 24 h. The solvent was evaporated, crude was diluted with sat. NaHCO$_3$ solution (25 mL) and CH$_2$Cl$_2$ (50 mL). The organic layer was separated and aqueous layer was extracted into CH$_2$Cl$_2$ (2 25 mL). The combined organic layer was washed with brine (20 mL) and dried (Na$_2$SO$_4$). The solvent was evaporated and the crude product was purified by column chromatography on silica gel (2 M NH$_3$ in methanol: CH$_2$Cl$_2$, 3:97) to obtain compound 87 (0.6 g, quantitative) as a foam. $^1$H NMR (DMSO-$d_6$) δ 1.40-1.56 (m, 11H), 1.90-1.94 (m, 2H), 2.86-2.94 (m, 3H), 4.02-4.06 (m, 2H), 6.26 (s, 1H), 6.64 (dd, 1H, J=1.2, 8.4 Hz), 6.99 (s, 1H), 7.05 (d, 1H, J=1.8 Hz), 7.09 (dd, 1H, J=3.6, 4.9 Hz), 7.27 (d, 1H, J=8.4 Hz), 7.59 (d, 1H, J=5.1 Hz), 7.71 (d, 1H, J=3.3 Hz), 10.63 (s, 1H); ESI-MS m/z (%): 425 (MH$^+$, 100).

Dihydrochloride salt of N-(3-(piperidin-4-yl)-1H-indol-5-yl)thiophene-2-carboximidamide (88): A solution of compound 87 (0.3 g, 0.706 mmol) was treated with 1 N HCl solution (20 mL) and refluxed for 2 h. The reaction was brought to room temperature, solid was filtered off and washed with water (5 mL). The water layer was evaporated and crude was recrystallised from ethanol/ether to obtain compound 88 (0.29 g, 72%) as a solid. Decomposed at 230° C. $^1$H NMR (DMSO-$d_6$) δ 1.90-2.10 (m, 4H), 3.00-3.13 (m, 3H), 3.31-3.35 (m, 2H), 7.11 (d, 1H, J=8.7 Hz), 7.28 (d, 1H, J=1.8 Hz), 7.39 (t, 1H, J=4.5 Hz), 7.53 (d, 1H, J=8.7 Hz), 7.77 (s, 1H), 8.16-8.20 (m, 2H), 8.58 (s, 1H), 9.18 (brs, 2H), 9.68 (s, 1H), 11.29 (s, 1H), 11.49 (s, 1H); ESI-MS m/z (%): 325 (MH$^+$, free base, 100), 242 (34), 163 (70); HRMS Calculated for C$_{18}$H$_{21}$N$_4$S (MH$^+$); Calculated: 325.1494; Found: 325.1481.

EXAMPLE 25

N-(3-(8-methyl-8-azabicyclo[3.2.1]oct-3-en-3-yl)-1H-indol-5-yl)thiophene-2-carboximidamide (90)

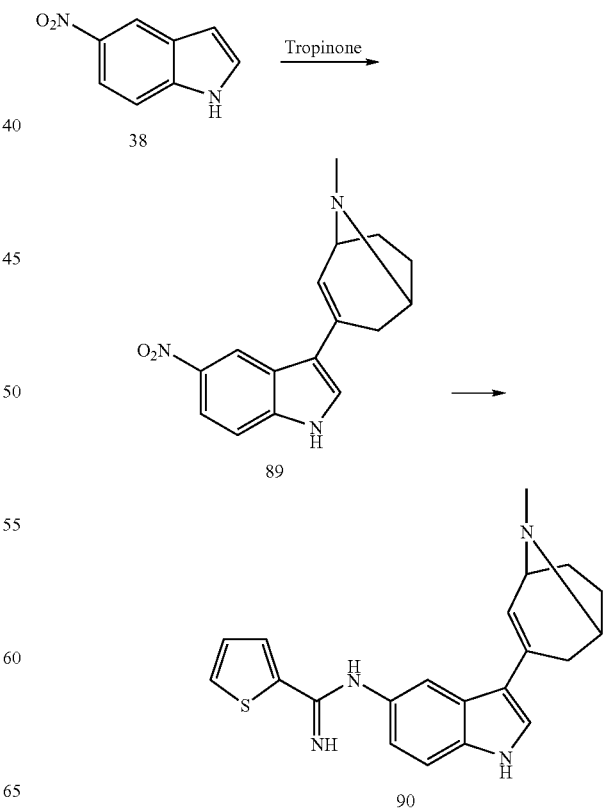

3-(8-Methyl-8-azabicyclo[3.2.1]oct-3-en-3-yl)-5-nitro-1H-indole (89): A solution of 5-nitroindole (38) (0.5 g, 3.083 mmol) in glacial acetic acid (10 mL) was treated with tropinone (0.85 g, 6.617 mmol), followed by 2 M $H_3PO_4$ in glacial acetic acid (5 mL) at 100° C. and the resulting solution was stirred at same temperature for 24 h. The reaction was brought to room temperature, poured in to ice-cold 10% $NH_4OH$ solution (50 mL) and product was extracted into $CH_2Cl_2$ (2 25 mL). The combined $CH_2Cl_2$ layer was washed with brine (15 mL) and dried ($Na_2SO_4$). The solvent was evaporated and crude material was purified by column chromatography on silica gel (2 M $NH_3$ in methanol: $CH_2Cl_2$, 1:9) to obtain compound 89 (0.27 g, 31%) as a solid. mp 234-236° C.; $^1H$ NMR (DMSO-$d_6$) δ 1.51-1.60 (m, 1H), 1.79-1.86 (m, 1H), 1.95-2.14 (m, 4H), 2.32 (s, 3H), 2.76-2.83 (m, 1H), 3.43 (t, 1H, J=5.4 Hz), 6.31 (d, 1H, J=5.1 Hz), 7.54 (d, 1H, J=8.7 Hz), 7.61 (s, 1H), 8.01 (dd, 1H, J=2.1, 9.0 Hz), 8.68 (d, 1H, J=2.4 Hz), 11.86 (s, 1H); ESI-MS m/z (%): 284 ($MH^+$, 100).

N-(3-(8-Methyl-8-azabicyclo[3.2.1]oct-3-en-3-yl)-1H-indol-5-yl)thiophene-2-carboximidamide (90): A solution of compound 89 (0.25 g, 0.882 mmol) in dry ethanol (10 mL) was treated with Pd—C (0.025 g) and purged with hydrogen gas. The reaction was stirred under hydrogen atm. (balloon pressure) for overnight (14 h). The solid was filtered off using celite bed and washed with ethanol (2 5 mL). The combine d ethanol layer was treated with thiophene-2-carboximidothioic acid methyl ester hydroiodide (0.5 g, 1.764 mmol) at room temperature and stirred for 24 h. Ethanol was evaporated and crude material was basified with sat. $NaHCO_3$ solution (20 mL) and product was extracted into $CH_2Cl_2$ (2 25 mL). The combined $CH_2Cl_2$ layer was washed with brine (15 mL) and dried ($Na_2SO_4$). The solvent was evaporated and crude was purified by column chromatography on silica gel (2 M $NH_3$ in methanol: $CH_2Cl_2$, 1:9) to obtain compound 90 (0.14 g, 44%) as a solid. mp 93-95° C.; $^1H$ NMR (DMSO-$d_6$) δ 1.60-1.65 (m, 1H), 1.84-1.90 (m, 1H), 2.02-2.26 (m, 4H), 2.41 (s, 3H), 2.83-2.89 (m, 1H), 3.46-3.55 (m, 1H), 6.20 (brs, 2H), 6.67 (d, 1H, J=7.8 Hz), 7.10 (s, 1H), 7.23-7.31 (m, 3H), 7.60-7.72 (m, 2H), 10.99 (s, 1H); ESI-MS m/z (%): 363 ($MH^+$, 65), 182 (100), 119 (48); ESI-HRMS calculated for $C_{21}H_{23}N_4S$ ($MH^+$), Calculated: 363.1633; Observed: 363.1637.

EXAMPLE 26

(R)—N-(3-((1-Methylpyrrolidin-2-yl)methyl)-1H-indol-5-yl)thiophene-2-carboximidamide (97)

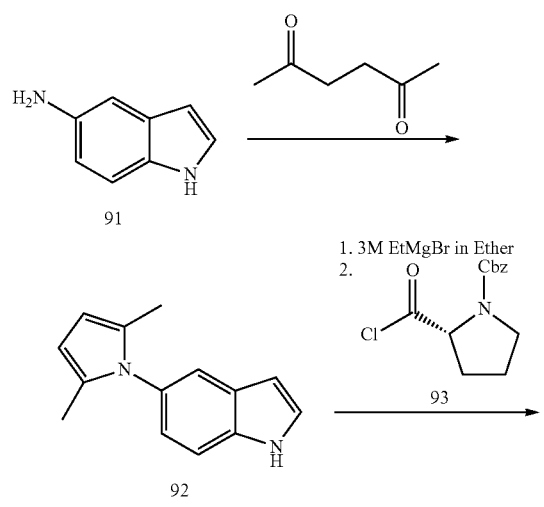

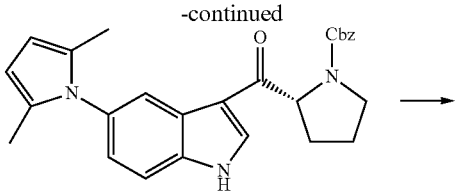

94

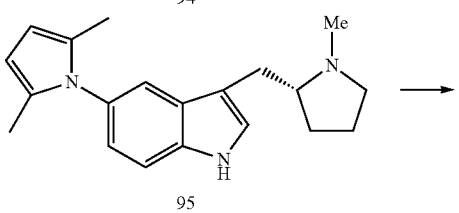

95

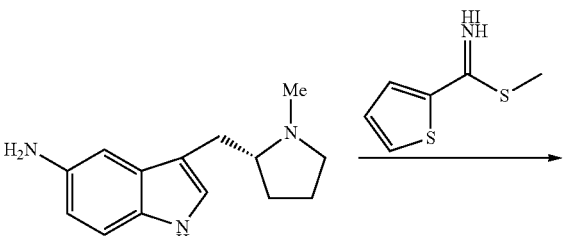

96

97

5-(2,5-dimethyl-1H-pyrrol-1-yl)-1H-indole (92) (Macor et. al. *J. Org. Chem.* 1994, 59(24), 7496): To a 250 mL argon purged round bottom flask containing a magnetic stirbar and a solution of 5-aminoindole (91) (15.00 g, 113 mmol) in anhydrous toluene (50 mL) was added acetonylacetone (25.4 mL, 216 mmol, 1.9 eq). The flask was fitted with a Dean-Stark trap with a 10 mL reservoir filled with toluene. The uppermost portion of the flask and the condensing arm of the trap were wrapped with foil and the reaction vessel placed into an oil bath preheated to a temperature of 125° C. The dark brown solution was allowed to stir under a continuous flow of argon at this temperature for 45 minutes, followed by draining of the trap solvent reservoir. After a total of 4 hours, TLC (5% ethyl acetate, 95% hexanes) revealed the reaction was complete. The reaction was cooled gradually to room temperature overnight. The reaction was poured onto a plug of silica gel and the solvent pulled through by vacuum filtration. The silica was washed with hexanes (200 mL). A white precipitate started to form almost immediately in the filtrate. The silica was washed again with a solution of 6% diethyl ether, 94% hexanes (800 mL). Crystals were collected from both washes, and the filtrates combined. The plug was washed with ether (150 mL) and the filtrate combined with the washes. The combined filtrates were concentrate to afford a brown oil. The oil was purified on the Biotage SP-1 (0-8% ether in hexanes). TLC revealed that all products were identical (white solids) and all products were combined. (Yield: 17.10 g of white solid, compound 92 (72%). $^1H$ NMR (CDCl$_3$) δ: 8.26 (bs, NH), 7.48-7.48 (d, 1H, J=1.2 Hz), 7.46-7.43 (d, 1H, J=8.7 Hz), 7.31-7.29 (t, 1H, J=2.7), 7.04-7.00 (dd, 1H, J=2.1, 8.4), 6.61 (s, 1H), 5.92 (s, 2H), 2.05 (s, 6H). MS-ESI m/z (%): 211 ($M^+$, 100).

(R)-benzyl 2-(5-(2,5-dimethyl-1H-pyrrol-1-yl)-1H-indole-3-carbonyl)pyrrolidine-1-carboxylate (94) (Macor et. al. *J. Org. Chem.* 1994, 59(24), 7496):

a) Formation of (R)-benzyl 2-(chlorocarbonyl)pyrrolidine-1-carboxylate (93): To an argon purged round bottom flask containing N-(benzyloxycarbonyl)-D-proline (10.00 g, 40.1 mmol) was added anhydrous dichloromethane (120 mL). The translucent reaction was treated with DMF (0.5 mL). Oxalyl chloride (5.25 mL, 60.2 mmol) was added gradually, resulting in effervescence. The react was stirred at room temperature under argon for 4 hours. The reaction was concentrate under reduced pressure and dried overnight under high vacuum to give an oil. The material was used as is in the next step.

b) To an argon purged 500 mL round bottom flask fitted with a magnetic stirbar and containing 93 (16.86 g, 80.2 mmol) was added anhydrous benzene (100 mL). The solution was placed in an ice-water bath and stirred for 10 minutes. A 3N ethyl magnesium bromide solution in diethyl ether (28 mL, 84 mmol) was added and the reaction stirred for 30 minutes, resulting in a dark yellow solution. A solution of 93 in benzene (50 mL) was added slowly by cannula over a period of 5 minutes. The reaction was stirred in an ice-water bath for 2 hours, becoming dark red in colour. The reaction was transferred to a separatory funnel and treated with saturated aqueous sodium bicarbonate solution (50 mL) and ethyl acetate (50 mL). The aqueous layer became milky and translucent. Additional sodium bicarbonate solution (30 mL) did not allow the precipitate to dissolve, however the phase boundary between the layers became more obvious. The aqueous layer was removed, and the organic layer poured out as a yellow solution by decantation. The aqueous layer was filtered to remove the solid, and the resulting colourless solvent was partitioned twice more with ethyl acetate (2×30 mL). The combined organics were washed with brine, dried over magnesium sulfate and filtered. The filtrate was concentrate to afford a yellow oil. The oil was treated with ether (100 mL). After stirring for 15 minutes an off white solid had formed. The reaction was stirred for 1 hr. The precipitate which formed was collected by vacuum filtration and dried under high vacuum. It was purified by filtration through a plug of silica gel using ether, followed by ethyl acetate, as eluents. Yield: 9.5 g of white solid, compound 94 (from precipitate). $^1$H NMR (CDCl$_3$) δ: 9.54, 9.20 (2s, 1H), 8.29-8.28 and 8.15-8.15 (2d, 1H, J=1.2 Hz), 7.81-7.80 and 7.76-7.75 (2d, 1H, J=2.7 Hz), 7.42-7.30 (m, 4H), 7.13-6.93 (m, 3H), 5.90 (bs, 2H), 5.25-4.97 (m, 3H), 3.80-3.58 (m, 2H), 2.41-2.20 (m, 1H), 2.16-1.88 (m, 2H), 2.04-1.99 (d, 8H), 1.64 (m, 1H). MS-ESI m/z (%) 442 (M$^+$, 100).

(R)-5-(2,5-dimethyl-1H-pyrrol-1-yl)-3-((1-methylpyrrolidin-2-yl)methyl)-1H-indole (95) (Macor et. al. *J. Org. Chem.* 1994, 59(24), 7496): To an argon purged round bottom flask containing a magnetic stirbar and a solution of lithium aluminum hydride (1.93 g, 50.9 mmol) in anhydrous THF (20 mL) was added a solution of 94 (5.00 g, 11.3 mmol) in anhydrous THF (30 mL). The flask was fitted with a condenser and placed in an oil bath. The reaction was heated to 75° C. and stirred at reflux with an argon flow for 4.5 hrs. The reaction was judged to be complete by TLC (10% 2M NH$_3$ in methanol, 90% CH$_2$Cl$_2$) and was cooled gradually to room temperature. The reaction was cooled further by placing the flask in an ice-water bath, followed by the portion-wise addition of solid sodium sulfate decahydrate (20 g). The reaction was diluted with cold water (50 mL) followed by ethyl acetate (50 mL) and the mixture stirred under argon for 17 hrs. The reaction was transferred into a separatory funnel. Residual solid in the flask was washed with both water and ethyl acetate and the washes transferred to the funnel. The aqueous layer was extracted twice more with ethyl acetate. The combined organics were washed with brine, dried over sodium sulfate and concentrated after decanting to afford a yellow oil. The product was purified by silica gel column chromatography (10% 2M NH$_3$ in methanol, 90% CH$_2$Cl$_2$) to afford the desired product as well as some recovered starting material. Yield: 1.827 g of white solid, compound 95 (52.5%). 1H NMR (CDCl$_3$) δ: 8.26 (bs, 1H), 7.45-7.44 (d, 1H, J=1.5 Hz), 7.41-7.38 (d, 1H, 8.7 Hz), 7.13-7.12 (d, 1H, J=2.1 Hz), 7.02-6.99 (dd, 1H, J=1.8, 8.1 Hz), 5.92 (bs, 2H), 3.49 (s, 1H), 3.20-3.12 (m, 2H), 2.68-2.61 (q, 1H, J=9.3, 14.1 Hz), 2.52-2.40 (m, 1H), 2.44 (s, 3H), 2.28-2.19 (q, 1H, J=9, 17.1 Hz), 2.05 (bs, 6H), 1.89-1.56 (m, 4H). MS-ESI m/z (%): 308 (M$^+$, 100).

(R)-3-((1-methylpyrrolidin-2-yl)methyl)-1H-indol-5-amine (96) (Macor et. al. *J. Org. Chem.* 1994, 59(24), 7496): To an argon purged round bottom flask fitted with a magnetic stirbar and containing a yellow solution of 95 (1.80 g, 5.85 mmol) in anhydrous 2-propanol (50 mL) and water (15 mL) was added solid hydroxylamine hydrochloride (8.14 g, 117.1 mmol) in one portion. Triethylamine (8.15 mL, 58.5 mmol) was added via syringe and the flask was fitted with a condenser. The vessel was placed in an oil bath and heated to reflux. The reaction was stirred at reflux under argon for 5 hours. TLC (10% 2M NH$_3$ in methanol, 90% CH$_2$Cl$_2$) revealed some starting material was still present. The reaction was cooled to room temperature and stirred overnight. The reaction was returned to reflux and stirred for an additional 2 hours. The reaction was cooled to room temperature and sodium hydroxide pellets (2.34 g, 58.5 mmol) were added slowly. The reaction was stirred vigorously for 17.5 hours and the orange solution became yellow with a white precipitate. The reaction was filtered through celite, followed by washing of the celite with 2-propanol (40 mL) and concentration of the filtrate. The residue was purified by column chromatography (10% 2M NH$_3$ in methanol, 90% CH$_2$Cl$_2$) using a silica gel plug approximately 10 cm in diameter by 15 cm in height to afford an orange oil. This product was partitioned between brine (5 mL) and ethyl acetate (20 mL). The organic layer was dried with anhydrous sodium sulfate before being decanted. Concentration afforded an orange oil, compound 96 (815 mg, 60%).

(R) —N-(3-((1-methylpyrrolidin-2-yl)methyl)-1H-indol-5-yl)thiophene-2-carboximidamide dihydrochloride (97): To an argon purged round bottom flask was charged 96 (350 mg, 1.53 mmol) and methyl thiophene-2-carbimidothioate hydroiodide (870 mg, 3.05 mmol) followed by absolute ethanol (10 mL). The reaction was stirred using a magnetic stirbar for 18 hours at room temperature. TLC (10% 2M ammonia in methanol/90% dichloromethane) revealed all starting amine had reacted. The reaction as treated with ether (70 mL) and the resulting yellow precipitate was collected by vacuum filtration and washed with ether. The precipitate was washed from the filter using a solution of 1N sodium hydroxide (10 mL) followed by ethyl acetate (20 mL). This filtrate was transferred to a separatory funnel, and after agitation, the aqueous phase removed. The organics were collected, and the aqueous washed twice more with ethyl acetate (2×10 mL). The combined organic fractions were washed with brine, dried over magnesium sulfate, filtered and concentrated to afford a yellow oil. The product was purified by silica gel column chromatography (5-10% 2M ammonia in methanol/95-90% dichloromethane) to afford a yellow oil. The purified product was dissolved in anyhydrous dichloromethane (5 mL) and treated with 1M hydrogen chloride in ether (5 mL). After stirring for 30 minutes the precipitate was collected by vacuum filtration. The precipitate was washed with ether, dried under suction and dried further under high vacuum to provide compound 97 (470 mg of yellow solid, 74.7%). 1H NMR (DMSO-d$_6$) δ: 10.587 (s, 1H), 7.71-7.70 (d, J=3 Hz, 1H), 7.59-7.58 (d, J=4.8 Hz, 1H), 7.28-7.25 (d, J=8.4 Hz, 1H), 7.11-7.10 (d, J=4.5 Hz, 1H), 7.07-7.06 (d, J=1.5 Hz, 1H), 6.93 (s, 1H), 6.64-6.62 (d, J=8.1 Hz, 1H), 6.21 (bs, 2H), 3.18-3.16 (d, J=5.1 Hz, 1H), 3.03-2.94 (m, 2H), 2.44-2.33 (m, 4H), 2.14-2.05 (m, 1H), 1.71-1.30 (m, 4H). ESI-MS m/z (%): 339 (M+1, 100).

EXAMPLE 27

N-(3-(4-(methylamino)cyclohex-1-enyl)-1H-indol-5-yl) thiophene-2-carboximidamide (100)

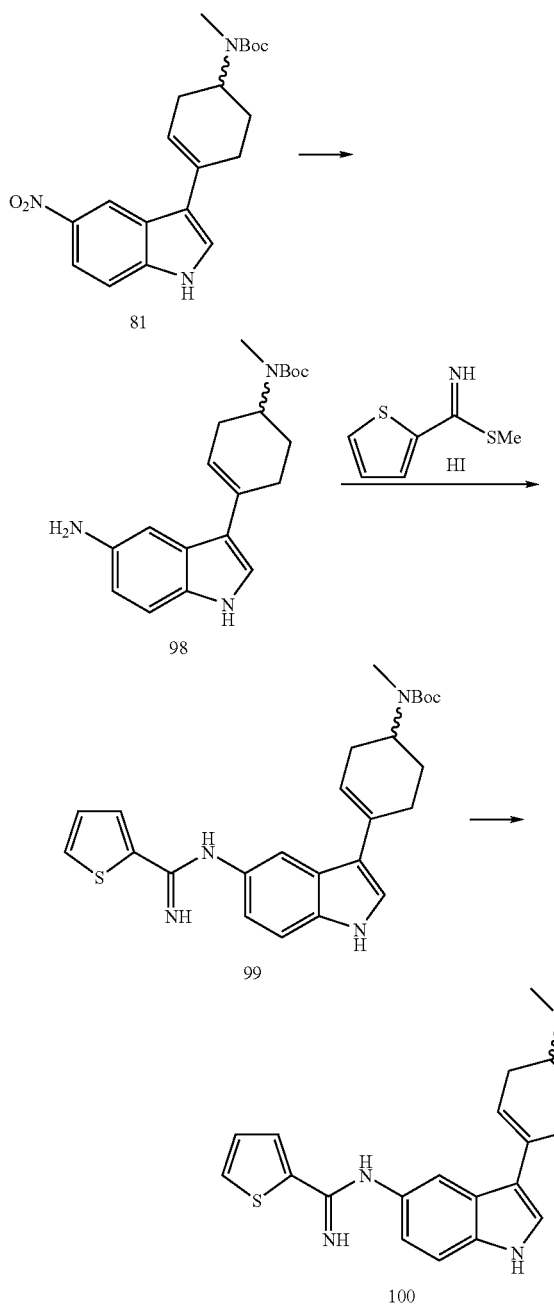

tert-Butyl methyl(4-(5-nitro-1H-indol-3-yl)cyclohex-3-enyl)carbamate (81): Please see Example 23 for synthetic details.

tert-Butyl 4-(5-amino-1H-indol-3-yl)cyclohex-3-enyl(methyl)carbamate (98): A solution of compound 81 (0.5 g, 1.346 mmol) in dry methanol (20 mL) was treated with hydrazine hydrate (0.41 mL, 13.461 mmol) followed by Raney-Ni (0.1 g) and the resulting mixture was refluxed for 30 min. The reaction was brought to room temperature, filtered through celite bed, washed with $CH_2Cl_2$:methanol (1:1, 3 20 mL). The combined organic layer was evaporated and crude was purified by column chromatography (EtOAC: Hexanes, 1:1) to obtain compound 98 (0.43 g, 94%) as a foam. $^1$H NMR (DMSO-$d_6$) δ: 1.38-1.41 (m, 11H), 1.76-1.86 (m, 2H), 2.14-2.42 (m, 2H), 2.73 (s, 3H), 4.05-4.15 (m, 1H), 4.49 (s, 2H), 6.00 (brs, 1H), 6.48 (dd, 1H, J=1.8, 8.2 Hz), 6.99 (d, 1H, J=1.5 Hz), 7.05 (d, 1H, J=8.4 Hz), 7.16 (d, 1H, J=2.7 Hz), 10.60 (s, 1H); ESI-MS m/z (%): 364 (M+Na$^+$, 7), 342 (MH$^+$, 11), 286 (100).

tert-Butyl methyl(4-(5-(thiophene-2-carboximidamido)-1H-indol-3-yl)cyclohex-3-enyl)carbamate (99): A solution of compound 98 (0.415 g, 1.215 mmol) in dry ethanol (20 mL) was treated with thiophene-2-carboximidothioic acid methyl ester hydroiodide (0.693 g, 2.430 mmol) at room temperature and the resulting solution was stirred for 24 h. The solvent was evaporated and crude was diluted with sat. $NaHCO_3$ solution (25 mL) and $CH_2Cl_2$ (50 mL). The organic layer was separated and aqueous layer was extracted with $CH_2Cl_2$ (2 25 mL). The combined organic layer was washed with brine (20 mL) and dried ($Na_2SO_4$). The solvent was evaporated and crude product was purified by column chromatography on silica gel (2M $NH_3$ in methanol: $CH_2Cl_2$, 5:95) to obtain compound 99 (0.37 g, 68%) as a foam. $^1$H NMR (DMSO-$d_6$) δ: 0.85 (t, 1H, J=7.2 Hz), 1.20-1.26 (m, 1H), 1.40 (s, 9H), 1.77-1.87 (m, 2H), 2.22-2.40 (m, 2H), 2.72 (s, 3H), 4.06-4.16 (m, 1H), 6.06 (s, 1H), 6.28 (brs, 1H), 6.66 (d, 1H, J=8.4 Hz), 7.10 (t, 1H, J=4.2 Hz), 7.22 (s, 1H), 7.25-7.32 (m, 2H), 7.60 (d, 1H, J=4.8 Hz), 7.72 (d, 1H, J=3.3 Hz), 10.94 (s, 1H); ESI-MS m/z (%): 451 (MH$^+$, 100).

N-(3-(4-(methylamino)cyclohex-1-enyl)-1H-indol-5-yl) thiophene-2-carboximidamide (100): A solution of compound 99 (0.35 g, 0.776 mmol) was treated with 20% TFA in $CH_2Cl_2$ (20 mL) at 0° C. and stirring was continued for 1 h at the same temperature. The solvent was evaporated and crude was diluted with 10% aq. $NH_3$ (15 mL) and product was extracted into $CH_2Cl_2$ (3 20 mL). The combined $CH_2Cl_2$ layer was washed with brine (10 mL) and dried ($Na_2SO_4$). The solvent was evaporated and the crude product was purified by column chromatography (2 M $NH_3$ in methanol: $CH_2Cl_2$, 1:9) to obtain compound 100 (0.2 g, 74%) as a solid. mp 167-169° C.: $^1$H NMR (DMSO-$d_6$) δ: 1.39-1.47 (m, 2H), 1.88-1.96 (m, 3H), 2.33 (s, 3H), 2.40-2.46 (m, 1H), 2.57-2.61 (m, 1H), 6.01 (s, 1H), 6.19 (brs, 2H), 6.65 (dd, 1H, J=1.5, 8.2 Hz), 7.09 (dd, 1H, J=4.2, 4.9 Hz), 7.20 (s, 1H), 7.28-7.31 (m, 2H), 7.59 (d, 1H, J==4.2 Hz), 7.71 (d, 1H, J=3.3 Hz), 10.87 (s, 1H); ESI-MS m/z (%): 351 (MH$^+$, 66), 320 (54), 160 (63), 119 (100); ESI-HRMS calculated for $C_{20}H_{23}N_4S$ (MH$^+$), Calculated: 351.1654. Observed: 351.1637.

EXAMPLE 28

(S)—N-(3-((1-methylpyrrolidin-2-yl)methyl)-1H-indol-5-yl)thiophene-2-carboximidamide (105)

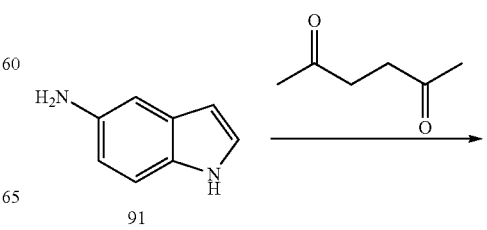

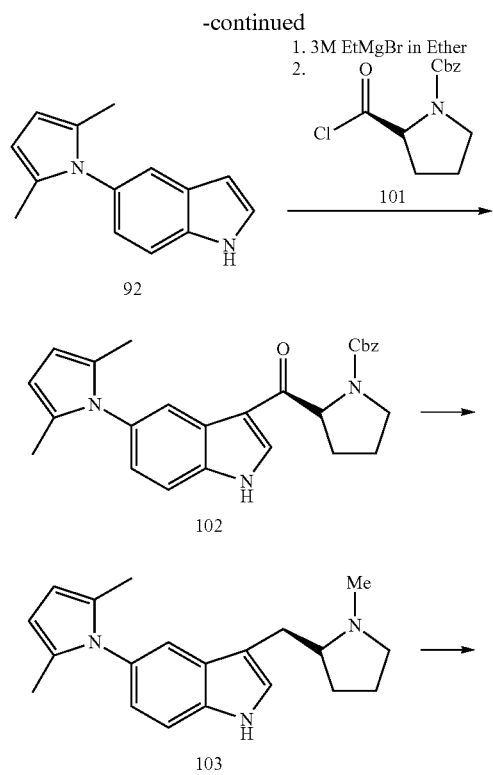

thesis of 95, Example 26, compound 103 was isolated as a white foam, 1.26 grams (44%). 1H NMR (CDCl$_3$) δ 8.11 (bs, 1H), 7.45-7.44 (d, 1H, J=1.5 Hz), 7.41-7.38 (d, 1H, 8.7 Hz), 7.12-7.11 (d, 1H, J=2.1 Hz), 7.03-6.99 (dd, 1H, J=1.8, 8.1 Hz), 5.92 (bs, 2H), 3.18-3.09 (m, 2H), 2.65-2.57 (q, 1H, J=9.3, 14.1 Hz), 2.42 (s, 4H), 2.28-2.19 (q, H, J=9, 17.1 Hz), 2.05 (s, 6H), 1.89-1.56 (m, 4H).

(S)-3-((1-methylpyrrolidin-2-yl)methyl)-1H-indol-5-amine (104). In a similar fashion to the synthesis of 96, Example 26, compound 104 was isolated as a brown oil, 149 mg (86%). 1H NMR (CDCl$_3$) is consistent with previous literature (Macor et. al. *J. Org. Chem.* 1994, 59(24), 7496).

(S)—N-(3-((1-Methylpyrrolidin-2-yl)methyl)-1H-indol-5-yl)thiophene-2-carboximidamide (105): In a similar fashion to the synthesis of 97, Example 26, treatment of 105 with methyl thiophene-2-carbimidothioate hydroiodide in ethanol gave the final product after purification as an orange solid (62 mg, 77%). 1H NMR (HCl salt) (DMSO-d6) (11.45 (d, J=19.8 Hz, 1H), 10.89 (m, 1H), 9.69 (bs, 1H), 8.63 (bs, 1H), 8.19-8.17 (d, J=4.2 Hz, 2H), 7.72-7.69 (m, 1H), 7.56-7.53 (d, J=8.4 Hz, 1H), 7.48-7.47 (d, 31.5 Hz, 1H), 7.41-7.38 (t, J=4.5 Hz, 1H), 7.17-7.14 (d, J=8.4 Hz, 1H), 3.58 (m, 2H), 3.43-3.37 (m, 1H), 3.17 (s, 1H), 3.11-2.99 (m, 2H), 2.81-2.80 (d, J=4.8 Hz, 3H), 2.10-1.70 (m, 5H), 1.28-1.23 (m, 3H), 0.90-0.85 (m, 2H). ESI-MS: MH$^+$=339 (100).

EXAMPLE 29

Preparation of (R)—N-(3-((1-Methylpyrrolidin-2-yl)methyl)-1H-indol-5-yl)furan-2-carboximidamide (106)

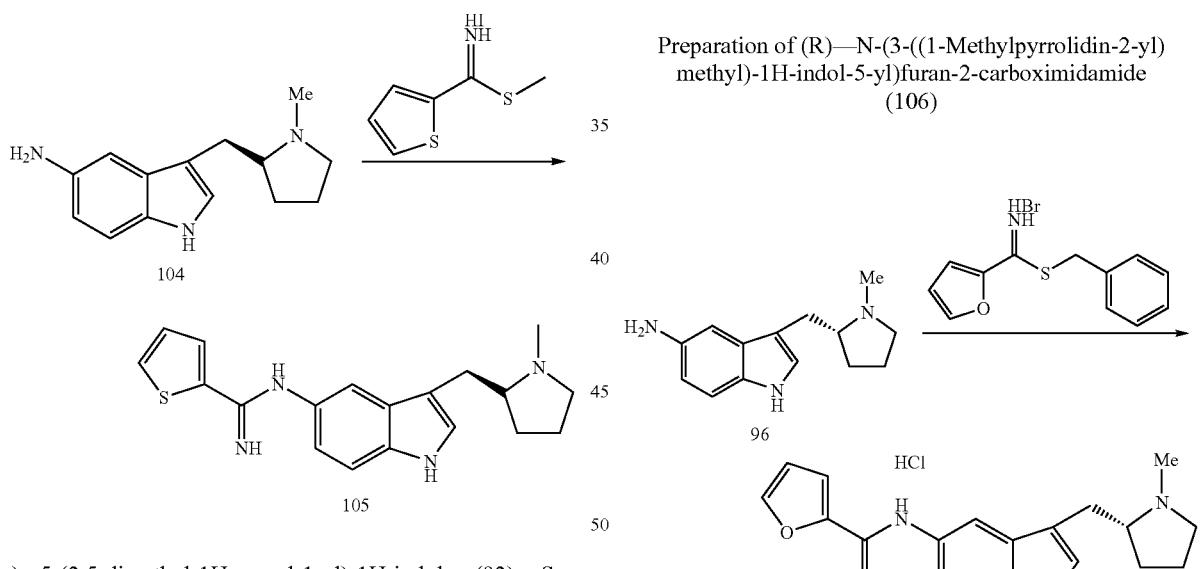

a) 5-(2,5-dimethyl-1H-pyrrol-1-yl)-1H-indole (92): See Example 26 for experimental details.
b) (S)-Benzyl 2-(5-(2,5-dimethyl-1H-pyrrol-1-yl)-1H-indole-3-carbonyl)pyrrolidine-1-carboxylate (102): (Macor et. al. *J. Org. Chem.* 1994, 59(24), 7496). In a similar fashion to the synthesis of 94, Example 26, compound 102 was isolated as an off white foam (4.35 g, 49%). $^1$H NMR (CDCl$_3$) δ: 9.46, 9.12 (2s, 1H), 8.28-8.28 and 8.16-8.16 (2d, 1H, J=1.2 Hz), 7.86-7.85 and 7.78-7.77 (2d, 1H, J=2.7 Hz), 7.44-7.34 (m, 4H), 7.14-6.96 (m, 3H), 5.90 (bs, 2H), 5.25-4.97 (m, 3H), 3.80-3.58 (m, 2H), 2.41-2.20 (m, 1H), 2.16-1.88 (m, 2H), 2.04-1.99 (d, 8H), 1.64 (m, 1H). MS-ESI m/z (%): 442 (M$^+$, 100).

(S)-5-(2,5-dimethyl-1H-pyrrol-1-yl)-3-((1-methylpyrrolidin-2-yl)methyl)-1H-indole (103): (Macor et. al. *J. Org. Chem.* 1994, 59(24), 7496).). In a similar fashion to the syn- (R)-3-((1-Methylpyrrolidin-2-yl)methyl)-1H-indol-5-amine) (96): See Example 26 for experimental details.

(R)—N-(3-((1-Methylpyrrolidin-2-yl)methyl)-1H-indol-5-yl)furan-2-carboximidamide (106): In a like fashion to compound 97, Example 26, using benzyl furan-2-carbimidothioate hydrobromide generated the title compound 106. (brown solid, 86 mg, 51.8% yield). 1H NMR (DMSO-d$_6$) δ: 10.68 (s, 1H), 7.84 (s, 1H), 7.31-7.28 (d, J=8.4 Hz, 1H), 7.28 (s, 1H), 7.11 (s, 1H), 7.07-7.06 (d, J=2.7 Hz, 1H), 6.74-6.71 (d, J=6.9 Hz, 1H), 6.65 (s, 1H), 3.18-3.16 (d, J=4.5 Hz, 1H),

EXAMPLE 30

(S)—N-(3-((1-methylpyrrolidin-2-yl)methyl)-1H-indol-5-yl)furan-2-carboximidamide dihydrochloride (107)

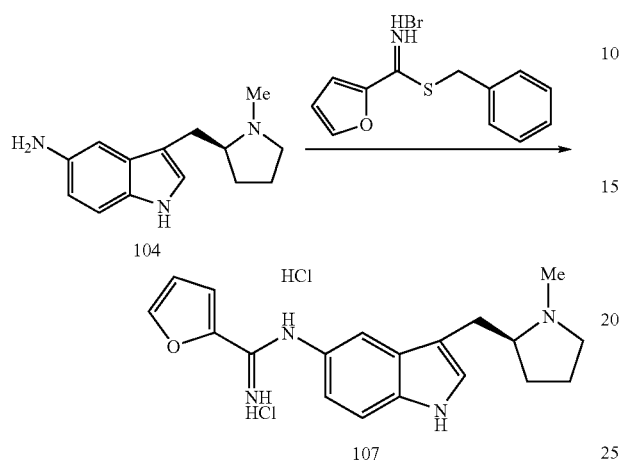

(S)-3-((1-Methylpyrrolidin-2-yl)methyl)-1H-indol-5-amine) (104): See Example 28 for experimental details.

(S)—N-(3-((1-methylpyrrolidin-2-yl)methyl)-1H-indol-5-yl)furan-2-carboximidamide dihydrochloride (107): In a like fashion to compound 105, Example 28, using benzyl furan-2-carbimidothioate hydrobromide generated the title compound 107 as pale orange solid (63 mg, 25%). $^1$H NMR (di-HCl salt) (DMSO-$d_6$) δ: 11.60 (s, 1H), 11.41-11.40 (d, J=1.2 Hz, 1H), 11.09 (bs, 1H), 9.71 (bs, 1H), 8.66 (bs, 1H), 8.25 (s, 1H), 7.99-7.97 (d, J=3.6 Hz, 1H), 7.70 (s, 1H), 7.55-7.52 (d, J=8.7 Hz, 1H), 7.48-7.47 (d, J=1.8 Hz, 1H), 7.13-7.10 (dd, J=1.8,9 Hz, 1H), 6.94-6.92 (dd, J=1.2, 3.6 Hz, 1H), 3.74 (m, 3H), 3.61-3.54 (m, 3H), 3.17 (s, 1H), 3.43-3.37 (dd, J=4.8, 13.8 Hz, 1H), 3.17 (s, 2H), 3.12-2.98 (m, 2H), 2.80-2.79 (d, J=4.5 Hz, 3H), 2.10-1.70 (m, 5H), 1.28-1.23 (m, 3H), 0.90-0.85 (m, 2H).

EXAMPLE 31

N-(3-(1-methylpyrrolidin-3-yl)-1H-indol-5-yl)thiophene-2-carboximidamide (110) and N-(3-(1-methylpyrrolidin-3-yl)-1H-indol-5-yl)furan-2-carboximidamide (111)

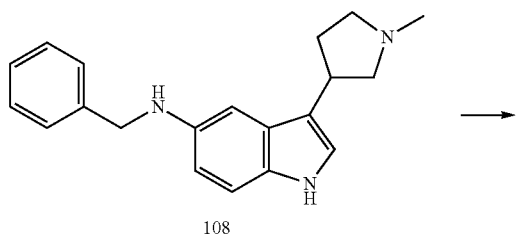

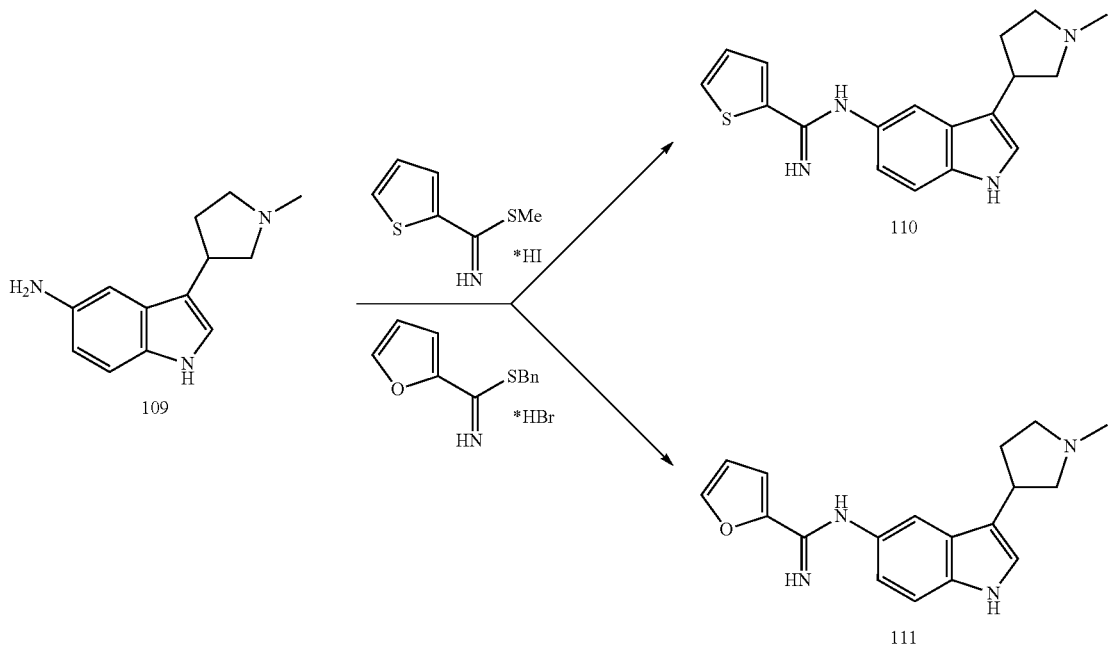

a) N-benzyl-3-(1-methylpyrrolidin-3-yl)-1H-indol-5-amine (108): Macor, J. E et. al J. Med. Chem., 37, 2509-2512, (1994).

(b) N-benzyl-3-(1-methylpyrrolidin-3-yl)-1H-indol-5-amine (110): N-benzyl-3-(1-methylpyrrolidin-3-yl)-1H-indol-5-amine 108, (500 mg, 1.637 mmol) was dissolved in anhydrous ethanol (10 mL) in a dry argon purged flask. Palladium hydroxide, 20 wt % on carbon, wet (560 mg, 0.796 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 48 hours, thin layer chromatography in a solvent system of (10% 2M $NH_3$ in methanol/90% dichloromethane) shows approximately 80-85% conversion to 109, 3-(1-methylpyrrolidin-3-yl)-1H-indol-5-amine. The mixture is filtered through a pad of celite to remove insolubles, the pad washed with anhydrous ethanol (10 mL) and the solvent evaporated and compound dried briefly on vacuum pump. The crude amine is dissolved in anhydrous ethanol (20 mL) and batch split into two portions. One half of the ethanolic solution of 109 (10 mL) is charged to a small, argon purged flask fitted with a magnetic stir bar. Thiophene-2-carboximidothioic acid methyl ester hydroiodide (350 mg, 1.227 mmol) is added to the flask and the reaction was stirred under Ar at ambient temperature for 96 hours, at which time the solvent was evaporated and the residue was partitioned between $H_2O$ and ethyl acetate and 1M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulfate, filtered, concentrated and the residue purified via chromatography on silica gel (5% 2M $NH_3$ in methanol/95% dichloromethane to 15% 2M $NH_3$ in methanol/85% dichloromethane) to yield a pale yellow solid 110 (96 mg, 36.2% yield); $^1$H NMR (DMSO-d6) δ: 10.59 (br s, 1H), 7.71 (d, 1H, J=3.2), 7.59 (d, 1H, J=5.1), 7.27 (d, 1H, J=8.5), 7.14-7.05 (2×m, 2H), 7.02 (s, 1H), 6.64 (dd, 1H, J=8.3, 1.5), 6.27 (br s, 2H), 3.56-3.45 (m, 1H), 2.93 (t, 1H, J=8.4), 2.72-2.65 (m, 1H), 2.58-2.50 (m, 2H), 2.31 (s, 3H), 2.28-2.15 (m, 1H), 1.98-1.86 (m, 1H); MS (ESI+): 325 (M+1, 100%). ESI-HRMS calculated for $C_{18}H_{21}N_4S$ (MH$^+$): 325.1488, Observed: 325.1481.

c) N-(3-(1-methylpyrrolidin-3-yl)-1H-indol-5-yl)furan-2-carboximidamide (111): The remaining half of the ethanolic solution of 109 (10 mL, see above) is charged to a small, argon purged flask fitted with a magnetic stir bar. Benzyl furan-2-carbimidothioate hydrobromide (366 mg, 1.227 mmol) is added to the flask and the reaction was stirred under Ar at ambient temperature for 24 hours, at which time the solvent was evaporated and the residue was partitioned between $H_2O$ and ethyl acetate and 1M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulfate, filtered, concentrated and the residue purified via chromatography on silica gel (5% 2M $NH_3$ in methanol/95% dichloromethane to 20% 2M $NH_3$ in methanol/80% dichloromethane) to yield a pale yellow foam 111 (170 mg, 67.4% yield); $^1$H NMR (DMSO-d6) δ: 10.61 (br s, 1H), 7.80 (s, 1H), 7.27 (d, 1H, J=8.5), 7.17-7.04 (2×m, 3H), 6.68 (d, 1H, J=8.2), 6.62 (s, 1H), 6.40 (br s, 1H), 3.55-3.44 (m, 1H), 2.94 (t, 1H, J=8.3), 2.74-2.66 (m, 1H), 2.59-2.50 (m, 2H), 2.31 (s, 3H), 2.28-2.16 (m, 1H), 1.97-1.86 (m, 1H); MS (ESI+): 309 (M+1, 100%). ESI-HRMS calculated for $C_{18}H_{21}N_4O$ (MH$^+$): 309.1717, Observed: 309.1709.

EXAMPLE 32

N-(3-(4-(dimethylamino)cyclohex-1-enyl)-1H-indol-5-yl)thiophene-2-carboximidamide (114)

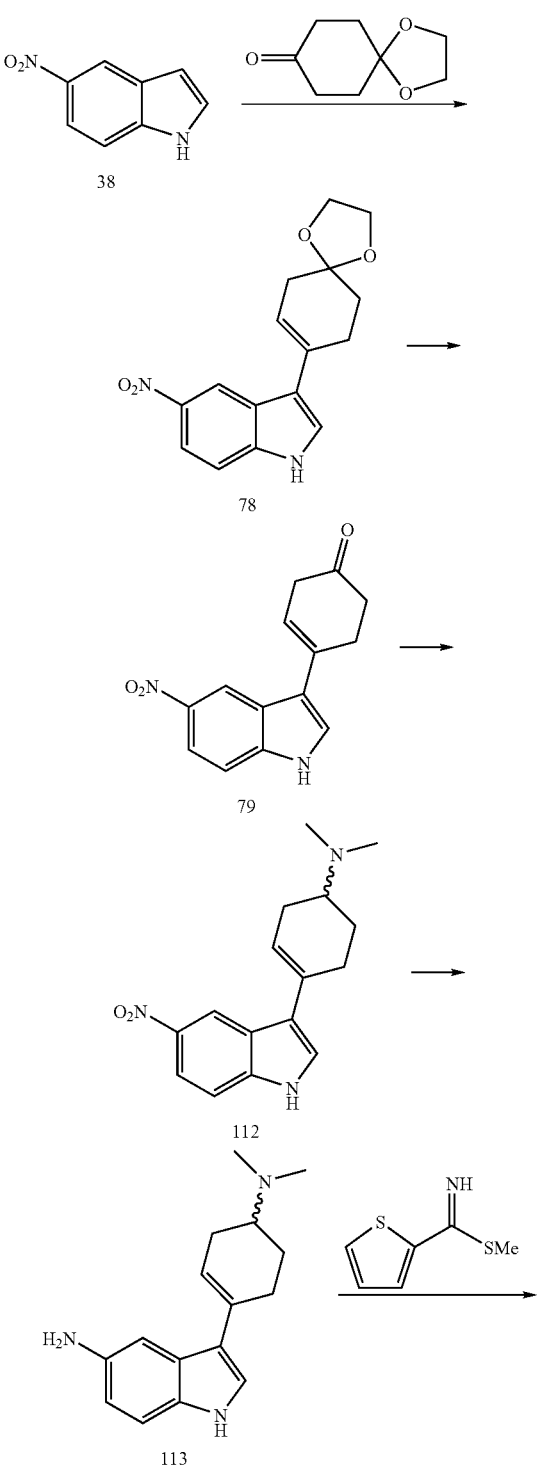

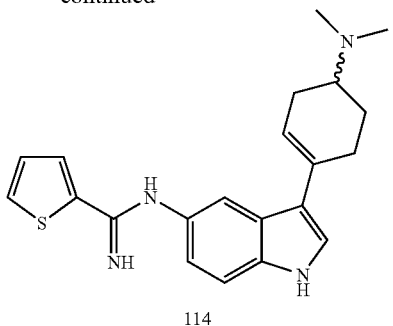

114

5-Nitro-3-(1,4-dioxaspiro[4.5]dec-7-en-8-yl)-1H-indole (78): A solution of 5-nitroindole (38) (3.0 g, 18.501 mmol) in dry methanol (50 mL) was treated with KOH (5.6 g) at room temperature. After stirring for 10 min., 1,4-cyclohexanedione monoethylene ketal (7.22 g, 46.253 mmol) was added and the resulting solution was refluxed for 36 h. The reaction was brought to room temperature and solvent was evaporated. Crude was diluted with water (50 mL), precipitated solid was filtered off and washed with water (2 10 mL). The precipitate was dried under vacuum to obtain compound 78 (4.7 g, 85%) as a solid. For spectral data, please see Example 23.

4-(5-Nitro-1H-indol-3-yl)cyclohex-3-enone (79): A solution of compound 78 (4.7 g, 15.650 mmol) in acetone (50 mL) was treated with 10% aq. HCl (50 mL) at room temperature and stirred for over night (14 h). Acetone was evaporated and crude was basified using 10% aq. NH$_4$OH solution (100 mL). The precipitate was filtered off, washed with 10% NH$_4$OH solution (2 10 mL) and water (2 10 mL). The product was dried under vacuum to obtain compound 79 (4.0 g, quantitative) as a solid. For spectral data, please see Example 23.

N,N-Dimethyl-4-(5-nitro-1H-indol-3-yl)cyclohex-3-enamine (112): A solution of compound 79 (1.0 g, 3.902 mmol) in dry 1,2-dichloroethane (10 mL) was treated with N,N-dimethyl amine hydrochloride (0.31 g, 3.902 mmol), AcOH (0.22 mL, 3.902 mmol), NaBH(OAc)$_3$ (1.24 g, 5.853 mmol) at room temperature and the resulting mixture was stirred for overnight (14 h). The reaction was diluted with 1 N NaOH (30 mL) and product was extracted into ethyl acetate (2 50 mL). The combined ethyl acetate layer was washed with brine (20 mL) and dried (Na$_2$SO$_4$). Solvent was evaporated and crude was purified by column chromatography (2 M NH$_3$ in methanol: CH$_2$Cl$_2$, 1:9) to obtain compound 112 (0.73 g, 66%) as a brown solid. mp 234-236° C.; $^1$H NMR (DMSO-d$_6$) δ 1.43-1.57 (m, 1H), 1.98-2.06 (m, 1H), 2.12-2.23 (m, 7H), 2.39-2.62 (m, 4H), 6.15 (t, 1H, J=1.5 Hz), 7.54 (d, 1H, J=9.0 Hz), 7.62 (s, 1H), 8.00 (dd, 1H, J=2.1, 9.0 Hz), 8.67 (d, 1H, J=2.1 Hz), 11.82 (s, 1H); ESI-MS m/z (%): 286 (MH$^+$, 100).

3-(4-(Dimethylamino)cyclohex-1-enyl)-1H-indol-5-amine (113): A solution of compound 112 (0.21 g, 0.735 mmol) in dry methanol (5 mL) was treated with Ra—Ni (0.05 g) followed by hydrazine hydrate (0.22 mL, 7.359 mmol) at room temperature. The reaction was placed in a pre-heated oil bath and refluxed for 5 min. The reaction brought to room temperature, filtered through celite bed and washed with methanol (2 10 mL). The solvent was evaporated and crude was purified by column chromatography (2 M NH$_3$ in methanol: CH$_2$Cl$_2$, 1:9) to obtain compound 113 (0.185 g, quantitative) as a foam. mp 63-65° C.; $^1$H NMR (DMSO-d$_6$) δ 1.40-1.52 (m, 1H), 1.97-2.02 (m, 1H), 2.08-2.57 (m, 11H), 4.47 (s, 2H), 5.99 (brs, 1H), 6.47 (dd, 1H, J=1.8, 8.4 Hz), 6.99 (d, 1H, J=0.9 Hz), 7.04 (d, 1H, J=8.7 Hz), 7.13 (d, 1H, J=2.4 Hz), 10.55 (s, 1H); ESI-MS m/z (%): 256 (MH$^+$, 100), 211 (41).

N-(3-(4-(dimethylamino)cyclohex-1-enyl)-1H-indol-5-yl)thiophene-2-carboximidamide (114): A solution of compound 113 (0.18 g, 0.704 mmol) in dry ethanol (10 mL) was treated with thiophene-2-carboximidothioic acid methyl ester hydroiodide (0.4 g, 1.409 mmol) at room temperature and stirred for 24 h. Solvent was evaporated and crude was diluted with sat. NaHCO$_3$ solution (20 mL) and product was extracted into CH$_2$Cl$_2$ (2 25 mL). The combined CH$_2$Cl$_2$ layer was washed with brine (20 mL) and dried (Na$_2$SO$_4$). Solvent was evaporated and crude was purified by column chromatography (2 M NH$_3$ in methanol: CH$_2$Cl$_2$, 1:9) to obtain compound 114 (0.24 g, 90%) as a solid. mp 113-115° C.; $^1$H NMR (DMSO-d$_6$) δ 1.42-1.53 (m, 1H), 1.97-2.02 (m, 1H), 2.08-2.22 (m, 8H), 2.31-2.60 (m, 3H), 6.03 (s, 1H), 6.21 (brs, 2H), 6.65 (dd, 1H, J=1.2, 8.4 Hz), 7.09 (t, 1H, J=4.2 Hz), 7.20 (s, 1H), 7.28-7.31 (m, 2H), 7.58 (d, 1H, J=4.5 Hz), 7.71 (d, 1H, J=2.7 Hz), 10.88 (s, 1H), ESI-MS m/z (%): 365 (MH$^+$, 39), 320 (38), 183 (76), 160 (100); ESI-HRMS calculated for C$_{21}$H$_{25}$N$_4$S (MH$^+$), Calculated: 365.1813: Observed: 365.1794.

EXAMPLE 33

N-(3-(4-(dimethylamino)cyclohexyl)-1H-indol-5-yl)thiophene-2-carboximidamide (116)

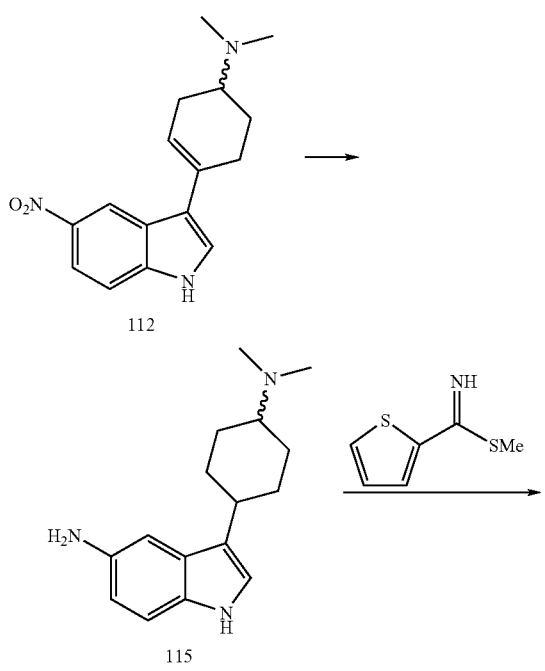

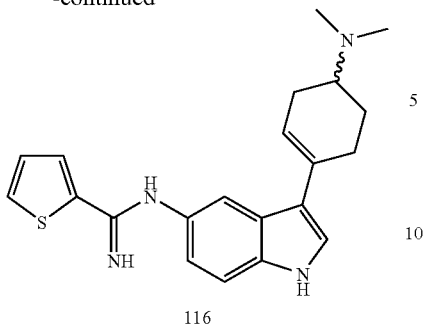

116

N,N-Dimethyl-4-(5-nitro-1H-indol-3-yl)cyclohex-3-enamine (112): For complete experimental details and spectral data, see Example 32.

N-(3-(4-(Dimethylamino)cyclohexyl)-1H-indol-5-yl)thiophene-2-carboximidamide (116): A solution of compound 112 (0.43 g, 1.506 mmol) in dry ethanol (5 mL) was treated with 10% Pd—C (0.04 g) and purged with hydrogen gas at room temperature. The reaction was stirred at the same temperature under a hydrogen atmosphere (balloon pressure) overnight (14 h). The reaction was filtered through a celite bed and washed with dry ethanol (2 5 mL). The combined ethanol layer was treated with thiophene-2-carboximidothioic acid methyl ester hydroiodide (0.85 g, 3.013 mmol) at room temperature and stirred for 24 h. The solvent was evaporated and crude material was diluted with sat. NaHCO$_3$ solution (20 mL) and product was extracted into CH$_2$Cl$_2$ (2 25 mL). The combined CH$_2$Cl$_2$ layer was washed with brine (20 mL) and dried (Na$_2$SO$_4$). The solvent was evaporated and crude was purified by column chromatography on silica gel (2 M NH$_3$ in methanol: CH$_2$Cl$_2$, 1:9) to obtain compound 116 (0.4 g, 72%, over two steps) as a yellow solid. mp 104-106° C.; $^1$H NMR (DMSO-d$_6$) δ: 1.39-1.60 (m, 3H), 1.66-1.72 (m, 1H), 1.82-1.94 (m, 3H), 2.05-2.08 (m, 1H), 2.23 (s, 3H), 2.34 (s, 3H), 2.64-2.71 (m, 1H), 2.91-2.96 (m, 1H), 6.48 (brs, 1H), 6.64 (dd, 1H, J=1.5, 8.4 Hz), 6.99-7.05 (m, 2H), 7.10 (t, 1H, J=4.2 Hz), 7.27 (d, 1H, J=8.4 Hz), 7.60 (d, 1H, J=5.4 Hz), 7.71 (d, 1H, J=3.3 Hz), 10.57 (s, 1H); ESI-MS i/z (%): 367 (MH$^+$, 31), 322 (18), 184 (100); ESI-HRMS calculated for C$_{21}$H$_{27}$N$_4$S (MH$^+$), Calculated: 367.1965; Observed: 367.1950.

EXAMPLE 34

N-(3-(4-(ethylamino)cyclohexyl)-1H-indol-5-yl)thiophene-2-carboximidamide (121)

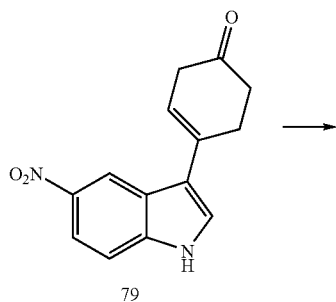

79

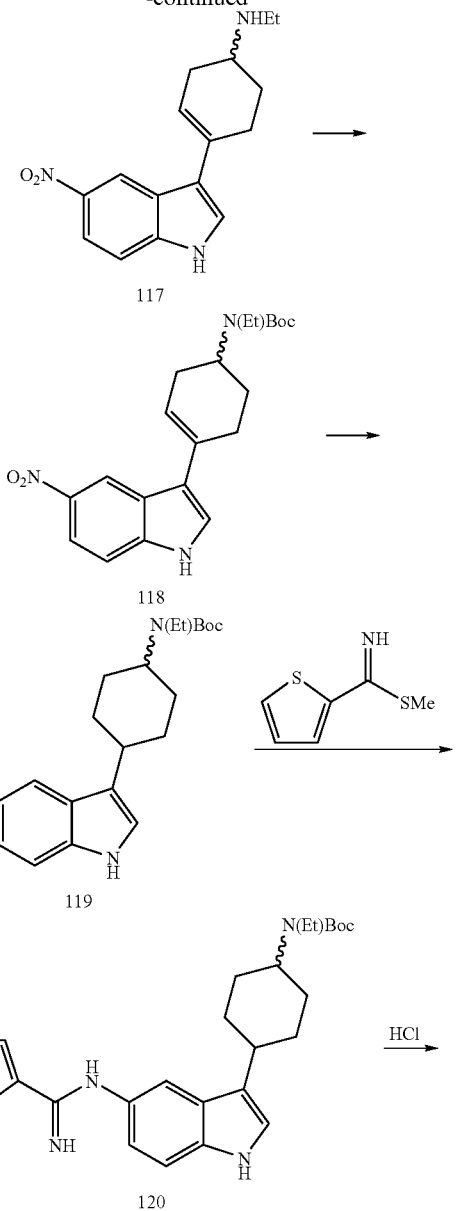

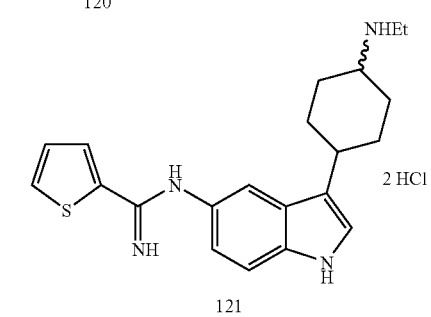

121

4-(5-Nitro-1H-indol-3-yl)cyclohex-3-enone (79): See Example 23 for complete experimental details and spectral data.

N-Ethyl-4-(5-nitro-1H-indol-3-yl)cyclohex-3-enamine (117): A solution of compound 79 (1.0 g, 3.902 mmol) in dry 1,2-dichloroethane (10 mL) was treated with ethylamine hydrochloride (0.31 g, 3.902 mmol), glacial acetic acid (0.22 mL, 3.902 mmol) and NaBH(OAc)$_3$ (1.24 g, 5.853 mmol) at room temperature and the resulting mixture was stirred for overnight (14 h). The reaction was diluted with 1 N NaOH (30 mL) and product was extracted into ethyl acetate (2 50 mL). The combined ethyl acetate layer was washed with brine (20 mL) and dried ($Na_2SO_4$). Solvent was evaporated and crude was purified by column chromatography (2 M $NH_3$ in methanol: $CH_2Cl_2$, 1:9) to obtain compound 117 (1.08 g, 97%) as a dark yellow solid. mp 177-179° C.; $^1$H NMR (DMSO-$d_6$) δ: 1.03 (t, 3H, J=6.9 Hz), 1.39-1.52 (m, 2H), 1.94-2.00 (m, 2H), 2.40-2.80 (m, 3H), 3.16 (s, 2H), 4.07 (brs, 1H), 6.13 (s, 1H), 7.54 (d, 1H, J=9.0 Hz), 7.62 (s, 1H), 8.00 (dd, 1H, J=2.4, 9.0 Hz), 8.67 (d, 1H, J=2.4 Hz), 11.83 (brs, 1H); ESI-MS m/z (%): 286 (MH$^+$, 100).

tert-Butyl ethyl(4-(5-nitro-1H-indol-3-yl)cyclohex-3-enyl)carbamate (118): A solution of compound 117 (1.05 g, 3.679 mmol) in dry 1,4-dioxane (20 mL) was treated with $Et_3N$ (1.02 mL, 7.359 mmol) followed by $(Boc)_2O$ (0.84 g, 3.863 indol) at room temperature and the resulting solution was stirred for overnight (14 h). Solvent was evaporated and crude was purified by column chromatography on silica gel (2 M $NH_3$ in methanol: $CH_2Cl_2$, 1:1) to obtain compound 118 (1.1 g, 78%) as a yellow solid. mp 217-219° C.: $^1$H NMR (DMSO-$d_6$) δ 1.09 (t, 3H, J=6.9 Hz), 1.42 (s, 9H), 1.83-1.96 (m, 2H), 2.27-2.43 (m, 2H), 2.56-2.62 (m, 2H), 3.14-3.18 (m, 2H), 4.05 (brs, 1H), 6.16 (s, 1H), 7.55 (d, 1H, J=9.0 Hz), 7.64 (s, 1H), 8.01 (dd, 1H, J=2.1, 8.7 Hz), 8.67 (d, 1H, J=2.1 Hz), 11.85 (s, 1H); ESI-MS m/z (%): 408 (M+Na, 95), 386 (MH$^+$, 9), 330 (73), 286 (100).

tert-Butyl 4-(5-amino-1H-indol-3-yl)cyclohexyl(ethyl)carbamate (119): A solution of compound 118 (0.55 g, 1.427 mmol) in 2 M $NH_3$ in methanol (10 mL) was treated with Pd—C (0.05 g) and flushed with hydrogen gas. The reaction was stirred at room temperature overnight (16 h) under hydrogen atmosphere (balloon pressure). The solution was filtered through a celite bed using methanol washes (2×10 mL). The solvent was evaporated and crude was purified by column chromatography (2 M $NH_3$ in methanol: $CH_2Cl_2$, 2.5:97.5) to obtain compound 119 (0.43 g, 84%) as a solid in 2:3 ratio of diastereomers. $^1$H NMR (DMSO-$d_6$) δ: 0.99, 1.07 (2t, 3H, J=7.2, 6.6 Hz), 1.37-1.51 (m, 11H), 1.63-1.78 (m, 4H), 2.01-2.18 (m, 2H), 2.98-3.04 (m, 1H), 3.11-3.17 (m, 2H), 3.68-3.80 (m, 1H), 4.52 (brs, 2H), 6.44-6.47 (m, 1H), 6.66-6.70 (m, 1H), 6.86-6.88, 6.99-7.06 (2m, 2H), 10.23, 10.27 (2s, 1H); ESI-MS m/z (%): 380 (M+Na, 6), 358 (MH$^+$, 5), 302 (100), 258 (54); ESI-HRMS calculated for $C_{21}H_{32}N_3O_2$ (MH$^+$). Calculated: 358.2507: Observed: 358.2489.

tert-Butyl ethyl(4-(5-(thiophene-2-carboximidamido)-1H-indol-3-yl)cyclohexyl)carbamate (120): A solution of compound 119 (0.4 g, 1.119 mmol) in dry ethanol (20 mL) was treated with thiophene-2-carboximidothioic acid methyl ester hydroiodide (0.63 g, 2.239 mmol) at room temperature and stirred for 24 h. The solvent was evaporated, diluted with sat. $NaHCO_3$ solution (20 mL) and product was extracted into $CH_2Cl$, (2×25 mL). The $CH_2Cl_2$ layer was washed with brine (20 mL) and dried ($Na_2SO_4$). The solvent was evaporated and crude material was purified by column chromatography on silica gel (2 M $NH_3$ in methanol: $CH_2Cl_2$, 5:95) to obtain compound 120 (0.4 g, 60%) as a yellow solid in 2:3 ratio of cis-trans diastereomers. $^1$H NMR (DMSO-$d_6$) δ 0.98-1.08 (m, 3H), 1.38-1.56 (m, 11H), 1.68-1.85 (m, 4H), 2.05-2.18 (m, 2H), 3.02-3.17 (m, 3H), 3.70-3.76 (m, 1H), 6.31 (brs, 2H), 6.62-6.67 (m, 1H), 6.96-7.01 (m, 1H), 7.09-7.11 (m, 1H), 7.22-7.30 (m, 2H), 7.60 (d, 1H, J=5.1 Hz), 7.70-7.72 (m, 1H), 10.59, 10.62 (2s, 1H); ESI-MS m/z (%): 467 (MH$^+$, 100).

N-(3-(4-(Ethylamino)cyclohexyl)-1H-indol-5-yl)thiophene-2-carboximidamide (121): Compound 120 (0.26 g, 0.557 mmol) was treated with 1 N aqueous HCl solution at room temperature and the resulting solution was refluxed for 2 h. The reaction was brought to room temperature, filtered and washed with water (5 mL). The solvent was evaporated and crude was recrystallised from ethanol/ether to obtain compound 121 (0.23 g, 94%) as a solid in 2:3 ratio of diastereomners. $^1$H NMR (DMSO-$d_6$) δ 1.22-1.29 (m, 3H), 1.53-1.62 (m, 2H), 1.80-2.16 (m, 6H), 2.74-3.23 (m, 4H), 7.08 (d, 1H, J=8.4 Hz), 7.24-7.52 (m, 3H), 7.68-7.72 (m, 1H), 8.14-8.18 (m, 2H), 8.59 (s, 1H), 8.97-9.09 (m, 2H), 9.64 (s, 1H), 11.20, 11.27 (2s, 1H), 11.42 (s, 1H); ESI-MS m/z (%): 367 (MH$^+$ for free base, 18), 322 (100), 184 (19), 119 (39); ESI-HRMS calculated for $C_{21}H_{27}N_4S$ (MH$^+$, free base), calculated: 367.1959; observed: 367.1950.

EXAMPLE 35

N-(3-(1-azabicyclo[2.2.2]oct-2-en-3-yl)-1H-indol-5-yl)thiophene-2-carboximidamide (125), N-(3-(quinuclidin-3-yl)-1H-indol-5-yl)thiophene-2-carboximidamide (126) and N-(3-(quinuclidin-3-yl)-1H-indol-5-yl)furan-2-carboximidamide (127)

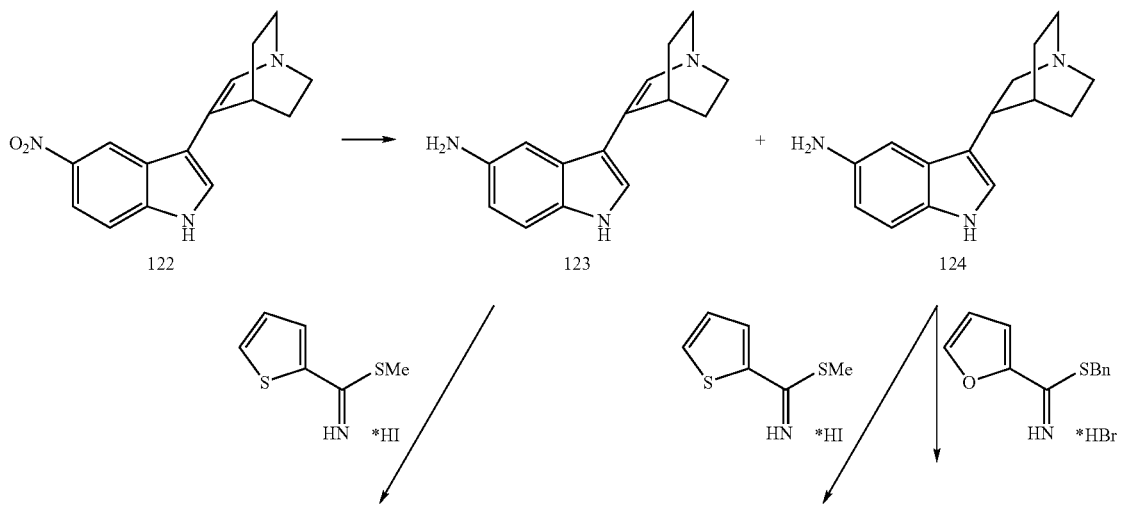

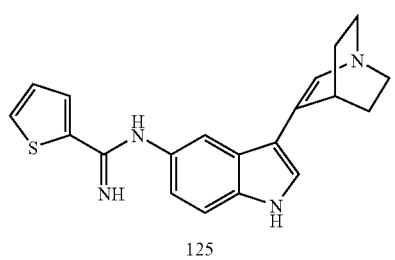
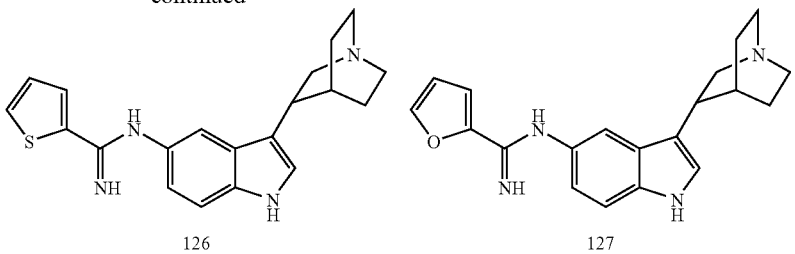

(a) 3-(5-Nitro-1H-indol-3-yl)-1-azabicyclo[2.2.2]oct-2-ene 1 (122): Schiemann et. al. US Pat App. US2004/012935 A1

(b) N-(3-(1-azabicyclo[2.2.2]oct-2-en-3-yl)-1H-indol-5-yl)thiophene-2-carboximidamide (125) and N-(3-(quinuclidin-3-yl)-1H-indol-5-yl)thiophene-2-carboximidamide (126): 3-(5-Nitro-1H-indol-3-yl)-1-azabicyclo[2.2.2]oct-2-ene (compound 122, 250 mg, 0.928 mmol) was dissolved in anhydrous methanol (10 mL) in a dry argon purged flask. Palladium, 10 wt % on activated carbon (49.2 mg, 0.0463 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 17 hours, thin layer chromatography in a solvent system of (20% 2M $NH_3$ in methanol/80% dichloromethane) shows complete consumption of starting material 122, and a mixture of 2 new products; compound 2,3-(1-azabicyclo[2.2.2]oct-2-en-3-yl)-1H-indol-5-amine (123) and 3,3-(quinuclidin-3-yl)-1H-indol-5-amine (124) in the ratio of 60/40 by TLC. The mixture is filtered through a pad of celite to remove insolubles, the pad washed with anhydrous methanol (10 mL) and solution of the two amines split into two portions. One half of the methanolic solution of 123 and 124 is charged to a small, argon purged flask fitted with a magnetic stir bar. Thiophene-2-carboximidothioic acid methyl ester hydroiodide (172 mg, 0.603 mmol) is added to the flask and the reaction was stirred under argon at ambient temperature for 24 hours, at which time the solvent was evaporated and the residue was partitioned between $H_2O$ and ethyl acetate and 1M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulfate, filtered, concentrated and the residue purified via chromatography on silica gel (10% 2M $NH_3$ in methanol/90% dichloromethane to 20% 2M $NH_3$ in methanol/80% dichloromethane) to yield 2 products; pale yellow solid 125 (50 mg, 31.0% yield); $^1$H NMR (DMSO) δ: 11.37 (br s, 1H), 7.75 (d, 1H, J=2.7), 7.72 (d, 1H, J=2.5), 7.65 (d, 1H, J=3.8), 7.40 (d, 1H, J=8.5), 7.19 (m, 1H), 7.15-7.12 (m, 1H), 6.84 (s, 1H), 6.79-6.76 (m, 1H), 6.50 (br s, 2H), 2.97-2.81 (m, 3H), 1.99-1.86 (m, 2H), 1.73-1.60 (m, 2H); MS (ESI+): 349 (M+1, 40%). ESI-HRMS calculated for $C_{20}H_{21}N_4S$ ($MH^+$): 349.1495, Observed: 349.1481 and pale yellow solid 126 (65 mg, 40.1% yield); $^1$H NMR (DMSO) δ: 10.72 (br s, 1H), 7.71 (d, 1H, J=3.4), 7.59 (d, 1H, J=5.2), 7.30-7.25 (2×m, 2H), 7.09 (dd, 1H, J=5.2, 3.8), 6.92 (s, 1H), 6.65 (dd, 1H, J=8.3, 1.5), 6.20 (br s, 2H), 3.32-3.19 (m, 2H), 3.05-2.99 (m, 2H), 2.95-2.90 (m, 2H), 2.84-2.72 (m, 1H), 1.98-1.79 (2×m, 2H), 1.72-1.57 (m, 2H), 1.37-1.26 (m, 1H); MS (ESI+): 351 (M+1, 10%), 176 (M++doubly charged, 100%). ESI-HRMS calculated for $C_{20}H_{23}N_4S$ ($MH^+$): 351.1651, Observed: 351.1637.

N-(3-(quinuclidin-3-yl)-1H-indol-5-yl)furan-2-carboximidamide (127):

A solution containing 123 and 124 (10 mL, 0.465 mmol) in methanol (see above) is charged to a small, argon purged flask fitted with a magnetic stir bar. Benzyl furan-2-carbimidothioate hydrobromide (207 mg, 0.696 mmol) is added to the flask and the reaction was stirred under argon at ambient temperature for 48 hours, at which time the solvent was evaporated and the residue was partitioned between $H_2O$ and ethyl acetate and 1M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulfate, filtered, concentrated and the residue purified twice via chromatography on silica gel (10% 2M $NH_3$ in methanol/90% dichloromethane to 30% 2M $NH_3$ in methanol/70% dichloromethane) to yield a beige solid 127 (51 mg, 32.9% yield); $^1$H NMR (DMSO) δ: 10.76 (br s, 1H), 7.79 (s, 1H), 7.31-7.28 (2×m, 2H), 7.09 (br s, 1H), 6.99 (s, 1H), 6.70 (d, 1H), 6.61 (s, 1H), 3.47-3.27 (m, 2H), 3.09-2.95 (2×m, 4H), 2.85-2.79 (m, 1H), 1.97-1.81 (2×m, 2H), 1.78-1.58 (2×m, 2H), 1.44-1.33 (m, 1H); MS (ESI+): 335 (M+1, 20%), 168 (M++doubly charged, 100%). ESI-HRMS calculated for $C_{20}H_{23}N_4O$ ($MH^+$): 335.1866, Observed: 335.1882.

EXAMPLE 36

N-(3-(3-fluoro-1-methyl-1,2,3,6-tetrahydropyridin-4-yl)-1H-indol-5-yl)thiophene-2-carboximidamide (134)

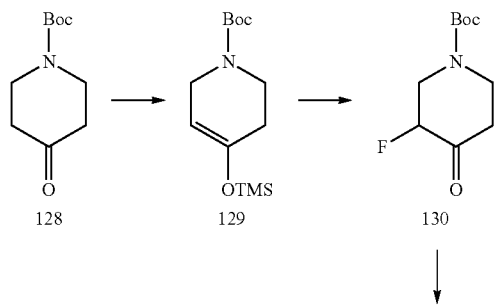

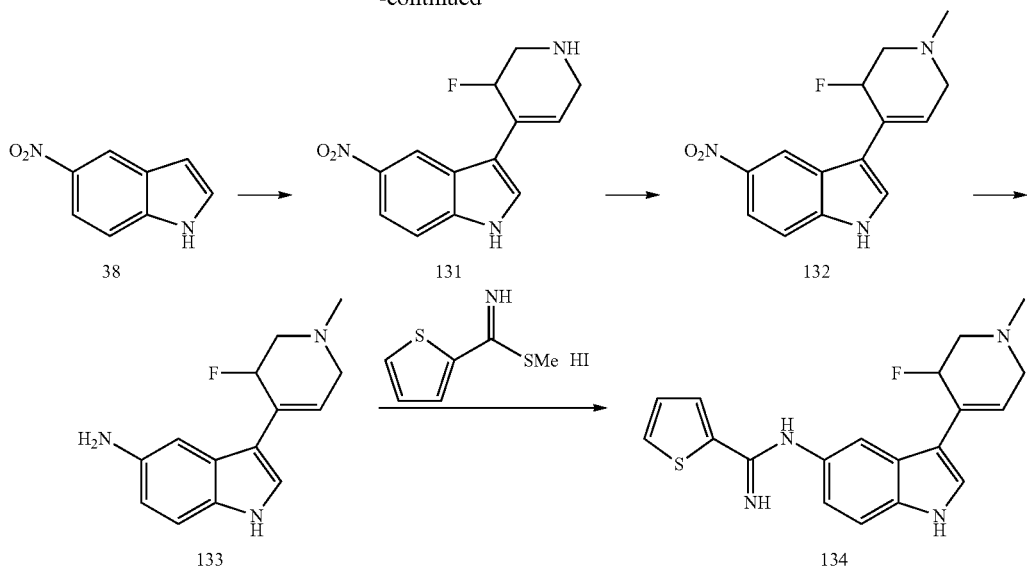

tert-Butyl 4-(trimethylsilyloxy)-5,6-dihydropyridine-1 (2H)-carboxylate (129): A solution of compound 128 (6.0 g, 30.112 mmol) in dry DMF (12 mL) was treated with trimethylsilylchloride (4.58 mL, 36.135 mmol), Et$_3$N (10.07 mL, 72.271 mmol) at room temperature (Caution: Foaming occurs) and the resulting solution was stirred at 80° C. for 16 h. The reaction was brought to room temperature and diluted with hexane (100 mL). The hexane layer was washed with cold saturated NaHCO$_3$ solution (3 20 mL) and dried (Na$_2$SO$_4$). Solvent was evaporated and crude was purified by column chromatography (EtOAc: Hexanes, 1:9) to obtain compound 129 (4.53 g, 55%) as a liquid with major recovery of starting material (2.6 g). $^1$H NMR is comparable with literature (J. Med. Chem. 1999, 42, 2087-2104).

tert-Butyl 3-fluoro-4-oxopiperidine-1-carboxylate (130): A solution of compound 129 (4.5 g, 16.578 mmol) in dry acetonitrile (175 mL) was treated with Selectfluor™ (6.46 g, 18.236 mmol) at room temperature and resulting solution was stirred for 75 min. at same temperature. The reaction was diluted with ethyl acetate (500 mL), washed with unsaturated brine (300 mL, water: saturated brine 1:1), saturated brine (100 mL) and dried (Na$_2$SO$_4$). The solvent was evaporated and crude was purified by column chromatography (ethyl acetate to 5% methanol in ethyl acetate) to obtain compound 130 (3.18 g, 88%) as a syrup. $^1$H NMR (CDCl$_3$) δ: 1.50 (s, 9H), 2.46-2.64 (m, 2H), 3.20-3.37 (m, 2H), 4.13-4.20 (m, 1H), 4.44-4.48 (m, 1H), 4.72-4.77, 4.88-4.93 (2m, 1H). $^1$H NMR comparable with literature (J. Med. Chem. 1999, 42, 2087-2104).

3-(3-Fluoro-1,2,3,6-tetrahydropyridin-4-yl)-5-nitro-1H-indole (131): A solution of 5-nitroindole (38) (1.0 g, 6.167 mmol) in glacial acetic acid (10 mL) at 90° C. was treated with compound 130 (1.33 g, 6.167 mmol) in glacial AcOH (5 mL), 1 M H$_3$PO$_4$ in glacial AcOH (5 mL) and the resulting solution was stirred at same temperature for 16 h. The reaction was brought to room temperature, poured into 15% cold aqueous ammonia solution (100 mL) and product was extracted into ethyl acetate (2 50 mL). The combined ethyl acetate layer was washed with brine (25 mL) and dried (Na$_2$SO$_4$). Solvent was evaporated and crude was purified by column chromatography (2 M NH$_3$ in methanol: CH$_2$Cl$_2$, 1:99 to 5:95) to obtain compound 131 (0.75 g, 47%) as a yellow solid. mp 205-207° C.; $^1$H NMR (DMSO-d$_6$) δ 2.35 (brs, 1H), 2.86-3.06 (m, 1H), 3.19-3.26 (m, 1H), 3.35-3.58 (m, 2H), 5.28 (d, 1H, J=49.5 Hz), 6.53-6.56 (m, 1H), 7.58 (d, 1H, J=8.7 Hz), 7.74 (s, 1H), 8.02 (dd, 1H, J=2.4, 9.0 Hz), 8.68 (d, 1H, J=2.4 Hz), 11.94 (s, 1H); ESI-MS m/z (%): 262 (MH$^+$, 100), 233 (50).

3-(3-Fluoro-1-methyl-1,2,3,6-tetrahydropyridin-4-yl)-5-nitro-1H-indole (132): A solution of compound 131 (0.2 g, 0.765 mmol) in dry methanol (5 mL) was treated with formaldehyde (0.07 mL, 0.918 mmol, 37% in water), AcOH (0.1 mL, 1.913 mmol) and NaBH$_3$CN (0.057 g, 0.918 mmol) at 0° C. The resulting mixture brought to room temperature and stirred for 3 h. The reaction was basified with 1 N NaOH (25 mL) and product was extracted into ethyl acetate (2 25 mL). The combined ethyl acetate layer was washed with brine (20 mL) and dried (Na$_2$SO$_4$). Solvent was evaporated and crude was purified by column chromatography (2 M NH$_3$ in methanol: CH$_2$Cl$_2$, 1:99 to 1:9) to obtain compound 132 (0.2 g, 95%) as a yellow solid. mp 94-96° C.; $^1$H NMR (DMSO-d$_6$) δ 2.32 (s, 3H), 2.48-2.63 (m, 1H), 2.78-2.87 (m, 1H), 3.03-3.12 (m, 1H), 3.38-3.48 (m, 1H), 5.45 (d, 1H, J=48.9 Hz), 6.48-6.50 (m, 1H), 7.58 (d, 1H, J=8.7 Hz), 7.75 (s, 1H), 8.03 (dd, 1H, J=2.1, 9.0 Hz), 8.68 (d, 1H, J=2.1 Hz), 11.96 (s, 1H) ESI-MS m/z (%): 276 (MH$^+$, 100).

3-(3-fluoro-1-methyl-1,2,3,6-tetrahydropyridin-4-yl)-1H-indol-5-amine (133): A solution of compound 132 (0.175 g, 0.635 mmol) in dry methanol (5 mL) was treated with hydrazine hydrate (0.198 mL, 6.357 mmol) followed by Ra—Ni (~0.05 g) at room temperature. The reaction was placed in a pre-heated oil bath and refluxed for 2 min. The reaction was brought to room temperature, filtered through celite bed, washed with methanol (3 10 mL). The combined methanol layer was evaporated and crude was purified by column chromatography (2 M NH$_3$ in methanol: CH$_2$Cl$_2$, 5:95) to obtain compound 133 (0.07 g, 45%) as a solid. mp 176-178° C.; $^1$H NMR (DMSO-d$_6$) δ 2.30 (s, 3H), 2.40-2.56 (m, 1H), 2.73-2.83 (m, 1H), 2.99-3.08 (m, 1H), 3.30-3.42 (m, 1H), 4.51 (s, 2H), 5.37 (d, 1H, J=48.9 Hz), 6.22-6.26 (m, 1H), 6.51 (dd, 1H, J=1.8, 8.5 Hz), 6.97 (d, 1H, J=1.8 Hz), 7.08 (d, 1H, J=8.4 Hz), 7.27 (t, 1H, J=1.8 Hz), 10.72 (s, 1H); ESI-MS m/z (%): 246 (MH$^+$, 12), 203 (100).

N-(3-(3-fluoro-1-methyl-1,2,3,6-tetrahydropyridin-4-yl)-1H-indol-5-yl)thiophene-2-carboximidamide (134): A solution of compound 133 (0.062 g, 0.252 mmol) in dry ethanol (5 mL) was treated with thiophene-2-carboximidothioic acid methyl ester hydroiodide (0.144 g, 0.505 mmol) at room temperature and stirred for 20 h. Solvent was evaporated, crude was diluted with sat. NaHCO$_3$ solution (20 mL) and product was extracted into CH$_2$Cl$_2$ (2 20 mL). The combined CH$_2$Cl$_2$ layer was washed with brine (15 mL) and dried (Na$_2$SO$_4$). Solvent was evaporated and crude was purified by column chromatography (2 M NH$_3$ in methanol: CH$_2$Cl$_2$, 0:100 to 1:9) to obtain compound 134 (0.052 g, 58%) as a solid. mp 127-129° C.; $^1$H NMR (DMSO-d$_6$) δ 2.29 (s, 3H), 2.42-2.57 (m, 1H), 2.72-2.81 (m, 1H), 3.00-3.09 (m, 1H), 3.32-3.42 (m, 1H), 5.41 (d, 1H, J=49.2 Hz), 6.30-6.40 (m, 3H), 6.69 (dd, 1H, J=1.2, 8.4 Hz), 7.10 (t, 1H, J=3.9 Hz), 7.22 (s, 1H), 7.34 (d, 1H, J=8.4 Hz), 7.42 (s, 1H), 7.60 (d, 1H, J=4.8 Hz), 7.73 (d, 1H, J=2.7 Hz), 11.05 (s, 1H); ESI-MS m/z (%): 355 (MH$^+$, 100), 335 (21), 312 (33); ESI-HRMS calculated for C$_{19}$H$_{20}$FN$_4$S (MH$^+$), Calculated: 355.1391; Observed: 355.1387.

EXAMPLE 37

N-(3-(3-fluoro-1-methylpiperidin-4-yl)-1H-indol-5-yl)thiophene-2-carboximidamide (137)

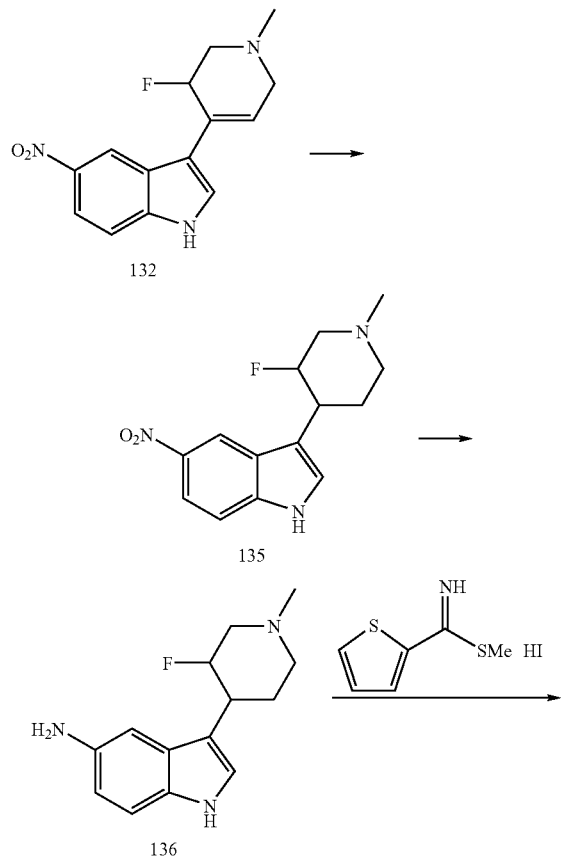

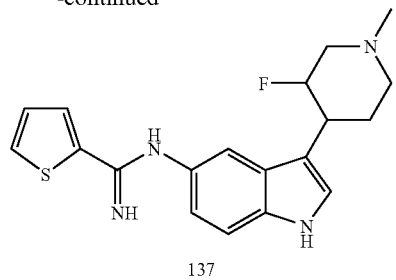

3-(3-Fluoro-1-methyl-1,2,3,6-tetrahydropyridin-4-yl)-5-nitro-1H-indole (132): For complete experimental details, see Example 36.

3-(3-Fluoro-1-methylpiperidin-4-yl)-5-nitro-1H-indole (135): A solution of compound 132 (0.22 g, 0.799 mmol) in TFA (5 mL) was treated with triethylsilane (0.22 mL, 1.438 mmol) at room temperature and stirred for 4 h. The reaction was carefully transferred to a beaker containing sat. NaHCO$_3$ solution (50 mL) and product was extracted into ethyl acetate (2 20 mL). The combined ethyl acetate layer was washed with brine (10 mL) and dried (Na$_2$SO$_4$). Solvent was evaporated and crude was purified by column chromatography (2 M NH$_3$ in methanol: CH$_2$Cl$_2$, 2.5:97.5) to obtain the trans diastereoisomers (mixture of enantiomers) compound 135 (0.102 g, 46%) as a solid. mp 105-107° C.; $^1$H NMR (DMSO-d$_6$) δ 1.80-1.96 (m, 2H), 2.02-2.15 (m, 2H), 2.29 (s, 3H), 2.78-2.81 (m, 1H), 2.98-3.09 (m, 1H), 3.16-3.21 (m, 1H), 4.62 (dddd, 1H, J=48.6, 4.8, 9.9, 9.9 Hz), 7.50-7.54 (m, 2H), 7.98 (dd, 1H, J=2.1, 9.0 Hz), 8.54 (d, 1H, J=2.1 Hz), 11.71 (s, 1H); ESI-MS m/z (%): 278 (MH$^+$, 100).

3-(3-Fluoro-1-methylpiperidin-4-yl)-1H-indol-5-amine (136): A solution of compound 135 (0.09 g, 0.324 mmol) in dry methanol (3 mL) was treated with hydrazine hydrate (0.1 mL, 3.245 mmol) followed by Ra—Ni (~0.05 g at room temperature. The reaction was placed in a pre-heated oil bath and refluxed for 5 min. The reaction was brought to room temperature, filtered through celite bed and washed with methanol (2 10 mL). The combined methanol layer was evaporated and crude was purified by column chromatography (2 M NH$_3$ in methanol: CH$_2$Cl$_2$, 5:95) to obtain compound 136 (0.08 g, quantitative) as a semi-solid. $^1$H NMR (DMSO-d$_6$) δ 1.78-1.86 (m, 2H), 1.95-2.07 (m, 2H), 2.26 (s, 3H), 2.69-2.78 (m, 2H), 3.11-3.17 (m, 1H), 4.41 (s, 2H), 4.68 (dddd, 1H, J=4.5, 9.9, 9.9, 48.7 Hz), 6.45 (dd, 1H, J=2.1, 8.5 Hz), 6.71 (d, 1H, J=1.5 Hz), 6.93-7.04 (m, 2H), 10.36 (s, 1H); ESI-MS m/z (%): 248 (MH$^+$, 100).

N-(3-(3-fluoro-1-methylpiperidin-4-yl)-1H-indol-5-yl)thiophene-2-carboximidamide (137): A solution of compound 136 (0.07 g, 0.283 mmol) in dry ethanol (5 mL) was treated with thiophene-2-carboximidothioic acid methyl ester hydroiodide (0.16 g, 0.566 mmol) at room temperature and stirred for overnight (16 h). Solvent was evaporated, crude was diluted with sat. NaHCO$_3$ solution (25 mL) and product was extracted into CH$_2$Cl$_2$ (2 20 mL). The combined CH$_2$Cl$_2$ layer was washed with brine (15 mL) and dried (Na$_2$SO$_4$). Solvent was evaporated and crude was purified by column chromatography (2 M NH$_3$ in methanol: CH$_2$Cl$_2$, 5:95) to obtain compound 137 (0.09 g, 90%) as a solid. mp 115-117° C.; $^1$H NMR (DMSO-d$_6$) δ 1.79-2.09 (m, 4H), 2.26 (s, 3H), 2.74-2.90 (m, 2H), 3.13-3.17 (m, 1H), 4.68 (dddd, 1H, J=4.8, 9.6, 9.6, 48.5 Hz), 6.23 (brs, 2H), 6.65 (d, 1H, J=8.1 Hz), 6.99 (s, 1H), 7.09 (t, 1H, J=4.2 Hz), 7.17 (d, 1H, J=1.5 Hz), 7.28 (d, 1H, J=8.4 Hz), 7.59 (d, 1H, J=5.1 Hz), 7.70 (d, 1H, J=3.3 Hz), 10.72 (s, 1H); ESI-MS m/z (%): 357

(MH+, 100), 179 (52); ESI-HRMS calculated for $C_{19}H_{22}FN_4S$ (MH+), Calculated: 357.1547, Observed: 357.1543.

EXAMPLE 38

N-(3-(1,2,3,5,8,8a-hexahydroindolizin-7-yl)-1H-indol-5-yl)thiophene-2-carboximidamide (142)

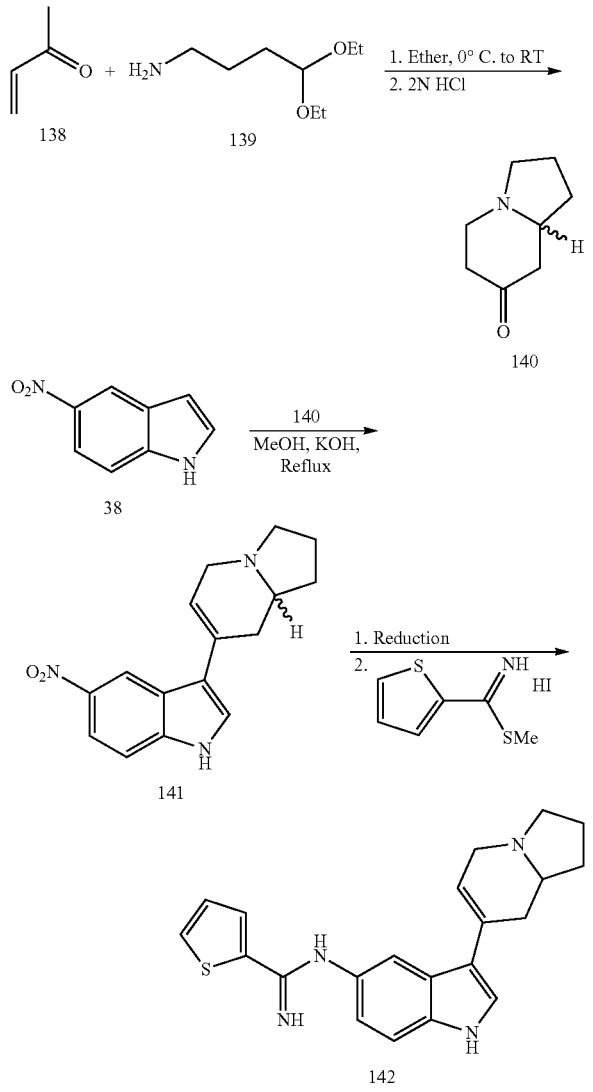

Hexahydroindolizin-7(1H)-one (140): Prepared according to WO0000487A1, U.S. Pat. No. 5,874,427, WO0017198A1.

3-(1,2,3,5,8,8a-Hexahydroindolizin-7-yl)-5-nitro-1H-indole (141): A solution of compound 38 (0.4 g, 2.466 mmol) in dry methanol (5 mL) was treated with KOH (1.12 g) at 0° C. and was stirred at room temperature for 10 min. Compound 140 (0.44 g, 3.206 mmol) in methanol (5 mL) was added and resulting mixture was refluxed for 30 h. The reaction was brought to room temperature and solvent was evaporated. Crude was diluted with water (20 mL) and product was extracted into $CH_2Cl_2$ (2 20 mL). The combined $CH_2Cl_2$ layer was washed with brine (15 mL) and dried ($Na_2SO_4$). Solvent was evaporated and crude was recrystallised from ethanol to obtain compound V (0.2 g, 29%) as solid. mp 205-207° C.; $^1H$ NMR (DMSO-$d_6$) δ 1.41-1.52 (m, 1H), 1.70-1.80 (m, 2H), 1.98-2.15 (m, 2H), 2.20-2.40 (m, 2H), 2.61-2.72 (m, 1H), 2.86-2.91 (m, 1H), 3.10-3.15 (m, 1H), 3.66 (dd, 1H, J=4.2, 16.5 Hz), 6.20 (s, 1H), 7.55 (d, 1H, J=9.0 Hz), 7.67 (s, 1H), 8.01 (dd, 1H, J=1.8, 9.0 Hz), 8.69 (d, 1H, J=2.1 Hz), 11.87 (s, 1H); ESI-MS (m/z, %) 284 (MH+, 100).

N-(3-(1,2,3,5,8,8a-Hexahydroindolizin-7-yl)-1H-indol-5-yl)thiophene-2-carboximidamide (142): A solution of compound 141 (0.12 g, 0.423 mmol) in dry methanol (5 mL) was treated with Ra—Ni (~0.05 g), hydrazine hydrate (0.13 mL, 4.235 mmol) at room temperature. The resulting mixture was refluxed for 2 min, in pre-heated oil bath. The reaction was brought to room temperature, filtered through celite bed and washed with methanol (2 20 mL). The combined methanol layer was evaporated and crude was purified by column chromatography (2 M $NH_3$ in MeOH: $CH_2Cl_2$, 95:5) to obtain 3-(1,2,3,5,8,8a-Hexahydroindolizin-7-yl)-1H-indol-5-amine, (0.087 g, 81%) as a solid. mp 208-210° C.; $^1H$ NMR (DMSO-$d_6$) δ 1.33-1.48 (m, 1H), 1.67-1.79 (m, 2H), 1.94-2.13 (m, 2H), 2.16-2.26 (m, 2H), 2.58-2.65 (m, 1H), 2.85 (d, 1H, J=15.6 Hz), 3.08-3.17 (m, 1H), 3.59 (dd, 1H, J=4.5, 15.7 Hz), 4.49 (s, 2H), 6.01 (d, 1H, J=4.5 Hz), 6.48 (dd, 1H, J=1.8, 9.1 Hz), 7.01 (d, 1H, J=1.5 Hz), 7.05 (d, 1H, J=8.4 Hz), 7.17 (d, 1H, J=2.7 Hz), 10.60 (s, 1H); ESI-MS (m/z, %) 254 (MH+, 62), 185 (100). A solution of the amine (0.053 g, 0.209 mmol) in dry ethanol (3 mL) was treated with thiophene-2-carboximidothioic acid methyl ester hydroiodide (0.12 g, 0.418 mmol) at room temperature and the solution was stirred for 24 h. Solvent was evaporated, crude was diluted with sat. $NaHCO_3$ solution (20 mL) and product was extracted into $CH_2Cl_2$ (2 20 mL). The combined $CH_2Cl_2$ layer was washed with brine (15 mL) and dried ($Na_2SO_4$). Solvent was evaporated and crude was purified by column chromatography (2 M $NH_3$ in MeOH: $CH_2Cl_2$, 5:95) to obtain compound 142 (0.06 g, 79%) as a solid. mp 122-124° C.; $^1H$ NMR (DMSO-$d_6$) δ 1.38-1.46 (m, 1H), 1.70-1.78 (m, 2H), 1.93-2.12 (m, 2H), 2.20-2.28 (m, 2H), 2.62-2.72 (m, 1H), 2.83 (d, 1H, J=15.9 Hz), 3.07-3.13 (m, 1H), 3.59 (dd, 1H, J=4.5, 16.0 Hz), 6.07 (d, 1H, J=3.9 Hz), 6.22 (brs, 2H), 6.66 (d, 1H, J=8.1 Hz), 7.09 (dd, 1H, J=3.9, 4.9 Hz), 7.22 (s, 1H), 7.30-7.32 (m, 2H), 7.58 (d, 1H, J=4.5 Hz), 7.71 (d, 1H, J=2.7 Hz), 10.92 (s, 1H); ESI-MS (m/z, %) 363 (MH+, 20), 294 (100), 182 (15), ESI-HRMS calculated for $C_{21}H_{23}N_4S$ (MH+), calculated: 363.1655; observed: 363.1637.

EXAMPLE 39

(R)—N-(3-(2-(1-Methylpyrrolidin-2-yl)ethyl)-1H-indol-5-yl)thiophene-2-carboximidamide (147)

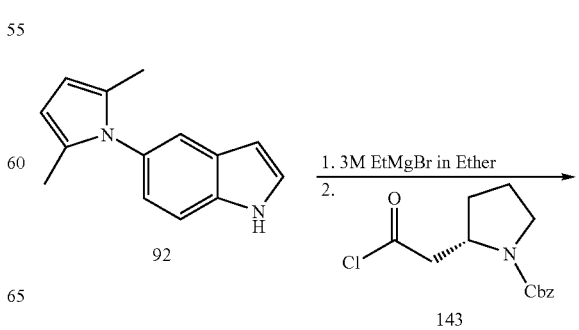

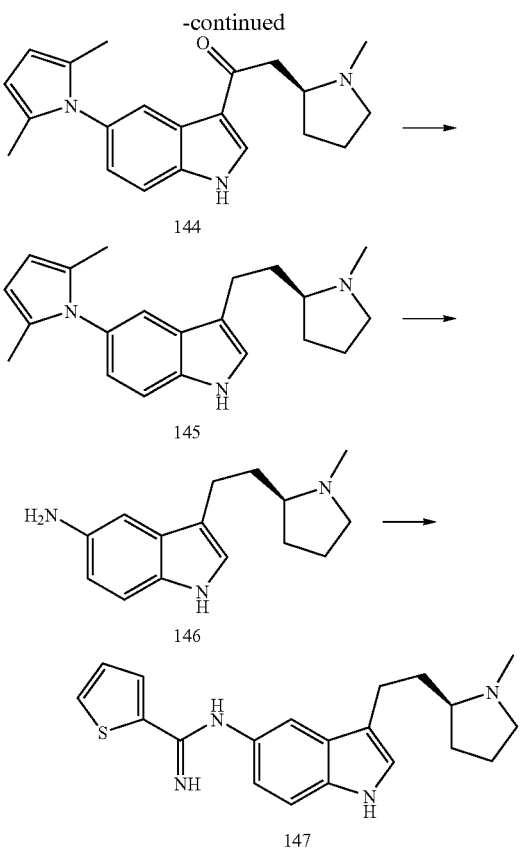

Preparation of 5-(2,5-dimethyl-1H-pyrrol-1-yl)-1H-indole (92): See Example 26 for experimental details.

Preparation of (S)-benzyl 2-(2-chloro-2-oxoethyl)pyrrolidine-1-carboxylate (143):

i) Formation of (S)-2-(1-(benzyloxycarbonyl)pyrrolidine-2-yl)acetic acid: To a reaction vial fitted with a magnetic stirbar was added L-B-Homoproline hydrochloride (250 mg, 1.51 mmol) as an off-white solid. The vessel was closed with a septum and cap, and placed in an ice-water bath. 2 N Sodium hydroxide solution (1.45 mL) was added, and the salt dissolved to give a brown solution. The septum was pierced with 2 syringes, one containing benzyl chloroformate (280 μL, 1.96 mmol), the second with 1.1 mL of 2 N sodium hydroxide (2.20 mmol). A $3^{rd}$ needle was added to relieve pressure. The two liquids were added alternatively, a little at a time to attempt to maintain a constant pH. After all reagents were added, the reaction was allowed to stir for 2 hours in the icewater bath. The reaction was transferred to a separatory funnel and ether (5 mL) was added. The ether layer was removed, and the aqueous acidified to a pH of 3 by the addition of 1 M aqueous HCl. The aqueous was extracted with ethyl acetate (3×5 mL). The combined organis were washed with brine, dried over sodium sulfate, decanted and concentrated to afford a yellow oil. Yield: 264 mg (66%) $^1$H NMR (DMSO-$d_6$) δ 12.22 (bs, 1H), 7.35 (m, 5H), 5.07 (s, 2H), 4.05-4.02 (t, J=7.2 Hz, 2H), 3.32-2.63 (m, 1H), 2.31-2.28 (m, 1H), 1.99 (s, 2H), 1.90-1.68 (m, 4H), 1.20-1.15 (t, J=7.2 Hz, 1H).

ii) To an argon purged round bottom flask fitted with a magnetic stirbar was added (S)-2-(1-(benzyloxycarbonyl)pyrrolidin-2-yl)acetic acid (235 mg, 0.893 mmol) followed by anhydrous dichloromethane (5 mL). The reaction was treated with anhydrous DMF (2 drops ~5 mL). The flow of argon was stopped, and the reaction vessel fitted with a balloon. Oxalyl chloride (0.12 mL, 1.38 mmol) was added in two portions, resulting in effervescence. The reaction was stirred at room temperature for 3 hours, before being concentrated to dryness under reduced pressure and dried overnight under high vacuum.

Preparation of (S)-benzyl 2-(2-(5-(2,5-dimethyl-1H-pyrrol-1-yl)-1H-indol-3-yl)-2-oxoethyl)pyrrolidine-1-carboxylate (144): In a similar fashion to the synthesis of compound 94, Example 26, compound 144 was isolated as a yellow solid (240 mg, 59%). $^1$H NMR (CDCl$_3$) δ: 8.72 and 8.44 (2s, 1H), 8.26 and 8.11 (2m, 1H), 7.45-7.39 (m, 7H), 7.44-7.34 (m, 4H), 7.11-7.09 (d, 1H, J=7.8 Hz), 5.89 (bs, 2H), 5.19 (s, 2H), 4.36 (m, 1H), 3.49 (s, 1H), 3.50-3.41 (m, 2H), 2.03 (s, 6H), 2.00-1.90 (m, 5H), MS-ESI m/z (%): 456 (M$^+$, 100).

Preparation of (R)-5-(2,5-dimethyl-1H-pyrrol-1-yl)-3-(2-(1-methylpyrrolidin-2-yl)ethyl)-1H-indole (145): To an argon purged round bottom flask fitted with a magnetic stirbar and containing a solution 144 (210 mg, 0.461 mmol) in anhydrous THF (5 mL) was added lithium aluminum hydride (79 mg, 2.08 mmol). The flask was fitted with a condenser and placed in an oil bath. The reaction was heated to 75° C. and stirred at reflux with an argon flow for 4.5 hrs. The reaction was revealed to be complete by TLC (10% 2M NH$_3$ in MeOH, 90% CH$_2$Cl$_2$) and was cooled gradually to room temperature. The reaction was quenched by the addition of water (0.2 mL), 3N sodium hydroxide (0.3 mL) and water (0.6 mL). The react was filtered through celite and partitioned with ethyl acetate (10 mL). The aqueous layer was extracted twice more with ethyl acetate (2×10 mL). The combined organics were washed with brine, dried over sodium sulfate and concentrated after decanting to afford a brown oil. The product was purified by silica gel column chromatography (1:1 Ethyl acetate/Hexanes to 5% 2M NH$_3$ in MeOH, 95% CH$_2$Cl$_2$) to afford the desired product as a yellow oil, compound 145. Yield: 105 mg (71%). $^1$H NMR (CDCl$_3$) δ 8.09 (bs, 1H), 7.44-7.43 (d, 1H, J=1.5 Hz), 7.41-7.38 (d, 1H, 8.7 Hz), 7.08 (d, 1H, J=2.1 Hz), 7.03-7.00 (dd, 1H, J=1.8, 8.1 Hz), 5.91 (bs, 2H), 3.49 (s, 1H), 3.15-3.10 (m, 2H), 2.86-2.65 (m, 3H), 2.34 (s, 4H), 2.03 (bs, 6H), 1.90-1.52 (m, 4H). MS-ESI (m/z, %) 322 (M$^+$, 100)

Preparation of (R)-3-(2-(1-methylpyrrolidin-2-yl)ethyl)-1H-indol-5-amine (146): To an argon purged round bottom flask fitted with a magnetic stirbar and containing a yellow solution of 145 (94 g, 0.292 mmol) in anhydrous 2-propanol (6 mL) and water (2 mL) was added solid hydroxylamine hydrochloride (406 mg, 5.84 mmol) in one portion. Triethylamine (407 mL, 2.92 mmol) was added via syringe and the flask was fitted with a condenser. The vessel was placed in an oil bath and heated to reflux. The reaction was stirred at reflux under argon for 6 hours. TLC (10% 2M NH$_3$ in MeOH, 90% CH$_2$Cl$_2$) revealed the reaction was complete, and so the reaction was cooled to room temperature. Sodium hydroxide pellets (120 mg, 3.0 mmol) were added slowly. The reaction was stirred vigorously overnight. The reaction was filtered through celite, followed by washing of the celite with 2-propanol (40 mL) and absorption of the filtrate onto silica gel. The product was purified by column chromatography (5-10% 2M NH$_3$ in MeOH, 90% CH$_2$Cl$_2$) using a silica gel plug approximately 15 mm in diameter by 30 mm in height to afford an orange solid. This product was partitioned between brine (5 mL) and ethyl acetate (10 mL). The organic was dried with anhydrous sodium sulfate before being decanted. Concentration afforded an orange oil, compound 146. Yield: 48 mg of orange oil (68%) $^1$H NMR (DMSO-$d_6$) δ 10.19 (s, 1H), 7.02-6.99 (d, J=5.4 Hz, 1H), 6.90-6.89 (d, J=2.1 Hz, 1H), 6.64-6.63 (d, J=1.5 Hz, 1H), 6.47-6.43 (dd, J=1.8, 8.7 Hz, 1H), 4.42 (bs, 1H), 2.97-2.90 (m, 1H), 2.59 (m, 2H), 2.20 (s, 3H), 2.05-1.97 (m, 4H), 1.69-1.40 (m, 4H).

Preparation of (R)—N-(3-(2-(1-methylpyrrolidin-2-yl)ethyl)-1H-indol-5-yl)thiophene-2-carboximidamide dihydrochloride (147): To an argon purged round bottom flask was charged 146 (40 mg, 0.164 mmol) and thiophene-2-carboximidothioic acid methyl ester hydroiodide (94 mg, 0.329 mmol) followed by absolute ethanol (3 mL). The reaction was stirred using a magnetic stirbar for 60 hours at room temperature. TLC (10% 2 M ammonia in methanol/90% dichloromethane) revealed all starting amine had reacted. The reaction as treated with ether (50 mL). The resulting yellow precipitate was collected by vacuum filtration and washed with ether. The precipitate was washed from the filter using methanol. The residue was concentrated, and purified by silica gel column chromatography (5-10% 2M ammonia in methanol/95-90% dichloromethane) to afford a yellow oil. The purified product was dissolved in anhydrous methanol (3 mL) and treated with 1M hydrogen chloride in ether (5 mL). After stirring for 30 minutes the precipitate was collected by vacuum filtration. The precipitate was washed with ether, followed by washing from the filter with methanol. The filtrate was concentrated and dried under high vacuum. Yield: 21 mg of yellow solid, compound 147 (30%) Melting point 212° C. $^1$H NMR (MeOD-d$_3$) δ 8.09 (br s, 2H), 7.76 (s, 1H), 7.59 (d, 1H, J=8.7 Hz), 7.41 (br s, 1H), 7.35 (s, 1H), 7.19 (d, 1H, J=8.7 Hz), 3.67 (br m, 1H), 3.19 (br m, 1H), 3.1-2.8 (br m, 2H), 2.91 (s, 3H), 2.46 (br m, 2H), 2.2-1.8 (br m, 5H). MS (TOF+): Exact calc. for $C_{20}H_{25}N_4S$ 353.1794 (MH$^+$), found 353.1782.

EXAMPLE 40

Preparation of N-[1-(3-morpholin-4-yl-propyl)-1H-indol-6-yl]-thiophene-2-carboxamidine Hydrochloride (151)

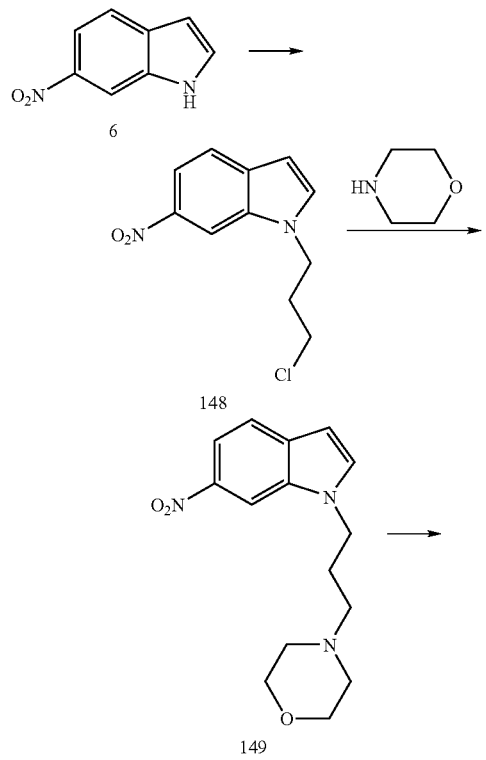

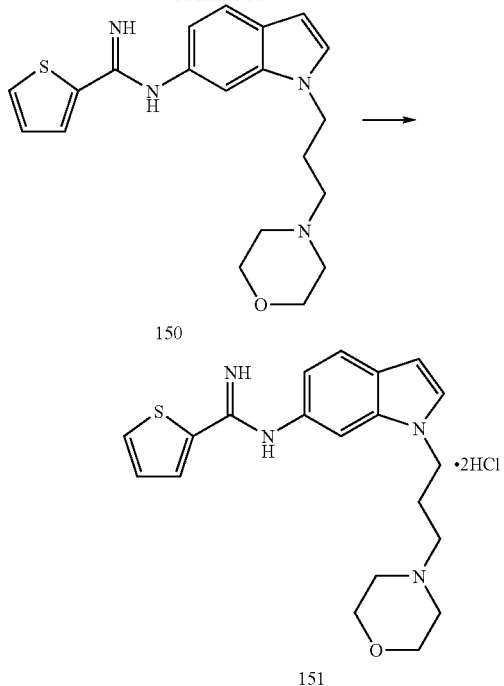

1-(3-Chloropropyl)-6-nitro-1H-indole (148): Sodium hydride (1.96 g, 49.337 mmol, 60% suspension in mineral oil) was treated with DMF (60 mL), followed by 6-nitroindole (6) (2.0 g, 12.334 mmol) in DMF (20 mL) over a period of 5 min at 0° C. After stirring for 15 min, the solution was treated with 1-chloro-3-iodopropane (3.9 mL, 37.002 mmol), the reaction was brought to room temperature and stirred for 3 h. The reaction was quenched with saturated brine (80 mL), water (80 mL) and cooled to 0° C. The solid was filtered off, washed with water (50-75 mL) and dried to obtain the crude product. The crude product was recrystallised from hot toluene (10 mL)/hexanes (5 mL) to obtain compound 148 (2.637 g, 90%) as solid. mp 85-87° C.; $^1$H-NMR (CDCl$_3$) δ 2.28-2.36 (m, 2H), 3.46 (t, 2H, J=5.7 Hz), 4.45 (t, 2H, J=6.6 Hz), 6.62 (d, 1H, J=2.7 Hz), 7.43 (d, 1H, J=3.0 Hz), 7.66 (d, 1H, J=8.7 Hz), 8.02 (dd, 1H, J=1.8, 7.9 Hz), 8.36 (d, 1H, J=0.9 Hz).

1-(3-Morpholin-4-yl-propyl)-6-nitro-1H-indole (149): A solution of compound 148 (2.35 g, 9.845 mmol) in dry CH$_3$CN (40 mL) was treated with K$_2$CO$_3$ (13.6 g, 98.458 mmol), KI (16.3 g, 98.458 mmol) and morpholine (8.58 mL, 98.458 mmol) at room temperature. The resulting mixture was refluxed for overnight (15 h). The reaction was brought to room temperature and the solvent was evaporated. The mixture was diluted with water (100 mL) and extracted with ethyl acetate (2×50 mL). The combined ethyl acetate layer was washed with water (25 mL), brine (20 mL) and dried (Na$_2$SO$_4$). The solvent was evaporated under reduced pressure and the crude product was purified by column chromatography (EtOAC: 2M NH$_3$ in methanol/CH$_2$Cl$_2$, 1:1) to obtain compound 149 (2.85 g, quantitative) as a syrup. $^1$H-NMR (CDCl$_3$) δ 1.97-2.06 (m, 2H), 2.23 (t, 2H, J=6.3 Hz), 2.38 (brs, 4H), 3.75 (t, 4H, J=4.5 Hz), 4.33 (t, 2H, J=6.6 Hz), 6.59 (d, 1H, J=3.0 Hz), 7.39 (d, 1H, J=3.0 Hz), 7.64 (d, 1H, J=8.7 Hz), 8.00 (dd, 1H, J=1.8, 8.7 Hz), 8.42 (brs, 1H).

N-[1-(3-Morpholin-4-yl-propyl)-1H-indol-6-yl]-thiophene-2-carboxamidine (150): A solution of compound 149 (2.0 g, 6.912 mmol) in abs. ethanol (20 mL) was treated with Pd—C (0.25 g), purged with hydrogen gas and stirred for overnight (15 h) under hydrogen atm. (balloon pressure). The reaction mixture was filtered through a celite pad and washed with abs. ethanol (2×20 mL). The combined ethanol layer was treated with thiophene-2-carboximidothioic acid methyl ester hydroiodide (3.94 g, 13.824 mmol) and the resulting mixture was stirred for overnight (16 h) at room temperature. The solvent was evaporated and the product was precipitated with ether (250 mL). The solid was dissolved into sat. NaHCO$_3$ sol.: CH$_2$Cl$_2$ (100 mL, 1:1). The org. layer was separated and aqueous layer was extracted with CH$_2$Cl$_2$ (2×50 mL). The combined CH$_2$Cl$_2$ layer was washed with brine (25 mL) and dried (Na$_2$SO$_4$). The solvent was evaporated and the crude product was purified by column chromatography (2M NH$_3$ in methanol: CH$_2$Cl$_2$, 5:95) to obtain compound 150 (2.348 g, 92%) as a foam. $^1$H-NMR (DMSO-d$_6$) δ 1.83-1.91 (m, 2H), 2.19 (t, 2H, J=6.6 Hz), 2.30 (brs, 4H), 3.56 (t, 4H, J=4.8 Hz), 4.14 (t, 2H, J=6.6 Hz), 6.34-6.35 (m, 3H), 6.58 (dd, 1H, J=1.2, 8.2 Hz), 6.95 (brs, 1H), 7.09 (dd, 1H, J=3.9, 5.1 Hz), 7.21 (d, 1H, J=3.0 Hz), 7.44 (d, 1H, J=8.1 Hz), 7.59 (d, 1H, J=3.9 Hz), 7.72 (dd, 1H, J=0.9, 3.6 Hz).

Hydrochloride salt of N-[1-(3-morpholin-4-yl-propyl)-1H-indol-6-yl]-thiophene-2-carboxamidine (151): A solution of compound 150 (0.65 g, 1.763 mmol) in methanol (5 mL) was treated with 1 N HCl in ether (5.3 mL, 5.291 mmol) at 0° C. The reaction was brought to room temperature and stirred for 30 min. The solvent was evaporated and the crude product was recrystallized from ethanol/ether to obtain compound 151 (0.66 g, 85%) as a solid. mp 100-105° C. ESI-MS m/z (%): 369 (M$^+$, 100).

EXAMPLE 41

Preparation of N-(1-(3-(diethylamino)propyl)-1H-indol-6-yl)thiophene-2-carboximidamide dihydrochloride (153)

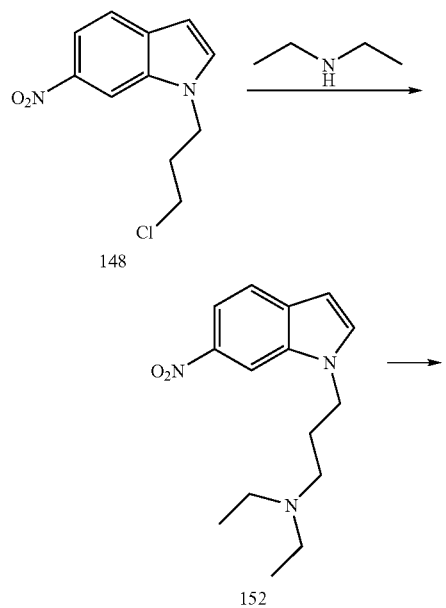

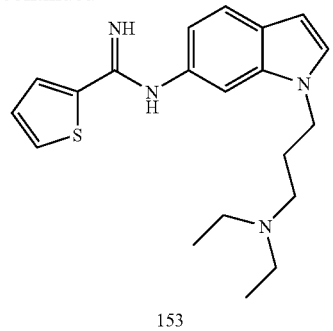

Preparation of 1-(3-chloropropyl)-6-nitro-1H-indole (148): Procedure described in Example 40. (Yield: 796.6 mg, greater than 100%)

Preparation of N,N-diethyl-3-(6-nitro-1H-indol-1-yl)propan-1-amine (152): Reaction performed as described in Example 40, using diethylamine as nucleophile. Product purified using silica gel column chromatography (2.5-5% 2M ammonia in methanol, 97.5-95% dichloromethane). Yield: 145.1 mg of compound 152 as a dark yellow oil (83.9%). $^1$H-NMR (CDCl$_3$) δ 8.37 (s, 1H), 8.02-7.99 (dd, J=2.1, 9 Hz, 1H), 7.66-7.63 (d, J=8.7 Hz, 1H), 7.43-7.42 (d, J=3 Hz, 1H), 6.60-6.58 (d, J=3 Hz, 1H), 4.32-4.27 (t, J=6.9 Hz, 2H), 2.57-2.50 (q, J=7.1 Hz, 4H), 2.43-2.39 (t, J=6.6 Hz, 2H), 2.07-1.98 (quintet, J=6.6 Hz, 2H), 1.03-0.99 (t, J=6.9 Hz, 6H).

Preparation of Amberlite Ion Exchange Resin Used for the Formation of FreeBase: to a 100 mL coarse buchner funnel was added Amberlite IRA-900 ion-exchange resin (15.25 g, approx 15 mmol) suspended in water (50 mL). The funnel was placed under vacuum to pack the solid. The solid was washed with water (50 mL) and the solvent removed through vacuum filtration. A solution of 10% sodium hydroxide (12.5 g, in 100 mL) was prepared and added to the resin in 25 mL portions. The resin was stirred with a glass stirring rod for 30 s after the addition of each portion before being put under vacuum. After the 4 basic washes, the resin was washed with water in 50 mL portions until the pH was neutral by pH paper (approx 400 mL water). The resin was dried under vacuum for 2 minutes. Denatured ethanol (2×50 mL) was used to wash the resin with stirring, followed by absolute ethanol (3×50 mL). The final product was dried under high vacuum for 15 minutes. Yield: 12.95 g of yellow beads.

Preparation of N-(1-(3-(diethylamino)propyl)-1H-indol-6-yl)thiophene-2-carboximidamide dihydrochloride (153): Reaction performed as described in Example 40, compound 150. Following isolation of the HI salt by precipitation, the salt was dissolved in ethanol. Amberlite resin (3.00 g) was added to the solution, and the mixture stirred at room temperature for 30 minutes. The reaction was diluted with ethyl acetate (30 mL) and filtered. The filtrate was concentrated to afford a yellow oil. The material was absorbed onto silica gel and purified by silica gel column chromatography (5% 2M ammonia in methanol, 95% dichloromethane). The resulting yellow oil was found to be the desired product, compound 152, by $^1$H-NMR analysis. The oil was dissolved in anhydrous dichloromethane (5 mL) and transferred to an argon purged reaction vial. The solution was treated with 1M hydrochloric acid in ether (3 mL) and the salt oiled out immediately. The reaction was stirred for 10 minutes and filtered. The vial and the filter were washed with ethyl acetate and the filtrate discarded. The yellow-brown oil which remained in the reaction vial was dissolved in methanol and the solution poured through the filter. The filter was washed with methanol and all organics combined and concentrated to afford a yellow oil. Additional drying under high vacuum afforded a yellow oil, compound 153. Yield: 80.1 mg of yellow oil. $^1$H-NMR (DMSO-d$_6$) δ 7.74-7.73 (d, J=3.3 Hz, 1H), 7.61-7.60 (d, J=4.5, 1H), 7.47-7.44 (d, J=8.1 Hz, 1H), 7.27 (s, NH), 7.22-7.21 (d, J=3 Hz, 1H), 7.11-7.08 (t, J=4.8 Hz, 1H), 6.92 (s, 1H), 6.60-6.57 (dd, J=1.2, 8.4 Hz, 1H), 6.34-6.33 (d, J=3 Hz, 2H), 4.16-4.12 (t, J=6.9 Hz, 2H), 2.46 (s, 4H), 2.36-2.31 (t, J=6.6 Hz, 2H), 1.93-1.83 (quintet, J=6.7 Hz, 2H), 1.67 (s, 4H) MW 353.

EXAMPLE 42

Preparation of N-(1-(3-(pyrrolidin-1-yl)propyl)-1H-indol-6-yl)thiophene-2-carboximidamide dihydrochloride (155)

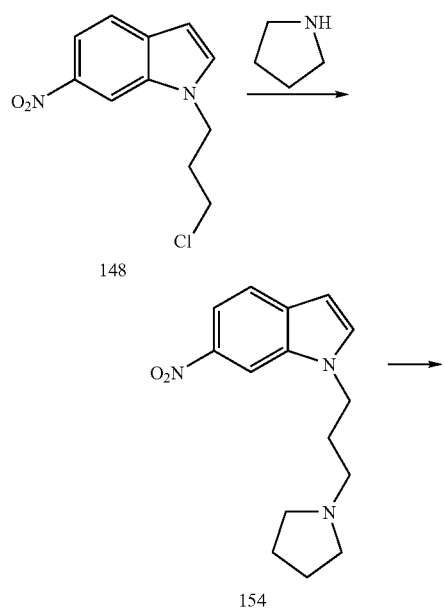

6.59 (d, J=3.3 Hz, 1H), 4.36-4.31 (t, J=6.9 Hz, 2H), 2.49 (bs, 4H), 2.41-2.37 (t, J=6.6 Hz, 2H), 2.10-2.01 (quintet, J=6.7 Hz, 2H), 1.85-1.81 (m, 4H)

Preparation of N-(1-(3-(pyrrolidin-1-yl)propyl)-1H-indol-6-yl)thiophene-2-carboximidamide dihydrochloride (155): Reaction performed as described in Example 40, compound 150. Following isolation of the HI salt by precipitation (193.5 mg), the salt was dissolved in ethanol. Treated amberlite resin (3.00 g) was added to the solution, and the mixture stirred at room temperature for 30 minutes. The reaction was diluted with ethyl acetate (30 mL) and filtered. The filtrate was concentrated to afford a yellow oil. The material was absorbed onto silica gel and purified by silica gel column chromatography (5-10% 2M ammonia in methanol, 95-90% dichloromethane). The resulting yellow oil was found to be the desired product, compound 154, by $^1$H-NMR. The oil was dissolved in anhydrous dichloromethane (5 mL) and transferred to an argon purged reaction vial. The solution was treated with 1M hydrochloric acid in ether (3 mL) and the salt oiled out immediately. The reaction was stirred for 10 minutes and filtered. The vial and the filter were washed with ethyl acetate and the filtrate discarded. The yellow-brown oil which remained in the reaction vial was dissolved in methanol and the solution poured through the filter. The filter was washed with methanol and all organics combined and concentrated to afford a yellow oil. Additional drying under high vacuum afforded a yellow solid, compound 155. Yield: 116 mg of yellow solid. $^1$H-NMR (DMSO-d$_6$) δ 7.73-7.72 (d, J=3.6 Hz, 1H), 7.60-7.59 (d, J=4.5, 1H), 7.46-7.43 (d, J=8.1 Hz, 1H), 7.21-7.20 (d, J=3 Hz, 1H), 7.11-7.08 (t, J=4.8 Hz, 1H), 6.92 (s, 1H), 6.60-6.57 (dd, J=1.2, 8.4 Hz, 1H), 6.34-6.33 (d, J=3 Hz, 2H), 4.16-4.12 (t, J=6.9 Hz, 2H), 2.46 (s, 4H), 2.36-2.31 (t, J=6.6 Hz, 2H), 1.93-1.83 (quintet, J=6.7 Hz, 2H), 1.67 (s, 4H). MW 353.

EXAMPLE 43

Preparation of N-(1-(3-(dimethylamino)propyl)-1H-indol-6-yl)thiophene-2-carboximidamide dihydrochloride (157)

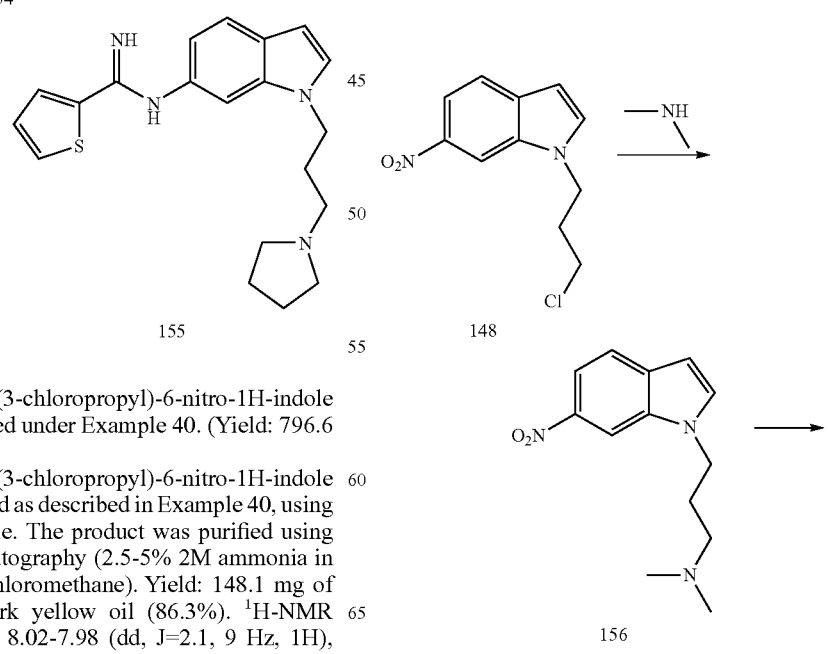

Preparation of 1-(3-chloropropyl)-6-nitro-1H-indole (148): Procedure described under Example 40. (Yield: 796.6 mg, greater than 100%)

Preparation of 1-(3-chloropropyl)-6-nitro-1H-indole (154): Reaction performed as described in Example 40, using pyrrolidine as nucleophile. The product was purified using silica gel column chromatography (2.5-5% 2M ammonia in methanol, 97.5-95% dichloromethane). Yield: 148.1 mg of compound 154 as a dark yellow oil (86.3%). $^1$H-NMR (CDCl$_3$) δ 8.43 (s, 1H), 8.02-7.98 (dd, J=2.1, 9 Hz, 1H), 7.66-7.63 (d, J=8.7 Hz, 1H), 7.43-7.42 (d, J=3 Hz, 1H), 6.60-

-continued

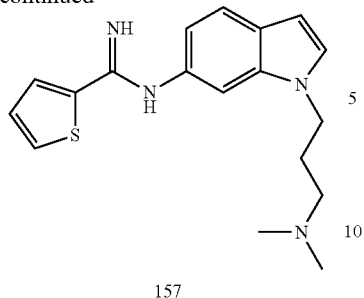

157

Preparation of 1-(3-chloropropyl)-6-nitro-1H-indole (148): Procedure described under Example 40. (Yield: 796.6 mg, greater than 100%)

Preparation of N,N-dimethyl-3-(6-nitro-1H-indol-1-yl)propan-1-amine (156): Reaction performed as described in Example 40, using dimethylamine as nucleophile. The product was purified using silica gel column chromatography (2.5-5% 2M ammonia in methanol, 97.5-95% dichloromethane). Yield: 121.4 mg of compound 156 as a dark yellow oil (88.3%). $^1$H-NMR (CDCl$_3$) δ 8.41-8.40 (d, J=1.8 Hz, 1H), 8.02-7.99 (dd, J=2.1, 9 Hz, 1H), 7.66-7.63 (d, J=8.7 Hz, 1H), 7.43-7.42 (d, J=3 Hz, 1H), 6.60-6.59 (d, J=3.3 Hz, 1H), 4.33-4.29 (t, J=6.9 Hz, 2H), 2.23-2.19 (m, 8H), 2.43 (s, 3H), 2.05-1.96 (quintet, J=6.7 Hz, 2H).

Preparation of N-(1-(3-(dimethylamino)propyl)-1H-indol-6-yl)thiophene-2-carboximidamide dihydrochloride (157): Reaction performed as described in Example 40, compound 150. Following isolation of the HI salt by precipitation (186.6 mg), the salt was dissolved in ethanol. Treated amberlite resin (3.00 g) was added to the solution, and the mixture stirred at room temperature for 30 minutes. The reaction was diluted with ethyl acetate (30 mL) and filtered. The filtrate was concentrated to afford a yellow oil. The material was absorbed onto silica gel and purified by silica gel column chromatography (5-10% 2M ammonia in methanol, 95-90% dichloromethane). The hydrochloride salt was formed using the procedure described for Example 40, compound 151. Yield: 61.7 mg of compound 157 as a yellow-orange solid. $^1$H-NMR (DMSO-d$_6$) δ 7.74-7.73 (d, J=3.9 Hz, 1H), 7.61-7.59 (d, J=4.5 Hz, 1H), 7.46-7.43 (d, J=8.1 Hz, 1H), 7.21-7.20 (d, J=3 Hz, 1H), 7.11-7.09 (t, J=4.8 Hz, 1H), 6.91 (s, 1H), 6.60-6.58 (d, J=8.1 Hz, 1H), 6.35-6.34 (d, J=3 Hz, 3H), 4.14-4.10 (t, J=6.9 Hz, 2H), 2.19-2.15 (t, J=6.6 Hz, 2H), 2.12 (s, 6H), 1.89-1.80 (quintet, J=6.7 Hz, 2H), 1.75 (s, 2H). ESI-MS m/z (%): 327 (M$^+$, 100).

EXAMPLE 44

Preparation of N-(1-(3-(methylamino)propyl)-1H-indol-6-yl)thiophene-2-carboximidamide dihydrochloride (159)

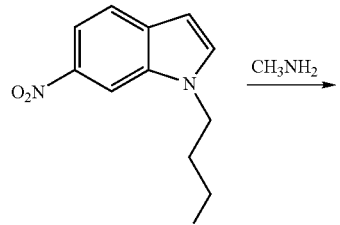

-continued

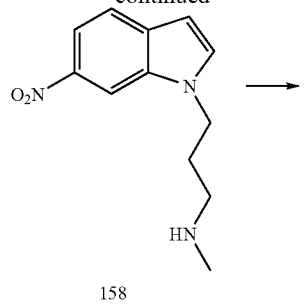

158

<div style="text-align:center">

NH
‖
thiophene-C-N(H)-indole-propyl-NH-CH$_3$

159

</div>

Preparation of 1-(3-chloropropyl)-6-nitro-1H-indole (148): Procedure described under Example 40. (Yield: 796.6 mg, greater than 100%)

Preparation of N-methyl-3-(6-nitro-1H-indol-1-yl)propan-1-amine (158): Reaction performed as described in Example 40, using methylamine as nucleophile. The product was purified using silica gel column chromatography (2.5-5% 2M ammonia in methanol, 97.5-95% dichloromethane). Yield: 91.7 mg of compound 158 as a dark yellow oil (94.1%). $^1$H-NMR (CDCl$_3$) δ 8.40-8.39 (d, J=1.8 Hz, 1H), 8.02-7.99 (dd, J=2.1, 9 Hz, 1H), 7.66-7.63 (d, J=8.7 Hz, 1H), 7.42-7.41 (d, J=3 Hz, 1H), 6.60-6.59 (d, J=3.3 Hz, 1H), 4.36-4.31 (t, J=6.9 Hz, 2H), 2.59-2.54 (t, J=6.6 Hz, 2H), 2.43 (s, 3H), 2.07-1.98 (quintet, J=6.7 Hz, 2H)

Preparation of N-(1-(3-(methylamino)propyl)-1H-indol-6-yl)thiophene-2-carboximidamide dihydrochloride (159): Reaction performed as described in Example 40, compound 150. Following isolation of the HI salt by precipitation (121.9 mg), the salt was dissolved in ethanol. Treated amberlite resin (3.00 g) was added to the solution, and the mixture stirred at room temperature for 35 minutes. The reaction was diluted with ethyl acetate (15 mL) and filtered. The filtrate was concentrated to afford a yellow oil. The material was absorbed onto silica gel and purified by silica gel column chromatography (5-10% 2M ammonia in methanol, 95-90% dichloromethane). Reaction converted to hydrochloride salt using procedure described in Example 40 for compound 151. Yield: 87.2 mg of compound 159 as a yellow-orange solid. $^1$H-NMR (DMSO-d$_6$) δ 7.74-7.73 (d, J=3.6 Hz, 1H), 7.61-7.59 (d, J=4.5, 1H), 7.46-7.43 (d, J=8.1 Hz, 1H), 7.21-7.20 (d, J=3 Hz, 1H), 7.11-7.09 (t, J=4.8 Hz, 1H), 6.92 (s, 1H0), 6.60-6.57 (dd, J=1.2, 8.4 Hz, 1H), 6.34-6.33 (d, J=3 Hz, 2H), 4.17-4.12 (t, J=6.9 Hz, 2H), 2.46-2.41 (t, J=6.6 Hz, 2H), 2.25 (s, 3H), 1.87-1.83 (quintet, J=6.7 Hz, 2H). ESI-MS m/z (%): 327 (M$^+$, 100).

EXAMPLE 45

Preparation of N-(2-benzyl-1-(2-(1-methylpyrrolidin-2-yl)ethyl)-1H-indol-6-yl)thiophene-2-carboximidamide (164)

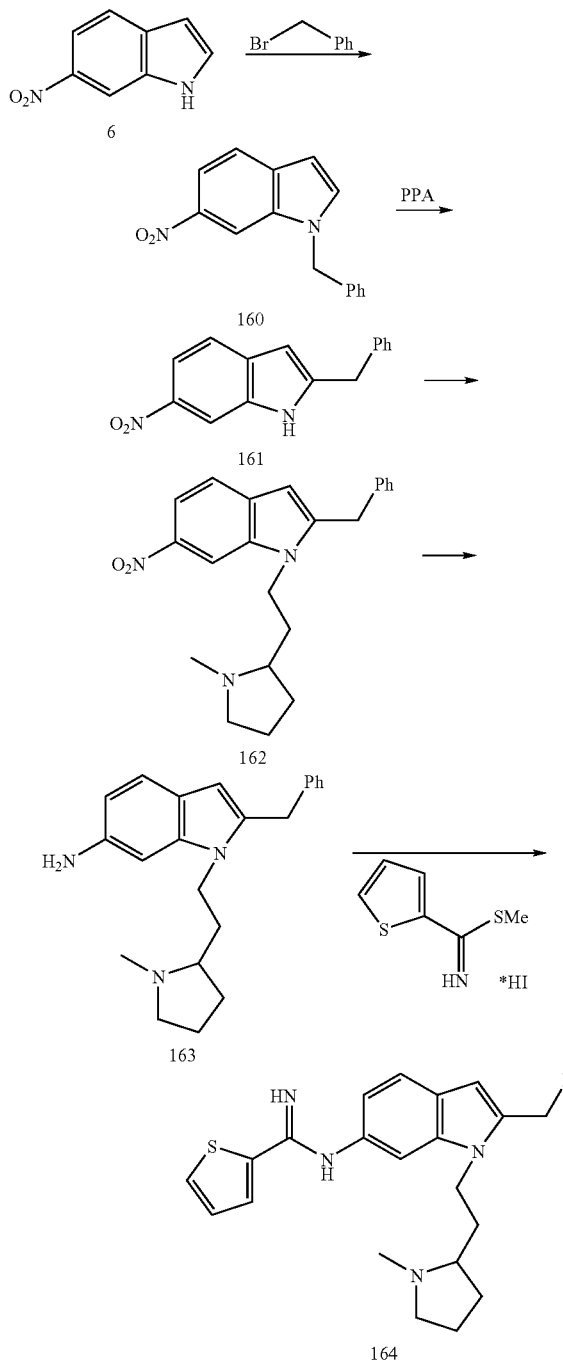

Preparation of compound 160: 6-nitroindole (6) (1.0 g, 6.167 mmol) was subjected to conditions as per Organic Syntheses, Coll. Vol. 6, p 104 and the crude product slurried in boiling hexanes, filtered and dried to yield compound 160. $^1$H-NMR (CDCl$_3$) δ 8.29 (m, 1H), 8.02 (dd, 1H, J=1.9, 8.8), 7.68 (d, 1H, J=8.5), 7.41 (d, 1H, J=3.1), 7.31 (m, 3H), 7.13, (m, 2H), 6.65 (d, 1H, J=3.0), 5.40 (s, 2H). MS (ESI+): 253 (M+1, 100%).

Preparation of compound 161: A solution of 1-benzyl-6-nitro-1H-indole (compound 160, 0.5 g, 1.982 mmol) was treated with Polyphosphoric Acid as per Synthetic Communications, 27(12), 2033-2039 (1997) and the crude product purified via silica gel column chromatography (2:8 ethyl acetate:hexanes) to provide compound 161 (115 mg, 23.0%); $^1$H-NMR (CDCl$_3$) δ 8.25-8.10 (2×m, 2H), 7.99 (dd, 1H, J=2.1, 8.9), 7.56 (d, 1H, J=8.7), 7.45-7.12 (m, 5H), 6.44 (d, 1H, J=1.6), 4.19 (s, 2H). MS (ESI+): 253 (M+1, 100%).

Preparation of compound 162: 2-benzyl-6-nitro-1H-indole (compound 161, 110 mg, 0.436 mmol), 2-(2-chloroethyl)-1-methylpyrrolidine hydrochloride (88.3 mg, 0.479 mmol), and powdered potassium carbonate (180.8 mg, 1.308 mmol) were placed in an argon-purged flask. DMF (5 mL, Aldrich sure seal™) was added and the mixture heated to 65° C. in an oil bath for 20 hours. The solution was cooled to room temperature and diluted with water (10 mL) and ethyl acetate (25 mL). The layers were separated and the aqueous phase extracted with ethyl acetate (2×25 mL). The organic extracts were combined, washed with brine (2×10 mL) and dried over magnesium sulfate. The sample was filtered, concentrated, and the resultant crude product purified using dry silica gel column chromatography eluting with 10-15 mL portions of solvent system (2.5% 2M NH$_3$ in methanol/95% dichloromethane) to afford a yellow residue 162 (47 mg, 29.7% yield); $^1$H-NMR (CDCl$_3$) δ 8.25 (s, 1H), 8.00 (dd, 1H, J=1.9, 8.8), 7.55 (d, 1H, J=8.7), 7.37-7.17 (m, 5H), 6.36 (s, 1H), 4.19 (d, 2H, J=3.4), 4.12 (m, 2H), 3.12 (m, 1H), 2.26 (s, 3H), 2.20 (m, 1H), 2.01-1.85 (m, 2H), 1.84-1.66 (m, 2H), 1.63-1.40 (m, 3H); MS (ESI+): 274.5 (M+1, 100%).

Preparation of compound 164: 2-benzyl-1-(2-(1-methylpyrrolidin-2-yl)ethyl)-6-nitro-1H-indole (compound 162, 40 mg, 0.110 mmol) was dissolved in anhydrous ethanol (5 mL) in a dry argon purged flask. Palladium, 10 wt % on activated carbon (11.7 mg, 0.011 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of (5% 2M NH$_3$ in methanol/95% dichloromethane) shows complete conversion to compound 163, 2-benzyl-1-(2-(1-methylpyrrolidin-2-yl)ethyl)-1H-indol-6-amine, which is utilized without isolation. The mixture is filtered through a pad of celite to remove insolubles, the pad washed with anhydrous ethanol (5 mL) and the ethanolic solution of the amine 163 is charged to a small, argon purged flask fitted with a magnetic stirbar. Thiophene-2-carboximidothioic acid methyl ester hydroiodide (40.8 mg, 0.143 mmol) is added to the flask and the reaction was stirred under Ar at ambient temperature for 48 hours. An additional amount of the thiophene-2-carboximidothioic acid methyl ester hydroiodide (0.3 eq) was added and stirring continued for an additional 18 hours. A further portion of thiophene-2-carboximidothioic acid methyl ester hydroiodide (0.3 eq) was added and stirring continued for an additional 18 hours, at which time the mixture was concentrated and the residue purified via chromatography on silica gel (2.5% 2M NH$_3$ in methanol/97.5% dichloromethane to 5% 2M NH$_3$ in methanol/95% dichloromethane) to afford yellow oil, compound 164 (38 mg, 78.0% yield); $^1$H-NMR (CDCl$_3$) δ 7.72 (d, 1H, J=3.2), 7.59 (d, 1H, J=4.7), 7.38 (d, 1H, J=8.1), 7.35-7.20 (m, 5H), 7.09 (m, 1H), 6.77 (s, 1H), 6.56 (d, 1H, J=7.4), 6.36 (br s, 2H), 6.14 (s, 1H), 4.14 (s, 2H), 3.96 (t, 2H, J=7.9), 2.94-2.86 (m, 1H), 2.09 (s, 3H), 2.06-1.94 (m, 2H), 1.89-1.78 (m, 1H), 1.69-1.51 (m, 3H), 1.45-1.35 (m, 2H); MS (ESI+): 443 (M+1, 70%) 219 (100%).

EXAMPLE 46

Preparation of N-(1-(4-(1H-imidazol-1-yl)butyl)-1H-indol-6-yl)thiophene-2-carboximidamide (168)

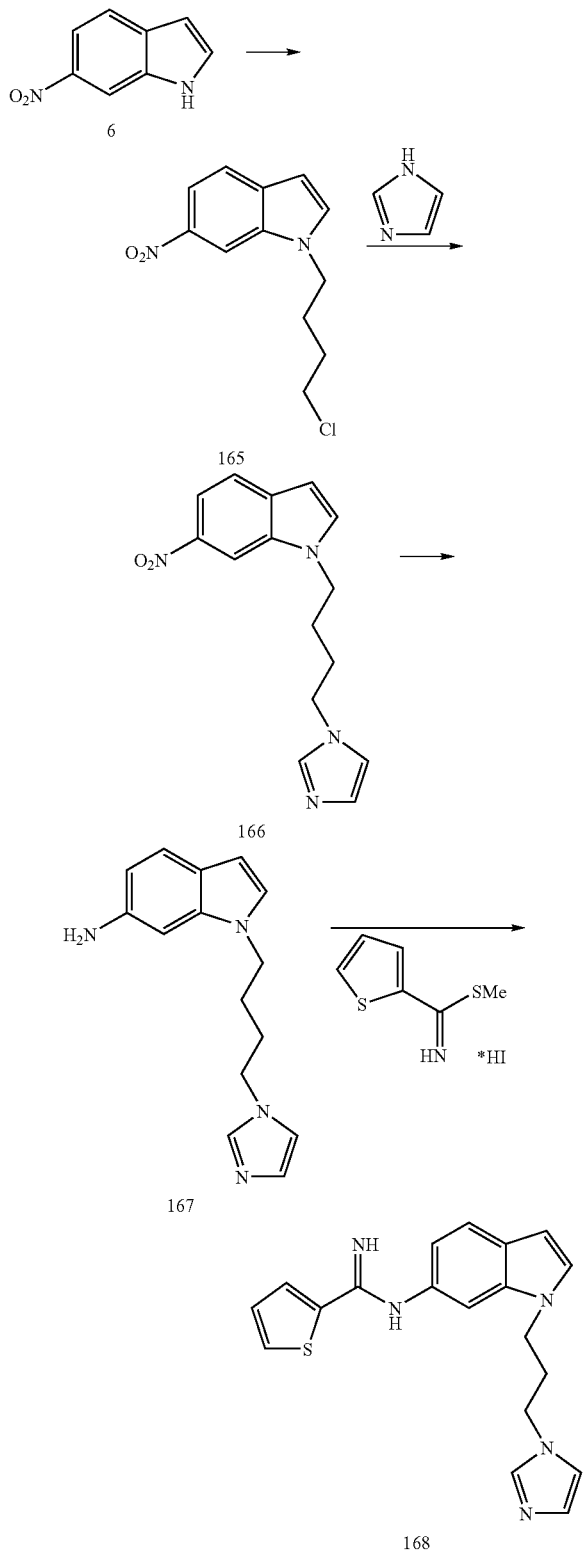

Preparation of compound 165: To sodium hydride (0.987 g, 24.68 mmol) in a 100 mL argon-purged flask fitted with a stir bar and an Argon atmosphere was added anhydrous DMF (10 mL) and the mixture was cooled to 0° C. in an ice bath. A solution of 6-nitroindole (6) (1.00 g, 6.17 mmol) in DMF (10 mL) was added slowly to the NaH mixture and after addition was complete the ice bath was removed and the reaction stirred at room temperature for ~5 min. In a second oven dried argon purged flask fitted with a stir bar was charged 1-Chloro-4-iodo-butane (2.26 mL, 18.51 mmol) and DMF (10 mL). The indole solution was added via cannula to the chlorobutane solution over a period of 10 min and the mixture was stirred at RT. After 20 min, the reaction was placed in an ice bath and quenched with brine (10 mL). The reaction was diluted with ethyl acetate and water and transferred to a separatory funnel. The organic layer was separated and the aqueous layer further extracted with EtOAc. The combined organics were washed with brine, dried with magnesium sulfate, filtered and concentrated to afford a brown oil. The crude product was purified via chromatography on silica gel (20% Ethyl acetate/80% Hexanes) to afford compound 165 (1.52 g, 97.6% yield); $^1$H-NMR (DMSO-d$_6$) δ 8.57 (d, 1H, J=1.8), 7.93-7.88 (m, 1H), 7.84 (d, 1H, J=3.0), 7.75-7.72 (m, 1H), 6.67 (d, 1H, J=3.0), 4.39 (t, 2H, J=7.0), 3.66 (t, 2H, J=6.6), 1.95-1.82 (m, 2H), 1.73-1.64 (m, 2H); MS (ESI+): 253 (M+1, 100%).

Preparation of compound 166: To an over dried, Argon purged 50 mL flask fitted with stir bar and condenser, 1H-Imidazole (0.673 g, 9.893 mmol), potassium iodide (1.642 g, 9.893 mmol) and potassium carbonate (1.367 g, 9.893 mmol) were added as solids. 1-(4-chlorobutyl)-6-nitro-1H-indole (compound 165, 0.250 g, 0.989 mmol) in a solution of acetonitrile (5 mL) was charged to the flask and stirring began. Mixture was heated at 50° C. for 16 hours then heated to reflux for 4 hours. The reaction was cooled to room temperature and diluted with dichloromethane (10 mL) and filtered through a pad of celite. The pad was washed further with dichloromethane and the solution was concentrated to afford a crude yellow solid. The product was purified by silica gel column chromatography using a solvent system of (5% 2M NH$_3$ in methanol/95% dichloromethane) to yield a yellow residue, compound 166 (182 mg, 64.7% yield); $^1$H-NMR (DMSO-d$_6$) δ 8.54 (d, 1H, J=1.5), 7.94-7.88 (m, 1H), 7.81 (d, 1H, J=3.0), 7.74-7.72 (m, 1H), 7.59 (s, 1H), 7.12 (s, 1H), 6.86 (s, 1H), 6.66 (d, 1H, J=3.0), 4.35 (t, 2H, J=6.4), 3.97 (t, 2H, J=6.4), 1.76-1.61 (m, 4H); MS (ESI+): 307 (M+Na, 100%).

Preparation of compound 168: 1-(4-(1H-imidazol-1-yl)butyl)-6-nitro-1H-indole (compound 166, 145 mg, 0.510 mmol) was dissolved in anhydrous ethanol (7 mL) in a dry argon purged flask. Palladium, 10 wt % on activated carbon (54.2 mg, 0.051 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of (10% 2M NH$_3$ in methanol/90% dichloromethane) shows complete conversion to compound 167, 1-(4-(1H-imidazol-1-yl)butyl)-1H-indol-6-amine, which is utilized without isolation. The mixture is filtered through a pad of celite to remove insolubles, the pad washed with anhydrous ethanol (7 mL) and the ethanolic solution of the amine 167 is charged to a small, argon purged flask fitted with a magnetic stir bar. Thiophene-2-carboximidothioic acid methyl ester hydroiodide (189.1 mg, 0.663 mmol) is added to the flask and the reaction was stirred under Ar at ambient temperature for 20 hours, at which time the solution was diluted with diethyl ether (100 ml) resulting in the formation of a sticky solid which could not be isolated via filtration. As a result the product was washed off the funnel with methanol, combined with the filtrate and solvents evaporated to leave a crude residue. The residue was partitioned between H$_2$O and ethyl acetate and 3M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulfate, filtered, concentrated and the residue purified via chromatography on silica gel (2.5% 2M NH$_3$ in methanol/97.5% dichloromethane) to yield yellow solid, compound 168 (101 mg, 54.5% yield); $^1$H-NMR (DMSO-d$_6$) δ 7.74 (d, 1H, J=3.0), 7.60 (d, 1H, J=5.2), 7.56 (s, 1H), 7.45 (d, 1H, J=8.3), 7.21 (d, 1H, J=3.0), 7.13-7.06 (m, 2H), 6.92 (s, 1H), 6.85 (s, 1H), 6.59 (d, 1H, J=8.0), 6.42-6.30 (br, 2×m, 3H), 4.17-4.06 (m, 2H), 3.99-3.92 (m, 2H), 1.75-1.58 (m, 4H); MS (ESI+): 364 (M+1, 100%).

EXAMPLE 47

Preparation of N-(1-(4-(dimethylamino)butyl)-1H-indol-6-yl)thiophene-2-carboximidamide (171)

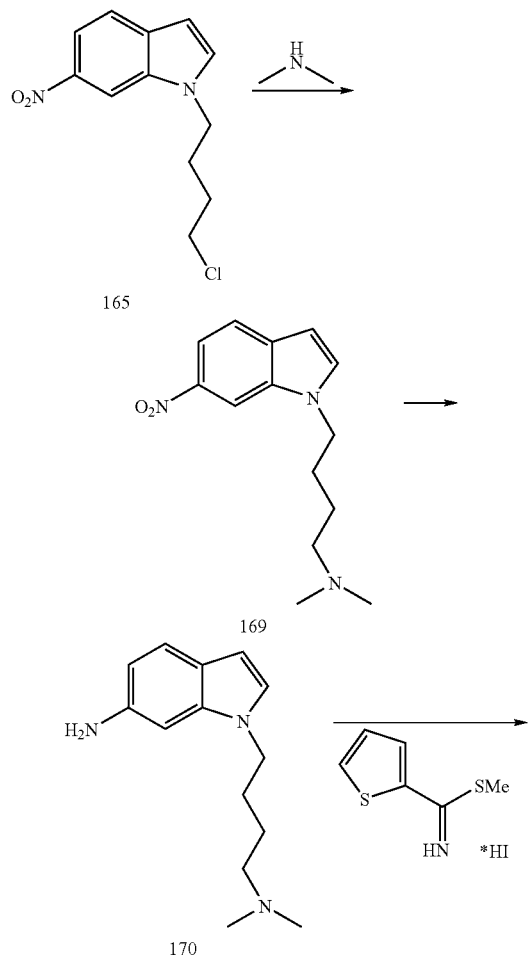

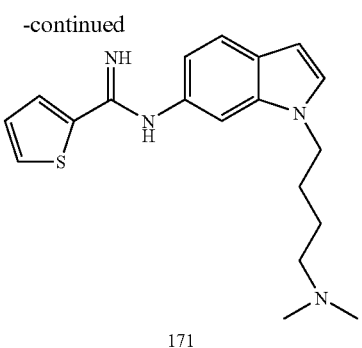

Preparation of compound 165: 1-(4-chlorobutyl)-6-nitro-1H-indole: Please see Example 46 for complete experimental details and spectral data.

Preparation of compound 169: To an oven dried, Argon purged 50 mL flask fitted with stir bar and condenser, dimethylamine hydrochloride (0.806 g, 9.893 mmol), potassium iodide (1.642 g, 9.893 mmol) and potassium carbonate (1.367 g, 9.893 mmol) were added as solids. 1-(4-chlorobutyl)-6-nitro-1H-indole (compound 165, 0.250 g, 0.989 mmol) in a solution of acetonitrile (5 mL) was charged to the flask and stirring began. Mixture was heated at 50° C. for 16 hours. The reaction was diluted with 3-4 mL of anhydrous acetonitrile due to loss of some solvent then heated to reflux for 8 hours. The reaction was cooled to room temperature and stirred at room temperature over the weekend. After a total of 88 hours the reaction was diluted with dichloromethane (10 mL) and filtered through a pad of celite. The pad was washed further with dichloromethane and the solution was concentrated to afford a crude yellow solid. The product was purified by silica gel column chromatography using a solvent system of (5% 2M NH$_3$ in methanol/95% dichloromethane to 10% 2M NH$_3$ in methanol/90% dichloromethane) to yield 2 products, the major product as a yellow oil, compound 169 (100 mg, 38.8% yield); $^1$H-NMR (DMSO-d$_6$) δ 8.54 (d, 1H, J=1.5), 7.93-7.88 (m, 1H), 7.83 (d, 1H, J=3.0), 7.74-7.71 (m, 1H), 6.66 (d, H, J=3.0), 4.34 (t, 2H, J=7.1), 2.18 (t, 2H, J=7.0), 2.06 (s, 6H), 1.78 (quintet, 2H, J=7.5), 1.36 (quintet, 2H, J=7.5). MS (ESI+): 262 (M+1, 100%).

Preparation of compound 171: N,N-dimethyl-4-(6-nitro-1H-indol-1-yl)butan-1-amine (compound 169, 88 mg, 0.337 mmol) was dissolved in anhydrous ethanol (5 mL) in a dry argon purged flask. Palladium, 10 wt % on activated carbon (35.8 mg, 0.033 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 3 hours, thin layer chromatography in a solvent system of (10% 2M NH$_3$ in methanol/90% dichloromethane) shows complete conversion to 170, 1-(4-(dimethylamino)butyl)-1H-indol-6-amine, which is utilized without isolation. The mixture is filtered through a pad of celite to remove insolubles, the pad washed with anhydrous ethanol (5 mL) and the ethanolic solution of the amine 170 is charged to a small, argon purged flask fitted with a magnetic stir bar. Thiophene-2-carboximidothioic acid methyl ester hydroiodide (124.9 mg, 0.438 mmol) is added to the flask and the reaction was stirred under Ar at ambient temperature for 20 hours, at which time the solution was diluted with diethyl ether (100 ml) resulting in the formation of a sticky solid which could not be isolated via filtration. As a result the product was washed off the funnel with methanol, combined with the filtrate and solvents evaporated to leave a crude residue. The residue was partitioned between H₂O and ethyl acetate and 3M sodium hydroxide solution added to adjust pH to 9. The mixture was transferred to a separatory funnel and the organic layer collected. The aqueous layer was further extracted with ethyl acetate and the combined organic layers were washed with brine, dried over magnesium sulfate, filtered, concentrated and the residue purified via chromatography on silica gel (5% 2M NH₃ in methanol/95% dichloromethane) to yield yellow oil, compound 171 (102 mg, 89.0% yield); ¹H-NMR (DMSO-d₆) δ 7.73 (d, 1H, J=3.4), 7.60 (d, 1H, J=5.1), 7.45 (d, 1H, J=8.2), 7.22 (d, 1H, J=3.0), 7.13-7.06 (m, 1H), 6.91 (s, 1H), 6.58 (d, 1H, J=8.2), 6.39-6.28 (br, 2×m, 3H), 4.10 (t, 2H, J=6.9), 2.16 (t, 2H, J=7.0), 2.05 (s, 6H), 1.73 (quintet, 2H, J=7.5), 1.37 (quintet, 2H, J=7.5); MS (ESI+): 341 (M+1, 100%).

EXAMPLE 48

Preparation of N-[1-(3-Morpholin-4-yl-propyl)-1H-indol-6-yl]-thiophene-3-carboxamidine dihydrochloride (173)

Dihydrochloride salt of N-[1-(3-Morpholin-4-yl-propyl)-1H-indol-6-yl]-thiophene-3-carboxamidine (173): A solution of compound 149 (0.25 g, 0.864 mmol) in dry ethanol (5 mL) was treated with Pd—C (0.025 g), purged with hydrogen gas and stirred for overnight (15 h) under hydrogen atm. (balloon pressure). The reaction mixture was filtered through celite bed and washed with dry ethanol (2×20 mL). The combined ethanol layer was treated with thiophene-3-carboximidothioic acid benzyl ester hydrobromide (0.54 g, 1.728 mmol) and the resulting mixture was stirred for over night (16 h) at room temperature. The solvent was evaporated and product was precipitated with ether (100 mL). The solid was dissolved into sat. NaHCO₃ sol.: CH₂Cl₂ (50 mL, 1:1). The org. layer was separated and aqueous layer was extracted with CH₂Cl₂ (2×30 mL). The combined CH₂Cl₂ layer was washed with brine (20 mL) and dried (Na₂SO₄). The solvent was evaporated and crude was purified by column chromatography (2M NH₃ in methanol: CH₂Cl₂, 5:95) to obtain compound 172 as a free base. Foam, ¹H-NMR (DMSO-d₆) δ 1.83-1.92 (m, 2H), 2.19 (t, 2H, J=6.9 Hz), 2.30 (brs, 4H), 3.56 (t, 4H, J=4.5 Hz), 4.13 (t, 2H, J=6.9 Hz), 6.05 (brs, 2H), 6.34 (d, 1H, J=3.0 Hz), 6.57 (d, 1H, J=8.4 Hz), 6.93 (brs, 1H), 7.20 (d, 1H, J=3.3 Hz), 7.44 (d, 1H, J=8.4 Hz), 7.54 (dd, 1H, J=2.7, 4.8 Hz), 7.63 (d, 1H, J=5.4 Hz), 8.12 (dd, 1H, J=1.2, 3.0 Hz); ESI-MS (m/z, %): 369 (M⁺, 100). A solution of above free base in methanol (5 mL) was treated with 1 M HCl in ether (2.6 mL, 2.592 mmol) and stirred for 30 min. at room temperature. The solvent was evaporated and crude was recrystallized from ethanol/ether to obtain compound 172 (0.287 g, 75%) as a solid. mp 105-108° C.

EXAMPLE 49

Preparation of N-[1-(3-morpholin-4-yl-propyl)-1H-indol-6-yl]-furan-2-carboxamidine dihydrochloride (175)

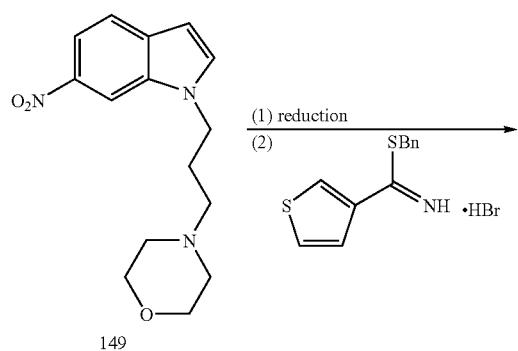

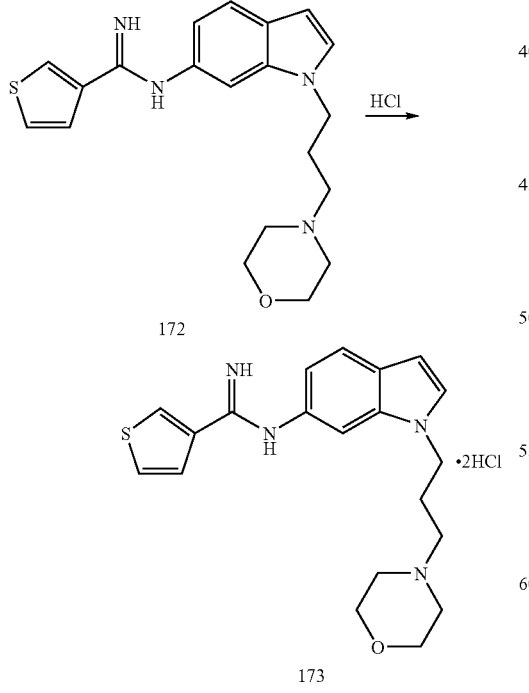

1-(3-Morpholin-4-yl-propyl)-6-nitro-1H-indole (149): Please see Example 40 for experimental details.

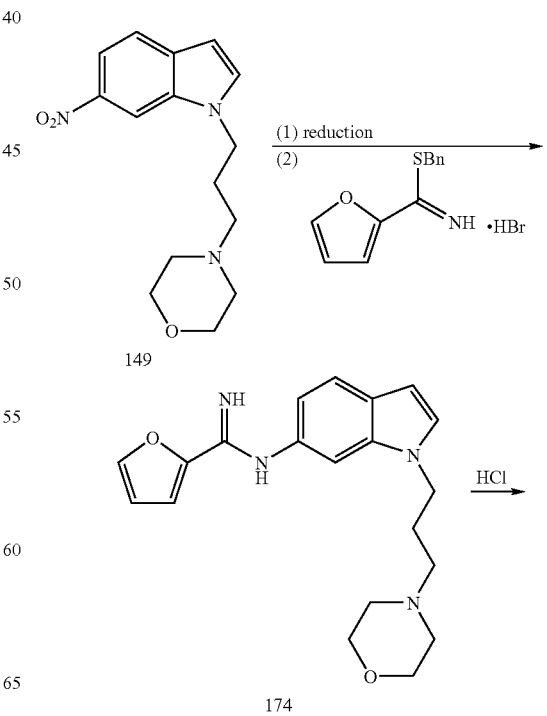

-continued

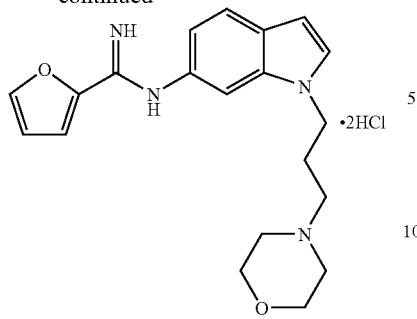

175

1-(3-Morpholin-4-yl-propyl)-6-nitro-1H-indole (149): Please see Example 40 for experimental details.

Dihydrochloride salt of N-[1-(3-morpholin-4-yl-propyl)-1H-indol-6-yl]-furan-2-carboxamidine (175): A solution of compound 149 (0.25 g, 0.864 mmol) in dry ethanol (5 mL) was treated with Pd—C (0.025 g), purged with hydrogen gas and stirred for overnight (15 h) under hydrogen atm. (balloon pressure). The reaction mixture was filtered through celite bed and washed with dry ethanol (2×20 mL). The combined ethanol layer was treated with benzyl furan-2-carbimidothioate hydrobromide (0.51 g, 1.728 mmol) and the resulting mixture was stirred for over night (16 h) at room temperature. The solvent was evaporated and product was precipitated with ether (100 mL). The solid was dissolved into sat. NaHCO$_3$ sol.: CH$_2$Cl$_2$ (50 mL, 1:1). The org. layer was separated and aqueous layer was extracted with CH$_2$Cl$_2$ (2×30 mL). The combined CH$_2$Cl$_2$ layer was washed with brine (20 mL) and dried (Na$_2$SO$_4$). The solvent was evaporated and crude was purified by column chromatography (2M NH$_3$ in methanol: CH$_2$Cl$_2$, 5:95) to obtain compound 174 as a free base. Foam: $^1$H-NMR (DMSO-d$_6$) δ 1.83-1.92 (m, 2H), 2.19 (t, 2H, J=6.9 Hz), 2.30 (brs, 4H), 3.56 (t, 4H, J=4.2 Hz), 4.13 (t, 2H, J=6.9 Hz), 6.00-6.20 (m, 2H), 6.33 (d, 1H, J=3.0 Hz), 6.55-6.62 (m, 2H), 6.98 (brs, 1H), 7.09 (d, 1H, J=3.3 Hz), 7.20 (d, 1H, J=3.0 Hz), 7.43 (d, 1H, J=8.1 Hz), 7.78 (brs, 1H); ESI-MS (m/z, %): 353 (M$^+$, 100). A solution of above free base in methanol (5 mL) was treated with 1 N HCl in ether (2.6 mL, 2.592 mmol) and stirred for 30 min. at room temperature. The solvent was evaporated and crude was recrystallized from ethanol/ether to obtain compound 175 (0.262 g, 71%) as a solid. mp 87-90° C.

EXAMPLE 50

Preparation of N-[1-(3-morpholin-4-yl-propyl)-1H-indol-6-yl]-furan-3-carboxamidine dihydrochloride (177)

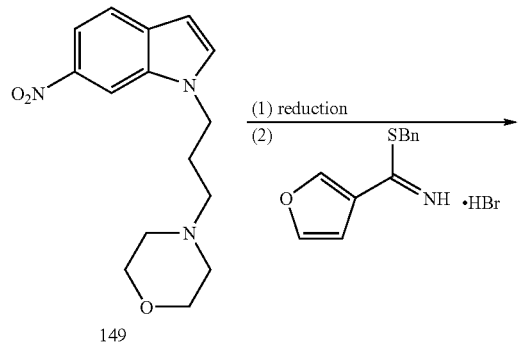

-continued

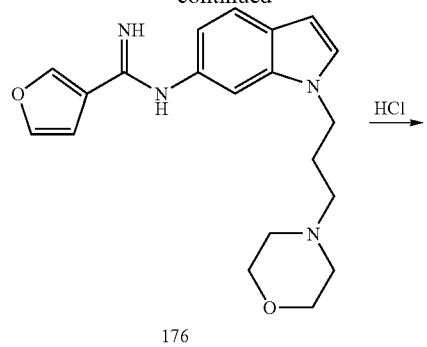

176

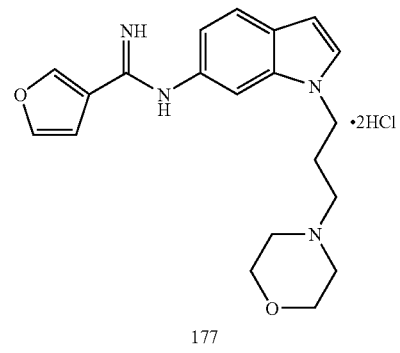

177

1-(3-Morpholin-4-yl-propyl)-6-nitro-1H-indole (149): Please see Example 40 for experimental details.

Dihydrochloride salt of N-[1-(3-morpholin-4-yl-propyl)-1H-indol-6-yl]-furan-3-carboxamidine (177): A solution of compound 149 (0.25 g, 0.864 mmol) in dry ethanol (5 mL) was treated with Pd—C (0.025 g), purged with hydrogen gas and stirred for overnight (15 h) under hydrogen atm. (balloon pressure). The reaction mixture was filtered through celite bed and washed with dry ethanol (2×20 mL). The combined ethanol layer was treated with benzyl furan-3-carbimidothioate hydrobromide (0.51 g, 1.728 mmol) and the resulting mixture was stirred for over night (16 h) at room temperature. The solvent was evaporated and product was precipitated with ether (100 mL). The solid was dissolved into sat. NaHCO$_3$ sol.: CH$_2$Cl$_2$ (50 mL, 1:1). The org. layer was separated and aqueous layer was extracted with CH$_2$Cl$_2$ (2×30 mL). The combined CH$_2$Cl$_2$ layer was washed with brine (20 mL) and dried (Na$_2$SO$_4$). The solvent was evaporated and crude was purified by column chromatography (2M NH$_3$ in methanol: CH$_2$Cl$_2$, 5:95) to obtain compound 176 as a free base. Foam; $^1$H-NMR (DMSO-d$_6$) δ 1.85-1.91 (m, 2H), 2.19 (t, 2H, J=6.6 Hz), 2.30 (brs, 4H), 3.56 (t, 4H, J=4.2 Hz), 4.13 (t, 2H, J=6.3 Hz), 6.00-6.07 (m, 2H), 6.34 (d, 1H, J=3.0 Hz), 6.56 (d, 1H, J=7.8 Hz), 6.90-6.92 (m, 2H), 7.20 (d, 1H, J=3.0 Hz), 7.43 (d, 1H, J=8.4 Hz), 7.70 (brs, 1H), 8.22 (brs, 1H); ESI-MS (m/z, %): 353 (M$^+$, 100). A solution of above free base in methanol (5 mL) was treated with 1 N HCl in ether (2.6 mL, 2.592 mmol) and stirred for 30 min. at room temperature. The solvent was evaporated and crude was recrystallized from ethanol/ether to obtain compound 177 (0.286 g, 78%) as a solid. mp 95-98° C.

EXAMPLE 51

Preparation of N-(3-(3-morpholinopropyl)-1H-indol-5-yl)thiophene-2-carboximidamide hydrochloride (181)

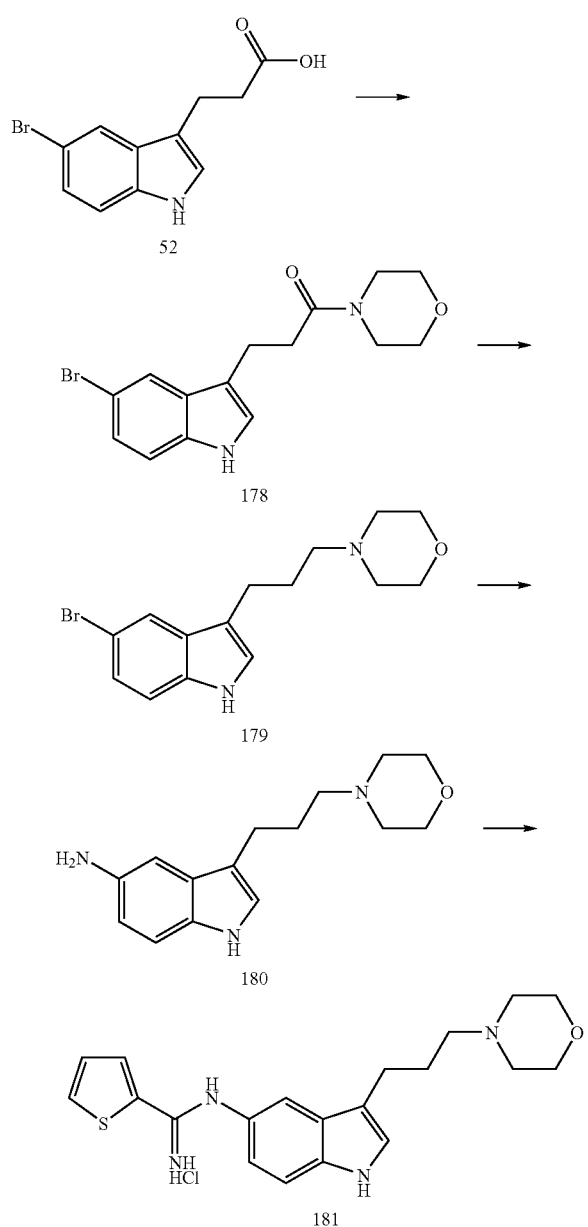

Preparation of 3-(5-bromo-1H-indol-3-yl)-N-morpholinepropanamide (178): To an argon purged vial fitted with a magnetic stirbar was charged 5-bromo-indol-3-propionic acid (52) (542 mg, 2.02 mmol), 1-[3-(dimethylamino)propyl]-3-ethylcarbodiimide hydrochloride (426 g, 2.22 mmol) and 1-hydroxybenzotriazole (273 mg, 2.02 mmol). Anhydrous DMF (5 mL) was added, followed by morpholine (0.18 mL, 2.06 mmol) and triethylamine (0.65 mL, 4.66 mmol). The reaction was stirred for 21.5 hours at room temperature. The reaction was diluted with ice-cold water (10 mL) and ethyl acetate (10 mL). The reaction was transferred to a separatory funnel and the product was extracted into the organic layer. The aqueous phase was extracted twice more with ethyl acetate (2×10 mL). The combined organics were washed with brine (10 mL), dried over magnesium sulfate, filtered and concentrated to afford a brown oil. Further drying under high vacuum afforded a pale orange solid, compound 178. Yield: 541 mg orange solid (79.4%) $^1$H NMR (DMSO) δ 11.00 (br s, NH), 7.68-7.67 (d, 1H, J=1.5), 7.31-7.28 (d, 1H, J=8.4 Hz), 7.72-7.14 (td, 2H, J=1.8, 8.4 Hz), 2.93-2.81 (m, 8H), 2.64-2.59 (t, J=7.5 Hz, 2H).

Preparation of 4-(3-(5-bromo-1H-indol-3-yl)propyl)morpholine (179): To an argon purged vial fitted with a magnetic stirbar containing compound 178(518 mg, 1.54 mmol) was added lithium aluminum hydride (146 mg, 3.84 mmol) followed by anhydrous tetrahydrofuran (15 mL). The vial was placed in a metal heating block and heated to reflux. After stirring at reflux for 21 hours, the reaction was cooled to room temperature. The cooled reaction was quenched with water (0.15 mL), 3N sodium hydroxide (0.25 mL), and water (0.45 mL) sequentially. The reaction was filtered through celite to remove the white solid and the pale yellow filtrate concentrated to afford a pale yellow oil. Drying under high vacuum afforded a pale yellow solid, compound 179. Yield: 407 mg of pale yellow solid (82%) $^1$H NMR (CDCl$_3$) δ 7.99 (s, 1H), 7.75 (s, 1H), 7.28-7.20 (m, 1H), 6.99 (s, 1H), 3.76-3.73 (t, J=4.5 Hz, 4H), 2.77-2.72 (t, J=7.5 Hz, 2H), 2.46-2.39 (m, 6H), 1.94-1.91 (m, 2H).

Preparation of 3-(3-morpholinopropyl)-1H-indol-5-amine (180): To an argon purged vial fitted with a magnetic stirbar was charged a solution of compound 179 (407 mg, 1.26 mmol) in anhydrous THF (8 mL). The orange solution was treated with solid Pd$_2$(dba)$_3$ (58 mg, 0.063 mmol) which resulted in a dark red reaction mixture. Tri-t-butyl phosphine solution (10%, 0.37 mL, 0.13 mmol) was added and the reaction was stirred at room temperature for 5 minutes. A 1M solution of lithium bis(trimethylsily)amide in THF (3.78 mL, 3.78 mmol) was added, and the yellow-brown solution placed in a metal heating block and heated to reflux. The reaction was stirred at this temperature for 16 hours. TLC (10% 2M ammonia in methanol, 90% dichloromethane) revealed all starting material had reacted. The reaction was cooled to room temperature and quenched with 1M aqueous hydrogen chloride (15 mL). The acidic reaction was extracted with ethyl acetate (3×10 mL). The aqueous phase was basified with 3N sodium hydroxide (8 mL) and partitioned into ethyl acetate (3×10 mL). The organics were washed with brine, dried over magnesium sulfate, and treated with charcoal. Filtration through celite, concentration and further drying under high vacuum afforded a dark yellow oil. Purification of the product was performed using silica gel column chromatography (5-10% 2M ammonia in methanol, 95-90% dichloromethane) Yield: 102 mg of brown oil, compound 180 (31.2%). $^1$H NMR (CDCl3) δ 7.72 (br s, NH), 7.17-7.14 (d, 1H, J=8.4 Hz), 6.92-6.89 (dd, 2H, J=2.1, 4.5 Hz), 6.67-6.64 (dd, J=2.1, 8.4 Hz, 1H), 3.77-3.74 (t, J=4.5 Hz, 4H), 2.74-2.69 (t, J=7.5, 2H), 2.49-2.43 (m, 6H), 1.97-1.89 (m, 2H).

Preparation of N-(3-(3-morpholinopropyl)-1H-indol-5-yl)thiophene-2-carboximidamide hydrochloride (181): To an argon purged vial fitted with a magnetic stirbar was charged a solution of 180 (28 mg, 0.108 mmol) in absolute ethanol (3 mL). Methyl thiophene-2-carbimidothioate hydroiodide (62 mg, 0.217 mmol) was added as a yellow solid in one portion. The reaction was stirred at room temperature for 17 hours. The reaction was complete by TLC (10% 2M ammonia in methanol, 90% dichloromethane). The reaction was diluted with ether (15 mL) and the solid which precipitated was collected by vacuum filtration. The precipitate was washed with ether (10 mL). The product was collected by washing the filter with methanol (10 mL) and collecting the filtrate. The filtrate was returned to the reaction vial and DOWEX-66 (3 g) was added. The reaction was stirred for 2 hours. The reaction was filtered and the filtrate concentrated to afford a brown solid. The solid was taken up in dichloromethane (10 mL) and partitioned with saturated sodium bicarbonate (2 mL). The organic phase was treated with brine, dried over magnesium sulfate and filtered. The filtrate was treated with 1M hydrogen chloride in ether (3 mL). After stirring for 1 hours the reaction was concentrated on the rotary evaporator. The resulting yellow solid was dried further on the high vacuum line. Yield: 45 mg of yellow solid, compound 181 (96%). $^1$H NMR (DMSO) δ 10.91 (br s, 1H), 7.96 (s, 2H), 7.42-7.39 (d, J=8.4 Hz, 2H), 7.36 (s, 1H), 7.29-7.25 (t, J=4.5 Hz, 1H), 7.24 (s, 1H), 6.92-6.89 (d, J=8.7 Hz, 1H), 3.58 (s, 4H), 2.72-2.67 (t J=7.5 Hz, 2H), 2.38 (m, 6H), 1.83-1.78 (m, 2H). MS (ESI+): 369 (MH+, 100%).

NOS In Vitro Inhibition Assays

The compounds of formula I of the present invention have been found to exhibit selective inhibition of the neuronal isoform of NOS (nNOS). Compounds may be examined for their efficacy in preferentially inhibiting nNOS over iNOS and/or eNOS by a person skilled in the art, for example, by using the methods described in Examples 11a and 11b, herein below.

EXAMPLE 52a nNOS (Rat), eNOS (Bovine) and iNOS (Murine) Enzyme Assay

The NOS isoforms used in this example were recombinant enzymes expressed in *E. coli*. Rat nNOS was expressed and purified as described previously (Roman et al., *Proc. Natl. Acad. Sci. USA* 92:8428-8432, 1995). The bovine eNOS isoform was isolated as reported (Martasek et al., *Biochem. Biophys. Res. Commun.* 219:259-365, 1996) and murine macrophage iNOS was expressed and isolated according to the procedure of Hevel et al. (*J. Biol. Chem.* 266:22789-22791, 1991). IC$_{50}$ values and percent inhibition of NOS by the compounds of the invention were determined under initial velocity measurement conditions with the hemoglobin capture assay as previously described (Hevel and Marletta, *Methods Enzymol.* 133:250-258, 1994). In this assay, nitric oxide reacts with oxyhemoglobin to yield methemoglobin, which was detected at 401 nm (e=19,700 M$^{-1}$ cm$^{-1}$) on a Perkin-Elmer Lamda 10 UV/vis spectrophotometer. The assays were performed using varying test compound concentrations. Assay mixtures for nNOS or eNOS contained 10 mM L-arginine, 1.6 mM CaCl$_2$, 11.6 mg/mL calmodulin, 100 mM NADPH, 6.5 mM BH$_4$ and 3 mM oxyhemoglobin in 100 mM Hepes (pH 7.5). Assay mixtures for iNOS contained 10 mM of L-arginine, 100 mM NADPH, 6.5 mM BH$_4$ and 3 mM oxyhemoglobin in 100 mM Hepes (pH 7.5). All assays were conducted in a final volume of 600 μL and were initiated with enzyme. Results for exemplary compounds of the invention are shown in Table 2a. These results indicate the selectivity of the compounds of the invention for nNOS inhibition.

TABLE 2a

Selective inhibition of NOS by compounds of the Invention

| Compound | Rat nNOS (μM) | Murine iNOS (μM) | Bovine eNOS (μM) |
|---|---|---|---|
| 4 | 29.6 | 46.9 | 164 |
| 5 | 57.6 | — | 643 |
| 9 | 9.4 | | 29.2 |
| 12 | 8.8 | 109 | 211 |
| 15 | 2.3 | 56 | 51.1 |
| 18 | 3.3 | 43.5 | 248 |
| 24 | 3.7 | 213.3 | 103 |
| 27 | 14.6 | 159.2 | >300 |
| 32 | 4.1 | 67.2 | 6.2 |

EXAMPLE 52b nNOS (Human), eNOS (Human) and iNOS (Human) Enzyme Assay

Recombinant human inducible NOS (iNOS), human endothelial constitutive NOS (eNOS) or human neuronal constitutive NOS (nNOS) were produced in Baculovirus-infected Sf9 cells (ALEXIS). In a radiometric method, NO synthase activity was determined by measuring the conversion of [$^3$H]L-arginine to [$^3$H]L-citrulline. To measure iNOS, 10 μL of enzyme was added to 100 μL of 100 mM HEPES, pH=7.4, containing 1 mM CaCl$_2$, 1 mM EDTA, 1 mM dithiothreitol, 1 mM FMN, 1 μM FAD, 10 μM tetrahydrobiopterin, 120 μM NADPH, and 100 nM CaM. To measure eNOS or nNOS, 10 μL of enzyme was added to 100 μL of 40 mM HEPES, pH=7.4, containing 2.4 mM CaCl$_2$, 1 mM MgCl$_2$, 1 mg/mL BSA, 1 mM EDTA, 1 mM dithiothreitol, 1 μM FMN, 1 μM FAD, 10 μM tetrahydrobiopterin, 1 mM NADPH, and 1.2 μM CaM.

To measure enzyme inhibition, a 15 μL solution of a test substance was added to the enzyme assay solution, followed by a pre-incubation time of 15 min at RT. The reaction was initiated by addition of 20 μL L-arginine containing 0.25 μCi of [$^3$H] arginine/mL and 24 μM L-arginine. The total volume of the reaction mixture was 150 μL in every well. The reactions were carried out at 37° C. for 45 min. The reaction was stopped by adding 20 μL of ice-cold buffer containing 100 mM HEPES, 3 mM EGTA, 3 mM EDTA, pH=5.5. [$^3$H]L-citrulline was separated by DOWEX (ion-exchange resin DOWEX 50 W X 8-400, SIGMA) and the DOWEX was removed by spinning at 12,000 g for 10 min in the centrifuge. An 70 μL aliquot of the supernatant was added to 100 μL of scintillation fluid and the samples were counted in a liquid scintillation counter (1450 Microbeta Jet, Wallac). Specific NOS activity was reported as the difference between the activity recovered from the test solution and that observed in a control sample containing 240 mM of the inhibitor L-NMMA. All assays were performed at least in duplicate. Standard deviations were 10% or less. Results for exemplary compounds of the invention are shown in Table 2b. These results again show the selectivity of the compounds of the invention for nNOS inhibition.

TABLE 2b

Selective inhibition of human NOS by compounds of the Invention

| Compound | Human nNOS (μM) | Human iNOS (μM) | Human eNOS (μM) |
|---|---|---|---|
| 12 | 1.2 | 60 | 15 |
| 18 | 2.6 | 12 | 26 |
| 27 | 12 | 320 | >100 |
| 32(+) | 0.32 | 72.8 | 16 |
| 32(−) | 0.2 | 72.6 | 24 |
| 37 | 0.49 | 21 | 3.8 |

Neuroprotection Studies

The neurotoxic effects of glutamate through the activation of NMDA receptors and $Ca^{2+}$ influx contribute to neuronal degeneration in several neurological diseases (Choi, *J. Neurobiol.* 23:1261, 1992; Dingledine et al., *Trends Pharmacol. Sci.* 11:334-338, 1990; Meldrum and Garthwaite, *Trends Pharmacol. Sci.* 11:379-387, 1990). Thus, compounds that prevent cell death associated with activation of NMDA receptors, either directly via NMDA antagonism (Example 12-15), or indirectly through blocking NMDA mediated NO synthesis, are candidate neuroprotective agents for the treatment of neurodegenerative diseases.

EXAMPLE 53

Neuroprotection of Rat Cortical Cells Against NMDA Challenge

According to a previously reported procedure (Tremblay et al., *J Neurosci.* 20(19):7183-92, 2000), test compounds were added for a 60-minute pre-incubation period to rat cortical neuronal cultures, which were then exposed for 30 minutes to 25 µM NMDA in buffer. After 24 hrs cultures were treated with propidium iodide and the % cell death determined and compared to control cells. As shown in FIG. 1, compounds 9, 12, and 18 protected neuronal cells from death upon NMDA challenge, indicating their efficacy as neuroprotective agents.

EXAMPLE 54

Neuroprotection of Rat Hippocampal Slices after Oxygen-Glucose Deprivation (OGD)

Figure 2:
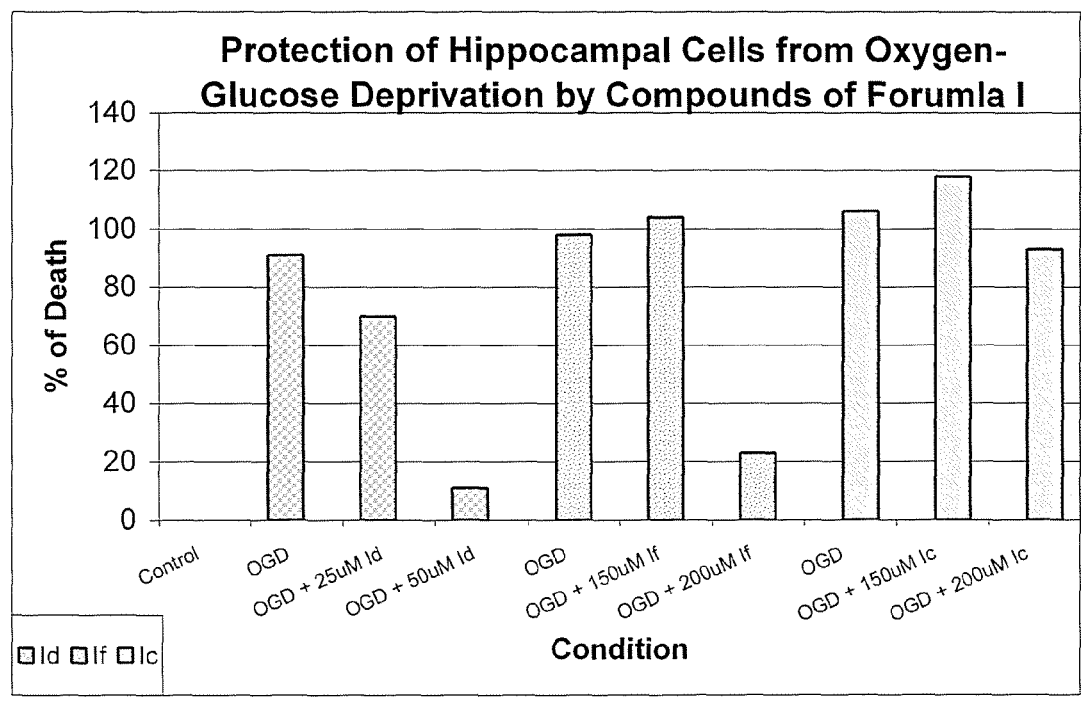
FIG. 2 is a bar graph showing the neuroprotective effect of compounds 9, 12, and 18 after challenge of oxygen-glucose-deprived (OGD) rat hippocampal slices.

Given that during stroke, ischemia, and trauma, the brain is deprived of oxygen and nutrients, OGD represents a more "physiological" insult to cortical cultures and thus is a relevant model of neuroprotection. Neuronal cultures were exposed to 90 minutes of hypoxia in glucose-free buffer with or without compound 9, 12, or 18. A 60-minute pre-incubation period with compound 12 was used in those cultures treated with this compound. After 24 hours, propidium iodide was used to determine cell death. As shown in FIG. 2, a concentration of 25 µM of compound 12 protected neurons against the 90-minute OGD insult, indicating its efficacy as a neuroprotective agent.

EXAMPLE 55

Effects on NMDA Induced $Ca^{2+}$ Influx by Compound 12

Figure 3:
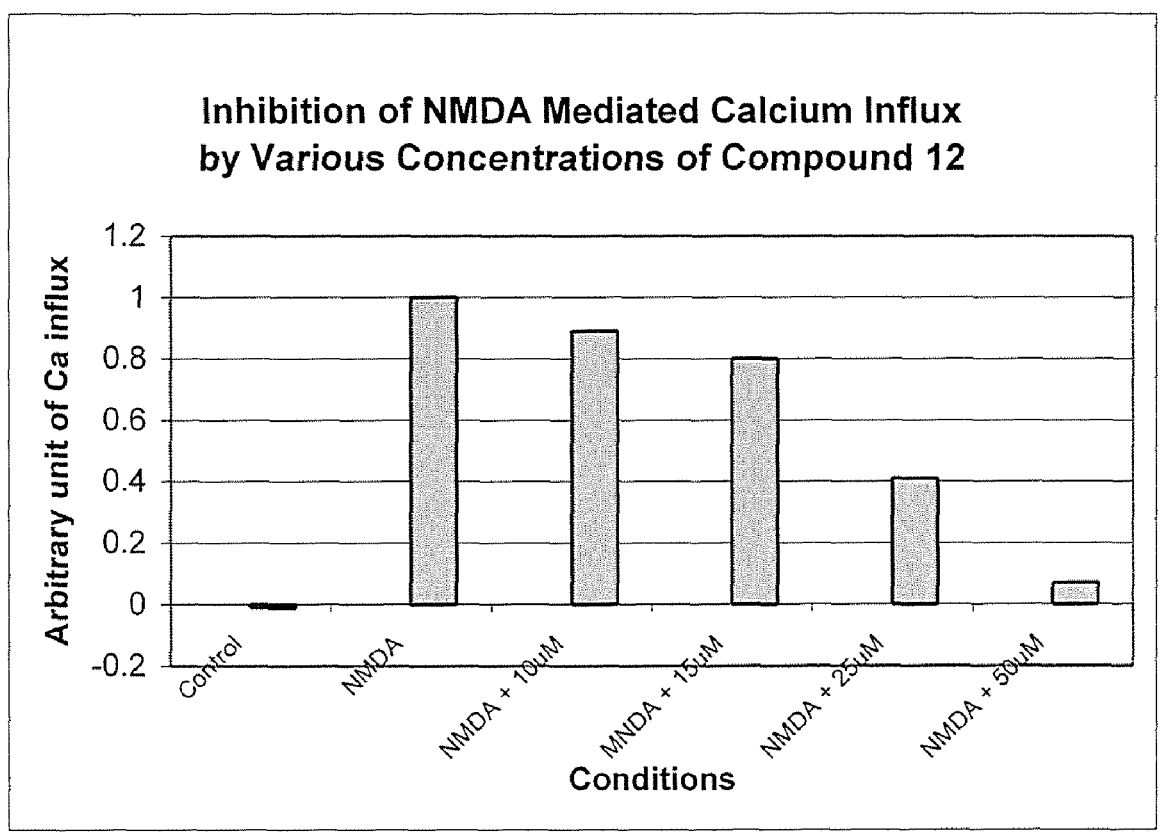
FIG. 3 is a bar graph showing the effect of compound 12 on NMDA-mediated $Ca^{2+}$ influx as measured using the fluorescent $Ca^{2+}$ sensitive dye Fluo-4FF.

To measure intracellular $[Ca^{2+}]_i$ concentrations in neuronal cultures, cells were loaded with the fluorescent $Ca^{2+}$-sensitive dye Fluo-4FF. Flourescence was read on a plate reader before and after a 15 minute application of NMDA (25 µM). NMDA induces a rapid transient elevation of $[Ca^{2+}]_i$. As shown in FIG. 3, compound 12 caused a dose-dependent (10-50 µM) inhibition of NMDA-induced $Ca^{2+}$ influx, indicating its efficacy as an NMDA antagonist and as a neuroprotective agent.

EXAMPLE 56

Effects on NMDA-Induced Whole-Cell Currents in Rat Cortical Neurons by Compound 12

Figure 4:
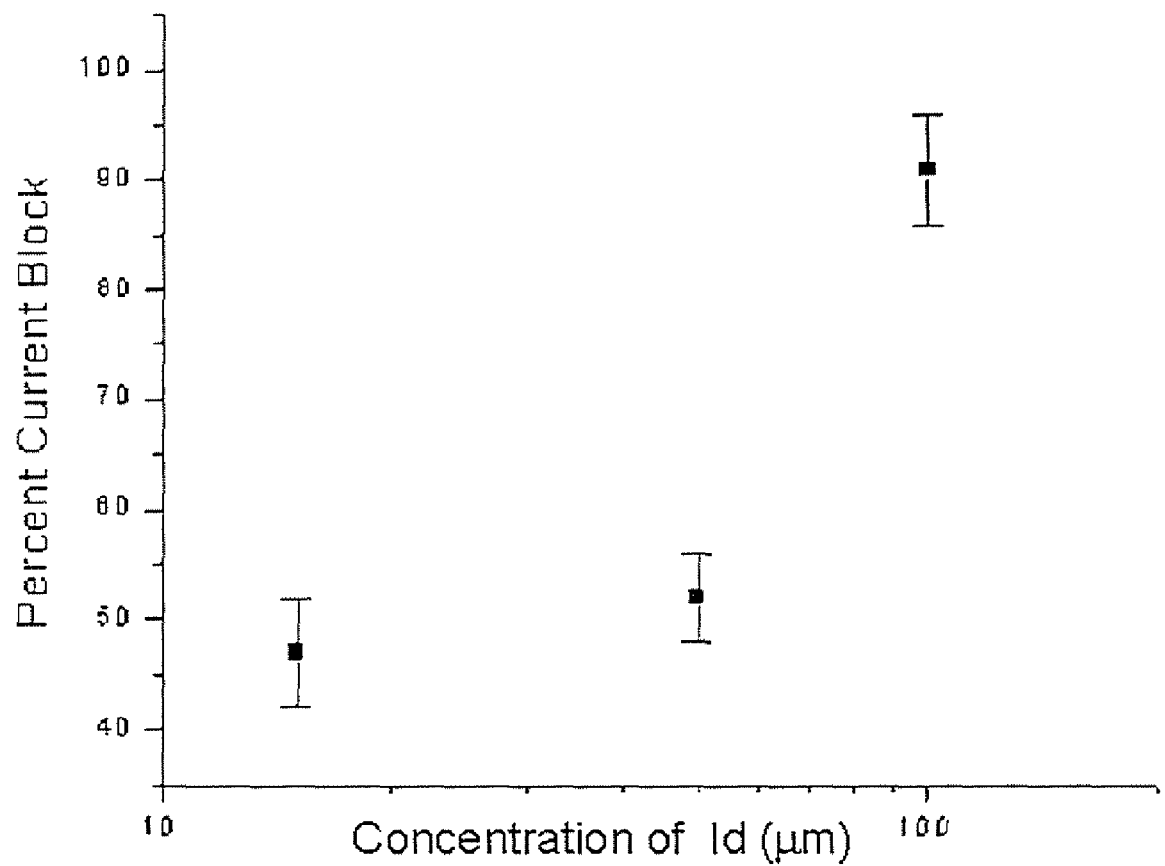
FIG. 4 is a graph showing the effects of compound 12 on NMDA-mediated whole-cell currents in rat cortical neurons.

Effects of compound 12 on NMDA-induced currents in whole-cell rat cortical neurons was performed according to literature procedures (Mealing et. al. *J Pharmacol Exp Ther.* 2001 297(3), 906-14). As shown in FIG. 4, compound 12 effectively blocked NMDA-induced currents in rat whole-cell cortical neurons in a dose-dependent manner, demonstrating its efficacy as an NMDA antagonist and as a neuroprotective agent.

EXAMPLE 57

Effects of NOS Inhibitors on Formalin-Induced Paw Licking in Mice

Formalin Induced Hyperalgesia and Inflammation: In an experimental model of sustained inflammatory nociception associated with long term intracellular changes of nociceptive processing at the level of the spinal cord, mice or rats are subjected to a subplantar injection of formalin into a paw (Chapman et al., *Brain Res.* 697:258-261, 1995; Meller and Gebhart, *Pain* 52:127-136, 1993). Two distinct phases of spontaneous nociceptive behaviour exist: The first phase (Phase I) last about 5 minutes, followed by a second phase (Phase II), lasting approximately 40 minutes characterized by persistent shaking or licking of the injected paw (Fu et al., *Neuroscience* 101(4):1127-1135, 2000). Longer periods after injection of formalin results in the development of allodynia and hyperalgesia (1-4 weeks). It has been shown previously that 7-NI exhibits anti-nociceptive activity in mice without increasing blood pressure (Moore et al., *Br. J. Pharmacol.* 102:198-202, 1992). Thus, compounds possessing n-NOS inhibitory activity should be effective for the treatment of inflammatory pain and neuropathic pain symptoms of allodynia and hyperalgesia resulting from inflammation.

Figure 5:
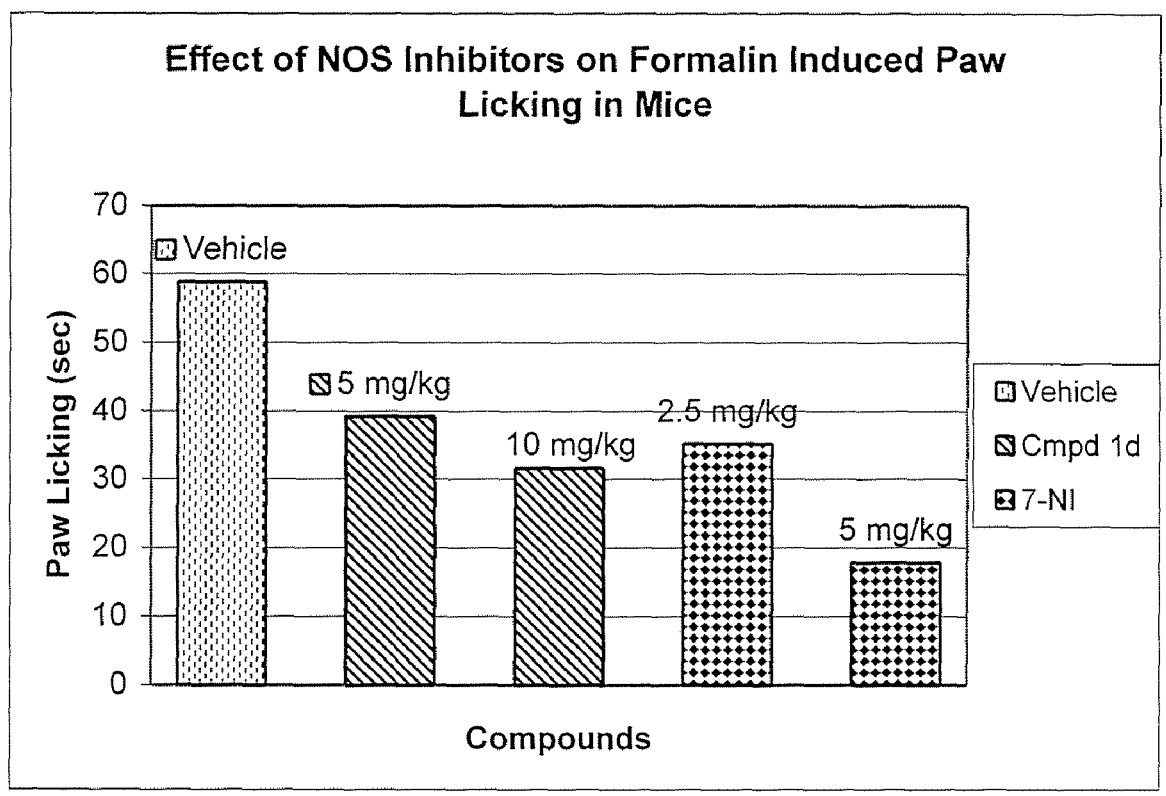
FIG. 5 is a graph showing formalin-induced paw licking in mice after treatment with (a) vehicle, (b) compound 12 at 5 mg/kg and 10 mg/kg, (c) treatment with the non-selective inhibitor 7-nitroindazole (7-NI) at 2.5 mg/kg and 5 mg/kg.

Test compounds, including compound 12 and 7-NI, were dissolved in 1% DMSO/2% Tween 80/0.9% NaCl. Male or female ICR-derived mice weighing 23±2 g were housed in APEC® cages and maintained in a controlled temperature (22° C.-24° C.) and humidity (60%-80%) environment with 12 hr light-dark cycles for 1 week prior to use. Free access to standard lab chow and tap water was granted. Test substances were administered intraperitoneally to 6 groups of 5 ICR-derived mice, weighing 23±2 g, 30 minutes before subplantar injection of formalin (0.02 mL, 1%). The reduction of formalin-induced hind paw licking time was recorded during the following 20 to 30 minute period (Phase II). As shown in FIG. 5, administration of both compound 12 and 7-NI resulted in a reduction in the frequency of paw licking in the subject mice, indicating the efficacy of this compound as a treatment for pain.

EXAMPLE 58

Neuroprotective Effect in a Mouse Model of Traumatic Brain Injury (TBI) by Compound of Formula 12

Traumatic Brain Injury Test: Male Swiss mice (Iffa Credo, France), weighing 21 to 24 g, were given water and food ad libidum before the experiment. The traumatic brain injury (TBI) model used in the experiment was the closed head injury model described by Hall (*J. Neurosurg.* 62:882-887, 1985) and modified according to Mésenge (*J. Neurotrauma* 13:209-214, 1996). Mice were held by the dorsal skin of the neck and the head was positioned under the injury apparatus, with the chin resting firmly on the base of the apparatus. The injury weight was then released, falling freely to hit a metal impounder resting on the top of the head. A 50-g weight was dropped 24 cm resulting in a 1200 g/cm impact injury. Injury caused immediate unconsciousness, as judged by the loss of righting reflex and the loss of any pain reflex. The loss of consciousness lasted 2-5 min. Of the mice 20-30% died in the first post-traumatic seconds. There was no delayed mortality or prostration in the surviving mice, with test animals taking water and food similarly to control animals.

Neurological Deficit Evaluation: Neurological examinations were performed in a blinded fashion 1 h, 4 h, and 24 h after TBI on compound 12-treated uninjured mice and, control mice treated with vehicle alone, and compound 12-treated injured mice. Sensorimotor status was evaluated blindly by a grip test and a string test, as described by Hall (*J. Neurosurg.*, 62:882-887, 1985). Each mouse was picked up by the tail and placed on a taut string 60 cm long suspended between two upright bars 40 cm above a padded table. The grip score was measured as the length of time (in seconds) during which the mouse remained on the string in some manner, with a cut-off of 30 seconds. The string test, scoring from 0 (severely impaired) to 5 (normal) evaluated the way mice could hang and move on the string, with the following scoring criteria: 0—mice fall during the 30-second period evaluation; 1—mice hang on the string during the 30-second period evaluation, using only one paw; 2—mice hang on the string using the four paws, at least 5 seconds; 3—mice hang on the string using four paws and the tail, at least 5 seconds; 4—mice hang on the string using the four paws and the tail and move, at least 5 seconds; and 5—mice reach one of the upright bars during the 30-second period evaluation.

Figure 6:
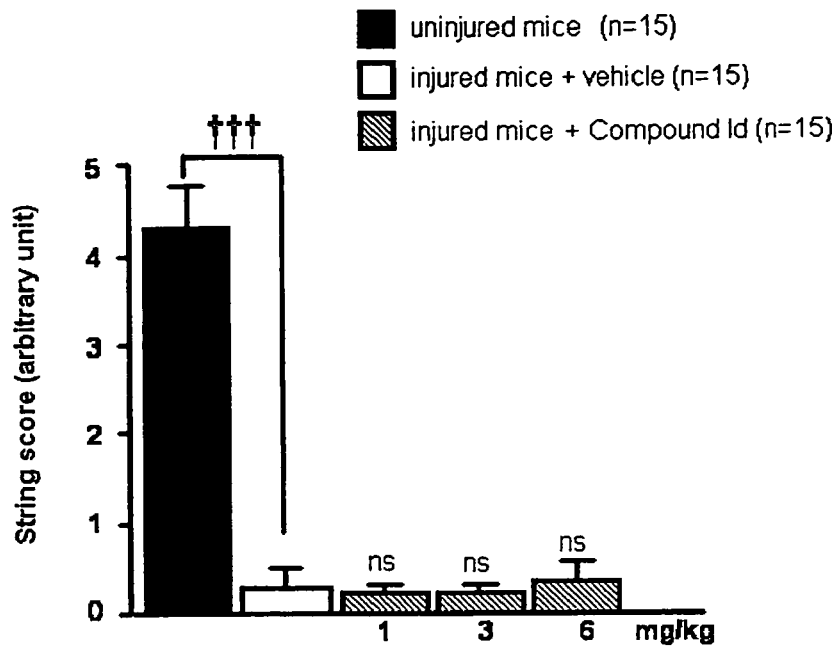
FIG. 6 is a bar graph showing the dose-related effect of compound 12 on the string score evaluated 1 hour after traumatic brain injury in mice. Compound 12 or vehicle was given s.c. 5 minutes post-injury. ††† P<0.001 versus uninjured mice; ns: non-significant versus vehicle-treated injured mice.
Figure 7:
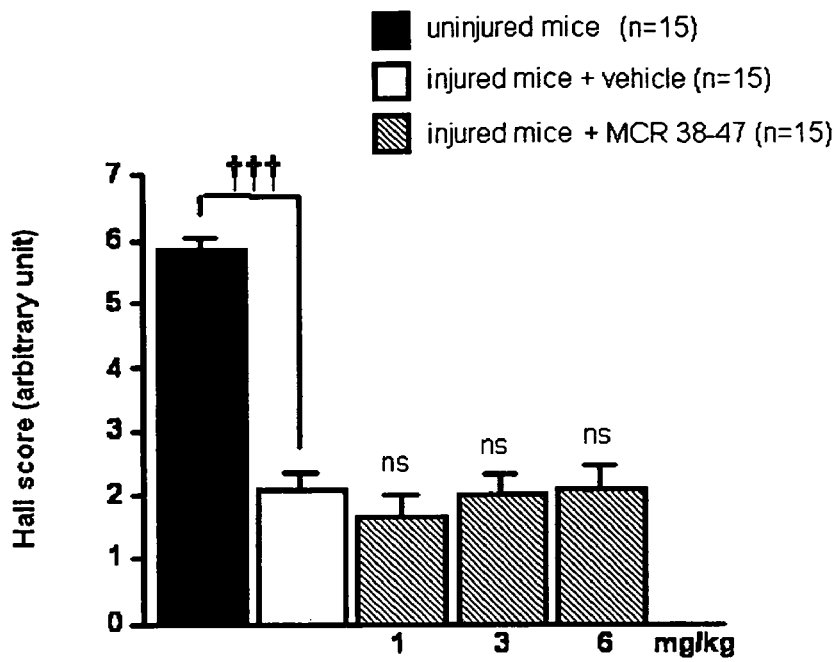
FIG. 7 is a bar graph showing the dose-related effect of compound 12 on the Hall score evaluated 1 hour after traumatic brain injury in mice. Compound 12 or vehicle was given s.c. 5 minutes post-injury. †††  $P<0.001$ versus uninjured mice; ns: non-significant versus vehicle-treated injured mice.
Figure 8:
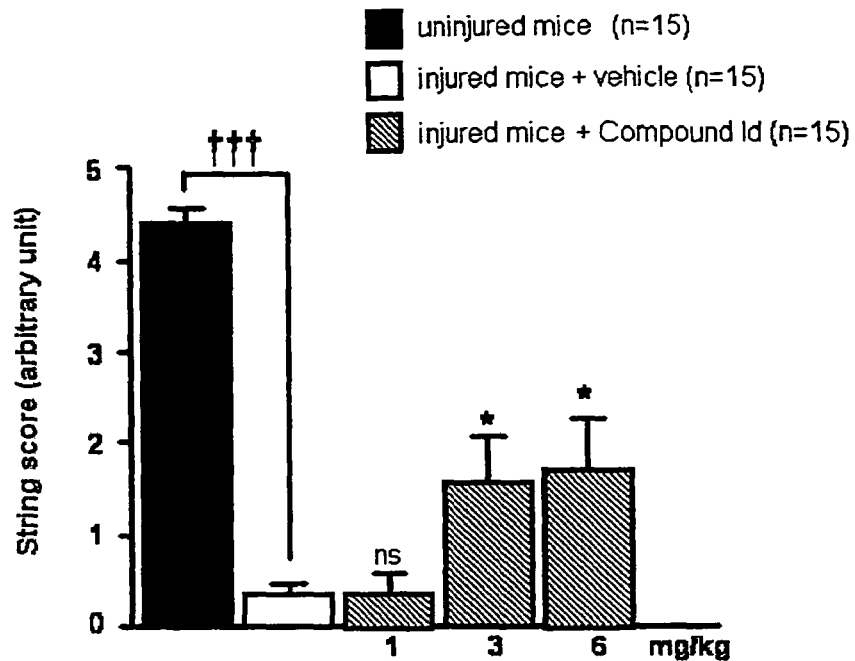
FIG. 8 is a bar graph showing the dose-related effect of compound 12 on the string score evaluated 4 hours after traumatic brain injury in mice. Compound 12 or vehicle was given s.c. 5 minutes post-injury. ††† $P<0.001$ versus uninjured mice; *$P<0.05$ versus vehicle-treated injured mice; ns: non-significant versus vehicle-treated injured mice.
Figure 9:
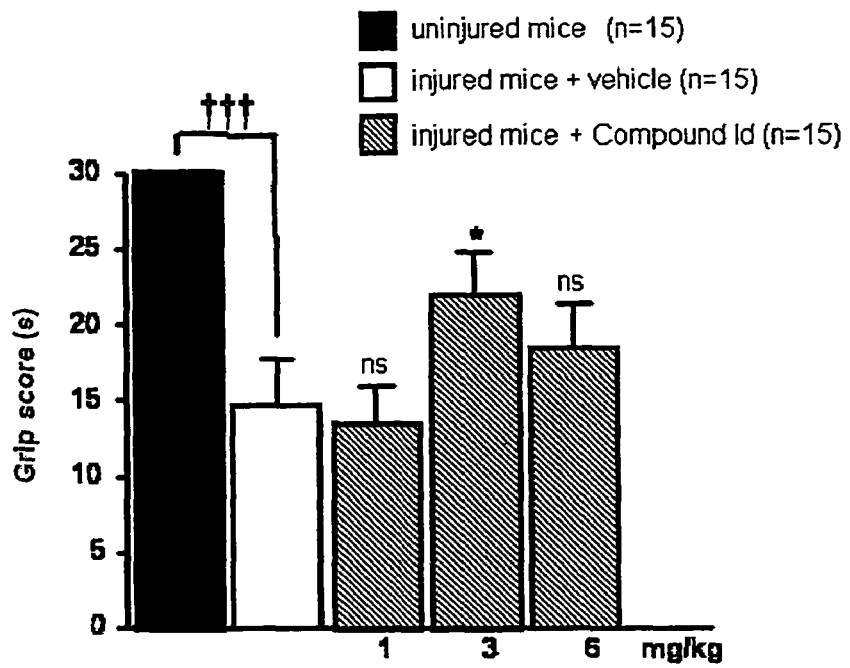
FIG. 9 is a bar graph showing the dose-related effect of compound 12 on the grip score evaluated 4 hours after traumatic brain injury in mice. Compound 12 or vehicle was given s.c. 5 minutes post-injury. ††† $P<0.001$ versus uninjured mice; *$P<0.05$ versus vehicle-treated injured mice; ns: non-significant versus vehicle-treated injured mice.
Figure 10:
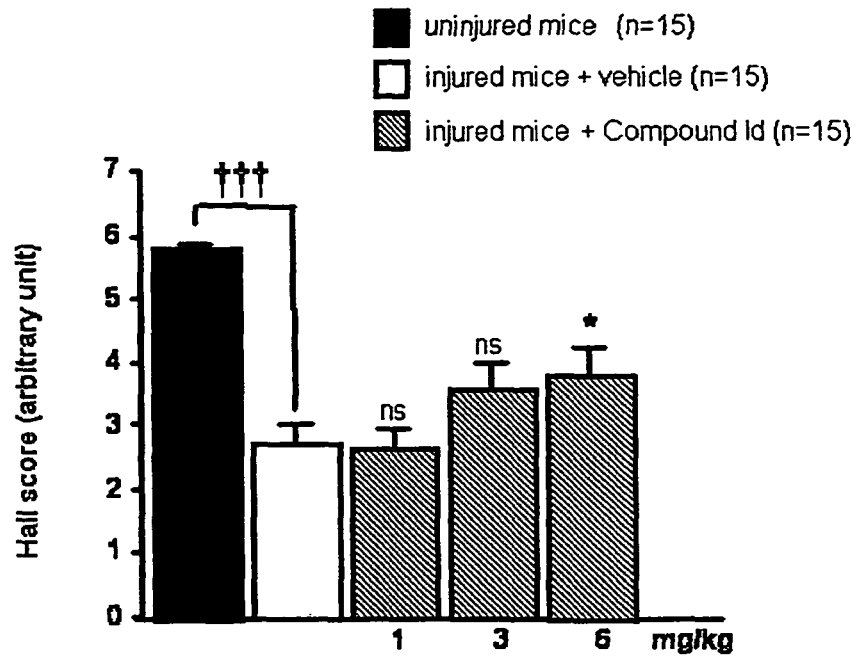
FIG. 10 is a bar graph showing the dose-related effect of compound 12 on the Hall score evaluated 4 hours after traumatic brain injury in mice. Compound 12 or vehicle was given s.c. 5 minutes post-injury. ††† $P<0.001$ versus uninjured mice; *$P<0.05$ versus vehicle-treated injured mice; ns: non-significant versus vehicle-treated injured mice.

One hour after TBI, no significant improvement in the string score (FIG. 6, Table 3) or in the Hall scores (FIG. 7, Table 4) was observed in the control mice or in the treated mice. However, 4 hours following TBI, a significant improvement in the string scores (FIG. 8, Table 5) for the 3 and 6 mg/kg treatment group and in grip score for the 3 mg/kg treatment group with a trend towards improvement in the 6 mg/kg group (FIG. 9, Table 6). A significant improvement in the Hall score was observed for the 6 mg/kg treatment group 4 hours after TBI (FIG. 10, Table 7). A non-significant trend towards improvement was observed after 24 hours in the string, grip and Hall scores for treated groups relative to control was observed after a single s.c. dose of compound 12. These results indicate a neuroprotective effect of compound 12 following traumatic brain injury.

Figure 11:
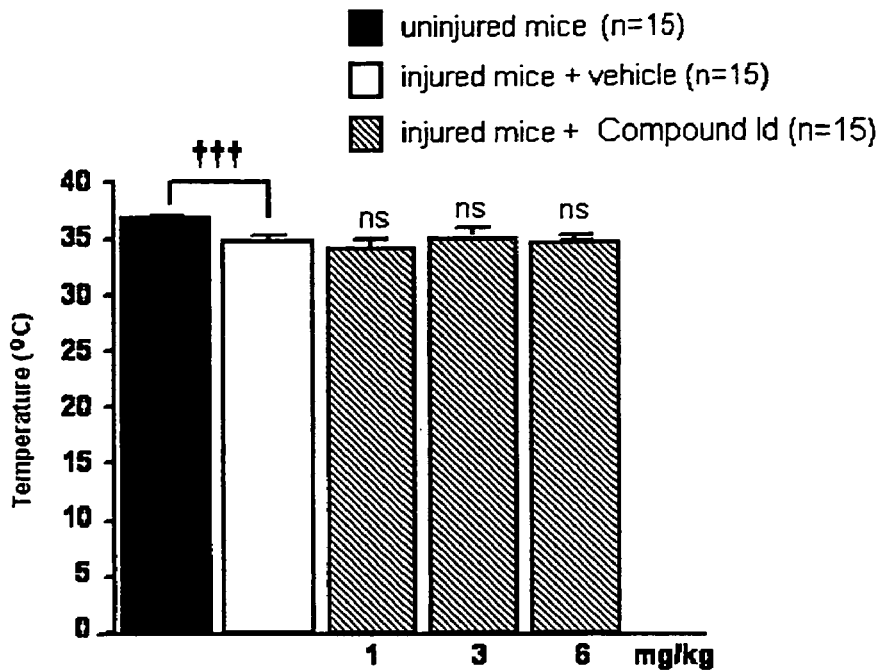
FIG. 11 is a bar graph showing the dose-related effect of compound 12 on body temperature evaluated 1 hour after traumatic brain injury in mice. Compound 12 or vehicle was given s.c. 5 minutes post-injury. ††† $P<0.001$ versus uninjured mice; ns: non-significant versus vehicle-treated injured mice.
Figure 12:
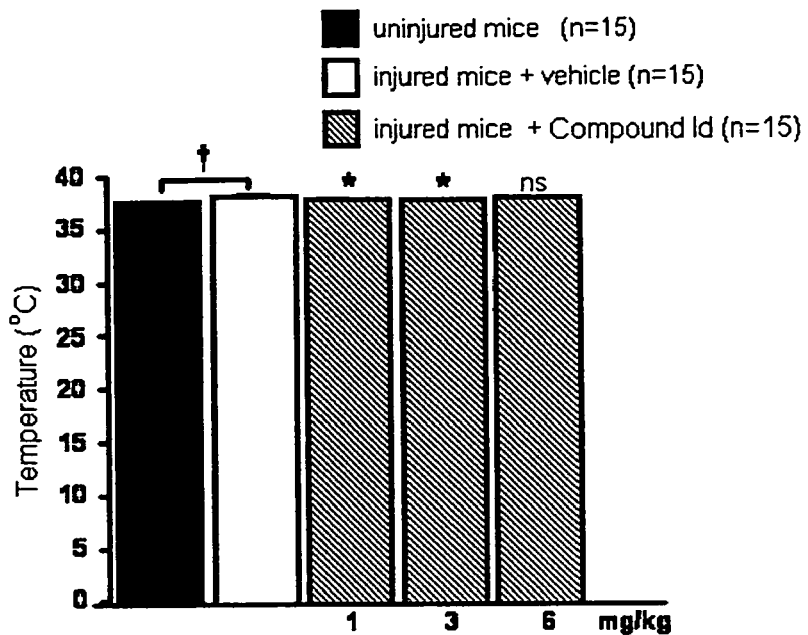
FIG. 12 is a bar graph showing the dose-related effect of compound 12 on body temperature evaluated 4 hours after traumatic brain injury in mice. Compound 12 or vehicle was given s.c. 5 minutes post-injury. † $P<0.05$ versus uninjured mice; *$P<0.05$ versus vehicle-treated injured mice; ns: non-significant versus vehicle-treated injured mice.

Body Temperature and Weight Loss: Body temperature and weight loss were recorded for uninjured mice, and for injured treated and control mice at 1, 4, and 24 hours after injury. One hour post TBI, a significant drop in body temperature was noted in injured mice, with no difference between treated and control mice (FIG. 11, Table 8). At 4 hours post TBI, untreated animals had a significant elevated body of 37.1 while the average body temperature of the treated mice was similar to uninjured mice (FIG. 12, Table 9). At 24 hours injured control mice and low-dose treated mice (1 mg/kg) had a lower body temperature than uninjured or injured mice treated with 3 or 6 mg/kg.

Figure 13:
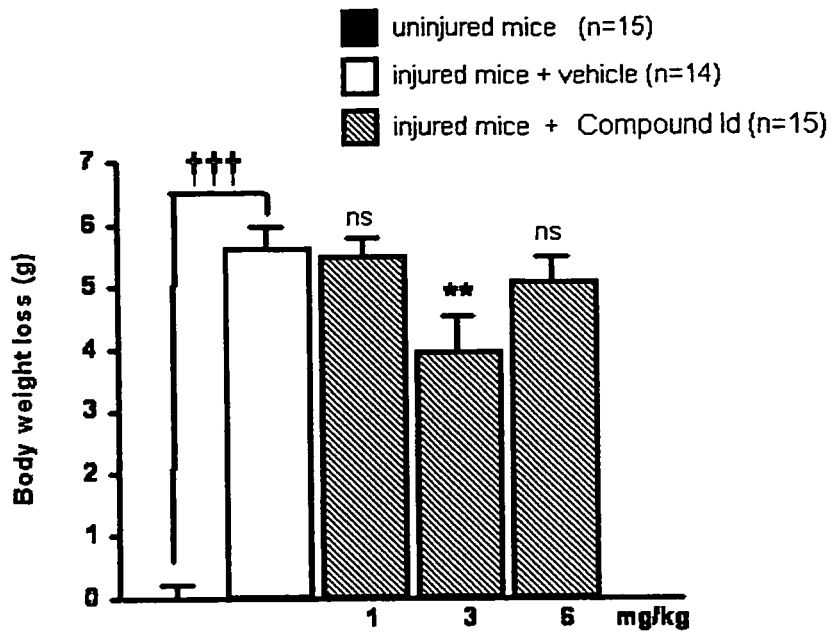
FIG. 13 is a bar graph showing the dose-related effect of compound 12 on body weight loss evaluated 24 hours after traumatic brain injury in mice. Compound 12 or vehicle was given s.c. 5 minutes post-injury. ††† $P<0.001$ versus uninjured mice; *$P<0.05$ versus vehicle-treated injured mice; ns: non-significant versus vehicle-treated injured mice.

Injured mice had a significant loss of body weight 24 hours after TBI relative to uninjured mice (FIG. 13, Table 10). However, a significant improvement in body weight was observed for mice in the 3 mg/kg treatment group. A reduction of body mass and growth rate is a characteristic secondary phenomenon associated with acute brain trauma partly due to hypercatabolism of the damaged brain tissue (J. L. Pepe and C. A. Barba, *J. Head Trauma Rehabil.* 14: 462-474, 1999; Y. P. Tang et al. *J. Neurotrauma* 14: 851-862, 1997). Therefore, a reduction in the loss of body weight is further indication of the neuroprotective effect of compound 12 following traumatic brain injury.

EXAMPLE 59

Neuroprotection in CA1 Hippocampal Slices after OGD

Brain slice preparations are a valuable tool to study mechanisms underlying neurotoxicity and to assess the protective potential of new neuroprotective therapeutic agents. For example, nitric oxide inhibitors have been shown to attenuate OGD-induced damage (Izumi et al., *Neuroscience Letters* 210:157-160, 1996) and to block anoxic preconditioning (Centeno et al., *Brain Research* 836:62-69, 1999) in acute rat hippocampal slices. Slice preparations allow precise control of the neuronal environment, thus allowing both ionic and pharmacological manipulations not possible in vivo. The hippocampal slice model is especially useful for studying ischemia-induced neurotoxicity, since its CA1 neurons are among the most sensitive to neuronal injury. Furthermore, the hippocampal slice preserves physiological neuronal-glial cell interactions and synaptic circuitry, and retains its functional viability well beyond 6 h. Orthodromic stimulation of the Schaffer collateral input to neurons in the CA1 and subsequent measurement of field potentials near the pyramidal cell bodies of the CA1 neurons has been a method of choice for assessing viability in this model (see FIG. 14).

Brain injury can be measured in brain sections by incubating sections of fresh brain in 2,3,5-triphenyltetrazolium chloride (TTC). TTC, which is colorless, is reduced by mitochondrial succinate dehydrogenase in living tissue to a red formazan product. Combinations of photography or scanning and image analysis are then used to measure the area of normal (red) and damaged (uncolored) tissue at the surface of each section face and estimate the extent of damage. The TTC staining technique has been further refined by members of the Experimental Stroke Group at IBS (Study Host: University of Ottawa, Canada) using a solvent to extract the colored formazan product from tissue sections and measured it spectrophotometrically, thus obtaining a simple, objective measure of damage (Preston and Webster, *J. Neurosci. Meth.* 94(2):187-92, 1999). Watson et al. (*J. Neurosci. Meth.* 53:203-208, 1994) have demonstrated a correlation between TTC reaction product and population spike amplitude. A modified version of the technique of Preston and Webster was applied to hippocampal slices in combination with field potential measurements of population spike amplitude to screen for neuroprotective effects of compounds of the invention, such as, for example, compound 12.

Slice Preparation: Male Wistar rats, 180-200 gm, were anesthetized with halothane and decapitated. Their brains were removed and placed in artificial cerebral spinal fluid (ACSF) at 0.5° C. within 60 s of decapitation. Composition of the ACSF was (in mM): 127 NaCl, 2 KCl, 1.2 $KH_2PO_4$, 26 $NaHCO_3$, 2 $MgSO_4$, 2 $CaCl_2$, 10 glucose, equilibrated with 95% $O_2$/5% $CO_2$, pH 7.4. Brains were hemisected and hippocampi were dissected out and sectioned into 400 μM thick slices using a McIlwain Tissue chopper (Mickle Laboratory Engineering Co. Gomshall, GB). Sectioning was initiated approximately 1 mm from the rostral end of the hippocampus and approximately 12 slices were harvested from each hippocampus. Slices were distributed into groups in a rotational manner so that each group contained slices from all sectioned regions of the hippocampus. The hippocampal slices were placed on nylon mesh platforms in interface-type incubation chambers (6-8 slices per platform; 1 platform per chamber) for 90 min at 35° C. The ACSF in these chambers, and the atmosphere above it, was continuously gassed with 95% $O_2$/5% $CO_2$. In some instances, after an initial 60 min stabilization period, slices received a pre-insult treatment by transferring the slices on their nylon mesh platform to another chamber for a 30 min incubation in the appropriate ACSF. The slices that were subjected to a 10 min oxygen-glucose deprivation (OGD) were transferred on their nylon mesh platforms to incubation chambers that contained anoxic, low glucose (4 mM) ACSF. The ACSF in these chambers and the atmosphere above it was continuously gassed with 95% $N_2$/5% $CO_2$. Following this 10 min insult the platforms supporting the slices were returned to their original incubation chambers and maintained for a period of 4 h.

Treatment Groups: For every experiment, three control groups were run: control live (4 h after sham insult), control dead (4 h after 10 min OGD insult), and control protection (4 h post 10 min OGD insult in 0.3 mM Ca, with 30 min preincubation). In experiments where control live slices didn't survive, control dead slices didn't die, or control protection slices were not significantly better than those in the control dead group, the entire experiment was rejected.

(a) Preservation of Evoked Field Potentials: The efficacy of synaptic transmission in these slices was evaluated using electrophysiological techniques. Slices were transferred to an interface recording chamber (Haas et al., *J. Neurosci. Meth.* 1:323-325, 1979) and perfused at a rate of 1 mL/min at 35.0±0.5° C. Orthodromic field potentials were evoked by stimulating the Schaffer collaterals with a concentric bipolar tungsten electrode. Stimulation consisted of 2 ms duration constant-current pulses separated by 30 s intervals. Evoked potentials (EP) were recorded in the CA1 from the stratum pyrimidale using glass micropipettes (2-5 megohms) filled with 150 mM NaCl. Population spike (PS) amplitude was measured from the peak downward deflection to the midway point between the 2 positive peaks. PS amplitude was optimized by adjusting the recording electrode within the slice, usually to a depth of about 50 μM. In slices whose PS was less than 3 mV in amplitude, a $2^{nd}$ and, if necessary, a $3^{rd}$ attempt was made to obtain a more robust PS, by relocating the recording electrode within the CA1. The largest amplitude PS from these multiple recording attempts was tabulated.

Figure 14:
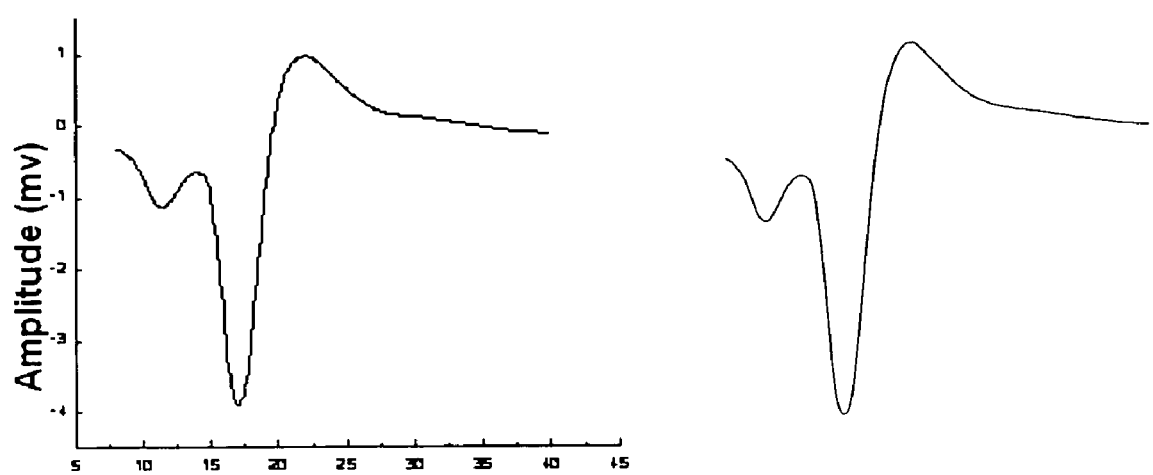
FIG. 14 shows the effects of compound 12 (50 µM) on population spike (PS) amplitude in hippocampal cells. Traces show PSs recorded prior to (left), or 5 min after starting perfusion with 50 µM compound 12 (right). Results are typical of 3 experiments. Each trace is the average of 10 consecutively recorded field potentials; 0.03 Hz stimulation. Left shows the population spike in normal CA1 hippocampal cells evoked by stimulation of the Schaffer collaterals with 2 millisecond pulses. Right shows that application of compound 12 does not modify normal evoked field potentials in normal CA1 cells.
Figure 15:
FIG. 15 shows the effects of compound 12 (50 µM) on population spike (PS) amplitude in hippocampal cells; control slices (left), slices subjected to OGD (middle); and slices subjected OGD in 0.3 mM $Ca^{2+}$. Each trace is the average of 10 consecutively recorded field potentials; 0.03 Hz stimulation.
Figure 16:
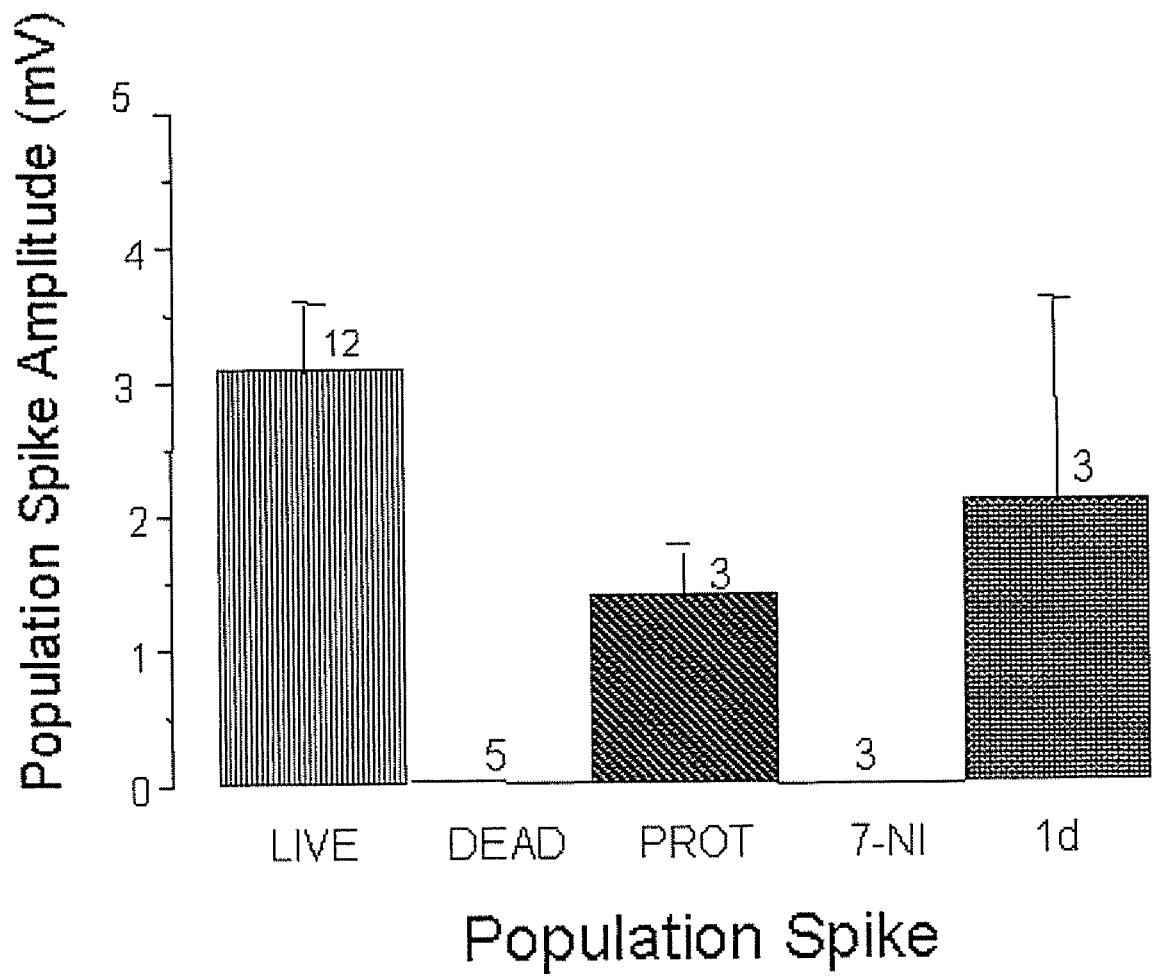
FIG. 16 shows the effects of treatment with 0.3 M $Ca^{2+}$, and NOS inhibitors 7-NI (100 µM) and compound 12. Either protection by low $Ca^{2+}$ concentration (0.3 mM) or compound 12 (50 µM) shows preservation of population spike, while 7-NI (100 µM) treatment did not preserve population spike in hippocampal slices.

In control slices, PS amplitude was not affected by 50 μM compound 12 (FIG. 14; control left, compound 12 right). In FIG. 15, traces show PS's recorded from control slices (left), slices subjected to OGD (middle) and slices subjected OGD in 0.3 mM $Ca^{2+}$. Each trace is the average of 10 consecutively recorded field potentials; 0.03 Hz stimulation. Hippocampal slices not subjected to an OGD insult (control live) had a PS amplitude of 3.5±0.5 mV (n=12). Slices exposed to 10 min OGD (control dead) showed fiber volleys, but no PSs (n=5), whereas slices exposed to the same insult, but incubated in 0.3 mM $Ca^{2+}$ 30 min prior to and during the insult (control protection) had a PS amplitude of 1.4±0.3 mV (n=3) (FIG. 16).

Slices incubated in 0.05% DMSO alone (the maximum concentration of vehicle used for 7-NI) and exposed to OGD, as per the treatment groups, had PS amplitudes not significantly different from the control dead group. Slices incubated with 100 μM 7-NI showed fiber volleys, but no PSs (n=3). Slices treated with 50 μM compound 12 had PS amplitudes of 2.1±1.5 mV (n=3). All of these results indicate a neuroprotective effect of compound 12.

Figure 17:
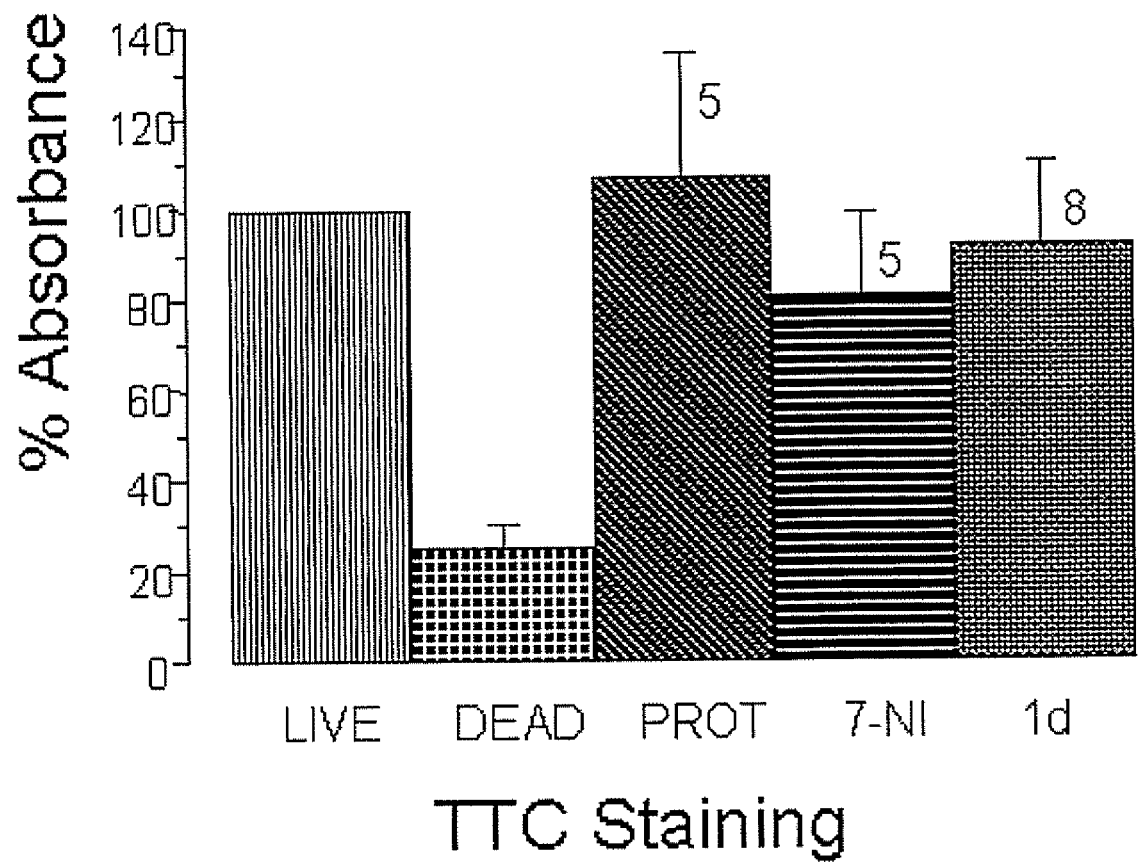
FIG. 17 shows the effects of 0.3M $Ca^{2+}$ (PROT), 7-NI (100 µM) or compound 12 (50 µM) on the preservation of mitochondrial respiration in hippocampal slices after 10 min of OGD.

(b) Preservation of Mitochondrial Metabolic Activity by compound 12 using TTC staining: Hippocampal slices exposed to 10 min OGD (control dead) retained 25±5% (n=5 groups of 4-5 slices) of the absorbance of slices not subjected to an insult (control live—normalized to 100%), whereas slices preincubated in 0.3 mM calcium 30 min prior to and during OGD retained 107±27% (n=5) of their absorbance (control protection). Slices incubated in 0.05% DMSO alone (the maximum concentration of vehicle used for 7-NI) and exposed to OGD, as per the compound treatment groups, had absorbances not significantly different from the control dead group (data not shown). Slices treated with 100 μM 7-NI retained 81±18% (n=5) of their absorbance, while slices treated with 50 μM compound 12 retained 92±18% (n=8) of their absorbance (see FIG. 17). These results again indicate a neuroprotective effect for compound 12.

EXAMPLE 60

Efficacy in Models Predictive of Neuropathic-Like Pain States

The efficacy of the compounds of the invention for the treatment of neuropathic pain was assessed using standard animal models predictive of anti-hyperalgesic and anti-allodynic activity induced by a variety of methods, each described in more detail below.

Figure 18:
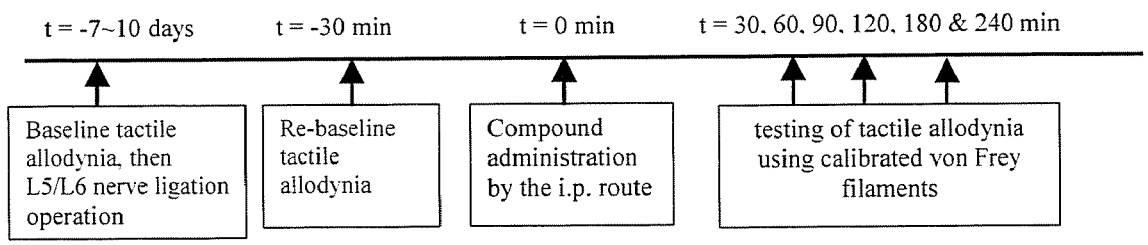
FIG. 18 shows flow charts of the experimental designs used in the Chung Spinal Nerve Ligation (SNL) model assays (tactile allodynia and thermal hyperalgesia) for neuropathic pain.
Figure 18:
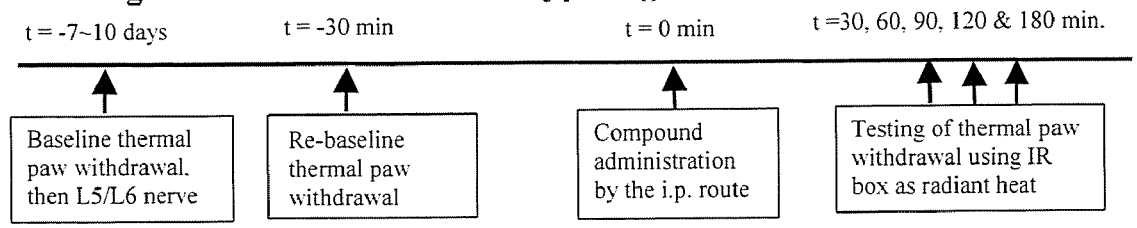

(a) Chung Model of Injury-induced Neuropathic-like Pain: The experimental designs for the Chung Spinal Nerve Ligation SNL Model assay for neuropathic pain are depicted in FIG. 18. Nerve ligation injury was performed according to the method described by Kim and Chung (Kim and Chung, *Pain* 50:355-363, 1992). This technique produces signs of neuropathic dysesthesias, including tactile allodynia, thermal hyperalgesia, and guarding of the affected paw. Rats were anesthetized with halothane and the vertebrae over the L4 to S2 region were exposed. The L5 and L6 spinal nerves were exposed, carefully isolated, and tightly ligated with 4-0 silk suture distal to the DRG. After ensuring homeostatic stability, the wounds were sutured, and the animals allowed to recover in individual cages. Sham-operated rats were prepared in an identical fashion except that the L5/L6 spinal nerves were not ligated. Any rats exhibiting signs of motor deficiency were euthanized. After a period of recovery following the surgical intervention, rats show enhanced sensitivity to painful and normally non-painful stimuli.

Figure 19:
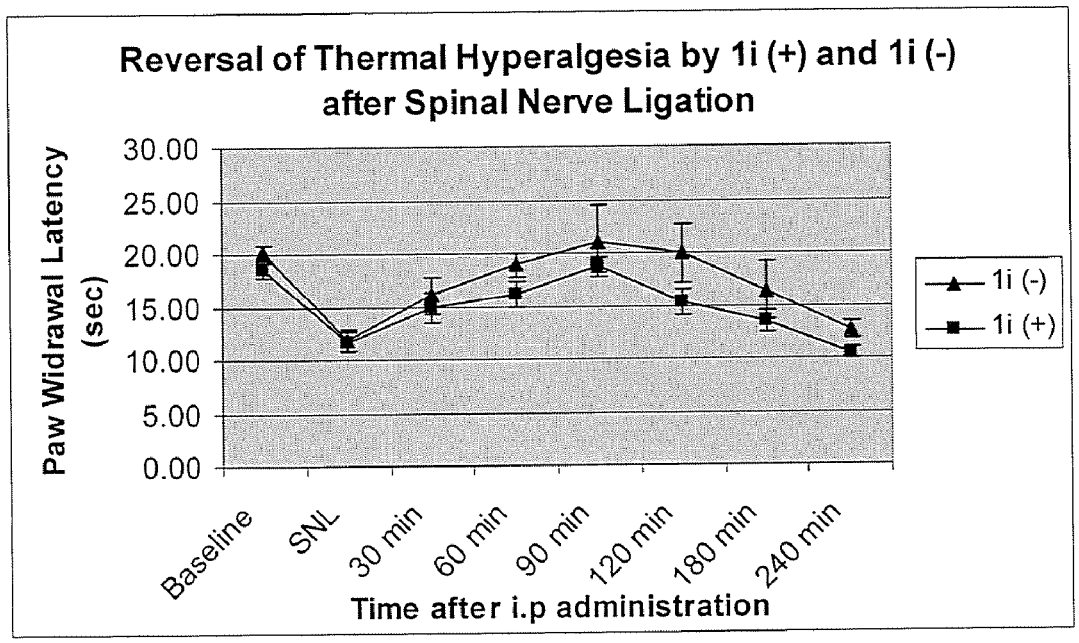
FIG. 19 shows the effect of 30 mg/kg i.p. administration of compounds 32(+) and 32(−) on the reversal of thermal hyperalgesia in rats after L5/L6 spinal nerve ligation (Chung neuropathic pain model).
Figure 20:
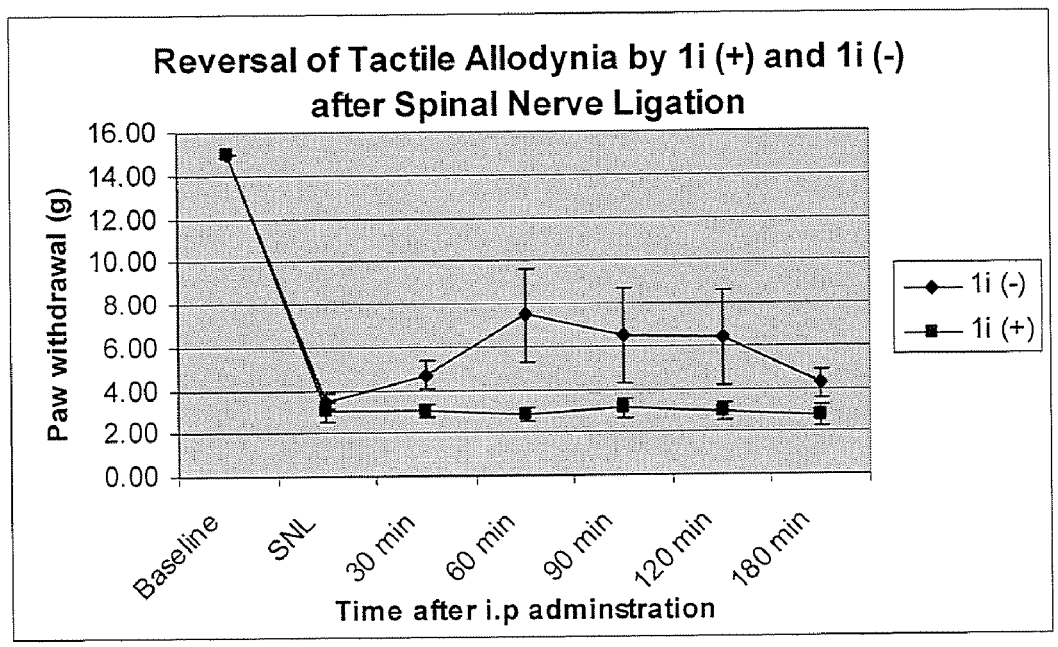
FIG. 20 shows the effect of 30 mg/kg i.p. administration of compounds 32(+) and 32(−) on the reversal of tactile allodynia in rats after L5/L6 spinal nerve ligation (Chung neuropathic pain model).
Figure 21:
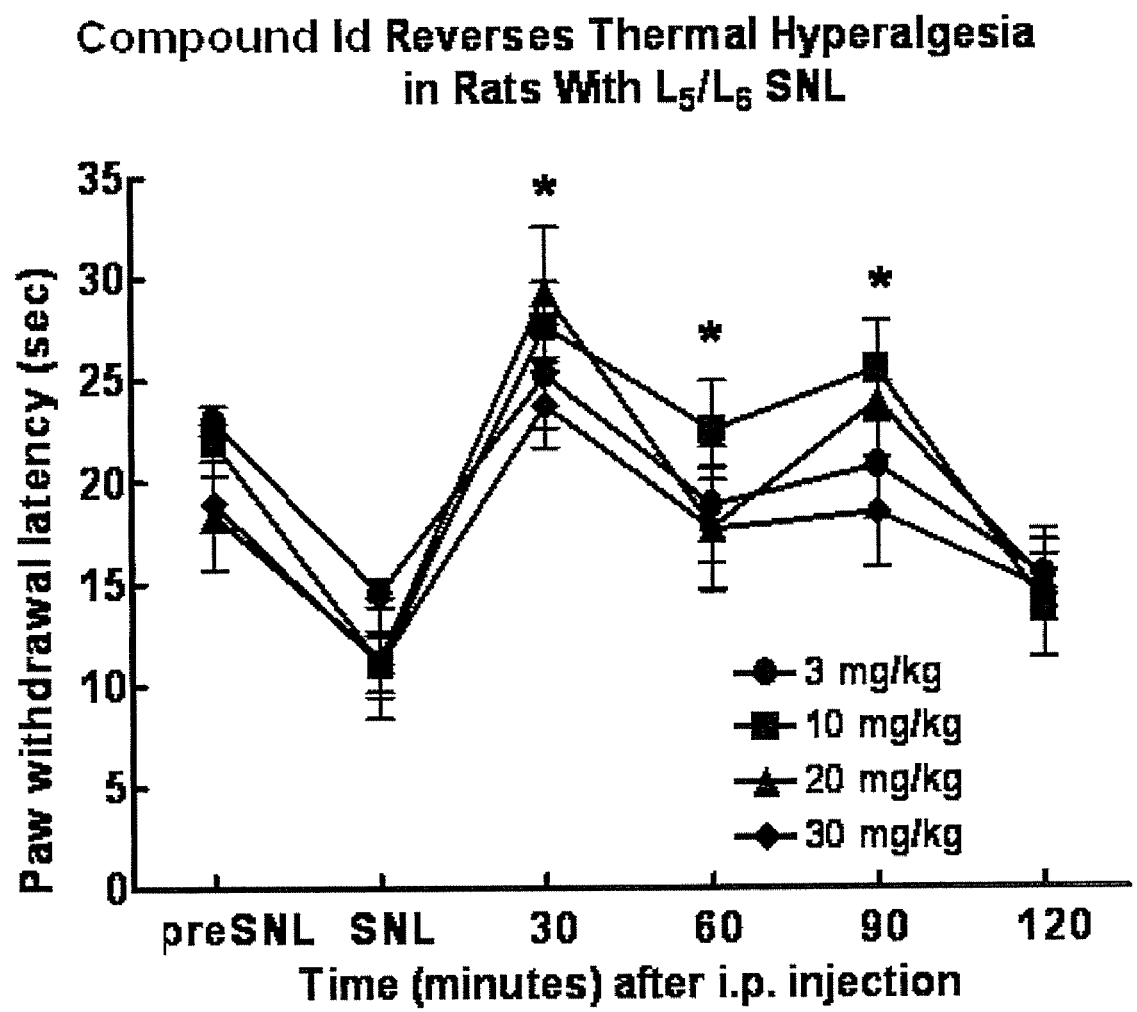
FIG. 21 shows the dose response (3 mg/kg-30 mg/kg) of compound 12 on the reversal of thermal hyperalgesia in rats after L5/L6 spinal nerve ligation (Chung neuropathic pain model).
Figure 22:
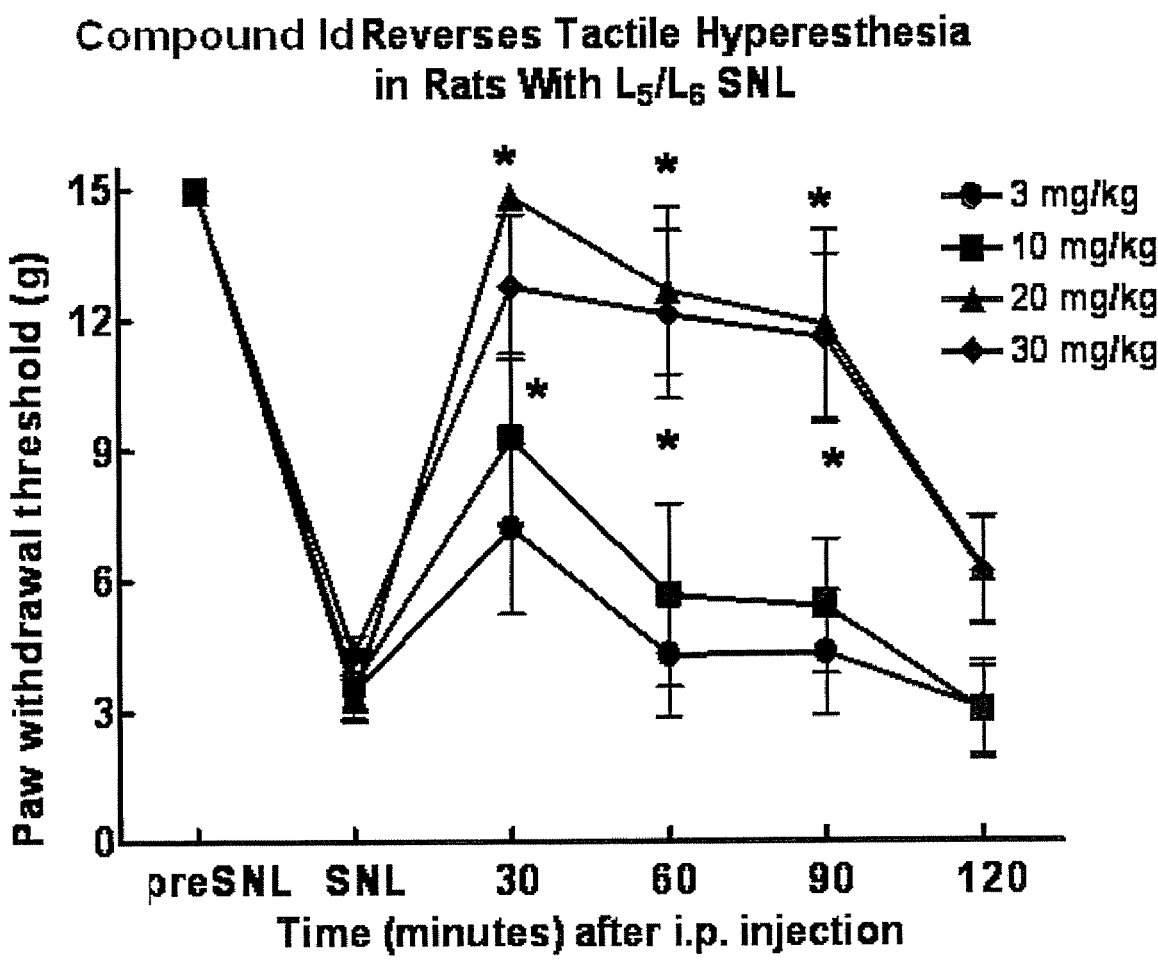
FIG. 22 shows the dose response (3 mg/kg-30 mg/kg) of compound 12 on the reversal of tactile hyperthesia in rats after L5/L6 spinal nerve ligation (Chung neuropathic pain model).

After one standard dose (10 mg/kg) injected IP according to the published procedure, there is a clear antihyperalgesic effect of nNOS selective compounds 32(−), 32(+) (see FIG. 19), and 12 (see FIG. 21). Administration of compounds 32(−), 32(+), and 12 to test animals also resulted in a reversal of tactile hyperthesia (see FIGS. 20 and 22, respectively). A clear difference between the two enantiomers of compound 32 was observed in this model of neuropathic pain.

EXAMPLE 61

Experimental Migraine Model

Animals. Male, Sprague Dawley rats (275-300 g) were purchased from Harlan Sprague Dawley (Indianapolis, Ind.). Animals were given free access to food and water. Animals were maintained on a 12 hour light (7 am to 7 pm) and 12 hour dark cycle (7 pm to 7 am). All procedures were in accordance with the policies and recommendations of the International Association for the Study of Pain and the National Institutes of Health guidelines and use of laboratory animals as well as approved by the Animal Care and Use Committee of the University of Arizona.

Surgical Preparation.

Migraine cannulation: Male Sprague Dawley rats were anesthetized using ketamine/xylazine (80 mg/kg, i.p.), the top of the head was shaved using a rodent clipper (Oster Golden A5 w/size 50 blade), and the shaved area was cleaned with betadine and 70% ethanol. Animals were placed into a stereotaxic apparatus (Stoelting model 51600) and the body core temperatures of 37° C. were maintained using a heating pad placed below the animals. Within the shaved and cleaned area on the head, a 2 cm incision was made using a scalpel with a #10 blade and any bleeding was cleaned using sterile cotton swabs. Location of bregma and midline bone sutures were identified as references and a small hole 1 mm in diameter was made using a hand drill without breaking the dura but deep enough to expose the dura. Two additional holes (1 mm in diameter) 4 to 5 mm from the previous site were made in order to mount stainless steel screws (Small Parts #A-MPX-080-3F) securing the cannula through which an inflammatory soup could be delivered to induce experimental migraine. A modified intracerebroventricular (ICV) cannula (Plastics One #C313G) was placed into the hole without penetrating into or through the dura. The ICV cannula was modified by cutting it to a length of 1 mm from the bottom of the plastic threads using a Dremel mototool and a file to remove any steel burrs. Once the modified migraine cannula was in place, dental acrylic was placed around the migraine cannula and stainless steel screws in order to assure that the cannula was securely mounted. Once the dental acrylic was dry (i.e., after 10-15 min) the cap of the cannula was secured on top to avoid contaminants entering the cannula and the skin was sutured back using 3-0 silk suture. Animals were given an antibiotic injection (Amikacin C, 5 mg/kg, i.m.) and removed from the stereotaxic frame and allowed to recover from anesthesia on a heated pad. Animals were placed in a clean separate rat cage for a 5 day recovery period.

Injections. Subcutaneous injections: Subcutaneous (s.c.) injections were performed by manually holding the animal and inserting a 25 gauge disposable needle on a disposable 1 cc syringe into the abdominal region of the animal assuring that the needle remained between the muscle and the skin of the animal. Injections of compounds were performed over a 5 sec period and were noted as positive by the development of an out-pocketing of the skin at the site of injection. Oral delivery was accomplished by using an 18 gauge gavage needle attached to a 1 cc syringe.

Migraine cannula injections: An injection cannula (Plastics One, C313I cut to fit the modified ICV cannulas) connected to a 25 μl Hamilton Syringe (1702SN) by tygon tubing (Cole-Palmer, 95601-14) was used to inject 10 μl of the inflammatory mediators solution onto the dura.

Behavioral Testing. Naïve animals prior to the day of migraine surgery are placed in suspended plexiglass chambers (30 cm L×15 cm W×20 cm H) with a wire mesh bottom (1 cm$^2$) and acclimated to the testing chambers for 30 minutes.

Hindpaw sensory thresholds to non-noxious tactile stimuli in rats

The paw withdrawal thresholds to tactile stimuli were determined in response to probing, with calibrated von Frey filaments (Stoelting, 58011). The von Frey filaments were applied perpendicularly to the plantar surface of the hind paw of the animal until it buckles slightly, and is held for 3 to 6 sec. A positive response was indicated by a sharp withdrawal of the paw. The 50% paw withdrawal threshold was determined by the non-parametric method of Dixon (1980). An initial probe equivalent to 2.00 g was applied and if the response was negative the stimulus was increased one increment, otherwise a positive response resulted in a decrease of one increment. The stimulus was incrementally increased until a positive response was obtained, then decreased until a negative result was observed. This "up-down" method was repeated until three changes in behavior were determined. The pattern of positive and negative responses was tabulated. The 50% paw withdrawal threshold is determined as $(10^{[Xf+kM]})/10,000$, where Xf=the value of the last von Frey filament employed, k=Dixon value for the positive/negative pattern, and M=the mean (log) difference between stimuli. Only naïve animals with baselines of 11 to 15 g were used in the experiment. Fifteen grams was used as the maximal cut-off. Five days post migraine surgery animals paw withdrawal thresholds were re-tested using the same habituation and von Frey procedure as stated above. Data were converted to % "antiallodynia" by the formula: % activity=100×(post-migraine value−baseline value)/(15 g−baseline value). Only animals that demonstrated no difference in their tactile hypersensitivity as compared to their pre-migraine surgery values were used in all studies.

After establishing baseline paw withdrawal thresholds, individual animals were removed from the testing chamber, the cap of the migraine cannula was removed and animals received an injection of either a mixture of inflammatory mediators (1 mM Histamine, 1 mM 5-HT [Serotonin], 1 mM Bradykinin, 1 mM PGE$_2$) or vehicle at 10 uL volume via the migraine cannula over a 5 to 10 second period. The inflammatory mediator (IM) cocktail was made fresh on the day of each experiment. The cap of the migraine cannula was replaced, individual animals were placed back into their corresponding testing chamber and paw withdrawal thresholds were measured at 1 hour intervals over a 6 hour time course. Data were converted to % "antiallodynia" by the formula: % activity=100×(post-IM value−pre-IM baseline value)/(15 g−pre-IM baseline value).

Figure 23:
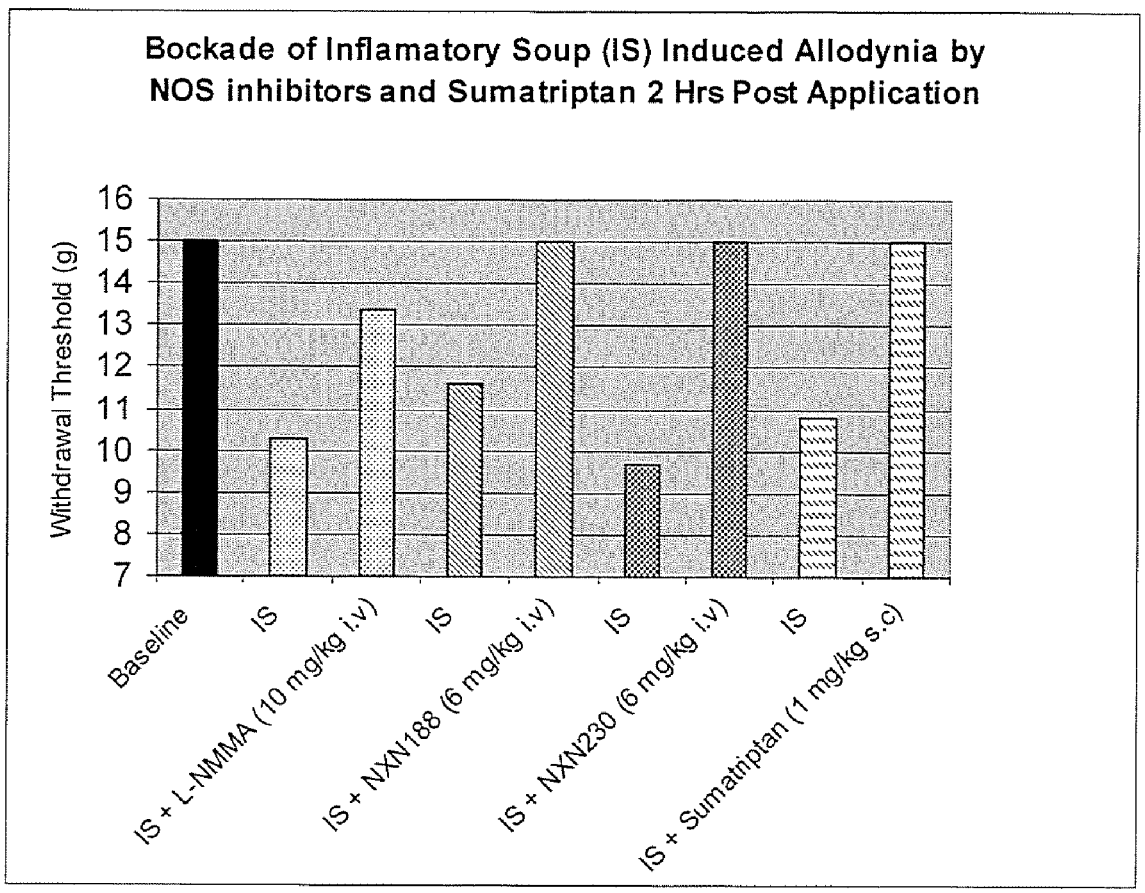
FIG. 23 is a bar graph showing the effects of various NOS inhibitors (i.v.) or Sumatriptan succinate (s.c.) on the reversal of hindpaw allodynia in rats 2 hours after exposure of the dura with an inflammatory soup.

Data on selected compounds of the invention obtained using this model are shown in FIG. 23. Application of an inflammatory soup (IS) onto the dura results in a decrease in the hindpaw withdrawal threshold upon stimulation with von Frey filaments. Administration of Sumatriptan succinate (1 mg/kg s.c.) 5 minutes prior to the addition of the soup results in the prevention of the development of hindpaw allodynia as measured two hours after IS administration. Similarly the non-selective NOS inhibitor L-NMMA (10 mg/kg i.v) or 42 and 97 (6 mg/kg i.v.) 10 minutes prior to IS prevents the development of hindpaw allodynia. Thus non selective NOS inhibitors such as L-NMMA, or more selective nNOS inhibitors (e.g., compound 97) or mixed nNOS/5HT1D/1B compounds (e.g., compound 42) should be effective for the treatment of migraine.

EXAMPLE 62

Serotonin 5HT1D/1B Binding Assays

5-HT1D binding assays (agonist radioligand) were performed using bovine caudate membranes according to the methods of Heuring and Peroutka (J. Neurosci 1987, 7: 894-903). 5-HT1B (rat cerebral cortex) binding assays (agonist radioligand) were performed according to the method of Hoyer et. al. (Eur. J. Pharmacol. 1995, 118: 1-12). For the purpose of result analysis, the specific ligand binding to the receptors is defined as the difference between the total binding and the nonspecific binding as determined in the presence of an excess of unlabelled ligand. The results are expressed as a percent of control specific binding obtained in the presence of the test compounds. IC$_{50}$ values (concentration causing a half-maximal inhibition of control specific binding) and Hill coefficients ($n_H$) were determined by non-linear regression analysis of the competition curves using Hill equation curve fitting and the inhibition constants (K$_i$) were calculated from the Cheng Prusoff equation ($K_i=IC_{50}/(1+(L/K_D))$, where L=concentration of radioligand in the assay, and $K_D$=affinity of the radioligand for the receptor).

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:

1. A compound having the formula:

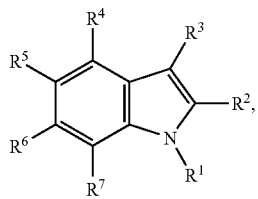

or a pharmaceutically acceptable salt or prodrug thereof, wherein,
- $R^1$ is H, optionally substituted $C_{1-6}$ alkyl, optionally substituted $C_{1-4}$ alkaryl, optionally substituted $C_{2-9}$ heterocyclyl, or optionally substituted $C_{1-4}$ alkheterocyclyl;
- $R^2$ is H, Hal, optionally substituted $C_{1-6}$ alkyl, optionally substituted $C_{6-10}$ aryl, optionally substituted $C_{1-4}$ alkaryl, optionally substituted $C_{2-9}$ bridged heterocyclyl, optionally substituted $C_{1-4}$ bridged alkheterocyclyl, optionally substituted $C_{2-9}$ heterocyclyl, or optionally substituted $C_{1-4}$ alkheterocyclyl;
- $R^3$ is H, Hal, optionally substituted $C_{1-6}$ alkyl, optionally substituted $C_{6-10}$ aryl, optionally substituted $C_{1-4}$ alkaryl, optionally substituted $C_{2-9}$ bridged heterocyclyl, optionally substituted $C_{1-4}$ bridged alkheterocyclyl, optionally substituted $C_{2-9}$ heterocyclyl, or optionally substituted $C_{1-4}$ alkheterocyclyl;
- each of $R^4$ and $R^7$ is, independently, H, F, $C_{1-6}$ alkyl, or $C_{1-6}$ alkoxy;
- $R^5$ is H, $R^{5A}C(NH)NH(CH_2)_{r5}$ or $R^{5B}NHC(S)NH(CH_2)_{r5}$, wherein r5 is an integer from 0 to 2, $R^{5A}$ is optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl; $R^{5B}$ is optionally substituted $C_{1-6}$ thioalkoxy, optionally substituted $C_{1-4}$ thioalkaryl, or optionally substituted $C_{1-4}$ thioalkheterocyclyl; and
- $R^6$ is H or $R^{6A}C(NH)NH(CH_2)_{r6}$ or $R^{6B}NHC(S)NH(CH_2)_{r6}$, wherein r6 is an integer from 0 to 2, $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl; $R^{6B}$ is optionally substituted $C_{6-10}$ aryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl;
wherein one, but not both, of $R^5$ and $R^6$ is H.

2. The compound of claim 1, wherein,
- $R^1$ is H, optionally substituted $C_{1-6}$ alkyl, optionally substituted $C_{1-4}$ alkaryl, or optionally substituted $C_{1-4}$ alkheterocyclyl;
- each of $R^2$ and $R^3$ is, independently, H, Hal, optionally substituted $C_{1-6}$ alkyl, optionally substituted $C_{6-10}$ aryl, optionally substituted $C_{1-4}$ alkaryl, optionally substituted $C_{2-9}$ heterocyclyl, or optionally substituted $C_{1-4}$ alkheterocyclyl;
- each of $R^4$ and $R^7$ is, independently, H, F, $C_{1-6}$ alkyl, or $C_{1-6}$ alkoxy;
- $R^5$ is H or $R^{5A}C(NH)NH(CH_2)_{r5}$, wherein r5 is an integer from 0 to 2, $R^{5A}$ is optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted $C_{1-4}$ thioalkheterocyclyl; and
- $R^6$ is H or $R^{6A}C(NH)NH(CH_2)_{r6}$, wherein r6 is an integer from 0 to 2, $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted $C_{1-4}$ thioalkheterocyclyl.

3. The compound of claims 1 or 2, wherein $R^5$ is $R^{5A}C(NH)NH(CH_2)_{r5}$, and $R^{5A}$ is thiomethoxy, thioethoxy, thio-n-propyloxy, thio-i-propyloxy, thio-n-butyloxy, thio-i-butyloxy, thio-t-butyloxy, phenyl, benzyl, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, and 4-isothiazole.

4. The compound of claim 1 or 2, wherein $R^6$ is $R^{6A}C(NH)NH(CH_2)_{r6}$, and $R^{6A}$ is methyl, fluoromethyl, ethyl, n-propyl, i-propyl, n-butyl, i-butyl, t-butyl, thiomethoxy, thioethoxy, thio-n-propyloxy, thio-i-propyloxy, thio-n-butyloxy, thio-i-butyloxy, thio-t-butyloxy, phenyl, benzyl, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, and 4-isothiazole.

5. The compound of claims 1 or 2, wherein one or more of $R^1$, $R^2$, and $R^3$ is not H.

6. The compound of claims 1 or 2, wherein $R^1$ is $(CH_2)_{m1}X^1$, wherein $X^1$ is selected from the group consisting of:

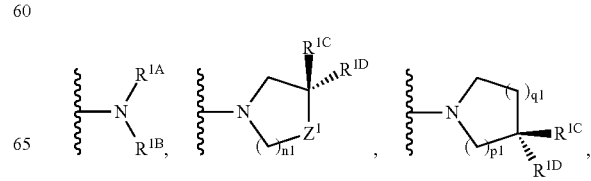

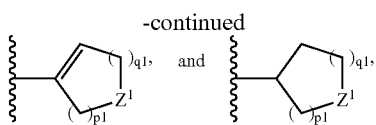

wherein
- each of $R^{1A}$ and $R^{1B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;
- each of $R^{1C}$ and $R^{1D}$ is, independently, H, OH, $CO_2R^{1E}$, or $NR^{1F}R^{1G}$, wherein each of $R^{1E}$, $R^{1F}$, and $R^{1G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{1C}$ and $R^{1D}$ together with the carbon they are bonded to are C=O;
- $Z^1$ is $NR^{1H}$, $NC(O)R^{1H}$, $NC(O)OR^{1H}$, $NC(O)NHR^{1H}$, $NC(S)R^{1H}$, $NC(S)NHR^{1H}$, $NS(O)_2R^{1H}$, O, S, S(O), or $S(O)_2$, wherein $R^{1H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;
- m1 is an integer of 2 to 6;
- n1 is an integer of 1 to 4;
- p1 is an integer of 0 to 2; and
- q1 is an integer of 0 to 5.

7. The compound of claims 1 or 2, wherein $R^3$ is $(CH_2)_{m3}X^3$, wherein $X^3$ is selected from the group consisting of:

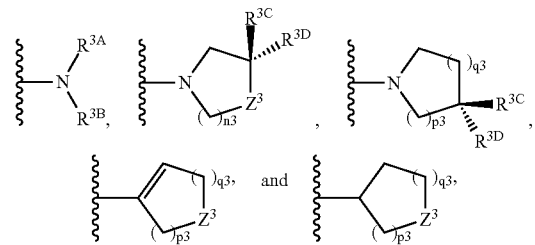

wherein
- each of $R^{3A}$ and $R^{3B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;
- each of $R^{3C}$ and $R^{3D}$ is, independently, H, OH, $CO_2R^{3E}$, or $NR^{3F}R^{3G}$, wherein each of $R^{3E}$, $R^{3F}$, and $R^{3G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{3C}$ and $R^{3D}$ together with the carbon they are bonded to are C=O;
- $Z^3$ is $NR^{3H}$, $NC(O)R^{3H}$, $NC(O)OR^{3H}$, $NC(O)NHR^{3H}$, $NC(S)R^{3H}$, $NC(S)NHR^{3H}$, $NS(O)_2R^{3H}$, O, S, S(O), or $S(O)_2$, wherein $R^{3H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;
- m3 is an integer of 2 to 6;
- n3 is an integer of 1 to 4;
- p3 is an integer of 0 to 2; and
- q3 is an integer of 0 to 5.

8. The compound of claim 1, wherein said compound selectively inhibits neuronal nitric oxide synthase (nNOS) over endothelial nitric oxide synthase (eNOS) or inducible nitric oxide synthase (iNOS).

9. The compound of claim 8, wherein said compound selectively inhibits nNOS over both eNOS and iNOS.

10. The compound of claim 1, wherein $R^5$ is $R^{5B}NHC(S)NH(CH_2)_{r5}$, and $R^{5B}$ is thiomethoxy, thioethoxy, thio-n-propyloxy, thio-i-propyloxy, thio-n-butyloxy, thio-i-butyloxy, or thio-t-butyloxy.

11. The compound of claim 1, wherein $R^6$ is $R^{6B}NHC(S)NH(CH_2)_{r6}$, and $R^{6B}$ is thiomethoxy, thioethoxy, thio-n-propyloxy, thio-i-propyloxy, thio-n-butyloxy, thio-i-butyloxy, thio-t-butyloxy, phenyl, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, or 4-isothiazole.

12. The compound of claim 1, wherein $R^1$ or $R^3$ is optionally substituted $C_{2-9}$ heterocyclyl or optionally substituted $C_{1-4}$ alkheterocyclyl, wherein the heterocyclyl moiety is a bicyclic, nitrogen containing heterocyclyl.

* * * * *

UNITED STATES PATENT AND TRADEMARK OFFICE
CERTIFICATE OF CORRECTION

| | | |
|---|---|---|
| PATENT NO. | : 7,951,940 B2 | |
| APPLICATION NO. | : 12/047963 | |
| DATED | : May 31, 2011 | |
| INVENTOR(S) | : Maddaford et al. | |

It is certified that error appears in the above-identified patent and that said Letters Patent is hereby corrected as shown below:

Cover page, under OTHER PUBLICATIONS, Col. 2 in Perregaared et al.,
   replace "Perregaared" with --Perregaard--.

Page 2, under OTHER PUBLICATIONS, in Cooper et al., replace
   "Pptimisation" with --Optimisation--.

Column 1, Line 37, replace "while m" with --while--;

Lines 42-43, replace "therapeutice" with --therapeutic--.

Column 63, Lines 24-25, replace "acid-7-chlorothiokynurenic
   acid;" with --acid; 7-chlorothiokynurenic acid;--.

Column 65, Line 56, replace "PD patients" with --AD patients--.

Column 78, Line 62, replace "$NH_{13}$" with --$NH_3$--.

Column 89, Line 13, replace "J-1.8" with --J=1.8--.

Column 94, Line 3, replace "filtered off though celite bed" with
   --filtered off through celite bed--;

Line 29, replace "7.27 (d, H, J=8.4 Hz)" with --7.27 (d, 1H, J=8.4 Hz)--.

Column 96, Line 46, replace "ESI-MS i/z" with --ESI-MS m/z--;

Line 47, replace "321 (M, 100)." with --321 ($M^+$, 100).--.

Signed and Sealed this
Third Day of July, 2012

David J. Kappos
*Director of the United States Patent and Trademark Office*

CERTIFICATE OF CORRECTION (continued)
U.S. Pat. No. 7,951,940 B2

Column 102, Line 3, replace "(q 2H, J=4.5 Hz)" with --(q, 2H, J=4.5 Hz)--;

Line 4, replace "3.10-3.04 (t J=7.5, 2H)" with --3.10-3.04 (t, J=7.5, 2H)--.

Column 106, Line 20, replace "(1.23 cg, 92%)" with --(1.23 g, 92%)--.

Column 109, Line 19, replace "crude was product was purified"
with --crude product was purified--.

Column 115, Lines 9-10, replace "(ethyla acetate)" with --(ethyl acetate)--.

Column 119, Line 24, replace "combine d" with --combined--.

Column 121, Line 10, replace "The react was stirred" with --The reaction was stirred--.

Column 126, Line 6, replace "(q, H, J=9, 17.1 Hz)" with --(q, 1H, J=9, 17.1 Hz)--.

Column 128, Line 14, replace "J=1.8.9 Hz" with --J=1.8, 9 Hz--.

Column 136, Lines 29-30, replace "2:3 ratio of diastereomners"
with --2:3 ratio of diastereomers--.

Column 145, Line 57, replace "organis" with --organics--.

Column 146, Line 28, replace "The react" with --The reaction--.